United States Patent
Bolli et al.

(10) Patent No.: US 7,238,685 B2
(45) Date of Patent: Jul. 3, 2007

(54) BENZO-FUSED HETEROCYCLES AS ENDOTHELIN ANTAGONISTS

(75) Inventors: Martin Bolli, Allschwil (CH);
Christoph Boss, Allschwil (CH);
Martine Clozel, Binningen (CH);
Walter Fischli, Allschwil (CH);
Thomas Weller, Binningen (CH);
Judith Marfurt, Oberwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 325 days.

(21) Appl. No.: 10/486,602

(22) PCT Filed: Jul. 31, 2002

(86) PCT No.: PCT/EP02/08523

§ 371 (c)(1),
(2), (4) Date: Sep. 28, 2004

(87) PCT Pub. No.: WO03/013545

PCT Pub. Date: Feb. 20, 2003

(65) Prior Publication Data

US 2005/0124605 A1    Jun. 9, 2005

(30) Foreign Application Priority Data

Aug. 9, 2001   (EP) ................. PCT/EP01/09235

(51) Int. Cl.
*C07D 243/24*   (2006.01)
*C07D 217/16*   (2006.01)
*C07D 401/12*   (2006.01)
*A61K 31/5513*  (2006.01)
*A61P 19/00*    (2006.01)

(52) U.S. Cl. .................. 514/211.09; 514/212.07; 514/217.12; 514/220; 514/221; 514/307; 540/504; 540/552; 540/562; 540/563; 540/566; 540/573; 540/593; 546/144

(58) Field of Classification Search ........... 540/504, 540/552, 562, 563, 566, 573, 593; 546/144; 514/211.09, 212.07, 217.12, 220, 221, 307
See application file for complete search history.

(56) References Cited

OTHER PUBLICATIONS

Kocienski, P.J., "Protecting Groups," 1994, New York, Table of Contents.
March, J., "Advanced Organic Chemistry," 1984, New York, Table of Contents.
Romeo, G., et al., "Nuclear Magnetic Resonance of Psychotherapeutic Agents," Organic Magnetic Resonance, vol. 15, No. 1, 1981, pp. 33-36.
Hiroshi, A., et al., "Cloning and expression of a cDNA encoding an endothelin receptor," Nature, vol. 348, Dec. 1990.
Effland, R.C., et al., Synthesis of 1,4-Benzodiazepino[4,5-d][1,4]benzoxazepines, May-Jun. 1982, pp. 537-539.

Walser, A., et al., Quinazolines and 1,4-Benzodiazepines, XCIII. (1). Synthesis of Imidazo[1,5-a][1,4]benzodiazepines from Nitrooximes, May-Jun. 1983, pp. 551-558.
Shridhar, D.R., et al., "Synthesis of B-Lactams using a New phosphorylating Agent, Phenyl N-Methyl-N-phenylphosphoramidochloridate", Communications, Oct. 1984, pp. 846-847.
Antilla, J.C., et al., "Copper-Catalyzed Coupling of Arylboronic Acids and Amines," Organic Letters, 2001, vol. 3, nol. 13, pp. 2077-2079.
Ogawa, Y., et al., "Molecular Cloning of a Non-Isopeptide-Selective Human Endothelin Receptor," Biochemical and Biophysical Research Communications, vol. 178, No. 1, Jul. 1991, pp. 248-255.
Ohlstein, E.H., et al., "Endothelin-1 Modulates Vascular Smooth Muscle Structure and Vasomotion: Implications in Cardiovascular Pathology," Drug Development Research 29, 1993, pp. 108-128.
McMillen, M.A., et al., "Endothelins: Polyfunctional Cytokines," Collective Review, Journal of the American College of Surgeons, May 1995, vol. 180, pp. 621-637.
Trybulski, E.J., et al., "2-Benzazepines. 9.1 Synthesis and Chemistry of 3H-2-Benzazepine and Pyrimido[4,5-d][2]benzazepine Derivatives," Journal of Organic Chemistry, Jun. 1986, vol. 51, No. 12, pp. 2191-2202.
Trybulski, E.J., et al., "2-Benzazepines. 1.1 Synthesis of 2-Benzazepine-4-ones and 5-ones via 2-Acetylenic Benzophenones," Journal of Organic Chemistry, Jun. 1982, vol. 47, No. 12, pp. 2441-2447.
Trybulski, E.J., et al., "2-Benzazepines. 9.1 Synthesis and Chemistry of 3H-2-Benzazepine and Pyrimido[4,5-d][2]benzazepine Derivatives," Journal of Organic Chemistry,Jun. 1986, vol. 51, No. 12, pp. 2191-2202.
Amin, S.G., et al., "A Convenient Method for the Synthesis of B-Lactams via 1-Methyl-2-halopyridinium Salts," Communications, Mar. 1979, pp. 210-213.
Shridhar, D.R., et al., "A Convenient Annelation of Imines to a-Substituted B-Lactams," Communications, Jan. 1982, pp. 63-65.
Merifield, E., et al., "Total synthesis of cytochalasin D: total synthesis and full structural assignment of cytochalsin O," J. Chem. So., 1999, pp. 3269-3283.
Ueda, T., et al., "Nucleosides. XVII. Pyrimidinyl Amino Acids," Nov. 1963, pp. 697-701.
Koppel H.C., "Pyrimidines. X. (Antibiotics.II) Synthesis of Bacimethrin, 2-Methoxy Analog of Thamine, and Related Alkoxypyridmides," Midwest Research Institute, vol. 27, May 1962, pp. 3614-3617.
Trybulski, E.J., et al., "2-Benzazepines. 5.1,2 Synthesis of Pyrimido[5,4-d][2]benzazepines and Their Evaluation as Anxiolytic Agents," J.Med.Chem., 1983, pp. 1589-1596.
Gall, M. et al., "Synthesis of Aminoalkyl-Substituted Imidazo[1,2-a]- and Imidazo [1,5-a]benzodiazepines," J. Org. Chem, 1981, pp. 1575-1585.

(Continued)

Primary Examiner—Bruck Kifle
(74) Attorney, Agent, or Firm—Dickstein Shapiro LLP

(57) ABSTRACT

The invention relates to novel benzo-fused heterocycles and their use as active ingredients in the preparation of pharmaceutical compositions. The invention also concerns related aspects including processes for the preparation of the compounds, pharmaceutical compositions containing one or more of those compounds and especially their use as endothelin receptor antagonists.

12 Claims, No Drawings

OTHER PUBLICATIONS

Gilman, N.W., et al., "Atropisomers of 1,4-Benzodiazepines. 2. Synthesis and Resolution of Imidazo[1,5-a][1,4]Benzodiazepines," J. Org. Chem., 1993, pp. 3285-3298.

Clader, J.W., et al., "2-Azetidinone Cholesterol Absorption Inhibitors: Structure-Activity Relationships on the Heterocyclic Nucleus," J.Med.Chem., 1996, pp. 3684-3693.

Fryer, R.I., et al., "Quinazolines and 1,4-Benzodiazepines. LXXIII. The Ring Expansion of 2-Chloromethylquinazoline 3-Oxides with Nitromethane," Jun. 1976, pp. 433-437.

Breslin, H.J., et al., "Synthesis and Anti-HIV-1 Activity of 4,5,6,7-Tetrahydro-5-methylimidazo-[4,5,1-jk][1,4]benzodiazepin-2(1H)-one (TIBO) Derivatives. 3," J.Med.Chem., 1995, pp. 771-793.

Sternbach, L.H., et al., "Quinazolines and 1,4-Benzodiazepines. XI. Synthesis and Transformations of 7-Choloro-2-3-dihydro(and 2,32,4,5-tetrahydro)-5-phenyl-1H-1,4-benzodiazepine," Notes, vol. 28, Mar. 1963, pp. 2456-2459.

Qui, J., et al., "2,6-Difluorophenol as a Bioisostere of a Carboxylic Acid: Bioisosteric Analogues of y-Aminobutyric Acid," J. Med. Chem., 1999, pp. 329-332.

Trybulski, E.J., et al., "2-Benzazepines. 6.1,2 Synthesis and Pharmacological Properties of the Metabolites of 9-Chloro-7-(2-chloropheny)-5H-pyrimido[5,4-d][p2]benzazepin," J.Med.Chem., 1983, pp. 1596-1601.

Hester, J.B., et al., "6-Phenyl-4H-s-triazolo[4,3-a][1,4]benzodiazepine Which Have Central Nervous System Depressant Activity," Journal of Medicinal Chemistry, 1971, vol. 14, No. 11, pp. 1078-1081.

Walser, A., et al., "Quinazolines and 1,4-Benzodiazepines. 84.1 Synthesis and Reactions of Imidazo[1,5-a][1.4] benzodiazepines," J.Org.Chem., vol. 43, No. 5, 1978, pp. 936-944.

Rubanyi, G.M., et al., "Endothelins: Molecular Biology, Biochemistry, Pharmacology, Physiology, and Pathophysiology," Pharmacological Review, vol. 46, No. 3, 1994, pp. 325-415.

Yanagisawa, M., et al., "A novel potent vasoconstrictor peptide produced by vascular endothelial cells," Nature, vol. 332, Mar. 1988, pp. 411-415.

Umemiya H., et al., "Regulation of Retinoidal Actions by Diazepinylbenzoic Acids. Retinoid Synergists Which Activate the RXR-RAR Heterodimers," J.Med.Chem., 1997, pp. 4222-4234.

Sakurai, T., et al., "Cloning of a cDNA encoding a non-isopeptide-selective subtype of the endothelin receptor," Nature, vol. 348, Dec. 1990, pp. 732-735.

Sharma, S.D., et al., "Studies on fuse B-lactams: Synthesis sterochemistry and antimicrobial activity of some new cepham analogues," Indian Journal of Chemistry, vol. 39B, Feb. 2000, pp. 156-159.

Arai, H., et al., "Cloning and expression of a cDNA endoing an endothelin receptor," Nature, vol. 348, Dec. 1990, pp. 730-732.

Miyake, M., et al., Synthesis of B-Lactams by Convenient Annelation of Imines, Synthetic Communications, vol. 14(4), 1984, pp. 353-362.

Sumner, M.J., et al., "Endothelin ETa and ETb receptors mediate vascular smooth muscle contraction, "Br. J. Pharmacol, 1992, pp. 858-860.

Martin, N.H., "75. Synthesis and Photo-oxygenation of Some Substituted 1-Benzyl-3,4-dihydroisoquinolines. Mechanisms of Enamine Photo-oxygenation," Helvetica Chimca Acta, vol. 65, 1982, pp. 762-774.

Hubschwelen, C., "218. An Enantioselective B-Lactam Synthesis Starting from L-(S)-Glyceraldehyde Acetonide," Helvetica Chimica Acta, vol. 66, 1983, pp. 2206-2209.

Bremner, J.B., et al., "Synthesis of 5-Aryl-1,4-benzoxazepine and 6-Phenyl-2H-1,5-benzoxazocine Derivative," Aust.J.Chem, 1984, pp. 129-141.

Brown, D.J., et al., "Isomerizations Akin to the Dimroth Rearrangement. III★The Conversion of Simple s-Triazolo[4,3-a]pyrimidines into Their [1,5-a] Isomers," Aust. J. Chem. 1997, pp. 2515-2525.

Walser, A., et al., "Quinazolines and 1,4-Benzodiazepines, XCV [1]. Synthesis of 1,4-Benzodiazepines by Ring Expansion of 2-Chloromethylquinazolines with Carbanions," 1986, pp. 1303-1314.

Fryer, R.I., et al., "Synthesis of Novel, Substituted 4H-Imidazo[1,5-a][1,4]benzodiazepines," Nov. 1991, pp. 1661-1669.

Manhas, M.S., et al., "Heterocyclic Compounds. X. Bis(2-chloroethyl)amino Substituted B-Lactams as Potential Antineoplastic Agents (1)," Mar. 1979, pp. 283-288.

Walser, A., et al., "Quinazolines and 1,4-Benzodlazepines. LXXXVII (1). Synthesis of 1-and 3 Phenylimidazo [1,5-a][1,4] benzodiazepines," Aug. 1978, pp. 855-858.

Fryer, R.I., et al., "Quinazolines and 1,4-Benzodiazepines. LXXIII. The Ring Expansion of 2-Chloromethylquinazoline 3-Oxides with Nitromethane," Jun. 1976, pp. 433-437.

Van Der Steen, F.H., et al., "The Synthesis of B-Lactams from Zinc Enolates of N,N-Disubstituted a-Aminoacid Esters and Imines: Substituents and Solvent Effects," Tetrahedron Letters, vol. 30, No. 6, 1989, pp. 765-768.

Breu, V., et al., "In vitro characterization of Ro 46-2005, a novel synthetic non-peptide endothelin antagonist of ETa and ETb receptors," FEBS Letters, Nov. 1993, vol. 334, No. 2, pp. 210-214.

BENZO-FUSED HETEROCYCLES AS ENDOTHELIN ANTAGONISTS

The present invention relates to novel benzo-fused heterocycles of the General Formula I and their use as active ingredients in the preparation of pharmaceutical compositions. The invention also concerns related aspects including processes for the preparation of the compounds, pharmaceutical compositions containing one or more compounds of the General Formula I and especially their use as endothelin receptor antagonists.

Endothelins (ET-1, ET-2, and ET-3) are 21-amino acid peptides produced and active in almost all tissues (Yanagisawa M et al.: Nature (1988) 332:411). Endothelins are potent vasoconstrictors and important mediators of cardiac, renal, endocrine and immune functions (McMillen M A et al.: J Am Coll Surg (1995) 180:621). They participate in bronchoconstriction and regulate neurotransmitter release, activation of inflammatory cells, fibrosis, cell proliferation and cell differentiation (Rubanyi G M et al.: Pharmacol Rev (1994) 46:328).

Two endothelin receptors have been cloned and characterized in mammals ($ET_A$, $ET_B$) (Arai H et al.: Nature (1990) 348:730; Sakurai T et al.: Nature (1990) 348:732). The $ET_A$ receptor is characterized by higher affinity for ET-1 and ET-2 than for ET-3. It is predominant in vascular smooth muscle cells and mediates vasoconstricting and proliferative responses (Ohlstein E H et al.: Drug Dev Res (1993) 29:108). In contrast, the $ET_B$ receptor has equivalent affinity for the 3 endothelin isopeptides and binds the linear form of endothelin, tetra-ala-endothelin, and sarafotoxin S6C (Ogawa Y et al.: BBRC (1991) 178:248). This receptor is located in the vascular endothelium and smooth muscles, and is also particularly abundant in lung and brain. The $ET_B$ receptor from endothelial cells mediates transient vasodilator responses to ET-1 and ET-3 through the release of nitric oxide and/or prostacyclin whereas the $ET_B$ receptor from smooth muscle cells exerts vasoconstricting actions (Sumner M J et al.: Brit J Pharmacol (1992) 107:858). $ET_A$ and $ET_B$ receptors are highly similar in structure and belong to the superfamily of G-protein coupled receptors.

A pathophysiological role has been suggested for ET-1 in view of its increased plasma and tissue levels in several disease states such as hypertension, sepsis, atherosclerosis, acute myocardial infarction, congestive heart failure, renal failure, migraine and asthma. As a consequence, endothelin receptor antagonists have been studied extensively as potential therapeutic agents. Endothelin receptor antagonists have demonstrated preclinical and/or clinical efficacy in various diseases such as cerebral vasospasm following subarachnoid hemorrhage, heart failure, pulmonary and systemic hypertension, neurogenic inflammation, renal failure and myocardial infarction.

Today, only one endothelin receptor antagonist is marketed, several are in clinical trials. However, these molecules possess a number of weaknesses such as complex synthesis, low solubility, high molecular weight, poor pharmacokinetics, or safety problems (e.g. liver enzyme increases).

The inhibitory activity of the compounds of General Formula I on endothelin receptors can be demonstrated using the test procedures described hereinafter:

For the evaluation of the potency and efficacy of the compounds of the General Formula I the following tests were used:

1) Inhibition of Endothelin Binding to Membranes from CHO Cells Carrying Human ET Receptors:

For competition binding studies, membranes of CHO cells expressing human recombinant $ET_A$ or $ET_B$ receptors were used. Microsomal membranes from recombinant CHO cells were prepared and the binding assay made as previously described (Breu V., et al, FEBS Lett 1993; 334:210).

The assay was performed in 200 uL 50 mM Tris/HCl buffer, pH 7.4, including 25 mM $MnCl_2$, 1 mM EDTA and 0.5% (w/v) BSA in polypropylene microtiter plates. Membranes containing 0.5 ug protein were incubated for 2 h at 20° C. with 8 pM [$^{125}$I]ET-1 (4000 cpm) and increasing concentrations of unlabelled antagonists. Maximum and minimum binding were estimated in samples without and with 100 nM ET-1, respectively. After 2 h, the membranes were filtered on filterplates containing GF/C filters (Unifilterplates from Canberra Packard S.A. Zürich, Switzerland). To each well, 50 uL of scintillation cocktail was added (MicroScint 20, Canberra Packard S.A. Zürich, Switzerland) and the filter plates counted in a microplate counter (TopCount, Canberra Packard S.A. Zürich, Switzerland).

All the test compounds were dissolved, diluted and added in DMSO. The assay was run in the presence of 2.5% DMSO which was found not to interfere significantly with the binding. $IC_{50}$ was calculated as the concentration of antagonist inhibiting 50% of the specific binding of ET-1. For reference compounds, the following $IC_{50}$ values were found: $ET_A$ cells: 0.075 nM (n=8) for ET-1 and 118 nM (n=8) for ET-3; $ET_B$ cells: 0.067 nM (n=8) for ET-1 and 0.092 nM (n=3) for ET-3.

The $IC_{50}$ values obtained with compounds of General Formula I are given in Table 1.

TABLE 1

| Compound of Example | $IC_{50}$ $ET_A$ [nM] | $IC_{50}$ $ET_B$ [nM] |
| --- | --- | --- |
| Example 27 | 13 | 126 |
| Example 39 | 29 | 701 |
| Example 40 | 8 | 52 |
| Example 49 | 17 | 240 |
| Example 50 | 12 | 507 |
| Example 51 | 7 | 26 |
| Example 52 | 11 | 23 |
| Example 56 | 4 | 83 |
| Example 58 | 2 | 29 |
| Example 68 | 1 | 4 |
| Example 78 | 3 | 23 |
| Example 107 | 1 | 42 |
| Example 111 | 3 | 10 |
| Example 115 | 1 | 3 |
| Example 117 | 61 | 749 |
| Example 129 | 6 | 353 |
| Example 167 | 36 | 947 |
| Example 170 | 15 | 368 |
| Example 187 | 18 | 180 |
| Example 211 | 6 | 62 |
| Example 213 | 3 | 29 |
| Example 218 | 5 | 39 |
| Example 223 | 7 | 12 |

2) Inhibition of Endothelin-induced Contractions on Isolated Rat Aortic Rings ($ET_A$ Receptors) and Rat Tracheal Rings ($ET_B$ Receptors):

The functional inhibitory potency of the endothelin antagonists was assessed by their inhibition of the contraction induced by endothelin-1 on rat aortic rings ($ET_A$ receptors) and of the contraction induced by sarafotoxin S6c on rat tracheal rings ($ET_B$ receptors). Adult Wistar rats were anesthetized and exsanguinated. The thoracic aorta or trachea were excised, dissected and cut in 3–5 mm rings. The endothelium/epithelium was removed by gentle rubbing of the intimal surface. Each ring was suspended in a 10 ml isolated organ bath filled with Krebs-Henseleit solution (in mM; NaCl 115, KCl 4.7, MgSO$_4$ 1.2, KH$_2$PO$_4$ 1.5, NaHCO$_3$ 25, CaCl$_2$ 2.5, glucose 10) kept at 37° C. and gassed with 95% O$_2$ and 5% CO$_2$. The rings were connected to force transducers and isometric tension was recorded (EMKA Technologies SA, Paris, France). The rings were stretched to a resting tension of 3 g (aorta) or 2 g (trachea). Cumulative doses of ET-1 (aorta) or sarafotoxin S6c (trachea) were added after a 10 min incubation with the test compound or its vehicle. The functional inhibitory potency of the test compound was assessed by calculating the concentration ratio, i.e. the shift to the right of the EC$_{50}$ induced by different concentrations of test compound. EC$_{50}$ is the concentration of endothelin needed to get a half-maximal contraction, pA$_2$ is the negative logarithm of the antagonist concentration which induces a two-fold shift in the EC$_{50}$ value.

The pA$_2$ values obtained with compounds of Formula I are given in Table 2.

TABLE 2

| Compound of Example | pA$_2$ (aortic rings) | pA$_2$ (trachea) |
|---|---|---|
| Example 48 | 8.19 | 6.28 |
| Example 49 | 6.87 | |
| Example 50 | 7.35 | |
| Example 51 | 7.39 | |
| Example 106 | 8.38 | 6.74 |
| Example 107 | 8.18 | 6.18 |
| Example 115 | 8.55 | 7.56 |
| Example 166 | 6.98 | |
| Example 203 | 7.95 | 6.11 |
| Example 211 | 9.04 | 7.07 |

Because of their ability to inhibit the endothelin binding, the described compounds can be used for treatment of diseases which are associated with an increase in vasoconstriction, proliferation or inflammation due to endothelin. Examples of such diseases are hypertension, coronary diseases, cardiac insufficiency, renal and myocardial ischemia, renal failure, cerebral ischemia, dementia, migraine, subarachnoidal hemorrhage, Raynaud's syndrome, portal hypertension, and pulmonary hypertension. They can also be used for atherosclerosis, prevention of restenosis after balloon or stent angioplasty, inflammation, pulmonary fibrosis, connective tissue diseases, stomach and duodenal ulcer, digital ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, pain as well as other diseases presently known to be related to endothelin.

The compounds can be administered orally, rectally, parenterally, e.g. by intravenous, intramuscular, subcutaneous, intrathecal or transdermal administration or sublingually or as ophthalmic preparation or administered as aerosol. Examples of applications are capsules, tablets, orally administered suspensions or solutions, suppositories, injections, eye-drops, ointments or aerosols/nebulizers.

Preferred applications are intravenous, intramuscular, or oral administrations as well as eye drops. The dosage used depends upon the type of the specific active ingredient, the age and the requirements of the patient and the kind of application. Generally, dosages of 0.1–50 mg/kg body weight per day are considered. The preparations with compounds can contain inert or as well pharmacodynamically active excipients. Tablets or granules, for example, could contain a number of binding agents, filling excipients, carrier substances or diluents.

The present invention relates to novel benzo-fused heterocycles of the General Formula I, General Formula I

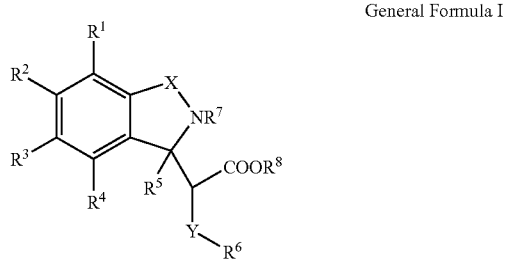

wherein

X represents —CH$_2$—CH$_2$—CH$_2$—; —NR$^9$—C(=O)—CH$_2$—; —NR$^{10}$—CH$_2$—CH$_2$—; —C(=O)—CH$_2$—CH$_2$—; —CH$_2$—C(=O)—CH$_2$—; —O—CH$_2$—CH$_2$—; —S—CH$_2$—CH$_2$—; —SO$_2$—CH$_2$—CH$_2$—; —NR$^9$—C(=O)—CH$_2$—CH$_2$—; —NR$^{10}$—CH$_2$—CH$_2$—CH$_2$—; —O—CH$_2$—CH$_2$—CH$_2$—;

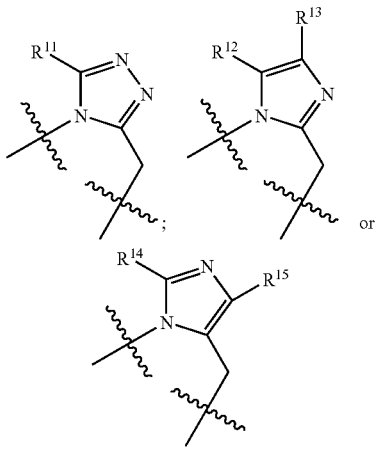

Y represents O; S; NH; N—CH$_3$ or CH$_2$;

R$^1$, R$^2$, R$^3$, R$^4$ represent hydrogen; or one or two of R$^1$, R$^2$, R$^3$, R$^4$ idependently represent halogen; hydroxy; lower alkyl; lower alkyloxy; lower alkyloxycarbonyl; hydroxy carbonyl; amino; lower alkylamino; di-(lower alkyl)-amino; lower alkylcarbonylamino; trifluoromethyl; and the others are hydrogen;

R$^5$ represents hydrogen; lower alkyl; phenyl; mono-, di-, or tri-substituted phenyl, substituted with lower alkyl, lower alkyloxy, halogen, amino, lower alkylamino, di-(lower alkyl)-amino, lower alkylthio; mono-, di-substituted phenyl, substituted with trifluoromethyl; pyridyl; benzyl or mono- or disubstituted benzyl, substituted at the phenyl ring with lower alkyl, lower alkyloxy, halogen, amino, lower alkylamino, di-(lower alkyl)-amino, trifluoromethyl, lower alkylthio;

$R^6$ represents phenyl; mono-, di-, or tri-substituted phenyl, substituted with lower alkyl, lower alkyloxy, halogen, amino, lower alkylamino, di-(lower alkyl)-amino, lower alkylthio, alkylenedioxy, ethylenoxy; mono-, di-substituted phenyl, substituted with trifluoromethyl; pyridyl; mono- or di-substituted pyridyl, substituted with lower alkyl, lower alkyloxy, halogen, amino, lower alkylamino, di-(lower alkyl)-amino, trifluoromethyl, lower alkylthio; pyrimidinyl; mono- or di-substituted pyrimidinyl, substituted with lower alkyl, lower alkyloxy, halogen, amino, lower alkylamino, di-(lower alkyl)-amino, lower alkylthio; mono-substituted pyrimidinyl, substituted with trifluoromethyl;

$R^7$ represents hydrogen; lower alkyl; cycloalkyl; lower alkylcarbonyl; benzyl; optionally substituted benzyl, substituted at the phenyl ring with lower alkyl, lower alkyloxy, halogen, amino, lower alkylamino, di-(lower alkyl)-amino, trifluoromethyl, lower alkylthio, alkylene-dioxy, ethylenoxy;

$R^8$ represents hydrogen; lower alkyl; lower alkylcarbonyloxy-lower alkyl;

$R^9$ represents hydrogen; lower alkyl; lower alkenyl; lower alkynyl; hydroxycarbonyl-lower alkyl whereby lower alkyl can be substituted with phenyl; lower alkyloxycarbonyl-lower alkyl whereby lower alkyl can be substituted with phenyl; tetrazol-5-yl-lower alkyl; 2,5-dihydro-5-oxo4H-1,2,4-oxadiazol-3-yl-lower alkyl; 2,5-dihydro-5-oxo-4H-1,2,4-thiadiazol-3-yl-lower alkyl; 2,5-dihydro-5-thioxo-4H-1,2,4-oxadiazol-3-yl-lower alkyl; 2-oxo-3H-1,2,3,5-oxathiadiazol-4-yl-lower alkyl; amino-lower alkyl; lower alkylamino-lower alkyl; di-(lower alkyliamino-lower alkyl; aminocarbonyl-lower alkyl; lower alkylamino carbonyl-lower alkyl; di-(lower alkyl)-aminocarbonyl-lower alkyl; hydroxy-lower alkyl; lower alkyloxy-lower alkyl; benzyl; mono- or di-substituted benzyl substituted at the phenyl ring with lower alkyl, lower alkyloxy, halogen, amino, lower alkylamino, di-(lower alkyl)-amino, trifluoromethyl, lower alkylthio, alkylene-dioxy, ethylenoxy;

$R^{10}$ represents hydrogen; lower alkyl; lower alkenyl; lower alkynyl; hydroxycarbonyl-lower alkyl whereby lower alkyl can be substituted with phenyl; lower alkyloxycarbonyl-lower alkyl whereby lower alkyl can be substituted with phenyl; tetrazol-5-yl-lower alkyl; 2,5-dihydro-5-oxo4H-1,2,4-oxadiazol-3-yl-lower alkyl; 2,5-dihydro-5-oxo-4H-1,2,4-thiadiazol-3-yl-lower alkyl; 2,5-dihydro-5-thioxo-4H-1,2,4-oxadiazol-3-yl-lower alkyl; 2-oxo-3H-1,2,3,5-oxathiadiazol-4-yl-lower alkyl; amino-lower alkyl; lower alkylamino-lower alkyl; di-(lower alkyl)-amino-lower alkyl; aminocarbonyl-lower alkyl; hydroxy-lower alkyl; lower alkyloxy-lower alkyl; benzyl; mono- or di-substituted benzyl substituted at the phenyl ring with lower alkyl, lower alkyloxy, halogen, amino, lower alkylamino, di-(lower alkyl)-amino, trifluoromethyl, lower alkylthio, alkylene-dioxy, ethylenoxy; benzylcarbonyl; mono- or di-substituted benzylcarbonyl substituted at the phenyl ring with lower alkyl, lower alkyloxy, halogen, amino, lower alkylamino, di-(lower alkylyamino, trifluoromethyl, lower alkylthio, alkylene-dioxy, ethylenoxy; lower alkylcarbonyl; phenylcarbonyl; mono- or di-substituted phenylcarbonyl substituted with lower alkyl, lower alkyloxy, halogen, amino, lower alkylamino, di-(lower alkyl)-amino, trifluoromethyl, lower alkylthio, alkylenedioxy, ethylenoxy; lower alkyloxycarbonyl; lower alkyloxy-lower alkylcarbonyl; hydroxycarbonyl-lower alkylcarbonyl;

$R^{11}$ represents hydrogen; lower alkyl; cycloalkyl; lower alkyloxy-lower alkyl; lower alkyloxycarbonyl; hydroxycarbonyl; lower alkyloxycarbonyl-lower alkyl; hydroxycarbonyl-lower alkyl; phenyl; mono- or di-substituted phenyl substituted with lower alkyl, lower alkyloxy, halogen, amino, lower alkylamino, di-(lower alkyl)-amino, trifluoromethyl, lower alkylthio; benzyl; mono- or di-substituted benzyl substituted at the phenyl ring with lower alkyl, lower alkyloxy, halogen, amino, lower alkylamino, di-(lower alkyl)-amino, lower alkylthio;

$R^{12}$ represents hydrogen; lower alkyl; cycloalkyl; lower alkyloxy-lower alkyl; phenyl; mono- or di-substituted phenyl substituted with lower alkyl, lower alkyloxy, halogen, amino, lower alkylamino, di-(lower alkylkamino, trifluoromethyl, lower alkylthio;

$R^{13}$ represents hydrogen; lower alkyl; cycloalkyl; lower alkyloxy-lower alkyl;

$R^{14}$ represents hydrogen; lower alkyl; cycloalkyl; lower alkyloxy-lower alkyl; phenyl; mono- or di-substituted phenyl substituted with lower alkyl, lower alkyloxy, halogen, amino, lower alkylamino, di-(lower alkyl)-amino, trifluoromethyl, lower alkylthio; benzyl; mono- or di-substituted benzyl substituted at the phenyl ring with lower alkyl, lower alkyloxy, halogen, amino, lower alkylamino, di-(lower alkyl)-amino, lower alkylthio; lower alkyloxycarbonyl; hydroxycarbonyl; lower alkyloxycarbonyl-lower alkyl; hydroxycarbonyl-lower alkyl lower; aminocarbonyl; alkylaminocarbonyl; di-(lower alkyl)-aminocarbonyl;

$R^{15}$ represents hydrogen; lower alkyl; cycloalkyl; lower alkyloxy-lower alkyl; lower alkyloxycarbonyl; hydroxycarbonyl; lower alkyloxycarbonyl-lower alkyl; hydroxycarbonyl-lower alkyl; aminocarbonyl; lower alkylaminocarbonyl; di-(lower alkyl)-aminocarbonyl;

and optically pure enantiomers, mixtures of enantiomers such as racemates, pure diastereomers, mixtures of diastereomers, diastereomeric racemates, mixtures of diastereomeric racemates and the meso-forms and pharmaceutically acceptable salts thereof.

In the definitions of the General Formula I if not otherwise stated—the expression lower alkyl or lower alkyloxy means straight and branched chain groups with one to seven carbon atoms, preferably 1 to 4 carbon atoms. Examples of lower alkyl and lower alkyloxy groups are methyl, ethyl, n-propyl, isopropyl, n-butyl, isobutyl, sec.-butyl, tert.-butyl, pentyl, hexyl, heptyl, methoxy, ethoxy, propoxy, butoxy, iso-butoxy, sec.-butoxy and tert.-butoxy. Lower alkylene-dioxy-groups are preferably methylene-dioxy, ethylene-dioxy, propylene-dioxy and butylene-dioxy groups. Examples of lower alkanoyl-groups are acetyl, n-propanoyl, i-propanoyl, n-butanoyl, i-butanoyl, sec-butanoyl and t-butanoyl. Lower alkenyl and lower alkynyl means groups like ethenyl, propenyl, butenyl, 2-methyl-propenyl, and ethynyl, propynyl, butynyl, pentynyl, 2-methyl-pentynyl etc. Lower alkenyloxy means allyloxy, vinyloxy, propenyloxy and the like. The expression cycloalkyl means a saturated cyclic hydrocarbon ring with 3 to 7 carbon atoms , e.g. cyclopropyl, cyclobutyl, cyclopentyl, cyclohexyl and cycloheptyl, which may be substituted with lower alkyl, hydroxy-lower alkyl, amino-lower alkyl and lower alkyloxy-lower alkyl groups.

It is understood that the substituents outlined relative to the expressions alkyl and cycloalkyl have been omitted in the definitions of the General Formula I in claims 1 to 8 for clarity reasons but the definitions in Formula I and in claims 1 to 8 should be read as if they are included therein.

The expression pharmaceutically acceptable salts encompasses either salts with inorganic acids or organic acids like hydrohalogenic acids, e.g. hydrochloric or hydrobromic acid; sulfuric acid, phosphoric acid, nitric acid, citric acid, formic acid, acetic acid, maleic acid, tartaric acid, methylsulfonic acid, p-toluolsulfonic acid and the like or in case the compound of Formula I is acidic in nature with an inorganic base like an alkali or earth alkali base, e.g. sodium hydroxide, potassium hydroxide, calcium hydroxide etc.

The compounds of the General Formula I might have one or more asymmetric carbon atoms and may be prepared in form of optically pure enantiomers or diastereomers, mixtures of enantiomers or diastereomers, diastereomeric racemates, mixtures of diastereomeric racemates and also in the meso-form. The present invention encompasses all these forms. Mixtures may be separated in a manner known per se, i.e. by column chromatography, thin layer chromatography, HPLC, crystallization etc.

Because of their ability to inhibit endothelin binding, the compounds of the General Formula I and their pharmaceutically acceptable salts may be used for the treatment of diseases which are associated with an increase in vasoconstriction, proliferation or inflammation due to endothelin. Examples of such diseases are hypertension, coronary diseases, cardiac insufficiency, renal and myocardial ischemia, renal failure, cerebral ischemia, dementia, migraine, subarachnoidal hemorrhage, Raynaud's syndrome, portal hypertension and pulmonary hypertension. They can also be used for atherosclerosis, prevention of restenosis after balloon or stent angioplasty, inflammation, stomach and duodenal ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, pain, as well as other diseases presently known to be related to endothelin.

These compositions may be administered in enteral or oral form e.g. as tablets, dragees, gelatine capsules, emulsions, solutions or suspensions, in nasal form like sprays or rectically in form of suppositories. These compounds may also be administered in intramuscular, parenteral or intravenous form, e.g. in form of injectable solutions.

These pharmaceutical compositions may contain the compounds of Formula I as well as their pharmaceutically acceptable salts in combination with inorganic and/or organic excipients which are usual in the pharmaceutical industry like lactose, maize or derivatives thereof, talcum, stearinic acid or salts of these materials.

For gelatine capsules vegetable oils, waxes, fats, liquid or half-liquid polyols etc. may be used. For the preparation of solutions and syrups e.g. water, polyols, saccharose, glucose etc. are used. Injectables are prepared by using e.g. water, polyols, alcohols, glycerin, vegetable oils, lecithin, liposomes etc. Suppositories are prepared by using natural or hydrogenated oils, waxes, fatty acids (fats), liquid or half-liquid polyols etc.

The compositions may contain in addition preservatives, stabilisation improving substances, viscosity improving or regulating substances, solubility improving substances, sweeteners, dyes, taste improving compounds, salts to change the osmotic pressure, buffer, antioxidants etc.

The compounds of Formula I may also be used in combination with one or more other therapeutically useful substances e.g. α- and β-blockers like phentolamine, phenoxybenzamine, atenolol, propranolol, timolol, metoprolol, carteolol etc.; vasodilators like hydralazine, minoxidil, diazoxide, flosequinan etc.; calcium-antagonists like diltiazem, nicardipine, nimodipine, verapamil, nifedipine etc.; ACE-inhibitors like cilazapril, captopril, enalapril, lisinopril etc.; potassium activators like pinacidil etc.; angiotensin II antagonists; diuretics like hydrochlorothiazide, chlorothiazide, acetolamide, bumetanide, furosemide, metolazone, chlortalidone etc.; sympatholitics like methyldopa, clonidine, guanabenz, reserpine etc.; and other therapeutics which serve to treat high blood pressure or any cardiac disorders.

The dosage may vary within wide limits but should be adapted to the specific situation. In general the dosage given daily in oral form should be between about 3 mg and about 3 g, preferably between about 10 mg and about 1 g, especially preferred between 5 mg and 300 mg, per adult with a body weight of about 70 kg. The dosage should be administered preferably in 1 to 3 doses per day which are of equal weight. As usual children should receive lower doses which are adapted to body weight and age.

Preferred compounds of General Formula I are the compounds wherein $R^1$, $R^2$, $R^3$, $R^4$, $R^5$, $R^7$, $R^8$, $R^9$, $R^{10}$, $R^{11}$, $R^{12}$, $R^{13}$, $R^{14}$, $R^{15}$ and X are as defined in General Formula I, and wherein $R^6$ represents pyrimidinyl; mono- or di-substituted pyrimidinyl, substituted with lower alkyl, lower alkyloxy, halogen, amino, lower alkylamino, di-(lower alkyl)-amino, lower alkylthio; mono-substituted pyrimidinyl, substituted with trifluoromethyl, and Y represents oxygen, and pharmaceutically acceptable salts thereof.

Another group of preferred compounds are compounds of General Formula I wherein $R^1$, $R^2$, $R^3$, $R^4$, $R^6$, $R^7$, $R^8$, $R^9$, $R^{10}$, $R^{11}$, $R^{12}$, $R^{13}$, $R^{14}$, $R^{15}$, X and Y are as defined in General Formula I, and wherein $R^5$ represents phenyl; mono-, di-, or tri-substituted phenyl, substituted with lower alkyl, lower alkyloxy, halogen, amino, lower alkylamino, di-(lower alkyl)-amino, lower alkylthio; mono-, di-substituted phenyl, substituted with trifluoromethyl and pharmaceutically acceptable salts thereof.

A third group of preferred compounds are compounds of General Formula I wherein $R^1$, $R^2$, $R^3$, $R^4$, $R^5$, $R^6$, $R^7$, $R^8$, $R^9$ $R^{10}$, $R^{11}$, $R^{12}$, $R^{13}$, $R^{14}$, $R^{15}$, and Y are as defined in General Formula I, and wherein X represents —$NR^9$—C(=O)—$CH_2$— and pharmaceutically acceptable salts thereof.

A fourth group of preferred compounds are compounds of General Formula I wherein $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, X and Y are as defined in General Formula I, and wherein $R^2$ represents hydrogen and pharmaceutically acceptable salts thereof.

A group of more preferred compounds are compounds of General Formula I wherein $R^3$, $R^5$, $R^6$, $R^7$, $R^8$, $R^9$, $R^{10}$, $R^{11}$, $R^{12}$, $R^{13}$, $R^{14}$, $R^{15}$, X and Y are as defined in General Formula I, and wherein $R^1$ represents hydrogen and
$R^2$ represents hydrogen and
$R^4$ represents hydrogen and pharmaceutically acceptable salts thereof.

A group of particulary preferred compounds are compounds of General Formula I wherein $R^5$, $R^6$, $R^7$, $R^8$, $R^9$, $R^{10}$, $R^{11}$, $R^{12}$, $R^{13}$, $R^{14}$, $R^{15}$, X and Y are as defined in General Formula I, and wherein
$R^1$ represents hydrogen and
$R^2$ represents hydrogen and
$R^3$ represents hydrogen or halogen and
$R^4$ represents hydrogen and and pharmaceutically acceptable salts thereof.

Another group of preferred compounds are compounds of General Formula I wherein $R^{10}$, $R^{11}$, $R^{12}$, $R^{13}$, $R^{14}$, $R^{15}$ are as defined in General Formula I, and wherein
$R^1$ represents hydrogen and
$R^2$ represents hydrogen and
$R^3$ represents hydrogen or halogen and
$R^4$ represents hydrogen and
$R^5$ represents phenyl; mono-, di-, or tri-substituted phenyl, substituted with lower alkyl, lower alkyloxy, halogen, amino, lower alkylamino, di-(lower alkyl)-amino, lower alkylthio; mono-, di-substituted phenyl, substituted with trifluoromethyl and
$R^6$ represents pyrimidinyl; mono- or di-substituted pyrimidinyl, substituted with lower alkyl, lower alkyloxy, halogen, amino, lower alkylamino, di-(lower alkyl)-amino, lower alkylthio; mono-substituted pyrimidinyl, substituted with trifluoromethyl and
$R^7$ represents hydrogen and
$R^8$ represents hydrogen and
$R^9$ represents lower alkyl; lower alkenyl; lower alkynyl; hydroxycarbonyl-lower alkyl whereby lower alkyl can be substituted with phenyl; lower alkyloxycarbonyl-lower alkyl whereby lower alkyl can be substituted with phenyl; hydroxy-lower alkyl; lower alkyloxy-lower alkyl; tetrazol-5-yl-lower alkyl; 2,5-dihydro-5-oxo-4H-1,2,4-oxadiazol-3-yl-lower alkyl; 2,5-dihydro-5-oxo-4H-1,2,4-thiadiazol-3-yl-lower alkyl; 2,5-dihydro-5-thioxo-4H-1,2,4-oxadiazol-3-yl-lower alkyl; 2-oxo-3H-1,2,3,5-oxathiadiazol-4-yl-lower alkyl; benzyl; mono- or di-substituted benzyl substituted at the phenyl ring with lower alkyl, lower alkyloxy, halogen, amino, lower alkylamino, di-(lower alkyl)-amino, trifluoromethyl, lower alkylthio, alkylene-dioxy, ethylenoxy, and
X represents —NR$^9$—C(=O)—CH$_2$— and
Y represents oxygen and pharmaceutically acceptable salts thereof.

Especially preferred compounds are:
(±)-(S*)-(4,6-dimethyl-pyrimidin-2-yloxy)-((6S*)-1-methyl-6-phenyl-5,6-dihydro-4H-2,3,5,10b-tetraaza-benzo[e]azulen-6-yl)-acetic acid;
(±)-(S*)-(4,6dimethyl-pyrimidin-2-yloxy)-((6S*)-6-phenyl-5,6-dihydro-4H-2,3,5,10b-tetraaza-benzo[e]azulen-6-yl)-acetic acid;
(±)-(S*)-((5S*)-7-chloro-1-methyl-2-oxo-5-phenyl-2,3,4,5-tetrahydro-1H-benzo[e][1,4]diazepin-5-yl)-(4,6-dimethoxy-pyrimidin-2-yloxy)-acetic acid;
(±)-(S*)-[(5S*)-1-(3,5-dimethoxy-benzyl)-2-oxo-5-phenyl-2,3,4,5-tetrahydro-1H-benzo[e][1,4]diazepin-5-yl]-(4,6-dimethoxy-pyrimidin-2-yloxy)-acetic acid;
(±)-4-{(5S*)-5-[(S*)-Carboxy-(4,6-dimethoxy-pyrimidin-2-yloxy)-methyl]-2-oxo-5-phenyl-2,3,4,5-tetrahydro-benzo[e][1,4]diazepin-1-ylmethyl}-benzoic acid methyl ester;
(±)-(S*)-(4,6-dimethoxy-pyrimidin-2-yloxy)-[(5S*)-5-phenyl-1-(2,4,6-trifluoro-benzyl)-2,3,4,5-tetra-hydro-1H-benzo[e][1,4]diazepin-5-yl]-acetic acid;
(±)-(S*)-(4,6-dimethyl-pyrimidin-2-yloxy)-((5S*)-1-methyl-2-oxo-5-phenyl-2,3,4,5-tetrahydro-1H-benzo[e][1,4]diazepin-5-yl)-acetic acid;
(±)-(S*)-((5S*)-1-Carboxymethyl-2-oxo-5-phenyl-2,3,4,5-tetrahydro-1H-benzo[e][1,4]diazepin-5-yl)-(4,6-dimethyl-pyrimidin-2-yloxy)-acetic acid;
(±)-(S*)-[(5S*)-1-(3,5-Dimethoxy-benzyl)-2-oxo-5-phenyl-2,3,4,5-tetra-hydro-1H-benzo[e][1,4]diazepin-5-yl]-(4,6-dimethyl-pyrimidin-2-yloxy)-acetic acid;
(±)-(S*)-(4,6-Dimethyl-pyrimidin-2-yloxy)-[(5S*)-1-(2-hydroxy-ethyl)-2-oxo-5-phenyl-2,3,4,5-tetrahydro-1H-benzo[e][1,4]diazepin-5-yl]-acetic acid;
(±)-(S*)-(4,6-dimethyl-pyrimidin-2-yloxy)-[(5S*)-2-oxo-5-phenyl-1-(1H-tetrazol-5-ylmethyl)-2,3,4,5-tetrahydro-1H-benzo[e][1,4]diazepin-5-yl]-acetic acid;
(±)-4-{(5S*)-5-[(S*)-Carboxy-(4,6-dimethyl-pyrimidin-2-yloxy)-methyl]-2-oxo-5-phenyl-2,3,4,5-tetrahydro-benzo[e][1,4]diazepin-1-ylmethyl}-benzoic acid methyl ester;
(±)-(S*)-(4,6-dimethyl-pyrimidin-2-yloxy)-[(5S*)-1-(4-methoxy-benzyl)-2-oxo-5-phenyl-2,3,4,5-tetrahydro-1H-benzo[e][1,4]diazepin-5-yl]-acetic acid;
(±)-(S*)-(4,6-dimethyl-pyrimidin-2-yloxy)-[(5S*)-2-oxo-5-phenyl-1-(4-trifluoromethyl-benzyl)-2,3,4,5-tetrahydro-1H-benzo[e][1,4]diazepin-5-yl]-acetic acid;
(±)-(S*)-[(5S*)-1-(3-chloro-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;
(±)-(S*)-[(5S*)-1-(3,5-bis-trifluoromethyl-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;
(±)-(S*)-(4,6-dimethyl-pyrimidin-2-yloxy)-{(5S*)-1-[2-(1-methyl-1H-indol-3-yl)-ethyl]-2-oxo-5-phenyl-2,3,4,5-tetrahydro-1H-benzo[e][1,4]diazepin-5-yl}-acetic acid;
(±)-(S*)-[(5S*)-1-(2-chloro-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;
(±)-(S*)-(4,6-dimethyl-pyrimidin-2-yloxy)-((5S*)-2-oxo-1-phenethyl-5-phenyl-2,3,4,5-tetrahydro-1H-benzo[e][1,4]diazepin-5-yl)-acetic acid;
(±)-(S*)-(4,6-dimethyl-pyrimidin-2-yloxy)-[(5S*)-2-oxo-5-phenyl-1-(4-trifluoromethoxy-benzyl)-2,3,4,5-tetrahydro-1H-benzo[e][1,4]diazepin-5-yl]-acetic acid;
(±)-(S*)-[(5S*)-1-(2,6-difluoro-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;
(±)-(S*)-(4,6-dimethyl-pyrimidin-2-yloxy)-{(5S*)-1-[2-(2-methoxy-ethoxy)-ethyl]-2-oxo-5-phenyl-2,3,4,5-tetrahydro-1H-benzo[e][1,4]diazepin-5-yl}-acetic acid;
(±)-(S*)-[(5S*)-1-(2,4-difluoro-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;
(±)-(S*)-(4,6-dimethyl-pyrimidin-2-yloxy)-[(5S*)-2-oxo-5-phenyl-1-(2,3,6-trifluoro-benzyl)-2,3,4,5-tetrahydro-1H-benzo[e][1,4]diazepin-5-yl]-acetic acid;
(±)-(S*)-(4,6-dimethyl-pyrimidin-2-yloxy)-[(5S*)-2-oxo-5-phenyl-1-(2,4,6-trifluoro-benzyl)-2,3,4,5-tetrahydro-1H-benzo[e][1,4]diazepin-5-yl]-acetic acid;
(±)-(S*)-(4,6-dimethyl-pyrimidin-2-yloxy)-[(5S*)-2-oxo-5-phenyl-1-(2,4,6-trimethyl-benzyl)-2,3,4,5-tetrahydro-1H-benzo[e][1,4]diazepin-5-yl]-acetic acid;
(±)-(S*)-(4,6-dimethyl-pyrimidin-2-yloxy)-[(5S*)-2-oxo-5-phenyl-1-(2,3,4-trifluoro-benzyl)-2,3,4,5-tetrahydro-1H-benzo[e][1,4]diazepin-5-yl]-acetic acid;
(±)-(S*)-[(5S*)-1-(4-butyl-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;
(±)-(S*)-[(5S*)-1-(2,6-dichloro-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-(4,6-dimethyl-pyrimidin-2-yloxy)-((5S*)-2-oxo-1,5-diphenyl-2,3,4,5-tetrahydro-1H-benzo[e][1,4]diazepin-5-yl)-acetic acid;

(±)-4-{(5S*)-5-[(S*)-carboxy-(4,6-diethyl-pyrimidin-2-yloxy)-methyl]-2-oxo-5-phenyl-2,3,4,5-tetrahydro-benzo[e][1,4]diazepin-1-ylmethyl}-benzoic acid methyl ester;

(±)-(S*)-(4,6-diethyl-pyrimidin-2-yloxy)-[(5S*)-1-(2-hydroxy-ethyl)-2-oxo-5-phenyl-2,3,4,5-tetrahydro-1H-benzo[e][1,4]diazepin-5-yl]-acetic acid;

(±)-(S*)-(4,6-diethyl-pyrimidin-2-yloxy)-[(5S*)-1-(3,5-dimethoxy-benzyl)-2-oxo-5-phenyl-2,3,4,5-tetrahydro-1H-benzo[e][1,4]diazepin-5-yl]-acetic acid;

(±)-(S*)-(4,6-diethyl-pyrimidin-2-yloxy)-[(5S*)-2-oxo-5-phenyl-1-(2,4,6-trifluoro-benzyl)-2,3,4,5-tetrahydro-1H-benzo[e][1,4]diazepin-5-yl]-acetic acid;

(±)-(S*)-(4,6-dimethyl-pyrimidin-2-yloxy)-[(5S*)-4-methyl-2-oxo-5-phenyl-1-(2,4,6-trifluoro-benzyl)-2,3,4,5-tetrahydro-1H-benzo[e][1,4]diazepin-5-yl]-acetic acid;

(±)-(S*)-[(5S*)-7-chloro-1-(3,5-dimethoxy-benzyl)-2-oxo-5-phenyl-2,3,4,5-tetrahydro-1H-benzo[e][1,4]diazepin-5-yl]-(3,5-dimethoxy-phenoxy)-acetic acid;

(±)-(1S*)-((5S*)-7-chloro-1-methyl-2-oxo-5-phenyl-2,3,4,5-tetrahydro-1H-benzo[e][1,4]diazepin-5-yl)-(4,6-dimethoxy-pyrimidin-2-yloxy)-acetic acid;

(±)-(1S*)-[(5S*)-7-chloro-1-(3,5-dimethoxy-benzyl)-2-oxo-5-phenyl-2,3,4,5-tetrahydro-1H-benzo[e][1,4]diazepin-5-yl]-(4,6-dimethoxy-pyrimidin-2-yloxy)-acetic acid;

(±)-(1S*)-((5S*)-7-chloro-1-methyl-2-oxo-5-phenyl-2,3,4,5-tetra-hydro-1H-benzo[e][1,4]diazepin-5-yl)-(4,6-dimethyl-pyrimidin-2-yloxy)-acetic acid;

(±)-(S*)-[(5S*)-7-chloro-1-(4-methoxy-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-[(5S*)-1-(4-butylbenzyl)-7-chloro-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-[(5S*)-7-chloro-2-oxo-5-phenyl-1-(2,4,6-trifluoro-benzyl)-2,3,4,5-tetrahydro-1H-benzo[e][1,4]diazepin-5-yl]-(4,6-dimethyl-pyrimidin-2-yloxy)-acetic acid;

(±)-(S*)-[(5S*)-7-chloro-1-(2,6-dichloro-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-((5S*)-7-chloro-1-methyl-2-oxo-5-phenyl-2,3,4,5-tetrahydro-1H-benzo[e][1,4]diazepin-5-yl)-(4,6-diethyl-pyrimidin-2-yloxy)-acetic acid;

(±)-(S*)-(4,6-dimethyl-pyrimidin-2-yloxy)-[(5S*)-1-(4-methoxy-benzyl)-2-oxo-5-m-tolyl-2,3,4,5-tetrahydro-1H-benzo[e][1,4]diazepin-5-yl]-acetic acid;

(±)-(S*)-(4,6-dimethyl-pyrimidin-2-yloxy)-[(5S*)-5-(3-ethyl-phenyl)-1-(4-methoxy-benzyl)-2-oxo-2,3,4,5-tetrahydro-1H-benzo[e][1,4]diazepin-5-yl]-acetic acid;

(±)-(S*)-(4,6-dimethyl-pyrimidin-2-yloxy)-[(5S*)-5-(3-ethyl-phenyl)-2-oxo-1-(2,4,6-trimethyl-benzyl)-2,3,4,5-tetrahydro-1H-benzo[e][1,4]diazepin-5-yl]-acetic acid;

(±)-(S*)-(4,6-dimethyl-pyrimidin-2-yloxy)-[(5S*)-5-(3-ethyl-phenyl)-2-oxo-1-(2,3,4-trifluoro-benzyl)-2,3,4,5-tetrahydro-1H-benzo[e][1,4]diazepin-5-yl]-acetic acid;

(±)-(S*)-(4,6-dimethyl-pyrimidin-2-yloxy)-[(5S*)-5-(3-ethyl-phenyl)-2-oxo-1-(2,4,6-trifluoro-benzyl)-2,3,4,5-tetrahydro-1H-benzo[e][1,4]diazepin-5-yl]-acetic acid;

(±)-(S*)-(4,6-dimethyl-pyrimidin-2-yloxy)-[(5S*)-1-(4-methoxy-benzyl)-5-(3-methoxy-phenyl)-2-oxo-2,3,4,5-tetrahydro-1H-benzo[e][1,4]diazepin-5-yl]-acetic acid;

(±)-(S*)-(4,6-dimethyl-pyrimidin-2-yloxy)-[(5S*)-5-(3-methoxy-phenyl)-2-oxo-1-(2,4,6-trifluoro-benzyl)-2,3,4,5-tetrahydro-1H-benzo[e][1,4]diazepin-5-yl]-acetic acid;

(±)-(S*)-[(5S*)-1-carboxymethyl-5-(3-methoxy-phenyl)-2-oxo-2,3,4,5-tetrahydro-1H-benzo[e][1,4]diazepin-5-yl]-(4,6-dimethyl-pyrimidin-2-yloxy)-acetic acid;

(±)-(S*)-(4,6-dimethyl-pyrimidin-2-yloxy)-[(5S*)-5-(3-methoxy-phenyl)-2-oxo-1-(2,3,6-trifluoro-benzyl)-2,3,4,5-tetrahydro-1H-benzo[e][1,4]diazepin-5-yl]-acetic acid;

(±)-(S*)-[(5S*)-5-biphenyl-3-yl-1-(4-methoxy-benzyl)-2-oxo-2,3,4,5-tetrahydro-1H-benzo[e][1,4]diazepin-5-yl]-(4,6-dimethyl-pyrimidin-2-yloxy)-acetic acid;

(±)-(S*)-[(5S*)-5-biphenyl-3-yl-2-oxo-1-(2,4,6-trifluoro-benzyl)-2,3,4,5-tetrahydro-1H-benzo[e][1,4]diazepin-5-yl]-(4,6-dimethyl-pyrimidin-2-yloxy)-acetic acid;

(±)-(S*)-((5S*)-5-biphenyl-3-yl-1-carboxymethyl-2-oxo-2,3,4,5-tetrahydro-1H-benzo[e][1,4]diazepin-5-yl)-(4,6-dimethyl-pyrimidin-2-yloxy)-acetic acid;

(±)-(S*)-[(5S*)-5-biphenyl-3-yl-2-oxo-1-(2,3,6-trifluoro-benzyl)-2,3,4,5-tetrahydro-1H-benzo[e][1,4]diazepin-5-yl]-(4,6-dimethyl-pyrimidin-2-yloxy)-acetic acid;

(±)-(S*)-(4,6-dimethyl-pyrimidin-2-yloxy)-[(5S*)-5-(4-fluoro-3-methyl-phenyl)-1-(4-methoxy-benzyl)-2-oxo-2,3,4,5-tetrahydro-1H-benzo[e][1,4]diazepin-5-yl]-acetic acid;

(±)-(S*)-[(5S*)-5-butyl-1-(4-methoxy-benzyl)-2-oxo-2,3,4,5-tetrahydro-1H-benzo[e][1,4]diazepin-5-yl]-(4,6-dimethyl-pyrimidin-2-yloxy)-acetic acid;

(±)-(R*)-[(5S*)-7-chloro-1-(4-methoxy-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-[(5S*)-1-(4-butyl-benzyl)-5-(3-butyl-phenyl)-2-oxo-2,3,4,5-tetrahydro-1H-benzo[e][1,4]diazepin-5-yl]-(4,6-dimethyl-pyrimidin-2-yloxy)-acetic acid;

(±)-(S*)-[(5S)-5-(3-butyl-phenyl)-2-oxo-1-(2,4,6-trifluoro-benzyl)-2,3,4,5-tetrahydro-1H-benzo[e][1,4]diazepin-5-yl]-(4,6-dimethyl-pyrimidin-2-yloxy)acetic acid;

(±)-(S*)-[(5S*)-5-(3-Butyl-phenyl)-1-(2,6-dichloro-benzyl)-2-oxo-2,3,4,5-tetrahydro-1H-benzo[e][1,4]diazepin-5-yl]-(4,6-dimethyl-pyrimidin-2-yloxy)-acetic acid;

(±)-(S*)-(4,6-dimethyl-pyrimidin-2-yloxy)-[(5S*)-2-oxo-5-phenyl-1-(2,4,6-trifluoro-benzyl)-2,3,4,5-tetrahydro-1H-benzo[e][1,4]diazepin-5-yl]-acetic acid dimethylcarbamoylmethyl ester;

and pharmaceutically acceptable salts thereof.

Compounds of the General Formula I of the present invention can be prepared according to the general sequence of reactions outlined below. For simplicity and clarity reasons sometimes only parts of the synthetic possibilities which lead to compounds of General Formula I are described.

In case $R^7$ does not represent a hydrogen atom, the desired compounds of General Formula I can be prepared by reacting a compound of Formula II with an alkylating or acylating agent $R^7$—$G^1$, wherein $G^1$ represents a reactive group such as a chlorine, bromine, or an iodine atom. For final products of General Formula I wherein $R^7$ does not represent a hydrogen atom and wherein $R^8$ represents a hydrogen atom, this step is preferably performed with intermediates where $R^8$ represents an alkyl group (e.g methyl) which is then cleaved in a second step in water in the presence of either a base or an acid in the presence or absence of additional solvents (e.g. methanol, THF, etc.).

In case $R^7$ does represent a hydrogen atom, the desired compounds of General Formula I are directly obtained by reacting a compound of Formula III as mentioned below.

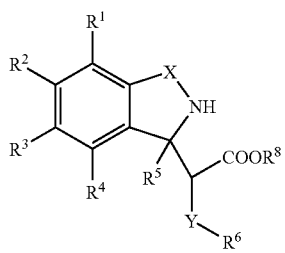

Formula II

The desired compounds of Formula II can be prepared by reacting a compound of the Formula III with water or an alcohol $R^8$—OH in the presence of either a base (e.g. LiOH, NaOH, KOH, triethylamine, DBU, DBN, etc.) or an acid (e.g. HCl, TFA) in the presence or absence of additional solvents such as methanol, ethanol, THF, dioxane, etc, at temperatures between zero and 100° C.

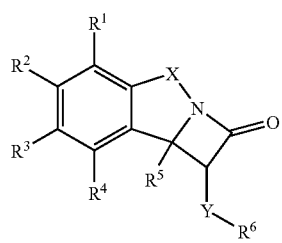

Formula III

In case Y represents O, S or NH and $R^6$ represents phenyl or substituted phenyl, compounds of Formula III are prepared by reacting a compound of Formula IV with a compound of Formula V in the presence of a base (e.g. triethylamine etc) and an activating agent such as bis(2-oxo-3-oxazolidinyl)-phosphinic chloride (BOP), phenyl N-methyl-N-phenylphosphoramidochloridate or 2-chloro-N-methylpyridinium iodide or the acide chloride of compound of Formula V in a solvent such as DCM, THF, etc. or mixtures thereof, at temperatures between zero and 80° C., as described in the literature: D. R. Shridhar, B. Ram, V. L. Narayana, *Synthesis,* (1982), 63–65; D. R. Shridhar, B. Ram, V. L. Narayana, A. K. Awasthi, G. J. Reddy, *Synthesis,* (1984), 846–847; S. G. Amin, R. D. Glazer, M. S. Manhas, *Synthesis,* (1979), 210–213; M. S. Manhas, S. G. Amin, R. D. Glazer, *J. Heterocyclic Chem.,* 16, (1979), 283–288; M. Miyake, N. Tokutake, M. Kirisawa, *Synthesis,* 14, (1984), 353–362, S. D. Sharma, A. Saluja, S. Bhaduri, *Indian J. Chem. Sect. B,* 39, (2000), 156–159. If Y represents NH, the compound of Formula V is previously protected with p-methoxy-benzyloxycarbonyl, for example, as described in U.S. Pat. No. 3,560,489, (1971); the obtained compound of Formula III is deprotected according to standard methodology (e.g. T. W. Greene, P. G. M. Wuts, Protective Groups in Organic Synthesis, 3$^{rd}$ Edition, Wiley New York, 1999; P. J. Kocienski, Protecting Groups, Thieme Stuttgart, 1994). In case Y represents N—CH$_3$ and $R^6$ phenyl or substituted phenyl or Y represents CH$_2$ and $R^6$ phenyl, substituted phenyl, pyridinyl, substituted pyridinyl, pyrimidinyl or substituted pyrimidinyl compounds of Formula III are prepared by reacting a compound of Formula IV with an ester derivative of compound of Formula V in analogy to procedures described by J. W. Clader, D. A. Duane, M. A. Caplen, M. S. Domalski, S. Dugar, *J. Med. Chem.*, 39, (1996), 3684–3693 and F. H. van der Steen, H. Kleijn, J. T. B. H. Jastrzebski, G. van Koten, *Tetrahedron Letters*, 30, (1989), 765–768.

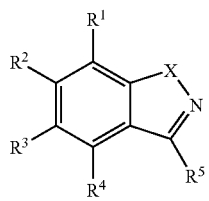

Formula IV

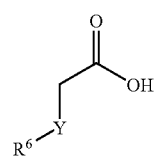

Formula V

Compounds of Formula IV are prepared according to procedures given in the literature: e.g. by N. H. Martin, C. W. Jefford in *Helv. Chim. Acta*, 75, (1982), 762–774; M. G. Bock, R. M. DiPardo, B. E. Evans, K. E. Rittle, D. F. Veber, R. M. Freidinger, J. Hirshfield, J. P. Springer, *J. Org. Chem.*, 52, (1987); by H. Umemiya, H. Fukasawa, M. Ebisawa, L. Eyrolles, E. Kawachi, G. Eisenmann, H. Gronemeyer, Y. Hashimoto, K. Shudo, H. Kagechika, *J. Med. Chem.*, 40, (1997); R. C. Effland, G. C. Helsey, J. J. Tegeler, *J. Heterocyclic Chem.* 19 (1982), 537–539 3232–3239.; J. B. Bremner, E. J. Browne, I. W. K. Gunawardana, *Aust. J. Chem.* 37 (1984) 129–141; E. J. Trybulski, R. I. Fryer, E. Reeder, A. Walser, J. Blount, *J. Med. Chem.* 26 (1983), 1596–1601; E. J. Trybuiski, E. Reeder, J. F. Blount, A. Walser, R. I. Fryer, *J. Org. Chem.* 47 (1982), 2441–2447; E. J. Trybulski, R. I. Fryer, E. Reeder, S. Vitone, L. Todaro, *J. Org. Chem.* 51 (1986), 2191–2202; E. J. Trybulski, L. E. Benjamin, J. V. Earley, R. I. Fryer, N. W. Gilman et al., *J. Med. Chem.* 26 (1983), 1589–1596; J. B. Hester, A. D. Rudzik, B. V. Kamdar, *J. Med. Chem.* 14 (1971), 1078–1081; A. Walser, R. I. Fryer, *J. Heterocyclic Chem.* 20 (1983), 551–558; A. Walser, L. E. Benjamin, T. Flynn, C. Mason, R. Schwartz, R. I. Fryer, *J. Org. Chem.* 43 (1978), 936–944; R. I. Fryer, J. V. Earley, N. W. Gilman, W. Zally, *J. Heterocyclic Chem.* 13 (1976), 433–437; R. I. Fryer, Z.-Q. Gu, C.-G. Wang, *J. Heterocyclic Chem.* 28 (1991), 1661–1669; M. Gall, B. V. Kamdar, *J. Org. Chem.* 46 (1981), 1575–1585; A. Walser, R. F. Lauer, R. I. Fryer, *J. Heterocyclic Chem.* 15 (1978), 855–858; N. W. Gilman, P. Rosen, J. V. Earley, C. M. Cook, J. F. Blount, L. M. Todaro, *J. Org. Chem.* 58 (1993), 3285–3298; A. Walser, T. Flynn, C. Mason, R. I. Fryer, *J. Heterocyclic Chem.* 23 (1986) 1303–1314; G. Romeo, M. C. Aversa, P. Giannetto, P. Ficarra, M. G. Vigorita, *Org. Magn. Reson.*, 15, (1981), 33–36; H. J. Breslin, M. J. Kukla, D. W. Ludovici, R. Mohrbacher, W. Ho, *J. Med. Chem.*, 38, (1995), 771–793.

Compounds of Formula V are prepared using standard methodology (e.g. J. March, Advanced Organic Chemistry, 3$^{rd}$ Edition, Wiley New York, 1985) e.g. from chloro-, bromo-, or iodo acetic acid and a compound $R^6$—YH in the presence of a base, or by reacting a compound of Formula VI, wherein $P^1$ represents a protecting group such as lower alkyl, with a compound of Formula VII, wherein $G^1$ represents a reactive group such as a chlorine atom, a bromine atom, or a methyl-sulfonyl group, in the presence of a base (e.g. triethylamine, $K_2CO_3$, NaH) in a solvent such as THF, DMF, etc., and subsequent ester cleavage.

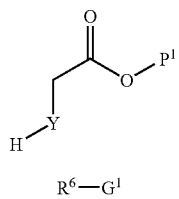

Formula VI

In case Y represents O, S NH or N—$CH_3$ and $R^6$ represents a pyridinyl, a substituted pyridinyl, a pyrimidinyl or a substituted pyrimidinyl group compounds of Formula III are preferably prepared by reacting a compound of Formula VIII with a compound of Formula VII in the presence of a base (e.g. $K_2CO_3$, triethylamine, NaH) in a solvent such as acetone, DMF, THF, DCM or mixtures thereof at temperatures between 0 and 80° C.

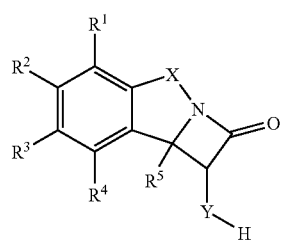

Formula VIII

Compounds of Formula VIII are prepared by cleavage of the protecting group $P^2$ in compounds of Formula IX, which in turn are prepared by reacting a compound of Formula IV with a compound of Formula X under conditions as described for the reaction of a compound of Formula IV with a compound of Formula V. A suitable protecting group $P^2$ is selected according to the nature of Y. For the cleavage of such a protecting group $P^2$, standard methodology is applied (e.g. T. W. Greene, P. G. M. Wuts, Protective Groups in Organic Synthesis, 3$^{rd}$ Edition, Wiley New York, 1999; P. J. Kocienski, Protecting Groups, Thieme Stuttgart, 1994). A benzyl protecting group, for example, is a preferred protecting group for compounds of Formula I wherein Y represents oxygen. For compounds of Formula I wherein Y represents NH a phthalimide protecting group for example is preferred, as described by C. Hubschwerlen, G. Schmid, *Helv. Chim. Acta* 66 (1983), 2206–2209. For compounds of Formula I wherein Y represents N—$CH_3$ a benzyloxycarbonyl protecting group for example is preferred. A dimethoxytriphenylmethyl or a triphenylmethyl protecting group, for example, is preferred for compounds of Formula I wherein Y represents a sulfur.

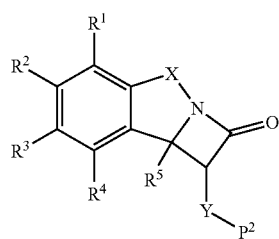

Formula IX

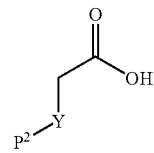

Formula X

EXAMPLES

The following examples illustrate the invention but do not at all limit the scope thereof. All temperatures are stated in ° C.

All compounds were characterized by $^1$H-NMR (300 MHz) and occasionally by $^{13}$C-NMR (75 MHz) (Varian Oxford, 300 MHz; chemical shifts are given in ppm relative to the solvent used; multiplicities: s=singlet, d=doublet, t=triplet; m=multiplet, br=broad, coupling constants are given in Hz), by LC-MS[1] (Finnigan Navigator with HP 1100 Binary Pump and DAD, column: 4.6×50 mm, Develosil RP Aqueous, 5 μm, 120A, gradient: 5–95% acetonitrile in water, 1 min, with 0.04% trifluoroacetic acid, flow: 4.5 ml/min) or LC-MS[2] (Waters Micromass; ZMD-platform with ESI-probe with Alliance 2790 HT and DAD 996, column: 2×30 mm, Gromsil ODS4, 3 μm, 120A; gradient: 0–100% acetonitrile in water, 6 min, with 0.05% formic acid, flow: 0.45 ml/min), $t_R$ is given in min; by tlc (tlc-plates from Merck, Silica gel 60 $F_{254}$) and occasionally by melting point. Some compounds were purified by preparative HPLC (two Varian SD-1 prep star pumps, PL-ELS 1000 detector, column 60×21.2 mm, Phenomenex AQUA, 5 μm, gradient: 10–95% acetonitrile in water, 3.5 min, with 0.5% formic acid) or by MPLC (Labomatic MD-80-100 pump, Linear UVIS-201 detector, column: 350×18 mm, Labogel-RP-18-5s-100, gradient: 10% methanol in water to 100% methanol).

List of Abbreviations:

aq. aqueous atm atmosphere

CyHex cyclohexane

DBN 1,5-Diazabicyclo[4.3.0]non-5-ene

DBU 1,8-Diazabicyclo[5.4.0]undec-7-ene

DCM dichloromethane

DMAP 4-dimethylaminopyridine

DME 1,2-dimethoxyethane

DMF dimethylformamide

DMSO dimethylsulfoxide

EA ethyl acetate

Hex hexane

HV high vacuum conditions

MCPBA m-chloroperbenzoic acid min minutes

THF tetrahydrofuran rt room temperature sat. saturated $t_R$ retention time tlc thin layer chromatography

Example 1

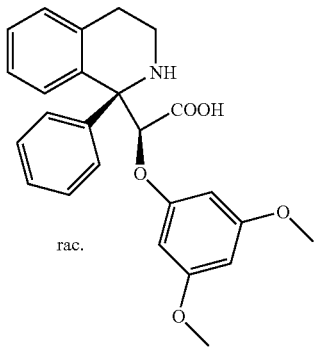

a) 1-Phenyl-3,4-dihydro-isoquinoline was prepared according to a procedure given in the literature (I. Lantos et al. *J. Org. Chem.* 51 (1986), 4147–4150). $^1$H-NMR (300 MHz, CDCl$_3$): 2.78–2.85 (m, 2H), 3.82–3.89 (m, 2H), 7.21–7.30 (m, 3H), 7.36–7.46 (m, 4H), 7.58–7.63 (m, 2H).

b) A mixture of 3,5-dimethoxy-phenol (5 g, 32.4 mmol), ethyl bromoacetate (3.6 ml, 32.4 mmol) and potassium carbonate (6.7 g, 48.5 mmol) in acetone (50 ml) is refluxed for 5 h. The mixture is filtered and the fitrate evaporated to give (3,5-dimethoxy-phenoxy)-acetic acid ethyl ester (8 g) as a colourless oil. $^1$H-NMR (300 MHz, CDCl$_3$): 1.30 (t, J=7, 3H), 3.75 (s, 3H), 4.27 (d, J=7, 2H), 4.56 (s, 2H), 6.08 (d, J=2, 2H), 6.12 (t, J=2, 1H).

c) To a solution of (3,5-dimethoxy-phenoxy)-acetic acid ethyl ester (7.8 g, 32.5 mmol) in THF (50 ml) and methanol (20 ml) is added lithium hydroxyde monohydrate (3.4 g, 81.0 mmol), dissolved in water (50 ml), at 0° C. The solution is stirred at rt for 4 h, then poured into 1 M aq. HCl. The aqueous phase is extracted twice with EA. The organic phase is dried over Na$_2$SO$_4$ and evaporated to give (3,5-dimethoxy-phenoxy)acetic acid (6.75 g) as an orange solid. $^1$H-NMR (300 MHz, CDCl$_3$): 3.71 (s, 3H), 4.51 (s, 2H), 6.06–6.08 (m, 3H). LC-MS$^2$: $t_R$=4.38 min, [M+1]$^+$=241.27.

d) A solution of 1-phenyl-3,4-dihydro-isoquinoline (500 mg, 2.41 mmol), (3,5-dimethoxy-phenoxy)-acetic acid (511 mg, 2.41 mmol) and triethylamine (1.34 ml, 9.64 mmol) in DCM (12 ml) is cooled to 5° C. and then treated with bis(2-oxo-3-oxazolidinyl)phosphinic chloride (460 mg, 1.81 mmol). The mixture is stirred at 0–5° C. for 5 h before a second portion of bis(2-oxo-3-oxazolidinyl) phosphinic chloride (460 mg, 1.81 mmol) is added. The mixture is stirred at rt for 1.5 h before it is diluted with DCM, washed with sat. aq. NaHCO$_3$ and brine. The organic phase is dried over Na$_2$SO$_4$ and evaporated. The crude product is purified by column chromatography on silica gel eluting with heptane:EA 5:1 to furnish (±)-(1S*, 9bS*)-1-(3,5-dimethoxy-phenoxy)-9b-phenyl-1,4,5,9b-tetrahydro-azeto[2,1-a]isoquinolin-2-one (843 mg) as a colourless foam. $^1$H-NMR (300 MHz, CDCl$_3$): 2.58–2.71 (m, 1H), 2.76–2.85 (m, 1H), 3.66–3.74 (m, 2H), 3.67 (s, 6H), 5.51 (s, 1H), 6.06–6.08 (m, 2H), 6.11–6.14 (m, 1H), 7.17–7.20 (m, 1H), 7.28–7.43 (m, 7H), 7.50–7.54 (m, 1H).

e) To a solution of (±)-(1S*,9bS*)-1-(3,5-dimethoxy-phenoxy)-9b-phenyl-1,4,5,9b-tetrahydro-azeto[2,1-a]isoquinolin-2-one (1.8 g, 4.48 mmol) in THF (20 ml) and ethanol (10 ml) a solution of LiOH.H$_2$O (2.26 g, 53.8 mmol) in water (15 ml) is added. The mixture is stirred at 70° C. for 4 h before it was neutralised with 2 M HCl. Upon evaporation of the organic solvents a white precipitate forms. The precipitate is collected and desalted by HPL-chromatography on RP-C$_{18}$ silica gel. This furnishes (±)-(S*)-(3,5-dimethoxy-phenoxy)-((1S*)-1-phenyl-1,2,3,4-tetrahydro-isoquinolin-1-yl)-acetic acid (1.1 g) as a white solid. LC-MS$^2$: $t_R$=3.85 min, [M+1]$^+$=420.34, [M−1]$^-$=418.28. $^1$H-NMR (300 MHz, D$_6$-DMSO): 2.82–2.91 (m, 2H), 2.95–3.05 (m, 1H), 3.38–3.44 (m, 1H), 3.64 (s, 6H), 4.98 (s, 1H), 6.02 (t, J=2, 1H), 6.16 (d, J=2, 2H), 7.08–7.36 (m, 7H), 7.54–7.59 (m, 2H).

Example 2

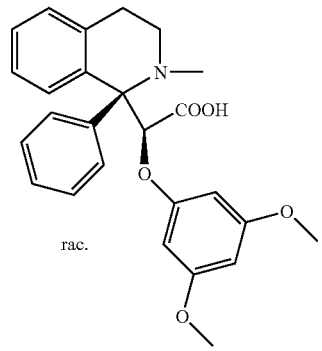

To a suspension of (±)-(S*)-(3,5-dimethoxy-phenoxy)-((1S*)-1-phenyl-1,2,3,4-tetrahydro-isoquinolin-1-yl)-acetic acid (200 mg, 0.477 mmol, Example 1) in THF (5 ml) Hünig's base (327 µl, 1.91 mmol) followed by chlorotrimethylsilane (72 µl, 0.572 mmol) is added. The mixture is stirred at 55° C. for 3 h before methyliodide (30 µl, 0.477 mmol) is added. Stirring at 55° C. is continued for another 16 h. The mixture is diluted with EA and extracted with water. The aqueous phase is acidified with 2 N HCl and extracted with EA. The EA-phase is dried over Na$_2$SO$_4$ and evaporated. The crude product is purified by prep. HPLC on Rp-C$_{18}$-silica gel to give (±)-(S*)-(3,5-dimethoxy-phenoxy)-((1S*)-2-methyl-1-phenyl-1,2,3,4-tetrahydro-isoquinolin-1-yl)-acetic acid (139 mg) as a white powder. LC-MS$^2$: $t_R$=4.03 min, [M+1]$^+$=434.34, [M−1]$^-$=432.32.

Example 3

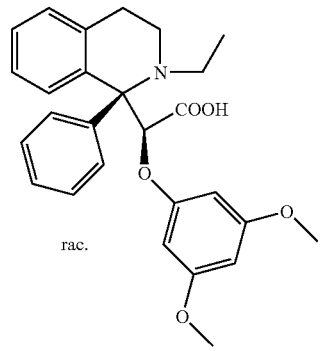

To a suspension of (±)-(S*)-(3,5-dimethoxy-phenoxy)-((1S*)-1-phenyl-1,2,3,4-tetrahydro-isoquinolin-1-yl)-acetic acid (200 mg, 0.477 mmol, Example 1) in acetonitrile (5 ml)

Hünig's base (327 μl, 1.91 mmol) followed by chlorotrimethylsilane (72 μl, 0.572 mmol) is added. The mixture is stirred at 55° C. for 3 h before ethyliodide (95 μl, 1.19 mmol) is added. Stirring at 55° C. is continued for another 16 h before water is added (about 200 μl). The solvent is removed under reduced pressure and the crude product is purified by prep. HPLC on Rp-C$_{18}$ silica gel to furnish (±)-(S*)-(3,5-dimethoxy-phenoxy)-((1S*)-2-ethyl-1-phenyl-1,2,3,4-tetrahydro-isoquinolin-1-yl)-acetic acid (58 mg) as a white solid. LC-MS$^2$: $t_R$=4.20 min, [M+1]$^+$=448.39, [M−1]$^−$=446.34.

Example 4

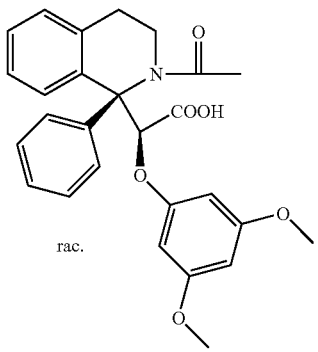

A solution of (±)-(S*)-(3,5-dimethoxy-phenoxy)-((1S*)-1-phenyl-1,2,3,4-tetrahydro-isoquinolin-1-yl)-acetic acid (100 mg, 0.238 mmol, Example 1), DMAP (6 mg, 0.048 mmol) and acetic anhydride (27 μl, 0.286 mmol) in pyridine (2 ml) is stirred at rt for 2.5 h. The reaction mixture is diluted with DCM, washed with 1 N aq. HCl. The organic phase is dried over Na$_2$SO$_4$ and evaporated. The crude product is purified by column chromatography on silica gel eluting with heptane:EA 1:1, EA, then methanol to give (±)-((1S*)-2-acetyl-1-phenyl-1,2,3,4-tetrahydro-isoquinolin-1-yl)-((S*)-3,5-dimethoxy-phenoxy)-acetic acid (57 mg) as yellow solid. LC-MS$^2$: $t_R$=4.57 min, [M+1]$^+$=462.38.

Example 5

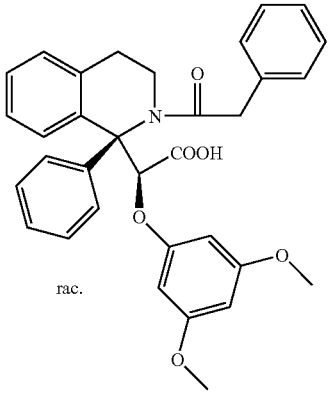

To a suspension of (±)-(S*)-(3,5-dimethoxy-phenoxy)-((1S*)-1-phenyl-1,2,3,4-tetrahydro-isoquinolin-1-yl)-acetic acid (60 mg, 0.143 mmol, Example 1) in THF (5 ml) Hünig's base (122 μl, 0.715 mmol) followed by chlorotrimethylsilane (22 μl, 0.172 mmol) is added at 5° C. The mixture is stirred at 55° C. for 3 h before phenylacetylchloride (29 μl, 0.215 mmol) is added. Stirring is continued at rt for 2 h before water (approx. 200 μl) is added. The mixture is diluted with DCM, washed twice with 2 N aq. HCl. The organic phase is dried over Na$_2$SO$_4$ and evaporated. The crude product is purified by prep. HPLC on Rp-C$_{18}$ silica gel to give (±)-(S*)-(3,5-dimethoxy-phenoxy)-((1S*)-1-phenyl-2-phenylacetyl-1,2,3,4-tetrahydro-isoquinolin-1-yl)-acetic acid (36 mg) as a white powder. LC-MS$^1$: $t_R$=0.98 min, [M+1]$^+$=538.13.

Example 6

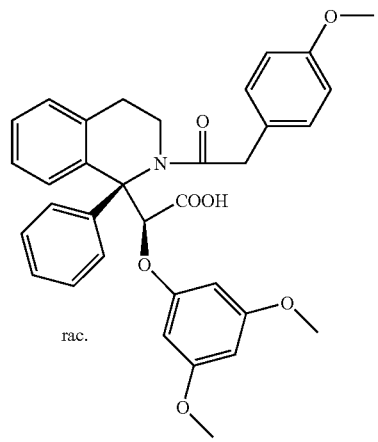

(±)-(S*)-(3,5-dimethoxy-phenoxy)-{(1S*)-2-[2-(4-methoxy-phenyl)-acetyl]-1-phenyl-1,2,3,4-tetrahydro-isoquinolin-1-yl}-acetic acid (74 mg) is prepared in analogy to Example 5 starting from (±)-(S*)-(3,5-dimethoxy-phenoxy)-((1S*)-1-phenyl-1,2,3,4-tetrahydro-isoquinolin-1-yl)-acetic acid (90 mg, 0.214 mmol, Example 1) and 4-methoxyphenylacetyl chloride (49 μl, 0.321 mmol). LC-MS$^2$: $t_R$=5.25 min, [M+1]$^+$=568.43, [M−1]$^−$=566.51.

Example 7

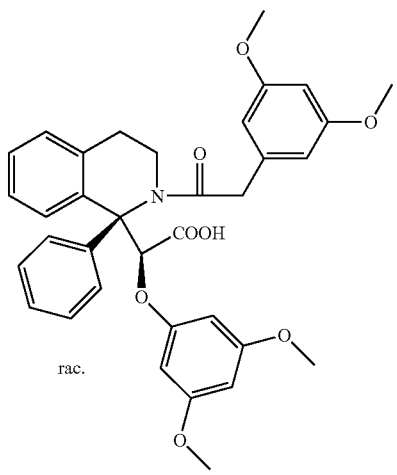

(±)-(S*)-(3,5-dimethoxy-phenoxy)-{(1S*)-2-[2-(3,5-dimethoxy-phenyl)-acetyl]-1-phenyl-1,2,3,4-tetrahydro-isoquinolin-1-yl}-acetic acid (77 mg) is prepared in analogy to Example 5 starting from (±)-(S*)-(3,5-dimethoxy-phenoxy)-((1S*)-1-phenyl-1,2,3,4-tetrahydro-isoquinolin-1- yl)-acetic acid (90 mg, 0.214 mmol, Example 1) and 3,5-dimethoxyphenylacetyl chloride (83 mg, 0.385 mmol). LC-MS²: $t_R$=5.23 min, [M+1]⁺=598.35, [M−1]⁻=596.29.

Example 8

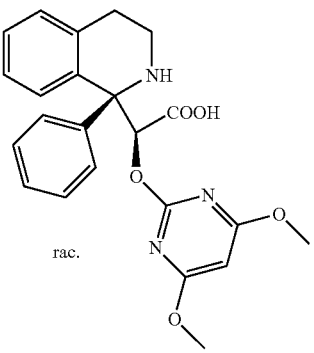

a) 4,6-dimethoxy-2-methylsulfanyl-pyrimidine is synthetized from 4,6-dichloro-2-(methylthio)pyrimidine as described by S. Batori, A. Messmer, *J. Heterocyclic Chem.*, 31, (1994), 1041–1046. ¹H-NMR (300 MHz, CDCl₃): 2.53 (s, 3H), 3.92 (s, 6H), 5.17 (s, 1H).

b) To 4,6-dimethoxy-2-methylsulfanyl-pyrimidine (2.67 g, 14.3 mmol), dissolved in DCM (20 ml), is added 39% peracetic acid in acetic acid (5.37 ml, 31.5 mmol) at 0° C. and the solution is stirred for 3 h at rt. The solution is poured into sat. aq. NaHCO₃. The aqueous phase is extracted twice with DCM. The organic phase is washed once with sat. aq. NaHCO₃, once with sat. aq. NaCl, dried over Na₂SO₄ and evaporated to give 2-methanesulfonyl-4,6-dimethoxy-pyrimidine (2.8 g) as a white solid. ¹H-NMR (300 MHz, CDCl₃): 3.32 (s, 3H), 4.03 (s, 6H), 6.18 (s, 1H).

c) At 5–10° C. a solution of hydroxy-acetic acid methyl ester (4.13 g, 45.8 mmol) in THF (40 ml) is slowly added to a suspension of NaH (1.83 g 60% in mineral oil, 45.8 mmol) in THF (60 ml). After completion of the addition, the mixture is stirred at rt for 20 min before a solution of 2-methanesulfonyl-4,6-dimethoxy-pyrimidine (5 g, 22.9 mmol) in THF (40 ml) is added. Stirring is continued at rt for 40 min before the mixture is diluted with EA and washed with sat. aq. NaHCO₃ and brine. The organic phase is dried over MgSO₄, evaporated and dried under HV to give (4,6-dimethoxy-pyrimidin-2-yloxy)-acetic acid methyl ester (5.99 g) as a colourless oil which was used without further purification. ¹H-NMR (300 MHz, CDCl₃): 3.75 (s, 3H), 3.88 (s, 6H), 4.85 (s, 2H), 5.72 (s, 1H).

d) At 10° C., a solution of LiOH.H₂O (2.88 g, 68.7 mmol) in water (37 ml) is slowly added to a solution of (4,6-dimethoxy-pyrimidin-2-yloxy)-acetic acid methyl ester (5.99 g, 22.9 mmol) in THF (63 ml) and methanol (25 ml). The mixture is stirred at rt for 1 h before it is diluted with EA and extracted twice with water and sat. aq. NaHCO₃. The aqueous phase is acidified with 37% aq. HCl and extracted three times with EA. The organic phase is dried over MgSO₄, evaporated and dried under HV to give (4,6-dimethoxy-pyrimidin-2-yloxy)-acetic acid (3.51 g) as a white powder. ¹H-NMR (300 MHz, CDCl₃): 3.90 (s, 6H), 4.90 (s, 2H), 5.76 (s, 1 H).

e) Bis(2-oxo-3-oxazolidinyl)phosphinic chloride (1.76 g, 6.9 mmol) is added to an ice-cold solution of 1-phenyl-3,4-dihydro-isoquinoline (950 mg, 4.6 mmol, Example 1) and (4,6-dimethoxy-pyrimidin-2-yloxy)-acetic acid (982 mg, 4.6 mmol) in DCM (25 ml). The mixture is allowed to slowly warm to rt and is stirred overnight before it is diluted with DCM and washed with sat. aq. NaHCO₃. The organic phase is dried over MgSO₄ and evaporated. The crude product is purified by column chromatography eluting with heptane:EA 5:1 to 2:1 to furnish (±)-(1S*,9bS*)-1-(4,6-dimethoxy-pyrimidin-2-yloxy)-9b-phenyl-1,4,5,9b-tetrahydro-azeto[2,1-a]isoquinolin-2-one (252 mg) as a white solid. LC-MS²: $t_R$=5.07 min, [M+1]⁺=404.33.

f) To a solution of (±)-(1S*,9bS*)-1-(4,6-dimethoxy-pyrimidin-2-yloxy)-9b-phenyl-1,4,5,9b-tetrahydro-azeto[2,1-a]isoquinolin-2-one (100 mg, 0.248 mmol) in THF (4 ml) is added 6 N aq. HCl (6 ml). The resulting solution is stirred at rt for 17 h, then at 70° C. for 2 h. The solvent is removed under reduced pressure, the water is coevaporated with toluene. The oily residue is precipitated twice from diethylether, the solid material is dissolved in DCM and washed with water. The organic phase is dried over Na₂SO₄ and evaporated to give (±)-(S*)-(4,6-dimethoxy-pyrimidin-2-yloxy)-((1S*)-1-phenyl-1,2,3,4-tetrahydro-isoquinolin-1-yl)-acetic acid (90 mg) as yellow oil. LC-MS²: $t_R$=3.76 min, [M+1]⁺=422.37.

Example 9

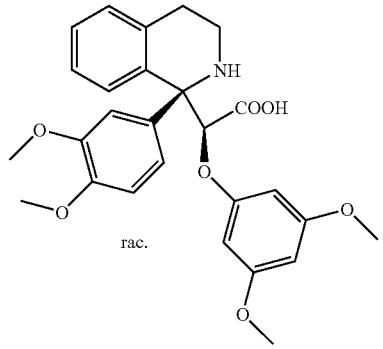

a) 1-(3,4-Dimethoxy-phenyl)-3,4-dihydro-isoquinoline was prepared in analogy to a literature procedure (I. Lantos et al. *J. Org. Chem.* 51 (1986), 4147–4150). ¹H-NMR(300 MHz, CDCl₃):3.00–3.17 (m, 2H), 3.58–3.62 (m, 1H), 3.88 (s, 3H), 3.92–3.98 (m, 4H), 6.82–6.98 (m, 2H), 7.20–7.26 (m, 1H), 7.38–7.46 (m, 1H), 7.52–7.58 (m, 1H), 7.62–7.70 (m, 2H). LC-MS²: $t_R$=2.68 min, [M+HCOOH]⁺=268.29.

b) Bis(2-oxo-3-oxazolidinyl)phosphinic chloride (400 mg, 1.57 mmol) is added to an ice-cold solution of 1-(3,4-dimethoxy-phenyl)-3,4-dihydro-isoquinoline (530 mg, 2.18 mmol) and (3,5-dimethoxy-phenoxy)-acetic acid (463 mg, 2.18 mmol, Example 1) in DCM (12 ml). The mixture is allowed to slowly warm to rt and is stirred for 52 h before a second portion of bis(2-oxo-3-oxazolidinyl)phosphinic chloride (432 mg, 1.70 mmol) is added. Stirring is continued for 16 h. The mixture is diluted with DCM and washed with sat. aq. NaHCO₃. The organic phase is dried over MgSO₄ and evaporated. The crude product is purified by column chromatography eluting with heptane:EA 2:1 to furnish (±)-(1S*,9bS*)-1-(3,5-dimethoxy-phenoxy)-9b-(3,4-dimethoxy-phenyl)-1,4,5,9b-tetrahydro-azeto[2,1-a]isoquinolin-2-one (730 mg) as a yellow foam. LC-MS²: $t_R$=4.95 min, [M+1]⁺=462.36.

c) A solution of (±)-(1S*,9bS*)-1-(3,5-dimethoxy-phenoxy)-9b-(3,4-dimethoxy-phenyl)-1,4,5,9b-tetrahydro-azeto[2,1-a]isoquinolin-2-one (100 mg, 0.216 mmol) in 1 ml dioxane is treated with 6 N aq. HCl. The mixture is stirred at 70° C. for 18 h before the solvent is evaporated. The crude product is purified by MPL-chromatography on Rp-$C_{18}$ silica gel to give (±)-(S*)-(3,5-dimethoxy-phenoxy)-[(1S*)-1-(3,4-dimethoxy-phenyl)-1,2,3,4-tetrahydro-isoquinolin-1-yl]-acetic acid (47 mg) as a beige solid. LC-MS$^2$: $t_R$=3.75 min, [M+1]$^+$=480.41.

Example 10

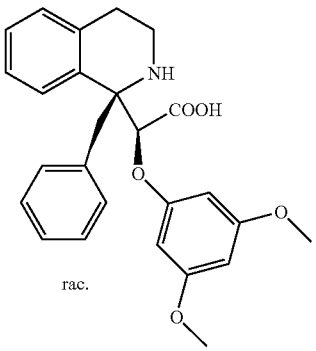

rac.

a) 1-Benzyl-3,4-dihydro-isoquinoline is prepared according to a procedure given in the literature (N. H. Martin, C. W. Jefford, *Helv. Chim. Acta* 65 (1982), 762–774). $^1$H-NMR (300 MHz, CDCl3): 2.72 (t, J=7.4, 2H), 3.77 (t, J=7.4, 2H), 4.09 (s, 2H), 7.14–7.38 (m, 8H), 7.47 (d, J=7.5, 1H). LC-MS$^2$: $t_R$=2.86 min, [M+1]$^+$=222.23.

b) Bis(2-oxo-3-oxazolidinyl)phosphinic chloride (1.58 g, 6.2 mmol) is added in two portions to an ice-cold solution of 1-benzyl-3,4-dihydro-isoquinoline (920 mg, 4.15 mmol) and (3,5-dimethoxy-phenoxy)-acetic acid (882 mg, 4.15 mmol, Example 1) in DCM (20 ml). The mixture is allowed to slowly warm to rt and is stirred for 4 h before it is diluted with DCM and washed three times with sat. aq. NaHCO$_3$. The aq. phase is extracted with additional DCM. The organic phase is dried over MgSO$_4$ and evaporated. The crude product is purified by column chromatography eluting with heptane:EA 2:1 to furnish (±)-(1S*,9bS*)-9b-benzyl-1-(3,5-dimethoxy-phenoxy)-1,4,5,9b-tetrahydro-azeto[2,1-a]isoquinolin-2-one (414 mg) as a yellow foam. LC-MS$^2$: $t_R$=5.59 min, [M+1]$^+$=416.19.

c) A solution of (±)-(1S*,9bS*)-9b-benzyl-1-(3,5-dimethoxy-phenoxy)-1,4,5,9b-tetrahydro-azeto[2,1-a]isoquinolin-2-one (312 mg, 0.751 mmol) in dioxane (10 ml) and 6 M aq. HCl (30 ml) is stirred at 95° C. for 3 h. The solvent is removed under reduced pressure and the resulting residue is dissolved water/ethanol. The solution is neutralized with 2 M aq. NaOH and evaporated. The residue is suspended in methanol and filtered. The filtrate is evaporated and purified by MPL-chromatography on Rp-$C_{18}$ silica gel to yield (±)-(S*)-((1S*)-1-benzyl-1,2,3,4-tetrahydro-isoquinolin-1-yl)-(3,5-dimethoxy-phenoxy)-acetic acid (97 mg) as a colourless foam. $^1$H-NMR (300 MHz, CDCl$_3$): 2.00–2.12 (m, 1H), 2.13–2.26 (m, 1H), 2.40–2.60 (m, 1H), 2.68–2.88 (m, 1H), 3.17 (d, J=13.4, 1H), 3.53 (d, J=13.4, 1H), 3.71 (s, 6H), 4.88 (s, 1H), 6.13 (s, 1H), 6.51 (s, 2H), 6.69 (d, J=7, 2H), 6.75 (d, J=7.5, 1H), 6.95 (d, J=7.5, 1H), 7.00–7.09 (m, 3H), 7.09–7.18 (m, 2H). LC-MS$^2$: $t_R$=4.01 min, [M+1]$^+$=434.24, [M−1]$^-$=432.31.

Example 11

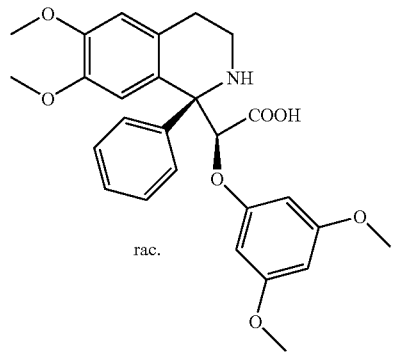

rac.

(±)-(S*)-(3,5-dimethoxy-phenoxy)-((1S*)-6,7-dimethoxy-1-phenyl-1,2,3,4-tetrahydro-isoquinolin-1-yl)-acetic acid is prepared in analogy to the procedures given in Example 1 and 9. $^1$H-NMR (300 MHz, CDCl$_3$): 2.50–2.64 (m, 1H), 2.70–2.90 (m, 2H), 2.96–3.10 (m, 1H), 3.71 (s, 6H), 3.85 (s, 3H), 3.87 (s, 3H), 5.08 (s, 1H), 6.11 (s, 1H), 6.38 (s, 2H), 6.79 (s, 1H), 7.22–7.32 (m, 2H), 7.40–7.50 (m, 3H). LC-MS$^2$: $t_R$=3.80 min, [M+1]$^+$=480.36, [M−1]$^-$=478.47.

Example 12

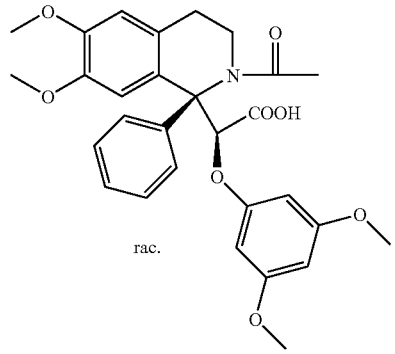

rac.

(±)-(S*)-(3,5-dimethoxy-phenoxy)-((1S*)-6,7-dimethoxy-1-phenyl-1,2,3,4-tetrahydro-isoquinolin-1-yl)-acetic acid (205 mg, 0.43 mmol) is acetylated in analogy to the procedure given in Example 5 to furnish (±)-(S*)-((1S*)-2-acetyl-6,7-dimethoxy-1-phenyl-1,2,3,4-tetrahydro-isoquinolin-1-yl)-(3,5-dimethoxy-phenoxy)-acetic acid (92 mg). LC-MS$^2$: $t_R$=4.40 min, [M+1]$^+$=522.37, [M−1]$^-$=520.32.

Example 13

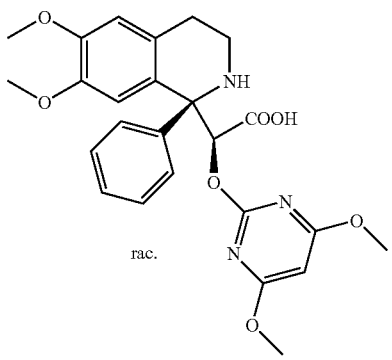

(±)-(S*)-((1S*)-6,7-Dimethoxy-1-phenyl-1,2,3,4-tetrahydro-isoquinolin-1-yl)-(4,6-dimethoxy-pyrimidin-2-yloxy)-acetic acid is prepared starting from 6,7-dimethoxy-1-phenyl-3,4-dihydro-isoquinoline in analogy to the procedures given in Example 8. $^1$H-NMR (300 MHz, CDCl$_3$): 2.72–2.87 (m, 1H), 3.10–3.40 (m, 3H), 3.61 (s, 3H), 3.75 (s, 6H), 3.81 (s, 3H), 5.57 (s, 1H), 6.06 (s, 1H), 6.53 (s, 1H), 6.60 (s, 1H), 7.18–7.24 (m, 3H), 7.56–7.62 (m, 2H). LC-MS$^2$: $t_R$=3.61 min, [M+1]$^+$=482.43, [M−1]$^−$=480.55.

Example 14

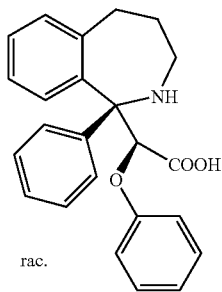

a) (±)-(1S*,9bS*)-1-Phenoxy-9b-phenyl-3,4,5,9b-tetrahydro-1H-2a-aza-benzo[a]cyclobuta[c]cyclohepten-2-one is prepared, starting from 1-phenyl-4,5-dihydro-3H-benzo[c]azepine (Example 15) and phenoxy-acetic acid, according to procedure described in Example 15. $^1$H-NMR (300 MHz, CDCl$_3$): 1.59–1.81 (m, 2H), 2.45 (dd, J=11.7, 14.5, 1H), 2.66 (dd, J=7.3, 14.8, 1H), 3.10 (dt, J$_d$=3.8, J$_t$=12.8, 1H), 4.09 (dt, J$_d$=13.6, J$_t$=3.6, 1H), 5.72 (s, 1H), 6.73–7.27 (m, 14H). LC-MS$^2$: $t_R$=5.51 min, [M+1]$^+$=356.23, [M−1]$^−$=354.17.

b) A solution of (±)-(1S*,9bS*)-1-phenoxy-9b-phenyl-3,4,5,9b-tetrahydro-1H-2a-aza-benzo[a]cyclobuta[c]cyclohepten-2-one (480 mg, 1.35 mmol) in dioxane (8 ml) and 6 M aq. HCl (7 ml) is stirred for 2 h at 75° C. and for 1 h at 90° C. 37% aq. HCl (1 ml) is added and the mixture is stirred for 30 h at 90° C. and for 64 h at rt. The organic solvent is evaporated in vacuo and the remaining solution acidified to pH 6. The residue is purified by preparative HPLC to give (±)-(1S*,1'S*)-phenoxy-(1'-phenyl-2',3',4',5'-tetrahydro-1H-benzo[c]azepin-1'-yl)-acetic acid (140 mg) as a white powder. LC-MS$^1$: $t_R$=0.79 min, [M+1]$^+$=374.06.

Example 15

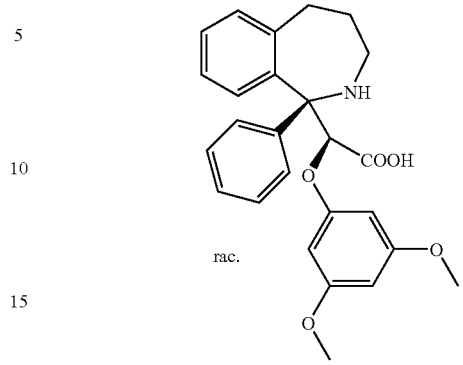

a) To a solution of 3-phenylpropylamine (10.6 ml, 74.0 mmol) in dry DCM (100 ml) and triethylamine (10.3 ml, 74.0 mmol) is added benzoylchloride (8.6 ml, 74.0 mmol) at 0° C. The suspension is stirred at rt for 16 h. The mixture is poured into water and extracted twice with EA. The organic phase is washed once with 2 M aq. HCl, once with sat. aq. NaHCO$_3$, and once with sat aq. NaCl. The organic phase is dried over Na$_2$SO$_4$ and evaporated to give N-(3-phenyl-propyl)-benzamide (17.8 g) as a light yellow oil. LC-MS$^2$: $t_R$=4.56 min, [M+1]$^+$=240.12.

b) 1-Phenyl-4,5-dihydro-3H-benzo[c]azepine is prepared from N-(3-phenyl-propyl)-benzamide, in analogy to procedures given by N. H. Martin, C. W. Jefford in *Helv. Chim. Acta*, 75, (1982), 762–774. LC-MS$^2$: $t_R$=2.95 min, [M+1]$^+$=222.09.

c) To a solution of 1-phenyl-4,5-dihydro-3H-benzo[c]azepine (440 mg, 1.99 mmol) and (3,5-dimethoxy-phenoxy)-acetic acid (507 mg, 2.39 mmol) in dry DCM (15 ml) and triethylamine (1.1 ml, 7.96 mmol) is added of bis(2-oxo-3-oxazolidinyl)phosphinic chloride (760 mg, 2.99 mmol) at 0° C. The suspension is stirred for 3 h at rt. The mixture is poured into DCM and the organic phase is washed once with sat. aq. NaHCO$_3$ and once with sat. aq. NaCl. The organic phase is dried over Na$_2$SO$_4$ and evaporated. The crude product is purified by column chromatography (silicagel, heptane:EA from 2:1 to 1:1) to give of (±)-(1S*,9bS*)-1-(3,5-dimethoxy-phenoxy)-9b-phenyl-3,4,5,9b-tetrahydro-1H-2a-aza-benzo[a]-cyclobuta[c]cyclohepten-2-one (250 mg) as a brown solid. LC-MS$^2$: $t_R$=5.51 min, [M+1]$^+$=416.32.

d) A solution of (±)-(1S*,9bS*)-1-(3,5-dimethoxy-phenoxy)-9b-phenyl-3,4,5,9b-tetrahydro-1H-2a-aza-benzo[a]cyclobuta[c]cyclohepten-2-one (250 mg, 602 µmol) in 2.4 M HCl in dioxane (7 ml) and water (20 µl) is stirred for 2 h at 55° C. After stepwise addition of 37% aq. HCl (2.75 ml) and stepwise heating to 75° C. for a total of 115 h the organic solvent is evaporated in vacuo. The remaining solution is acidified to pH 6 and the formed precipitate is filtered off. The brown solid is purified by preparative HPLC to give (±)-(1S*,1'S)-(3,5-dimethoxy-phenoxy)-(1'-phenyl-2',3',4',5'-tetrahydro-1H-benzo[c]azepin-1'-yl)-acetic acid (60 mg) as a red-brown solid. LC-MS$^2$: $t_R$=4.03 min, [M+1]$^+$=434.34, [M−1]$^−$=432.23.

Example 16

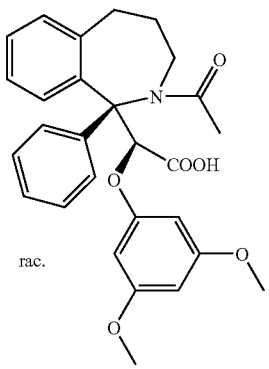

A solution of (±)-(1S*,1'S*)-(3,5-dimethoxy-phenoxy)-(1'-phenyl-2',3',4',5'-tetrahydro-1H-benzo[c]azepin-1'-yl)-acetic acid (34 mg, 78 μmol, Example 15), N-ethyldiisopropylamine (67 μl, 390 μmol) and chlorotrimethylsilane (12 μl, 94 μmol) in dry THF (4 ml) is stirred for 2 h at 55° C. The cloudy solution is cooled to rt and acetyl chloride (8.3 μl, 117 μmol) is added. The solution is stirred for 2 h at rt. The mixture is poured into 0.1 M aq. HCl. The aqueous phase is extracted twice with DCM. The organic phase is dried over Na$_2$SO$_4$ and evaporated. The crude product is purified by preparative HPLC to give (±)-(1S*,1'S*)-(2'-acetyl-1'-phenyl-2',3',4',5'-tetrahydro-1H-benzo[c]azepin-1'-yl)-(3,5-dimethoxy-phenoxy)-acetic acid (5 mg) as a white powder. LC-MS[1]: $t_R$=0.96 min, [M+1]$^+$=476.17.

Example 17

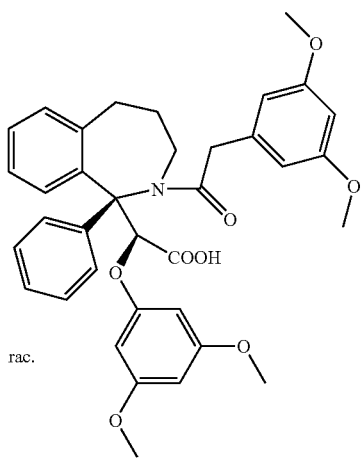

a) A suspension of (3,5-dimethoxyphenyl)acetic acid (75 mg, 383 μmol) in dry toluene (5 ml) and thionyl chloride (111 μl, 1.53 mmol) is stirred at 85° C. for 2 h and the solvent is evaporated to give crude (3,5-dimethoxy-phenoxy)-acetyl chloride as a slightly brown solid.

b) A solution of (±)-(1S*,1'S*)-1-(3,5-dimethoxy-phenoxy)-(1'-phenyl-2',3',4',5'-tetrahydro-1H-benzo[c]azepin-1'-yl)-acetic acid (34 mg, 78 μmol, Example 15), N-ethyldiisopropylamine (67 μl, 390 μmol) and chlorotrimethylsilane (12 μl, 94 μmol) in dry THF (4 ml) is stirred for 2 h at 55° C. The cloudy solution is cooled to rt and half of the crude (3,5-dimethoxy-phenoxy)-acetyl chloride, dissolved in dry THF (1 ml), is added. The solution is stirred for 2 h at rt. The mixture is poured into 0.1 M aq. HCl. The aqueous phase is extracted twice with DCM, the organic phase dried over Na$_2$SO$_4$ and evaporated. The crude product is purified by preparative HPLC to give (±)-(1S*,1'S*)-(3,5-dimethoxy-phenoxy)-{2'-[2-(3,5dimethoxy-phenyl)-acetyl]-1'-phenyl-2',3',4',5'-tetrahydro-1H-benzo[c]azepin-1'-yl}-acetic acid (4.3 mg) as a white powder. LC-MS[1]: $t_R$=1.06 min, [M+1]$^+$=612.20.

Example 18

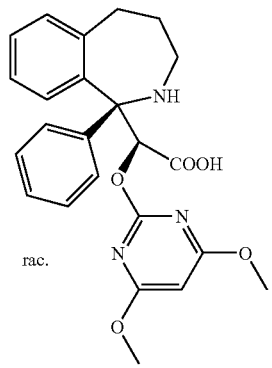

a) Benzyl alcohol (16.4 ml, 158 mmol), dissolved in dry THF (100 ml), is added to a suspension of NaH (60% in mineral oil) (13.2 g, 330 mmol) in dry THF (300 ml) at 0° C. The mixture is stirred for 30 min at 0° C., for 30 min at 45° C., then for 1 h at rt. Bromo-acetic acid (20 g, 144 mmol), dissolved in dry THF (100 ml), is added to the mixture. The suspension is stirred for 6 h at 65° C., then for 16 h at rt. The mixture is poured into water and extracted twice with EA. The aqueous phase is acidified, extracted twice with EA, which is dried over MgSO$_4$ and evaporated. Benzyloxy-acetic acid (18 g) is obtained as a light yellow oil. LC-MS[2]: $t_R$=3.17 min, [M+1]$^+$=165.02.

b) To a solution of 1-phenyl-4,5-dihydro-3H-benzo[c]azepine (1.16 g 5.24 mmol, Example 15), benzyloxy acetic acid (1.3 g, 7.86 mmol) and triethylamine (3.65 ml, 26.2 mmol) in DCM (30 ml) is added bis(2-oxo-3-oxazolidinyl)phosphinic chloride (2.67 g, 10.5 mmol) in two portions at 0° C. The mixture is allowed to come to rt and is stirred overnight before it is diluted with DCM and washed with sat. aq. NaHCO$_3$ and brine. The aq. phase is extracted again with DMC. The combined organic phase is dried over MgSO$_4$ and evaporated. The crude product is purified by column chromatography on silica gel eluting with DCM containing 0–10% of methanol to give (±)-(1S*,9bS*)-1-benzyloxy-9b-phenyl-3,4,5,9b-tetrahydro-1H-2a-aza-benzo[a]cyclobuta[c]cyclohepten-2-one (124 mg) as a yellow solid. $^1$H-NMR (300 MHz, CDCl$_3$): 1.56–1.76 (m, 1H), 1.76–1.92 (m, 1H), 2.44–2.56 (m, 1H), 2.66–2.80 (m, 1H), 3.08–3.26 (m, 1H), 4.12–4.25 (m, 1H), 4.36 (d, J=10.8, 1H), 4.52 (d, J=10.8, 1H), 5.21 (s, 1H), 6.90–7.04 (m, 3H), 7.09–7.51 (m, 11H). LC-MS[1]: $t^R$=1.11 min, [M+1]$^+$=370.10.

c) A mixture of (±)-(1S*,9bS*)-1-benzyloxy-9b-phenyl-3,4,5,9b-tetrahydro-1H-2a-aza-benzo[a]cyclobuta[c]cyclohepten-2-one (124 mg, 0.338 mmol) and Pd/C (104 mg, 10% Pd) in THF (6 ml), ethanol (6 ml) and acetic acid (0.2 ml) is stirred at 40° C. under 6 atm H$_2$ overnight. A second portion of Pd/C (104 mg) is added and stirring under 6 atm H$_2$ at 50° C. is continued for another 2 h. The mixture is filtered and the filtrate is evaporated to furnish (±)-

(1S*,9bS*)-1-hydroxy-9b-phenyl-3,4,5,9b-tetrahydro-1H-2a-aza-benzo[a]-cyclobuta[c]cyclohepten-2-one (92 mg) as a white powder. LC-MS¹: $t_R$=0.94 min, [M−1]⁻= 280.10, LC-MS²: $t_R$32 4.17 min, [M+1]⁺=280.13.

d) (±)-(1S*,9bS*)-1-Hydroxy-9b-phenyl-3,4,5,9b-tetrahydro-1H-2a-aza-benzo[a]-cyclobuta[c]cyclohepten-2-one (45 mg, 0.161 mmol) is added to a suspension of NaH (8.5 mg 60% in mineral oil, 0.209 mmol) in THF (2 ml). The mixture is stirred at rt for 1 h before 4,6-dimethoxy-2-methylsulfanyl-pyrimidine (45 mg, 0.209 mmol, Example 8) is added. Stirring is continued for 16 h. The mixture is partitioned between EA and sat. aq. NaHCO₃, the organic phase is washed with sat. aq. NaHCO₃ and brine, the aq. phase is extracted once more with EA. The combined organic phase is dried over MgSO₄ and evaporated. The crude product is purified by chromatography on prep. tlc plates with heptane:EA 3:7 to furnish (±)-(1S*,9bS*)-1-(4,6-dimethoxy-pyrimidin-2-yloxy)-9b-phenyl-3,4,5,9b-tetrahydro-1H-2a-aza-benzo[a]cyclobuta[c]cyclohepten-2-one (41 mg) as a solid. LC-MS¹: $t_R$=1.19 min, [M+1]⁺= 418.13.

e) At rt, a solution of LiOH.H₂O (8.2 mg, 0.2 mmol) in water (0.25 ml) is added to a solution of (±)-(1S*,9bS*)-1-(4,6-dimethoxy-pyrimidin-2-yloxy)-9b-phenyl-3,4,5,9b-tetrahydro-1H-2a-aza-benzo[a]cyclobuta[c]cyclohepten-2-one (41 mg, 0.1 mmol) in THF (0.5 ml) and methanol (0.25 ml). The resulting solution is stirred for 3 h before additional LiOH.H₂O (12 mg, 0.3 mmol) in water (0.1 ml) is added. After 4 h another portion of LiOH.H₂O (25 mg, 0.6 mmol) in water (0.1 ml) is added. Stirring is continued at rt for 16 h, then at 50° C. for 4 h. The reaction mixture is neutralized by adding 1N aq. HCl, and lyophilized. The crude product is purified by HPLC on Rp-C₁₈ silica gel to give (±)-(S*)-(4,6-dimethoxy-pyrimidin-2-yloxy)-((1S*)-1-phenyl-2,3,4,5-tetrahydro-1H-benzo[c]azepin-1-yl)-acetic acid (40 mg) as a white lyophilisate. LC-MS¹: $t_R$=0.85 min, [M+1]⁺=436.14.

Example 19

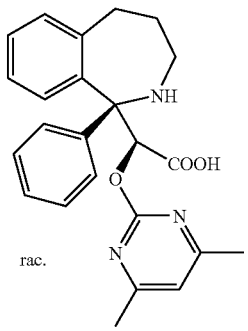

a) 2-Methanesulfonyl-4,6-dimethyl-pyrimidine is prepared by alkylation of 4,6-dimethyl-2-mercaptopyrimidine with methyliodide in aq. NaOH followed by the oxidation of the obtained 4,6-dimethyl-2-methylsulfanyl-pyrimidine with peracetic adic in DCM. ¹H-NMR (300 MHz, CDCl₃): 2.62 (s, 6H), 3.35 (s, 3H), 7.22 (s, 1H). LC-MS¹: $t_R$=0.72 min, [M+1]⁺=187.07.

b) (±)-(1S*,9bS*)-1-(4,6-dimethyl-pyrimidin-2-yloxy)-9b-phenyl-3,4,5,9b-tetrahydro-1H-2a-aza-benzo[a]cyclobuta[c]cyclohepten-2-one (61 mg) is prepared starting from (±)-(1S*,9bS*)-1-hydroxy-9b-phenyl-3,4,5,9b-tetrahydro-1H-2a-aza-benzo[a]-cyclobuta[c]cyclohepten-2-one (45 mg, 0.161 mmol, Example 18) and 2-methanesulfonyl-4,6-dimethyl-pyrimidine (39 mg, 0.209 mmol) as described in Example 18. LC-MS¹: $t_R$=1.13 min, [M+1]⁺= 386.13.

c) (±)-(S*)-(4,6-dimethyl-pyrimidin-2-yloxy)-((1S*)-1-phenyl-2,3,4,5-tetrahydro-1H-benzo[c]azepin-1-yl)-acetic acid (30 mg) is obtained as a white powder by reacting (±)-(1S*,9bS*)-1-(4,6-dimethyl-pyrimidin-2-yloxy)-9b-phenyl-3,4,5,9b-tetrahydro-1H-2a-aza-benzo[a]cyclobuta[c]-cyclohepten-2-one (61 mg, 0.38 mmol) with LiOH.H₂O as described in Example 18. LC-MS¹: $t_R$=0.82 min, [M+1]⁺=404.13.

Example 20

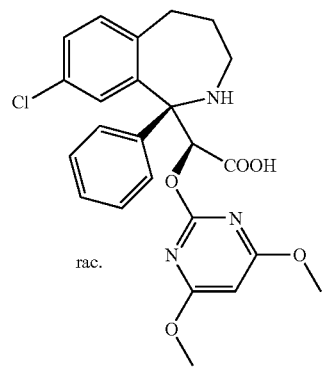

a) 8-Chloro-1-phenyl-4,5-dihydro-3H-benzo[c]azepine is prepared in analogy to Example 15. LC-MS¹: $t_R$=0.80 min, [M+1]⁺=256.02.

b) (±)-(1S*,9bS*)-1-Benzyloxy-8-chloro-9b-phenyl-3,4,5,9b-tetrahydro-1H-2a-aza-benzo[a]cyclobuta[c]cyclohepten-2-one is obtained starting from 8-chloro-1-phenyl-4,5-dihydro-3H-benzo[c]azepine following the procedure given in Example 15. LC-MS¹: $t_R$=1.28 min, [M+1]⁺= 404.02.

c) Hydrogenation of (±)-(1S*,9bS*)-1-benzyloxy-8-chloro-9b-phenyl-3,4,5,9b-tetrahydro-1H-2a-aza-benzo[a]cyclobuta[c]cyclohepten-2-one in THF/ethanol in the presence of 5% 4M HCl in dioxane gives (±)-(1S*,9bS*)-1-hydroxy-8-chloro-9b-phenyl-3,4,5,9b-tetrahydro-1H-2a-aza-benzo[a]cyclobuta[c]cyclohepten-2-one. ¹H-NMR (300 MHz, D₆⁻DMSO): 1.36–1.54 (m, 1H), 1.73–1.86 (m, 1H), 2.27 (dd, J=11.7, 14.0, 1H), 2.75 (dd, J=7.9, 15.0, 1H), 3.03 (dt, $J_d$=3.7, $J_t$=13.6, 1H), 3.93 (dt, $J_d$=13.6, $J_t$=3.3, 1H), 5.24 (d, J=6.4, 1H), 6.24 (d, J=6.4, 1H), 6.86–6.95 (m, 2H), 7.22–7.43 (m, 5H), 7.55 (d, J=2.2, 1H). LC-MS¹: $t_R$=0.92 min, [M+1]⁺=313.98.

d) Reaction of (±)-(1S*,9bS*)-1-hydroxy-8-chloro-9b-phenyl-3,4,5,9b-tetrahydro-1H-2a-aza-benzo[a]cyclobuta[c]cyclohepten-2-one with 2-methanesulfonyl-4,6-dimethoxy-pyrimidine (Example 8) followed by β-lactam hydrolysis as described in Example 18 yields (±)-(S*)-((1S*)-8-chloro-1-phenyl-2,3,4,5-tetrahydro-1H-benzo[c]azepin-1-yl)-(4,6-di-methoxypyrimidin-2-yloxy)-acetic acid as a white powder. LC-MS¹: $t_R$=0.90 min, [M+1]⁺= 470.12.

Example 21

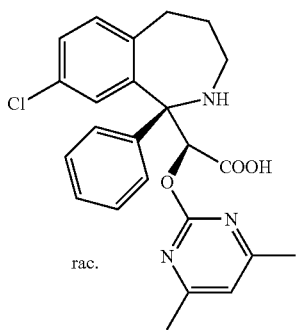

Following the procedures given in Example 18, (±)-(S*)-((1S*)-8-chloro-1-phenyl-2,3,4,5-tetrahydro-1H-benzo[c]azepin-1-yl)-(4,6-dimethylpyrimi-din-2-yloxy)-acetic acid is obtained as a white powder starting from (±)-(1S*,9bS*)-1-hydroxy-8-chloro-9b-phenyl-3,4,5,9b-tetrahydro-1H-2a-aza-benzo[a]cyclobuta[c]cyclohepten-2-one (Example 20) and 2-methanesulfonyl-4,6-dimethyl-pyrimidine (Example 19). LC-MS[1]: $t_R$=0.86 min, [M+1]$^+$=438.12.

Example 22

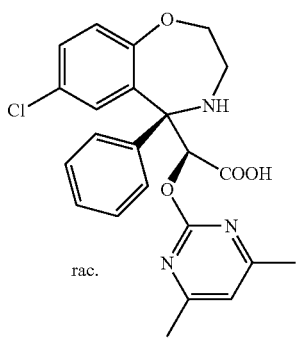

a) 7-Chloro-5-phenyl-2,3-dihydro-benzo[f][1,4]oxazepine is prepared according to procedures given by J. B. Bremner, E. J. Browne, I. W. K. Gunawardana in *Aust. J. Chem.* 37 (1984), 129–141.

b) To a solution of 7-chloro-5-phenyl-2,3-dihydro-benzo[f][1,4]oxazepine (2.0 g, 7.76 mmol) and benzyloxy-acetic acid (Example 5c) (1.93 g, 11.6 mmol) in dry DCM (20 ml) and triethylamine (5.4 ml, 38.7 mmol) bis(2-oxo-3-oxazolidinyl)phosphinic chloride (3.95 g, 15.5 mmol) is added at 0° C. The suspension is stirred at 0° C. and is allowed to slowly warm to rt. Stirring is continued for 18 h. The mixture is poured into sat. aq. NaHCO$_3$ and extracted three times with DCM. The organic phase is dried over MgSO$_4$ and evaporated. The crude product is purified by column chromatography (silica gel, heptane:EA 1:1) to give (±)-(1S*,9bS*)-1-benzyloxy-8-chloro-9b-phenyl-1,3,4,9b-tetrahydro-5-oxa-2a-aza-benzo[a]cyclobuta[c]cyclohepten-2-one (3.04 g) as a white solid. LC-MS[2]: $t_R$=5.39 min, [M+1]$^+$=406.15; $^1$H-NMR (300 MHz, CDCl$_3$): 3.38 (ddd, J=3.3, 9.3, 13.7, 1H), 3.78 (ddd, J=2.7, 9.5, 12.3, 1H), 4.08 (ddd, J=2.6, 3.5, 13.7, 1H), 4.20 (dt, $J_d$=12.3, $J_t$=3.5, 1H), 4.37 (d, J=11.2, 1H), 4.49 (d, J=11.2, 1H), 5.05 (d, 1H), 6.97–7.04 (m, 4H), 7.13–7.17 (m, 2H), 7.24–7.28 (m, 4H), 7.35–7.40 (m, 3H).

c) To a solution of (±)-(1S*,9bS*)-1-benzyloxy-8-chloro-9b-phenyl-1,3,4,9b-tetrahydro-5-oxa-2a-aza-benzo[a]cyclobuta[c]cyclohepten-2-one (1.0 g, 2.46 mmol) in ethanol (30 ml) and 1,2-dichlorobenzene (6 ml), a suspension of 10% Pd on charcoal (100 mg) in ethanol (1 ml) is added. The mixture is stirred for 70 min under an atmosphere of hydrogen gas (balloon). The catalyst is filtered and the filtrate is evaporated in vacuo. The remaining residue is suspended in diethyl ether, the solid material is collected, washed with diethyl ether and dried to give (±)-(1S*,9bS*)-8-chloro-1-hydroxy-9b-phenyl-1,3,4,9b-tetrahydro-5-oxa-2a-aza-benzo[a]cyclobuta[c]cyclohepten-2-one (707 mg) as an off-white powder. LC-MS[2]: $t_R$=4.10 min, [M+1]$^+$=316.05, [M−1]$^-$=313.81.

d) To a suspension of NaH (60% in mineral oil) (52 mg, 1.30 mmol) in dry THF (6 ml) and dry DMF (2 ml) (±)-(1S*,9bS*)-8-chloro-1-hydroxy-9b-phenyl-1,3,4,9b-tetrahydro-5-oxa-2a-aza-benzo[a]cyclobuta[c]cyclohepten-2-one (250 mg, 792 μmol) is added. The mixture is stirred for 5 min at rt before 2-methanesulfonyl-4,6-dimethyl-pyrimidine (Example 19) (221 mg, 1.19 mmol) is added. The mixture is stirred at rt for 3 h, diluted with EA and washed with sat. aq. NaHCO$_3$ and twice with water. The organic layer is dried over MgSO$_4$. The product slowly crystallises upon evaporation of the solvent. The solid material is collected, washed with diethyl ether and dried to give (±)-(1S*,9bS*)-8-chloro-1-(4,6-dimethyl-pyrimidin-2-yloxy)-9b-phenyl-1,3,4,9b-tetrahydro-5-oxa-2a-aza-benzo[a]cyclobuta[c]cyclohepten-2-one (269 mg) as white crystals. LC-MS[2]: $t_R$=4.99 min, [M+1]$^+$=422.17.

e) A solution of (±)-(1S*,9bS*)-8-chloro-1-(4,6-dimethyl-pyrimidin-2-yloxy)-9b-phenyl-1,3,4,9b-tetrahydro-5-oxa-2a-aza-benzo[a]cyclobuta[c]cyclohepten-2-one (200 mg, 474 μmol) in THF (3 ml), methanol (2 ml) and 2 N aq. lithium hydroxyde (2 ml) is stirred at 60° C. for 5 h. The pH is adjusted to 5 by the addition of 10% aq. acetic acid (approx. 2.5 ml) and the resulting mixture is extracted three times with DCM. The organic phase is dried over Na$_2$SO$_4$ and evaporated. The crude product is purified on prep. tlc plates (DCM containing 10% of methanol) to give (±)-(1S*,5'S*)-(7'-chloro-5'-phenyl-2',3',4',5'-tetrahydro-benzo[f][1,4]oxazepin-5'-yl)-(4,6-dimethyl-pyrimidin-2-yloxy)-acetic acid (143 mg) as a colourless foam. LC-MS[2]: $t_R$=3.63 min, [M+1]$^+$=440.21, [M−1]$^-$=438.08.

Example 23

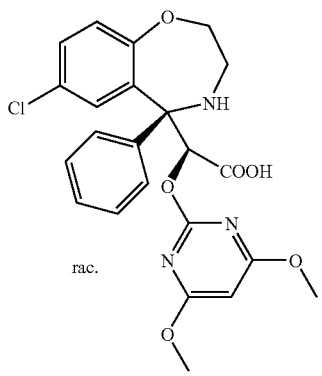

a) To a suspension of NaH (60% in mineral oil) (52 mg, 1.3 mmol) in dry THF (6 ml) and dry DMF (2 ml) (±)-(1S*, 9bS*)-8-chloro-1-hydroxy-9b-phenyl-1,3,4,9b-tetrahydro-5-oxa-2a-aza-benzo[a]cyclobuta[c]cyclohepten-2-one (Example 22) (250 mg, 792 µmol) is added. The mixture is stirred for 5 min at rt and 2-methanesulfonyl-4,6-dimethoxy-pyrimidine (Example 8) (260 mg, 1.19 mmol) is added. Stirring is continued for 3 h before the mixture is diluted with EA and washed with sat. aq. NaHCO$_3$ and twice with water. The organic layer is dried over MgSO$_4$ and evaporated. The product is crystallised from diethyl ether to give (±)-(1S*,9bS*)-8-chloro-1-(4,6-dimethoxy-pyrimidin-2-yloxy)-9b-phenyl-1,3,4,9b-tetrahydro-5-oxa-2a-aza-benzo[a]cyclobuta[c]cy-clohepten-2-one (329 mg) as white crystals. LC-MS$^2$: $t_R$=5.30 min, [M+1]$^+$=454.20.

b) A solution of (±)-(1S*,9bS*)-8-chloro-1-(4,6-dimethoxy-pyrimidin-2-yloxy)-9b-phenyl-1,3,4,9b-tetrahydro-5-oxa-2a-aza-benzo[a]cyclobuta[c]cy-clohepten-2-one (200 mg, 441 µmol) in THF (4 ml), methanol (3 ml) and 2 N aq. lithium hydroxyde (2 ml) is stirred at 50° C. for 6 h. The organic solvents are removed and the aqueous solution is diluted with water and acidified with 10% aq. acetic acid (approx. 3 ml). The mixture is extracted three times with DCM. The organic phase is evaporated and the crude product is purified on prep. tlc-plates (DCM:methanol:water:acetic acid 100:20:2:1) to give (±)-(1S*,5'S*)-(7'-chloro-5'-phenyl-2',3',4',5'-tetrahydro-benzo[f][1,4]oxazepin-5'-yl)-(4,6-dimethoxy-pyrimidin-2-yloxy)-acetic acid (96 mg) as a white powder. LC-MS$^2$: $t_R$=3.88 min, [M+1]$^+$=472.26, [M−1]$^-$=470.06.

Example 24

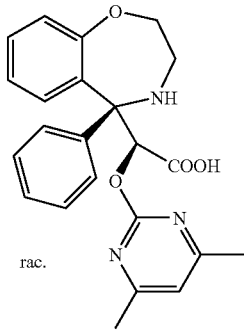

rac.

a) To a suspension of 10% Pd on charcoal (200 mg) in ethanol (10 ml) a solution of (±)-(1S*,9bS*)-1-benzyloxy-8-chloro-9b-phenyl-1,3,4,9b-tetrahydro-5-oxa-2a-aza-benzo[a]cyclobuta[c]cyclohepten-2-one (360 mg, 887 µmol, Example 22) in THF:ethanol 1:1 (15 ml), followed by acetic acid (approx. 0.5 ml), is added. The mixture is stirred at rt under an atmosphere of 7 atm hydrogen gas for 2.5 h. The catalyst is filtered off and the filtrate is evaporated. The crude product is purified by column chromatography (silica gel, EA) to give (±)-(1S*,9bS*)-1-hydroxy-9b-phenyl-1,3,4,9b-tetrahydro-5-oxa-2a-aza-benzo[a]cyclobuta[c]cyclo-hepten-2-one (235 mg) as a white crystaline solid. LC-MS$^2$: $t_R$=3.72 min, [M+1]$^+$=282.10, [M−H]$^-$=280.00.

b) To a solution of (±)-(1S*,9bS*)-1-hydroxy-9b-phenyl-1,3,4,9b-tetrahydro-5-oxa-2a-aza-benzo[a]cyclobuta[c]cy-clohepten-2-one (227 mg, 807 µmol) in dry THF (6 ml) and dry DMF (2 ml) NaH (60% in mineral oil) (46 mg, 1,15 mmol) is added. The mixture is stirred at rt for 5 min and 2-methanesulfonyl-4,6-dimethyl-pyrimidine (195 mg, 1.05 mmol, Example 19) is added. The resulting mixture is stirred at rt for 2 h before it is diluted with EA and washed with sat. aq. NaHCO$_3$ followed by water. The organic phase is evaporated. The product crystallises, the obtained crystals are collected, washed with diethyl ether and dried to furnish (±)-(1S*,9bS*)-(1-(4,6-dimethyl-pyrimidin-2-yloxy)-9b-phenyl-1,3,4,9b-tetrahydro-5-oxa-2a-aza-benzo[a]cyclobuta[c]cyclohepten-2-one (196 mg) as white crystals. LC-MS$^2$: $t_R$=4.66 min, [M+1]$^+$=388.19.

c) A solution of (±)-(1S*,9bS*)-(1-(4,6-dimethyl-pyrimidin-2-yloxy)-9b-phenyl-1,3,4,9b-tetrahydro-5-oxa-2a-aza-benzo[a]cyclobuta[c]cyclohepten-2-one (100 mg, 258 µmol) and lithium hydroxyde monohydrate (18 mg, 429 µmol) in THF (5 ml), methanol (5 ml) and water (2 ml) is stirred at 55° C. for 18 h, at 65° C. for 144 h before further lithium hydroxyde monohydrate (30 mg, 715 µmol) is added. Stirring of the solution is continued for 24 h at 65° C. The pH is adjusted to 5 by adding acetic acid. The solvent is removed and the crude product is purified by preparative HPLC. Product fractions are lyophilised to give (±)-(1S*,5'S*)-(4,6-dimethyl-pyrimidin-2-yloxy)-(5'-phenyl-2',3',4',5'-tetrahydro-benzo[f][1,4]oxazepin-5'-yl)-acetic acid (58 mg) as a white lyophilisate. LC-MS$^2$: $t_R$=3.38 min, [M+1]$^+$=406.10, [M−1]$^-$=404.09.

Example 25

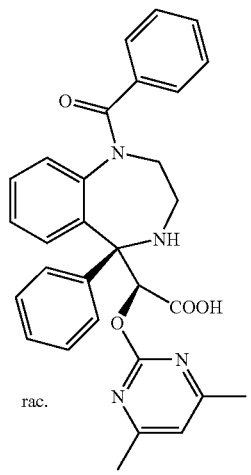

rac.

a) 5-Phenyl-2,3-dihydro-1H-benzo[e][1,4]diazepine is prepared starting from 5-phenyl-1,3-dihydro-benzo[e][1,4]diazepin-2-one (Example 27) as described in the literature (L. H. Sternbach, E. Reeder, G. A. Archer, *J. Org. Chem.* 28 (1963), 2456–2459). $^1$H-NMR (300 MHz, CDCl$_3$): 3.82–3.88 (m, 2H), 3.96–4.02 (m, 3H), 6.66–6.74 (m, 2H), 6.99–7.05 (m, 1H), 7.15–7.24 (m, 1H), 7.32–7.42 (m, 3H), 7.51–7.56 (m, 2H). LC-MS$^1$: $t_R$=0.76 min, [M+1]$^+$=223.05.

b) Benzoylchloride (0.64 ml, 5.5 mmol) is slowly added at 10° C. to a solution of 5-phenyl-2,3-dihydro-1H-benzo[e][1,4]diazepine (1.11 g, 5 mmol) and triethylamine (1.05 ml, 7.5 mmol) in DCM (25 ml). The mixture is stirred for 2 h at rt, diluted with EA and washed with water. The aq. phase is extracted once more with EA, the organic phase is washed with brine. The combined organic phase is dried over MgSO$_4$ and evaporated. The residue is suspended in boiling diethyl ether. The solid material is collected, washed with additional diethyl ether and dried to give phenyl-(5-phenyl-2,3-dihydro-benzo[e][1,4]diazepin-1-yl)-methanone (0.7 g) as beige crystals. LC-MS$^1$: $t_R$=0.69 min, [M+1]$^+$=327.03.

c) Benzyloxyacetyl chloride (0.45 ml, 2.74 mmol) is slowly added at 0° C. to a solution of phenyl-(5-phenyl-2,3-dihydro-benzo[e][1,4]diazepin-1-yl)-methanone (0.69 g, 2.11 mmol) and triethylamine (0.88 ml, 6.33 mmol) in DCM (15 ml). The mixture is allowed to come to rt and is stirred for 16 h before it is diluted with EA, washed with sat. aq. NaHCO$_3$, water and brine. The aq. phase is extracted once more with EA. The combined organic phase is dried over MgSO₄ and evaporated. The product is crystallised from EA/diethyl ether to furnish (±)-(1S*, 9bS*)-5-benzoyl-1-benzyloxy-9b-phenyl-3,4,5,9b-tetrahydro-1H-2a,5-diaza-benzo[a]cyclo-buta[c]cyclohepten-2-one (0.9 g) as a white powder. LC-MS¹: $t_R$=1.13 min, [M+1]⁺=475.05 d) A solution of (±)-(1S*,9bS*)-5-benzoyl-1-benzyloxy-9b-phenyl-3,4,5,9b-tetrahydro-1H-2a,5-diaza-benzo[a]cyclo-buta[c]cyclohepten-2-one (1.6 g, 3.35 mmol) in THF (45 ml), ethanol (15 ml) and acetic acid (0.5 ml) is treated with a suspension of Pd/C (0.5 g, 10% Pd) in THF (3 ml). The mixture is stirred at 45° C. under 7 atm of H₂ for 22 h. The catalyst is filtered off and the filtrate is evaporated. The residue is suspended in diethyl ether, filtered off, washed with diethyl ether and dried to yield (±)-(1S*, 9bS*)-5-benzoyl-1-hydroxy-9b-phenyl-3,4,5,9b-tetrahydro-1H-2a,5-diaza-benzo[a]cyclobuta[c]cyclohepten-2-one (1.23 g) as white crystals. LC-MS¹: $t_R$=0.89 min, [M+1]⁺=384.96.

e) A mixture of K₂CO₃ (1.25 g, 9 mmol), (±)-(1S*,9bS*)-5-benzoy-1-hydroxy-9b-phenyl-3,4,5,9b-tetrahydro-1H-2a,5-diaza-benzo[a]cyclobuta[c]cyclohepten-2-one (1.15 g, 3 mmol), and 2-methanesulfonyl-4,6-dimethyl-pyrimidine (0.67 g, 3.6 mmol, Example 19) in DMF (30 ml) is stirred at 40° C. for 58 h before it is diluted with EA and washed three times with water. The aq. phase is extracted once more with EA. The combined organic phase is dried over MgSO₄ and evaporated and dried to give crude (±)-(1S*,9bS*)-5-benzoyl-1-(4,6-dimethyl-pyrimidin-2-yloxy)-9b-phenyl-3,4,5,9b-tetrahydro-1H-2a,5-diaza-benzo[a]cyclobuta[c]cyclohepten-2-one (1.5 g) as a white powder. LC-MS¹: $t_R$=1.05 min, [M+1]⁺=491.00.

f) A 2 N solution LiOH.H₂O (2 ml) is added to a solution of crude (±)-(1S*,9bS*)-5-benzoyl-1-(4,6-dimethyl-pyrimidin-2-yloxy)-9b-phenyl-3,4,5,9b-tetrahydro-1H-2a,5-diaza-benzo[a]cyclobuta[c]cyclohepten-2-one (491 mg, 1 mmol) in THF (8 ml) and methanol (4 ml). The resulting solution is stirred at rt for 40 h before it is diluted with 10% aq. citric acid and extracted three times with DCM. The organic phase is washed with water, dried over MgSO₄ and evaporated. The crude product is purified on prep. tlc plates with DCM:methanol 9:1 to furnish (±)-(S*)-((5S*)-1-benzoyl-5-phenyl-2,3,4,5-tetrahydro-1H-benzo[e][1,4]diazepin-5-yl)-(4,6-dimethyl-pyrimidin-2-yloxy)-acetic acid (130 mg) as a white powder. LC-MS¹: $t_R$=0.95 min, [M+1]⁺=509.02.

Example 26

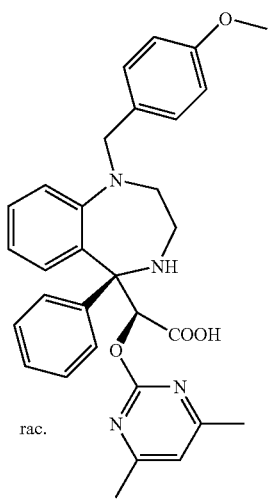

rac.

a) NaH is added (1.3 g, 55% in mineral oil, 29.7 mmol) in portions to an ice-cold solution of 5-phenyl-2,3-dihydro-1H-benzo[e][1,4]diazepine (6.0 g, 27 mmol, Example 25) in DMF (75 ml). The mixture is stirred at rt for 15 min before a solution of 4-methoxybenzyl chloride (4.53 ml, 32.4 mmol) in DMF (5 ml) is added. The orange suspension is stirred at rt for 8 h, diluted with EA and washed with cold water. The aq. phase is extracted two more times with EA. The organic phase is washed with brine, dried over MgSO₄ and evaporated. The crude product is purified by column chromatography on silica gel eluting with DCM:methanol 30:1 to 20:1 to furnish 1-(4-methoxy-benzyl)-5-phenyl-2,3-dihydro-1H-benzo[e][1,4]diazepine (8.0 g) as an orange solid. LC-MS¹: $t_R$=0.86 min, [M+1]⁺=343.07.

b) Starting from 1-(4-methoxy-benzyl)-5-phenyl-2,3-dihydro-1H-benzo[e][1,4]diazepine (27.31 g, 76.62 mmol), the [2+2]-cycloaddition and the hydrogenation is performed as described in Example 25 to give (±)-(1S*, 9bS*)-1-hydroxy-5-(4-methoxy-benzyl)-9b-phenyl-3,4,5,9b-tetra-hydro-1H-2a,5-diaza-benzo[a]cyclobuta[c]cyclohepten-2-one (28.87 g) as a white powder. ¹H-NMR (300 MHz, CDCl₃): 3.30 (d, J=15, 1H), 3.78 (s, 3H), 3.86 (d, J=13.5, 1H), 4.50 (d, J=13.5, 1H). 4.53 (d, J=15, 1H), 5.40 (s, 1H), 6.68–6.75 (m, 2H), 7.00–7.04 (m, 2H), 7.28–7.46 (m, 7H), 7.64–7.70 (m, 1H). LC-MS¹: $t_R$=0.96 min, [M+1]⁺=415.04.

c) The introduction of the 4,6-dimethylpyrimidine and the β-lactam cleavage are carried out as described in Example 25 to yield (±)-(S*)-(4,6-dimethyl-pyrimidin-2-yloxy)-[(5S*)-1-(4-methoxy-benzyl)-5-phenyl-2,3,4,5-tetrahydro-1H-benzo[e][1,4]diazepin-5-yl]-acetic acid as a white powder. LC-MS¹: $t_R$=0.95 min, [M+1]⁺=525.06.

Example 27

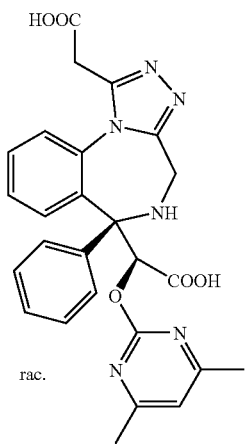

rac.

a) 5-Phenyl-1,3-dihydro-benzo[e][1,4]diazepin-2-one is prepared starting from 2-aminobenzophenone and bromoacetyl bromide in analogy to procedures given by M. G. Bock, R. M. DiPardo, B. E. Evans, K. E. Rittle, D. F. Veber, R. M. Freidinger, J. Hirshfield, J. P. Springer, *J. Org. Chem.*, 52, (1987), 3232–3239. LC-MS²: $t_R$=3.09 min, [M+1]⁺=237.00.

b) (6-Phenyl-4H-2,3,5,10b-tetraaza-benzo[e]azulen-1-yl)-acetic acid ethyl ester is prepared starting from 5-phenyl-1,3-dihydro-benzo[e][1,4]diazepin-2-one and ethyl 3-hydrazino-3-oxopropionate following the procedures described by A. Walser, T. Flynn, C. Mason, H. Crowley, C. Maresca, B. Yaremko, M. O'Donnell, *J. Med. Chem.* 34 (1991), 1209–1221. ¹H-NMR (300 MHz, CDCl₃): 1.18 (t, J=7.1, 3H), 4.04–4.17 (m, 5H), 5.49 (d, J=12.8, 1H), 7.31–7.48 (m, 5H), 7.51–7.70 (m, 4H). LC-MS²: $t_R$=3.91 min, [M+1]⁺=347.18, [M–1]⁻=344.81.

c) At 0° C. benzyloxyacetyl chloride (616 mg, 3.33 mmol) is added to a solution of (6-phenyl-4H-2,3,5,10b-tetraaza-benzo[e]azulen-1-yl)-acetic acid ethyl ester (770 mg, 2.22 mmol), trethylamine (1.55 ml, 11.11 mmol) in DCM (20 ml). The mixture is stirred at 0° C. for 40 min, then at rt for 20 h before it is diluted with EA and washed three times with sat. aq. NaHCO₃. The aq. phase is extracted with EA. The combined organic phase is dried over MgSO₄ and evaporated. The resulting solid is supsended in diethyl ether, filtered, washed with additional diethyl ether and dried to furnish (±)-((1S*,10bS*)-1-benzyloxy-2-oxo-10b-phenyl-1,10b-dihydro-2H,3H-2a,4,5,6a-tetraaza-benzo[h]cyclobuta[f]azulen-6-yl)-acetic acid ethyl ester (863 mg) as a beige powder. LC-MS²: $t_R$=4.53 min, [M+1]⁺=495.28, [M–1]⁻=493.17.

d) A suspension of Pd/C (500 mg, 10% Pd) in THF is added to a solution of (±)-((1S*,10bS*)-1-benzyloxy-2-oxo-10b-phenyl-1,10b-dihydro-2H,3H-2a,4,5,6a-tetraaza-benzo[h]cyclobuta[f]azulen-6-yl)-acetic acid ethyl ester (860 mg, 1.74 mmol) in THF (25 ml), ethanol (10 ml) and acetic acid (2 ml). The mixture is stirred at 50° C. under 7 atm H₂ for 57 h. The Pd-catalyst is filtered off and the filtrate is evaporated. The residue is dissolved in DCM (10 ml), diluted with EA (250 ml) and washed twice with sat. aq. NaHCO₃, once with water. The organic phase is dried over MgSO₄ and evaporated to give (±)-((1S*,10bS*)-1-hydroxy-2-oxo-10b-phenyl-1,10b-dihydro-2H,3H-2a,4,5,6a-tetraaza-benzo[h]cyclobuta[f]-azulen-6-yl)-acetic acid ethyl ester (491 mg) as a beige powder. ¹HNMR-(300 MHz, CDCl₃): 1.24 (t, J=7.1, 3H), 2.97 (d, J=16.8, 1H), 3.41 (d, J=17.0, 1H), 4.16 (q, J=7.1, 2H), 4.33 (d, J=14.6, 1H), 5.35 (d, J=14.8, 1H), 5.49(s, 1H), 6.90 (s br, 3H), 7.14–7.21 (m, 3H), 7.52 (d, J=7.7, 1H), 7.61 (t, J=7.7, 1H), 7.70 (t, J=7.5, 1H), 7.90 (d, J=7.7, 1H). LC-MS²: $t_R$=3.35 min, [M+1]⁺=405.35, [M–1]⁻=403.21.

e) At 50° C., K₂CO₃ (341 mg, 2.47 mmol) followed by 2-methanesulfonyl-4,6-dimethyl-pyrimidine (184 mg, 0.989 mmol, Example 19) is added to a solution of (±)-((1S*,8aS*)-1-hydroxy-2-oxo-8a-phenyl-1,8a-dihydro-2H,3H-2a,4,5,6a-tetraaza-benzo[h]cyclobuta[f]-azulen-6-yl)-acetic acid ethyl ester (200 mg, 0.495 mmol) in acetone (5 ml). The mixture is stirred for 5 h, diluted with EA (75 ml) and washed twice with water. The organic phase is evaporated and the crude product is purified by column chromatography on silica gel eluting with DMC containing 6% of methanol to furnish (±)-((1S*,10bS*)-1-(4,6-dimethylpyrimidin-2-yloxy)-2-oxo-10b-phenyl-1,10b-dihydro-2H,3H-2a,4,5,6a-tetraaza-benzo[h]cyclobuta[f]-azulen-6-yl)-acetic acid ethyl ester (205 mg) as a colourless foam. LC-MS²: $t_R$=4.13 min, [M+1]⁺=511.34, [M–1]⁻=509.06.

f) A 2 N aq. LiOH solution (2 ml) is added to a solution of (±)-((1S*, 10bS*)-1-(4,6-dimethylpyrimidin-2-yloxy)-2-oxo-10b-phenyl-1,10b-dihydro-2H,3H-2a,4,5,6a-tetraaza-benzo[h]cyclobuta[f]-azulen-6-yl)-acetic acid ethyl ester in THF (6 ml) and methanol (5 ml) and the mixture is stirred for 1 h at 50° C. before it is neutralised with acetic acid (0.24 ml). The organic solvents are evaporated under reduced pressure and the product is desalted over Rp-C₁₈ silica gel. The product fractions are lyophilized to give (±)-(S*)-((6S*)-1-carboxymethyl-6-phenyl-5,6-dihydro-4H-2,3,5,10b-tetraaza-benzo[e]azulen-6-yl)-(4,6-dimethoxy-pyrimidin-2-yloxy)-acetic acid (195 mg) as an off-white powder. LC-MS²: $t_R$=3.12 min, [M+1]⁺=501.41, [M–1]⁻=499.47.

Example 28

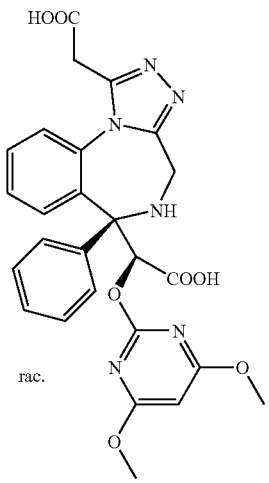

rac.

(±)-(S*)-((6S*)-1-carboxymethyl-6-phenyl-5,6-dihydro-4H-2,3,5,10b-tetraaza-benzo[e]azulen-6-yl)-(4,6-dimethoxy-pyrimidin-2-yloxy)-acetic acid is prepared in analogy to Example 27 by reacting (±)-((1S*,10bS*)-1-hydroxy-2-oxo-10b-phenyl-1,10b-dihydro-2H,3H-2a ,4,5,6a-tetraaza-benzo[h]cyclobuta[f]-azulen-6-yl)-acetic acid ethyl ester with 2-methanesulfonyl-4,6-dimethoxy-pyrimidine (Example 8), and subsequent cleaving of the ester and lactam functionality. LC-MS²: $t_R$=3.35 min, [M+1]⁺= 533.39, [M–1]⁻=531.33.

Example 29

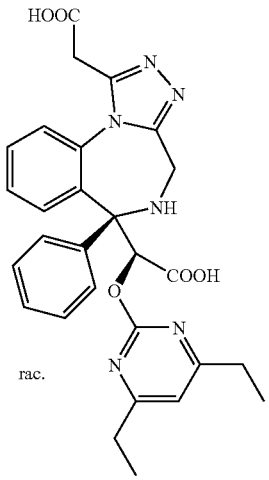

rac.

a) 37% aq. HCl (65 ml) is added dropwise to a suspension of heptane-3,5-dione (36.35 g, 0.284 mol) and thiourea (18 g, 0.236 mol) in ethanol (500 ml). The resulting yellow solution is stirred at 60° C. for 2 h, at 90° C. for 2 h and then at rt for 16 h. The solvent is removed under reduced pressure and the residue is suspended in boiling acetone. The solid material is collected, washed with acetone and dried to give 4,6-diethyl-pyrimidine-2-thiol (23 g) as yellow powder. The material is dissolved in 1 M aq. NaOH (600 ml) and treated with methyliodide (30 ml, 0.478 mol). The resulting emulsion is stirred at rt for 5 h before it is extracted twice with EA. The organic phase is washed with brine, dried over MgSO₄ and evaporated to give crude 4,6-diethyl-2-methylsulfanyl-pyrimidine (18.28 g) as a red oil. Peracetic acid (37 ml, 39% in acetic acid, 0.22 mol) is slowly added at 0° C. to a solution of the previously obtained oil in DCM (250 ml). The mixture is allowed to come to rt and is stirring is continued for 16 h before it is washed three times with sat. aq. NaHCO₃. The aq. phase is extracted once more with DCM. The combined organic phase is dried over MgSO₄. The product crystallises upon evaporation of the solvent. The solid material was dried under HV to give 4,6-diethyl-2-methanesulfonyl-pyrimidine (20.09 g) as pale pink crystals. ¹H-NMR (300 MHz, CDCl₃): 1.32 (t, J=7.5, 6H), 2.87 (q, J=7.5, 4H), 3.34 (s, 3H), 7.22 (s, 1H). LC-MS¹: $t_R$=0.78 min, [M+1]⁺=215.05.

b) (±)-(S*)-((6S*)-1-carboxymethyl-6-phenyl-5,6-dihydro4H-2,3,5,10b-tetraaza-benzo[e]azulen-6-yl)-(4,6-diethyl-pyrimidin-2-yloxy)-acetic acid is prepared in analogy to Example 27 by reacting (±)-((1S*,10bS*)-1-hydroxy-2-oxo-10b-phenyl-1,10b-dihydro-2H,3H-2a,4,5,6a-tetraaza-benzo[h]cyclobuta[f]-azulen-6-yl)-acetic acid ethyl ester with 4,6-diethyl-2-methanesulfonyl-pyrimidine, and cleaving of the ester and lactam functionality. LC-MS²: $t_R$=3.57 min, [M+1]⁺=529.32, [M–1]⁻=526.96.

Example 30

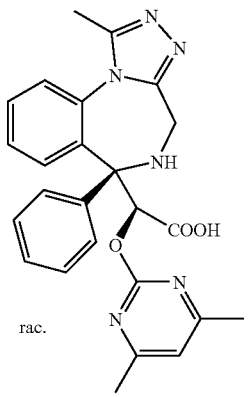

rac.

a) 8-Chloro-1-methyl-6-phenyl-4H-2,3,5,10b-tetraaza-benzo[e]azulene is prepared following the procedure given in A. Walser, T. Flynn, C. Mason, H. Crowley, C. Maresca, B. Yaremko, M O'Donnell, *J. Med. Chem.* 34 (1991), 1209–1221. ¹H-NMR (300 MHz, CDCl₃): 2.64 (s, 3H), 4.08 (d, J=12.8, 1H), 5.49 (d, J=12.8, 1H), 7.36–7.55 (m, 7H), 7.65 (dd, J=2.6, 8.6, 1H). LC-MS¹: $t_R$=0.88 min, [M+1]⁺=309.07.

b) 8-Chloro-1-methyl-6-phenyl-4H-2,3,5,10b-tetraaza-benzo[e]azulene (500 mg, 1.62 mmol) is reacted with benzyloxyacetyl chloride as described in Example 27 to give (±)-(1S*,10bS*)-1-benzyloxy-9-chloro-6-methyl-10b-phenyl-1,10b-dihydro-3H-2a,4,5,6a-tetraaza-benzo[h]cyclo-buta[f]azulen-2-one (397 mg) as a beige solid. LC-MS²: $t_R$=4.61 min, [M+1]⁺=457.26, [M+HCOOH–1]⁻= 500.99.

c) Hydrogenation of (±)-(1S*,10bS*)-1-benzyloxy-9-chloro-6-methyl-10b-phenyl-1,10b-dihydro-3H-2a,4,5, 6a-tetraaza-benzo[h]cyclobuta[f]azulen-2-one (397 mg) following the procedure given in Example 27 gives (±)-(1S*,10bS*)-1-hydroxy-6-methyl-10b-phenyl-1,10 b-dihydro-3H-2a,4,5,6a-tetraaza-benzo[h]cyclobuta[f]azulen-2-one (137 mg) as a beige solid. LC-MS²: $t_R$=2.92 min, [M+1]⁺=333.25,[M–1]⁻=331.07.

d) Reaction of (±)-(1S*,10bS*)-1-hydroxy-6-methyl-10b-phenyl-1,10b-dihydro-3H-2a,4,5,6a-tetraaza-benzo[h]cyclobuta[f]azulen-2-one with 2-methanesulfonyl-4,6-dimethyl-pyrimidine and subsequent lactam cleavage as described in Example 27 yields (±)-(S*)-(4,6-dimethyl-pyrimidin-2-yloxy)-((6S*)-1-methyl-6-phenyl-5,6-dihydro-4H-2,3,5,10b-tetraaza-benzo[e]azulen-6-yl)-acetic acid. LC-MS²: $t_R$=3.29 min, [M+1]⁺=457.41, [M–1]⁻=454.99.

or: A solution of (±)-(S*)-((6S*)-1-carboxymethyl-6-phenyl-5,6-dihydro-4H-2,3,5,10b-tetraaza-benzo[e]azulen-6-yl)-(4,6-dimethyl-pyrimidin-2-yloxy)-acetic acid (40 mg, 0.08 mmol, Example 27) in DMF (3 ml) is stirred at 80° C. for 90 min. The solvent is removed under reduced pressure and the remaining residue is suspended in diethyl ether. The solid material is collected, washed with diethyl ether and dried to give (±)-(S*)-(4,6-dimethyl-pyrimidin-2-yloxy)-((6S*)-1-methyl-6-phenyl-5,6-dihydro-4H-2,3,5,10b-tetraaza-benzo[e]azulen-6-yl)-acetic acid (34 mg) as a white powder. LC-MS²: $t_R$=3.29 min, [M+1]⁺=457.46, [M–1]⁻=455.32.

Example 31

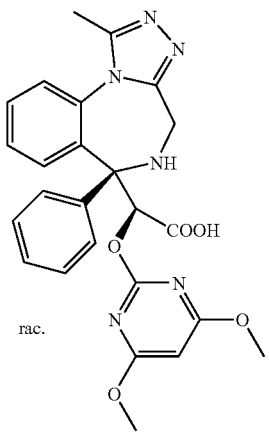

rac.

(±)-(S*)-(4,6-dimethoxy-pyrimidin-2-yloxy)-((6S*)-1-methyl-6-phenyl-5,6-dihydro-4H-2,3,5,10b-tetraaza-benzo[e]azulen-6-yl)-acetic acid is obtained starting from (±)-(1S*, 10bS*)-1-hydroxy-6-methyl-10b-phenyl-1,10b-dihydro-3H-2a,4,5,6a-tetraaza-benzo[h]cyclobuta[f]azulen-2-one (Example 30) and 2-methanesulfonyl-4,6-dimethoxy-pyrimidine (Example 8) following the procedures given in Example 30. LC-MS²: $t_R$=3.44 min, [M+1]⁺=489.34, [M–1]⁻=487.46.

Example 32

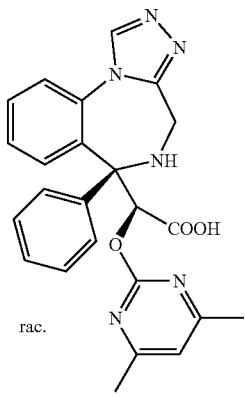

rac.

a) Methyl hydrazidooxalate is prepared according to the procedure given in the literature (J. Szmuszkovicz, M. E. Greig, *J. Med. Pharm. Chem.* 4 (1961), 259–296). $^1$H-NMR (300 MHz, $D_6$-DMSO): 3.74 (s, 3H), 4.59 (s br, 2H), 10.22 (s br,1H). $^{13}$C-NMR (75 MHz, $D_6$-DMSO): 53.4, 155.9, 161.4.

b) 6-Phenyl-4H-2,3,5,10b-tetraaza-benzo[e]azulene-1-carboxylic acid methyl ester is obtained as an off-white powder in analogy to the procedure given in the literature (A. Walser, T. Flynn, C. Mason, H. Crowley, C. Maresca, B. Yaremko, M O'Donnell, *J. Med. Chem.* 34 (1991), 1209–1221) starting from 5-phenyl-1,3-dihydro-benzo[e][1,4]diazepin-2-one (Example 27) and methyl hydrazidooxalate. $^1$H-NMR (300 MHz, $CDCl_3$): 4.01 (s, 3H), 4.07 (d, J=12.7, 1H), 5.55 (d, J=12.7, 1H), 7.34–7.65 (m, 9H). LC-MS$^2$: $t_R$=3.81 min, [M+1]$^+$=319.22, [M−1]$^-$=317.22.

c) The [2+2]-cycloaddition, the hydrogenation, the introduction of the 4,6-dimethylpyrimidine side chain are carried out as described for Example 27 to give (±)-(1S*, 10bS*)-1-(4,6-dimethyl-pyrimidin-2-yloxy)-2-oxo-10b-phenyl-1, 10b-dihydro-2H ,3H-2a,4,5,6a-tetraaza-benzo[h]cyclobuta[f]azulene-6-carboxylic acid methyl ester as a white solid. $^1$H-NMR (300 MHz, $CDCl_3$): 2.31 (s, 6H), 3.75 (s, 3H), 4.39 (d, J=14.8, 1H), 5.41 (d, J=14.8, 1H), 6.56 (s, 1H), 6.59 (s, 1H), 6.75–7.12 (m, 5H), 7.35 (dd, J=1.3, 8.1, 1H), 7.62 (dt, $J_d$=1.4, $J_t$=7.7, 1H), 7.77 (dt, $J_d$=1.3, $J_t$=7.7, 1H), 8.87 (dd, J=1.3, 8.1, 1H). LC-MS$^2$: $t_R$=4.02 min, [M+1]$^+$=483.54, [M−1]$^-$=317.12 d) A 2 N aq. solution of LiOH.$H_2$O (1.5 ml) is added to a suspension of (±)-(1S*,10bS*)-1-(4,6-dimethyl-pyrimidin-2-yloxy)-2-oxo-10b-phenyl-1,10b-dihydro-2H ,3H-2a ,4,5,6a-tetraaza-benzo[h]cyclobuta[f]azulene-6-carboxylic acid methyl ester (220 mg, 0.456 mmol) in THF (7 ml) and methanol (5 ml) and the resulting clear solution is stirred at 50° C. for 2 h. The solution is neutralised by adding acetic acid (0.24 ml) and evaporated. The crude product is desalted over Rp-$C_{18}$ silica gel to give (±)-(S*)-(4,6-dimethyl-pyrimidin-2-yloxy)-((6S*)-6-phenyl-5,6-dihydro-4H-2,3,5,10b-tetraaza-benzo[e]azulen-6-yl)-acetic acid (205 mg) as a white powder. LC-MS$^2$: $t_R$=3.30 min, [M+1]$^+$=443.25, [M−1]$^-$=441.05.

Example 33

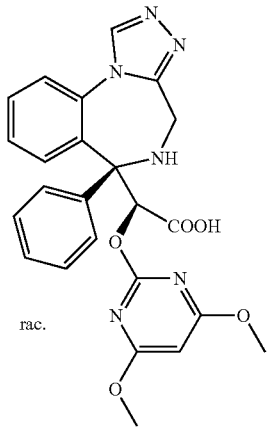

rac.

(±)-(S*)-(4,6-dimethoxy-pyrimidin-2-yloxy)-((6S*)-6-phenyl-5,6-dihydro-4H-2,3,5,10b-tetraaza-benzo[e]azulen-6-yl)-acetic acid is obtained in analogy to Example 32 as a white powder starting from (±)-(1S*,10bS*)-1-hydroxy-2-oxo-10b-phenyl-1,10b-dihydro-2H,3H-2a,4,5,6a-tetraaza-benzo[h]cyclobuta[f]azulene-6-carboxylic acid methyl ester and 2-methanesulfonyl-4,6-dimethoxy-pyrimidine (Example 8). LC-MS$^2$: $t_R$=3.49 min, [M+1]$^+$=475.36, [M−1]$^-$=473.21.

Example 34

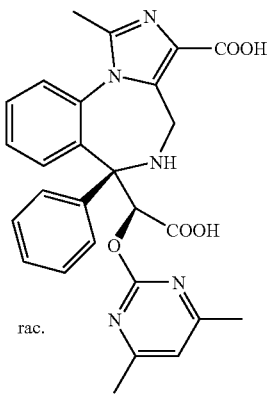

rac.

a) 8-Chloro-1-methyl-6-phenyl-4H-2,5,10b-triaza-benzo[e]azulene-3-carboxylic acid ethyl ester is prepared starting from 2-amino-5-chloro-benzophenone following the procedures given in the literature (R. I. Fryer, J. V. Earley, N. W. Gilman, W. Zally, *J. Heterocyclic Chem.* 13 (1976), 433–437; A. Walser, T. Flynn, C. Mason, R. I. Fryer, *J. Heterocyclic Chem.* 23 (1986), 1303–1314). $^1$H-NMR (300 MHz, $D_6$-DMSO): 1.29 (t, J=7.1, 3H), 2.49 (s, 3H), 3.96 (d, J=12.4, 1H), 4.21–4.30 (m, 2H), 5.69 (d, J=12.4, 1H), 7.33–7.55 (m, 6H), 7.81–7.86 (m, 2H). LC-MS$^1$: $t_R$=0.95 min, [M+1]$^+$=380.05.

b) The [2+2]-cycloaddition with 8-chloro-1-methyl-6-phenyl-4H-2,5,10b-triaza-benzo[e]azulene-3-carboxylic acid ethyl ester (1.02 g, 2.7 mmol) is carried out as described in Example 27 to give (±)-(1S*,10bS*)-1-benzyloxy-9-chloro-6-methyl-2-oxo-10b-phenyl-1,10b-dihydro-2H, 3H-2a,5,6a-triaza-benzo[h]cyclobuta[f]azulene-4-carboxylic acid ethyl ester (1.1 g) as white crystals. LC-MS[1]: $t_R$=1.07 min, [M+1]$^+$=528.14.

c) The hydrogenation of (±)-(1S*,10bS*)-1-benzyloxy-9-chloro-6-methyl-2-oxo-10b-phenyl-1,10b-dihydro-2H, 3H-2a,5,6a-triaza-benzo[h]cyclobuta-[f]azulene4-carboxylic acid ethyl ester is carried out at rt in analogy to Example 27 over a period of 30 h. This yields (±)-(1S*,10bS*)-1-hydroxy-6-methyl-2-oxo-10b-phenyl-1,10b-dihydro-2H ,3H-2a,5,6a-triaza-benzo[h]cyclobuta[f]azulene-4-carboxylic acid ethyl ester as a white powder. LC-MS[1]: $t_R$=0.78 min, [M+1]$^+$=404.08.

d) Introduction of the 4,6-dimethylpyrimidine, cleavage of the β-lactam and the ethyl ester are carried out as described in Example 27. The crude product is purified by prep. HPLC on Rp-C$_{18}$ silica gel to give (±)-(6S*)-6-[(S*)-carboxy-(4,6-dimethyl-pyrimidin-2-yloxy)-methyl]-1-methyl-6-phenyl-5,6-dihydro-4H-2,5,10b-triaza-benzo[e]azulene-3-carboxylic acid as an off-white solid. LC-MS[1]: $t_R$=0.69 min, [M+1]$^+$=500.17.

Example 35

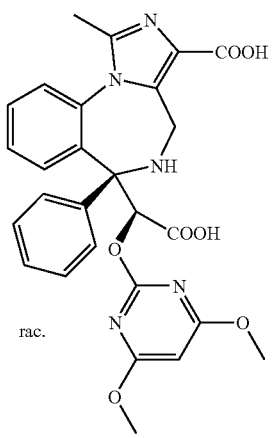

(±)-(6S*)-6-[(S*)-carboxy-(4,6-dimethoxy-pyrimidin-2-yloxy)-methyl]-1-methyl-6-phenyl-5,6dihydro-4H-2,5,10b-triaza-benzo[e]azulene-3-carboxylic acid is prepared in analogy to Example 34. LC-MS[1]: $t_R$=0.76 min, [M+1]$^+$=32.18.

Example 36

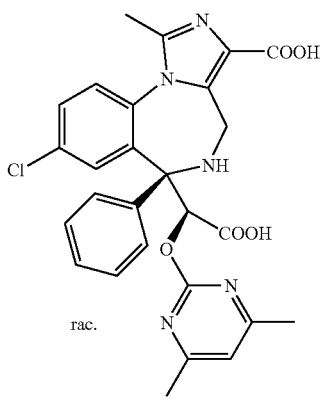

a) The hydrogenation of (±)-(1S*,10bS*)-1-benzyloxy-9-chloro-6-methyl-2-oxo-10b-phenyl-1,10b-dihydro-2H ,3H-2a,5,6a-triaza-benzo[h]cyclobuta-[f]azulene4-carboxylic acid ethyl ester (3.05 g, 5.76 mmol, Example 34) is carried out under 7 atm of H$_2$ at rt in THF (50 ml), ethanol (100 ml), 4 N HCl in dioxane (10 ml) with Pd/C (2 g, 10% Pd) over a period of 1.5 h. This furnishes (±)-(1S*,10bS*)-9-chloro-1-hydroxy-6-methyl-2-oxo-10b-phenyl-1,10b-dihydro-2H ,3H-2a ,5,6a-triaza-benzo[h]cyclobuta-[f]azulene-4-carboxylic acid ethyl ester (1.8 g) as white crystals. LC-MS[1]: $t_R$=0.84 min, [M+1]$^+$=438.08; LC-MS[2]: $t_R$=3.78 min, [M+1]$^+$=438.22, [M−1]$^-$=436.13.

b) The introduction of the 4,6-dimethylpyrimidine and the ester and β-lactam cleavage are performed as described in Example 34 to give (±)-(6S*)-6-[(S*)-carboxy-(4,6-dimethyl-pyrimidin-2-yloxy)-methyl]-8-chloro-1-methyl-6-phenyl-5,6-dihydro4H-2,5,10b-triaza-benzo[e]azulene-3-carboxylic acid as a white powder. LC-MS[1]: $t_R$=0.77 min, [M+1]$^+$=534.12.

Example 37

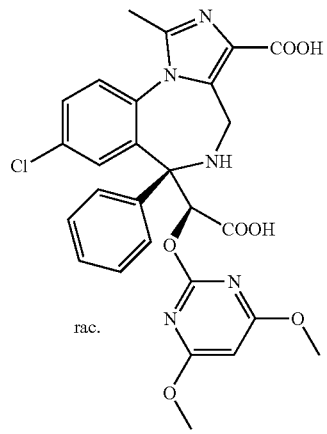

(±)-(6S*)-6-[(S*)carboxy-(4,6-dimethoxy-pyrimidin-2-yloxy)-methyl]-8-chloro-1-methyl-6-phenyl-5,6-dihydro-4H-2,5,10b-triaza-benzo[e]azulene-3-carboxylic acid is prepared in analogy to Example 36. LC-MS[1]: $t_R$=0.82 min, [M+1]$^+$=566.16.

Example 38

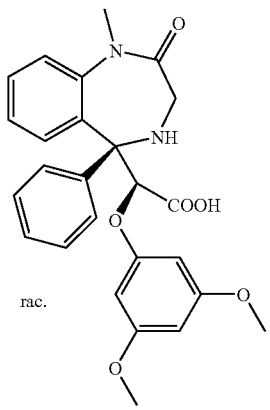

a) A solution of 5-phenyl-1,3-dihydro-benzo[e][1,4]diazepin-2-one (3.0 g, 12.7 mmol, Example 27) in DMF (8 ml) is slowly added to a suspension of NaH (630 mg, 55% in mineral oil, 1.2 mmol) in DMF (5 ml). The resulting slurry is cooled with an ice-bath before methyliodide (0.87 ml, 14.0 mmol) is added. The mixture is stirred at rt for 4 h, diluted with EA and washed with water. The aq. phase is extracted two more times with EA, the combined organic phase is dried over Na$_2$SO$_4$ and evaporated. The remaining oil crystallises upon addition of methanol. The crystals are collected, washed with methanol and dried to give 1-methyl-5-phenyl-1,3-dihydro-benzo[e][1,4]diazepin-2-one (2.94 g) as off-white crystals. LC-MS[1]: $t_R$=0.71 min, [M+1]$^+$=251.06.

b) 1-Methyl-5-phenyl-1,3-dihydro-benzo[e][1,4]diazepin-2-one (1.03 g, 4.1 mmol) is treated with triethylamine (2.9 ml, 20.5 mmol), (3,5-dimethoxy-phenoxy)-acetic (1.13 g, 5.33 mmol), and bis(2-oxo-3-oxazolidinyl)phosphinic chloride (2.1 g, 8.2 mmol) as described in Example 1 to furnish (±)-(1S*,9bS*)-1-benzyloxy-5-methyl-9b-phenyl-5,9b-dihydro-1H-2a,5-diaza-benzo[a]cyclobuta[c]cycloheptene-2,4-dione (780 mg) as a pale beige powder. $^1$H-NMR (300 MHz, CDCl$_3$): 2.56 (s, 3H), 3.68 (s, 6H), 3.81 (d, J=13.5, 1H), 4.43 (d, J=13.5, 1H), 5.78 (s, 1H), 5.98–6.03 (m, 2H), 6.08–6.12 (m, 1H), 7.22–7.36 (m, 6H), 7.42–7.56 (m, 2H), 7.66–7.71 (m, 1H). LC-MS[1]: $t_R$=0.97 min, [M+1]$^+$=445.10.

c) A solution of (±)-(1S*,9bS*)-1-benzyloxy-5-methyl-9b-phenyl-5,9b-dihydro-1H-2a,5-diaza-benzo[a]cyclobuta[c]cycloheptene-2,4dione (780 mg, 1.75 mmol) in dioxane (12 ml) and 6 N aq. HCl (8 ml) is stirred at 70° C. for 2.5 h. The organic solvent is removed under reduced pressure and the remaining solution is neutralised with aq. NaOH. The precipitate that forms is collected, and the filtrate is evaporated. Both, the precipitate and the filtrate are purified by HPL-chromatography on Rp-C$_{18}$ silica gel to furnish (±)-(S*)-(3,5-dimethoxy-phenoxy)-((5S*)-1-methyl-2-oxo-5-phenyl-2,3,4,5-tetrahydro-1H-benzo[e][1,4]diazepin-5-yl)-acetic acid (55 mg) as a pale beige solid. LC-MS[1]: $t_R$=0.83 min, [M+1]$^+$=463.09.

Example 39

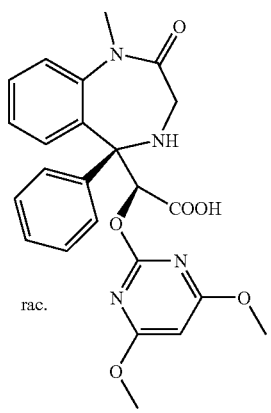

rac.

a) 7-Chloro-5-phenyl-1,3-dihydro-benzo[e][1,4]diazepin-2-one is prepared starting from 2-amino-5-chlorobenzophenone and bromo-acetyl bromide in analogy to procedures given by M. G. Bock, R. M. DiPardo, B. E. Evans, K. E. Rittle, D. F. Veber, R. M. Freidinger, J. Hirshfield, J. P. Springer, J. Org. Chem., 52, (1987), 3232–3239. LC-MS[2]: $t_R$=3.96 min, [M+1]$^+$=271.00.

b) 7-Chloro-5-phenyl-1,3-dihydro-benzo[e][1,4]diazepin-2-one (10 g, 36.9 mmol), dissolved in dry DMF (20 ml), is added to a suspension of NaH (60% in mineral oil) (1.77 g, 44.3 mmol) in dry DMF (60 ml) at 0° C. The mixture is stirred for 45 min at rt, then cooled to 0° C. and iodomethane (2.53 ml, 40.6 mmol), dissolved in dry DMF (10 ml), is added. The mixture is stirred at rt for 2 h. The suspension is added to water and extracted three times with EA. The organic phase is dried over MgSO$_4$ and evaporated. The crude product is purified by column chromatography (silicagel, heptane:EA from 4:1 to 2:1) to give of 7-chloro-1-methyl-5-phenyl-1,3-dihydro-benzo[e][1,4]diazepin-2-one (7.1 g) as a light brown solid. LC-MS[1]: $t_R$=0.92 min, [M+1]$^+$=284.98.

c) The [2+2]-cycloaddition is carried out with benzyloxy-acetic acid as described in Example 18. This furnishes (±)-(1S*,9bS*)-1-benzyloxy-8-chloro-5-methyl-9b-phenyl-5,9b-dihydro-1H-2a,5diaza-benzo[a]cyclo-buta[c]cycloheptene-2,4-dione as a pale beige solid. $^1$H-NMR (300 MHz, CDCl$_3$): 2.47 (s, 3H), 3.66 (d, J=13.6, 1H), 4.31 (d, J=13.6, 1 H), 4.39 (s, 2H), 5.11 (s, 1H), 6.91–7.40 (m, 13 H). LC-MS[2]: $t_R$=1.14 min, [M+1]$^+$=432.99.

d) (±)-(1S*,9bS*)-1-Benzyloxy-8-chloro-5-methyl-9b-phenyl-5,9b-dihydro-1H-2a,5-diaza-benzo[a]cyclo-buta[c]cycloheptene-2,4-dione is subjected to hydrogenolysis as described in Example 18 under 6 atm of H$_2$ at rt for 6 h. This gives a 5:4 mixture of (±)-(1S*,9bS*)-8-chloro-1-hydroxy-5-methyl-9b-phenyl-5,9b-dihydro-1H-2a,5-diaza-benzo[a]cyclo-buta[c]cyclo-heptene-2,4-dione and (±)-(1S*,9bS*)-1-hydroxy-5-methyl-9b-phenyl-5,9b-dihydro-1H-2a,5diaza-benzo[a]cyclo-buta[c]cycloheptene-2,4-dione which is not separated. LC-MS[2]: $t_R$=0.88 min, [M+1]$^+$=342.91; LC-MS[2] (dechlorinated product): $t_R$=0.81 min, [M+1]$^+$=309.00.

e) The introduction of the 4,6-dimethoxypyrimidine moiety to the mixture of (±)-(1S*,9bS*)-8-chloro-1-hydroxy-5-methyl-9b-phenyl-5,9b-dihydro-1H-2a,5-diaza-benzo[a]cyclo-buta[c]cyclo-heptene-2,4-dione and (±)-(1S*,9bS*)-1-hydroxy-5-methyl-9b-phenyl-5,9b-dihydro-1H-2a,5-diaza-benzo[a]cyclo-buta[c]cycloheptene-2,4-dione is performed as described in Example 18. The two products, (±)-(1S*,9bS*)-8-chloro-1-(4,6-dimethoxy-pyrimidin-2-yloxy)-5-methyl-9b-phenyl-5,9b-dihydro-1H-2a,5-diaza-benzo[a]cyclobuta[c]cycloheptene-2,4-dione and (±)-(1S*,9bS*)-1-(4,6-dimethoxy-pyrimidin-2-yloxy)-5-methyl-9b-phenyl-5,9b-dihydro-1H-2a,5-diaza-benzo[a]cyclobuta[c]cycloheptene-2,4-dione, are separated by column chromatography on silica gel eluting with heptane: EA 2:1. LC-MS[2]: $t_R$=1.12 min, [M+1]$^+$=481.00; LC-MS[2] (dechlorinated product): $t_R$=1.04 min, [M+1]$^+$=447.04.

f) (±)-(1S*,9bS*)-1-(4,6-dimethoxy-pyrimidin-2-yloxy)-5-methyl-9b-phenyl-5,9b-dihydro-1H-2a,5-diaza-benzo[a]cyclobuta[c]cycloheptene-2,4-dione is treated with LiOH.H$_2$O as described in Example 18 to give (±)-(S*)-((5S*)-1-methyl-2-oxo-5-phenyl-2,3,4,5-tetrahydro-1H-benzo[e][1,4]di-azepin-5-yl)-(4,6-dimethoxy-pyrimidin-2-yloxy)-acetic acid as a white solid. LC-MS[2]: $t_R$=0.63 min, [M+1]$^+$=465.04.

Example 40

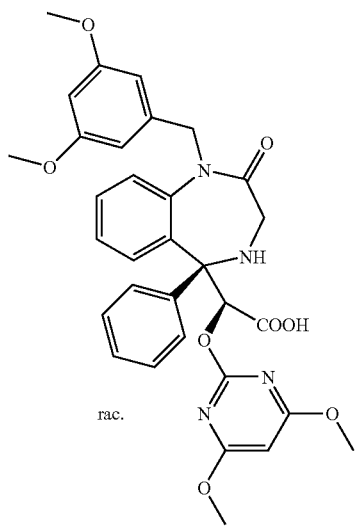

a) 5-Phenyl-1,3-dihydro-benzo[e][1,4]diazepin-2-one (15.0 g, 63.5 mmol, Example 27) is added in portions to a suspension of NaH (3.05 g, 55% in mineral oil, 76.2 mmol) in DMF (150 ml). The mixture is diluted with DMF (70 ml). 3,5-Dimethoxybenzylbromide (16.14 g, 69.8 mmol) is added and the mixture is stirred at rt for 16 h. The dark yellow solution is diluted with EA, washed with water. The aq. phase is extracted once more with EA, the combined organic phase is dried over $Na_2SO_4$ and evaporated. The residue is suspended in diethyl ether, filtered off, washed with additional diethyl ether and dried to yield 1-(3,5-dimethoxy-benzyl)-5-phenyl-1,3-dihydro-benzo[e][1,4]diazepin-2-one (14.97 g) as a pale yellow solid. LC-MS$^2$: $t_R$=0.94 min, [M+1]$^+$=387.13.

b) The [2+2]-cycloaddition is carried out with 1-(3,5-dimethoxy-benzyl)-5-phenyl-1,3-dihydro-benzo[e][1,4]diazepin-2-one (2.45 g, 6.34 mmol) as described in Example 18. Crystallisation of the product from EA/ethanol gives (±)-(1S*,9bS*)-1-benzyloxy-5-(3,5-dimethoxy-benzyl)-9b-phenyl-5,9b-dihydro-1H-2a,5-diaza-benzo[a]cyclobuta[c]cycloheptene-2,4-dione (2.0 g) as a pale beige crystals. LC-MS$^2$: $t_R$=1.20 min, [M+1]$^+$=535.07.

c) In analogy to Example 18, hydrogenolysis of (±)-(1S*,9bS*)-1-benzyloxy-5-(3,5-dimethoxy-benzyl)-9b-phenyl-5,9b-dihydro-1H-2a,5-diaza-benzo[a]cyclobuta[c]cycloheptene-2,4-dione (2.0 g, 3.7 mmol) at 50° C. under 7 atm $H_2$ for 20 h furnishes (±)-(1S*,9bS*)-5-(3,5-dimethoxy-benzyl)-1-hydroxy-9b-phenyl-5,9b-dihydro-1H-2a,5-diaza-benzo[a]-cyclobuta[c]cycloheptene-2,4-dione (1.85 g) as a colourless foam. LC-MS$^2$: $t_R$=0.97 min, [M+1]$^+$=445.05.

d) The introduction of the 4,6-dimethoxypyrimidine moiety to (±)-(1S*, 9bS*)-5-(3,5-dimethoxy-benzyl)-1-hydroxy-9b-phenyl-5,9b-dihydro-1H-2a,5-diaza-benzo[a]-cyclobuta[c]cycloheptene-2,4-dione (500 mg, 1.13 mmol) is carried out as described in Example 18. This gives (±)-(1S*, 9bS*)-5-(3,5-dimethoxy-benzyl)-1-(4,6-dimethoxy-pyrimidin-2-yloxy)-9b-phenyl-5,9b-dihydro-1H-2a,5-diaza-benzo[a]cyclobuta[c]cycloheptene-2,4-dione (357 mg) as a colourless foam. LC-MS$^2$: $t_R$=1.17 min, [M+1]$^+$=583.08.

e) (±)-(1S*,9bS*)-5-(3,5-dimethoxy-benzyl)-1-(4,6-dimethoxy-pyrimidin-2-yloxy)-9b-phenyl-5,9b-dihydro-1H-2a,5-diaza-benzo[a]cyclo-buta[c]cycloheptene-2,4-dione (28 mg, 0.048 mmol) is treated with LiOH.$H_2O$ as described in Example 18 to furnish (±)-(S*)-[(5S*)-1-(3,5-dimethoxy-benzyl)-2-oxo-5-phenyl-2,3,4,5-tetrahydro-1H-benzo[e][1,4]diazepin-5-yl]-(4,6-dimethoxy-pyrimidin-2-yloxy)-acetic acid (14 mg) as a white solid. LC-MS$^2$: $t_R$=0.98 min, [M+1]$^+$=601.12.

Example 41

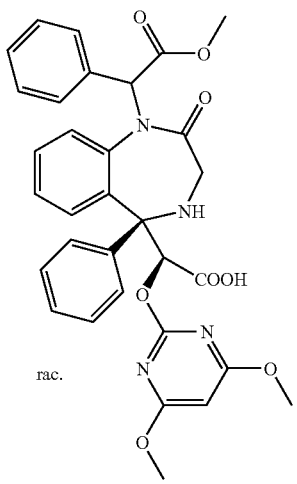

a) 5-Phenyl-1,3-dihydro-benzo[e][1,4]diazepin-2-one (12.0 g, 50.8 mmol, Example 27) is reacted with α-bromo-phenyl-acetic acid methyl ester (8.77 ml, 55.9 mmol) as described in Example 40 to give (±)-(2-oxo-5-phenyl-2,3-dihydro-benzo[e][1,4]diazepin-1-yl)-phenyl-acetic acid methyl ester (12.21 g) as a pale pink powder. LC-MS$^2$: $t_R$=0.98 min, [M+1]$^+$=385.11.

b) The [2+2]-cycloaddition is carried out as described in Example 27 with (±)-(2-oxo-5-phenyl-2,3-dihydro-benzo[e][1,4]diazepin-1-yl)-phenyl-acetic acid methyl ester (12.20 g, 31.7 mmol) and benzyloxyacetyl chloride (6.4 ml, 41.3 mmol). This furnishes (±)-(R/S)-((1S*,9bS*)-1-benzyloxy-2,4-dioxo-9b-phenyl-1,3,4,9b-tetrahydro-2H-2a,5-diaza-benzo[a]cyclobuta[c]cyclohepten-5-yl)-phenyl-acetic acid methyl ester (16.73 g) as a pale pink powder. No attempt is made to separate the diastereoisomers. LC-MS$^2$: $t_R$=1.19 min, [M+1]$^+$=533.21.

c) Hydrogenolysis of (±)-(R/S)-((1S*,9bS*)-1-benzyloxy-2,4-dioxo-9b-phenyl-1,3,4,9b-tetrahydro-2H-2a,5-diaza-benzo[a]cyclobuta[c]cyclohepten-5-yl)-phenyl-acetic acid methyl ester (16.73 mmol, 31.4 mmol) is carried out as described in Example 27 to give (±)-(R/S)-((1S*,9bS*)-2,4-dioxo-1-hydroxy-9b-phenyl-1,3,4,9b-tetrahydro-2H-2a,5-diaza-benzo[a]cyclobuta[c]cyclohepten-5-yl)-phenyl-acetic acid methyl ester (9.39 g) as a colourless foam. LC-MS$^2$: $t_R$=0.94 min, [M+1]$^+$=443.14.

d) Introduction of the 4,6-dimethoxypyrimidine (Example 8) is carried out as described in Example 27. This gives (±)-(R/S)-((1S*,9bS*)[1-(4,6-dimethoxy-pyrimidin-2-yloxy)-2,4-dioxo-9b-phenyl-1,3,4,9b-tetrahydro-2H-2a,5-diaza-benzo[a]cyclobuta[c]cyclohepten-5-yl]-phenyl-acetic acid methyl ester as a white powder. LC-MS$^2$: $t_R$=1.04 min, [M+1]$^+$=581.15.

e) In analogy to Example 27, treatment of (±)-(R/S)-((1S*, 9bS*)[1-(4,6-dimethoxy-pyrimidin-2-yloxy)-2,4-dioxo-9b-phenyl-1,3,4,9b-tetrahydro-2H-2a,5-diaza-benzo[a]

cyclobuta[c]cyclohepten-5-yl]-phenyl-acetic acid methyl ester (1.5 g, 2.6 mmol) with LiOH.H$_2$O (271 mg, 6.5 mmol) at rt for 16 h and at 55° C. for 2 h gives, after HPLC purification, (±)-(S*)-(4,6-dimethoxy-pyrimidin-2-yloxy)-[(5S*)-1-((R/S)-methoxycarbonyl-phenyl-methyl)-2-oxo-5-phenyl-2,3,4,5-tetrahydro-1H-benzo[e][1,4]diazepin-5-yl]-acetic acid (365 mg) as a white powder. LC-MS$^2$: t$_R$=0.93 min, [M+1]$^+$=599.19.

Example 42

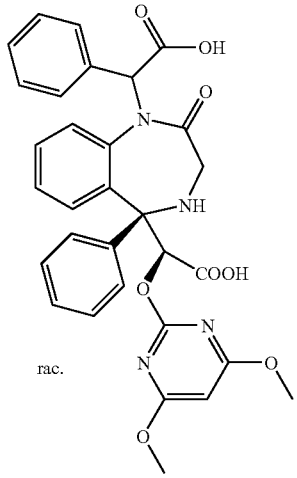

(±)-(R/S)-{(5S*)-5-[(S*)-carboxy-(4,6-dimethoxy-pyrimidin-2-yloxy)-methyl]-2-oxo-5-phenyl-2,3,4,5-tetrahydro-benzo[e][1,4]diazepin-1-yl}-phenyl-acetic acid (420 mg white powder) is isolated as the second product in step e) of Example 41. LC-MS$^2$: t$_R$=0.83 min, [M+1]$^+$=585.17.

Example 43

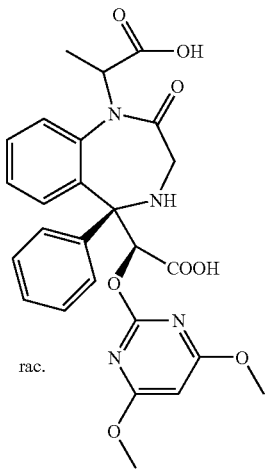

(±)-(2R/S)-2-{(5S*)-5-[(S*)-Carboxy-(4,6-dimethoxy-pyrimidin-2-yloxy)-methyl]-2-oxo-5-phenyl-2,3,4,5-tetrahydro-benzo[e][1,4]diazepin-1-yl}-propionic acid is prepared starting from 5-phenyl-1,3-dihydro-benzo[e][1,4]diazepin-2-one (Example 27) and (±)ethyl 2-bromopropionate in analogy to Example 41. LC-MS$^2$: t$_R$=0.86 min, [M+1]$^+$=523.14.

Example 44

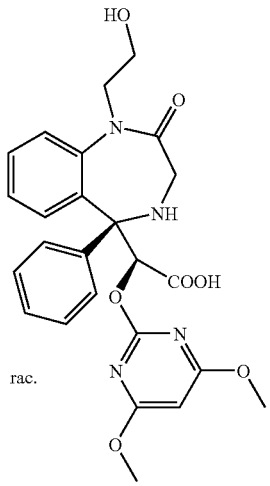

a) 5-Phenyl-1,3-dihydro-benzo[e][1,4]diazepin-2-one (3.0 g, 12.7 mmol, Example 27) is reacted with acetic acid 2-bromo-ethyl ester (2.33 g, 14.0 mmol) as described in Example 40 to give acetic acid 2-(2-oxo-5-phenyl-2,3-dihydro-benzo[e][1,4]diazepin-1-yl)-ethyl ester (4.0 g) as a pale yellow oil. LC-MS$^2$: t$_R$=0.81 min, [M+1]$^+$=323.09.

b) (±)-(S*)-(4,6-Dimethoxy-pyrimidin-2-yloxy)-[(5S*)-1-(2-hydroxy-ethyl)-2-oxo-5-phenyl-2,3,4,5-tetrahydro-1H-benzo[e][1,4]diazepin-5-yl]-acetic acid is prepared starting from acetic acid 2-(2-oxo-5-phenyl-2,3-dihydro-benzo[e][1,4]diazepin-1-yl)-ethyl ester following the procedures given in Example 27. LC-MS$^2$: t$_R$=0.81 min, [M+1]$^+$=495.17.

Example 45

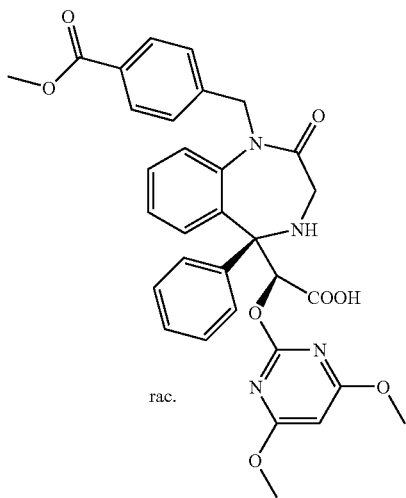

(±)-4-{(5S*)-5-[(S*)-Carboxy-(4,6-dimethoxy-pyrimidin-2-yloxy)-methyl]-2-oxo-5-phenyl-2,3,4,5-tetrahydro-benzo[e][1,4]diazepin-1-ylmethyl}-benzoic acid methyl ester is prepared starting from 5-phenyl-1,3-dihydro-benzo[e][1,4]diazepin-2-one (Example 27) and 4-bromomethyl-benzoic acid methyl ester following the procedures given in Example 41. LC-MS$^2$: t$_R$=0.92 min, [M+1]$^+$=599.22.

Example 46

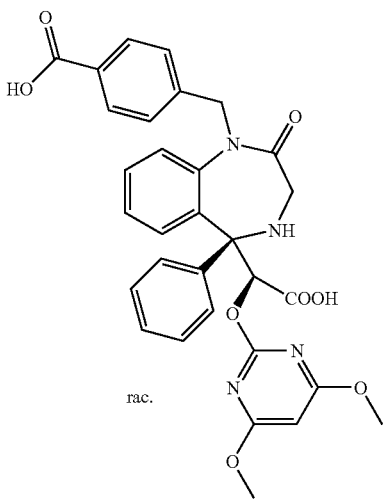

rac.

(±)-4-{(5S*)-5-[(S*)-Carboxy-(4,6-dimethoxy-pyrimidin-2-yloxy)-methyl]-2-oxo-5-phenyl-2,3,4,5-tetrahydro-benzo[e][1,4]diazepin-1-ylmethyl}-benzoic acid is isolated as a second product in the last step of the preparation of Example 45. LC-MS$^2$: $t_R$=0.81 min, [M+1]$^+$=585.19.

Example 47

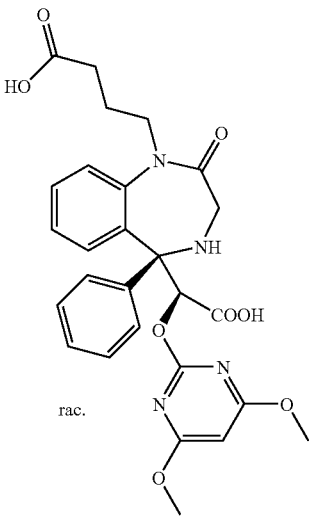

rac.

(±)-4-{(5S*)-5-[(S*)-Carboxy-(4,6-dimethoxy-pyrimidin-2-yloxy)-methyl]-2-oxo-5-phenyl-2,3,4,5-tetrahydro-benzo[e][1,4]diazepin-1-yl}-butyric acid is prepared starting from 5-phenyl-1,3dihydro-benzo[e][1,4]diazepin-2-one (Example 27) and 4-bromo-butyric acid ethyl ester following the procedures given in Example 41. LC-MS$^2$: $t_R$=0.73 min, [M+1]$^+$=537.17.

Example 48

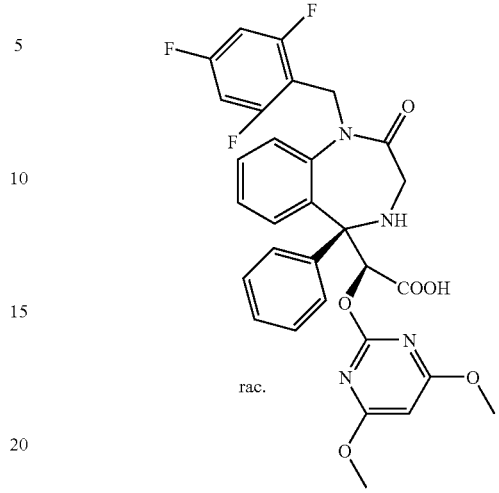

rac.

a) (±)-(1S*, 9bS*)-1-Hydroxy-5-(4-methoxy-benzyl)-9b-phenyl-3,4,5,9b-tetrahydro-1H-2a,5-diaza-benzo[a]cyclobuta[c]cyclohepten-2-one (2.0 g, 4.8 mmol, Example 26) is reacted with 2-methanesulfonyl-4,6-dimethoxy-pyrimidin (1.26 g, 5.8 mmol, Example 8) as described in Example 25 to furnish (±)-(1S*, 9bS*)1-(4,6-dimethoxy-pyrimidin-2-yloxy)-5-(4-methoxy-benzyl)-9b-phenyl-3,4,5,9b-tetrahydro-1H-2a,5-diaza-benzo[a]cyclo-buta[c]cyclohepten-2-one (2.49 g) as a white powder. LC-MS$^1$: $t_R$=1.18 min, [M+1]$^+$=553.10.

b) A solution of a ammonium cerium(IV)nitrate (7.41 g, 13.5 mmol) in water (25 ml) is added at 0° C. to a suspension of (±)-(1S*, 9bS*)-1-(4,6-dimethoxy-pyrimidin-2-yloxy)-5-(4-methoxy-benzyl)-9b-phenyl-3,4,5,9b-tetrahydro-1H-2a,5-diaza-benzo[a]cyclo-buta[c]cyclohepten-2-one (2.49 g, 4.5 mmol) in acetonitrile (60 ml). The mixture is stirred at rt for 4 h, diluted with water and extracted three times with DCM. The organic phase is washed twice with water, three times with brine, dried over MgSO$_4$ and evaporated. The remaining residue is suspended in diethyl ether, collected, washed with additional diethyl ether and dried to give (±)-(1S*, 9bS*)-1-(4,6-dimethoxy-pyrimidin-2-yloxy)-9b-phenyl-3,4,5,9b-tetrahydro-1H-2a,5-diaza-benzo[a]cyclobuta[c]cyclohepten-2-one (1.45 g) as a white powder. LC-MS$^1$: $t_R$=0.98 min, [M+1]$^+$=433.03.

c) A mixture of (±)-(1S*, 9bS*)-1-(4,6-dimethoxy-pyrimidin-2-yloxy)-9b-phenyl-3,4,5,9b-tetrahydro-1H-2a,5-diaza-benzo[a]cyclobuta[c]-cyclohepten-2-one (216 mg, 0.5 mmol), K$_2$CO$_3$ (208 mg, 1.5 mmol) and 2,4,6-trifluorobenzyl bromide (169 mg, 0.75 mmol) is stirred at 60° C. for 18 h. Further 2,4,6-trifluoroenzyl bromide (50 mg) and K$_2$CO$_3$ (50 mg) is added and stirring is continued at 50° C. for 18 h. The mixture is diluted with water, extracted twice with EA. The organic phase is washed with brine, dried over MgSO$_4$ and evaporated. The crude product is purified by chromatography on prep. tlc plates with EA:heptane 7:3 to furnish (±)-(1S*, 9bS*)-1-(4,6-dimethoxy-pyrimidin-2-yloxy)-9b-phenyl-5-(2,4,6-trifluoro-benzyl)-3,4,5,9b-tetrahydro-1H-2a,5-diaza-benzo[a]cyclo-buta[c]-cyclohepten-2-one (268 mg) as an almost colourless foam. LC-MS$^1$: $t_R$=1.18 min, [M+1]$^+$=577.05.

d) (±)-(1S*, 9bS*)-1-(4,6-dimethoxy-pyrimidin-2-yloxy)-9b-phenyl-5-(2,4,6-trifluoro-benzyl)-3,4,5,9b-tetrahydro-1H-2a,5-diaza-benzo[a]cyclo-buta[c]-cyclohepten-2-one (260 mg, 0.45 mmol) is treated with LiOH.H₂O (2 ml of 2N aq. solution) as described in Example 25 to give (±)-(S*)-(4,6-dimethoxy-pyrimidin-2-yloxy)-[(5S*)-5-phenyl-1-(2,4,6-trifluoro-benzyl)-2,3,4,5-tetra-hydro-1H-benzo[e][1,4]diazepin-5-yl]-acetic acid (150 mg) as a colourless foam. LC-MS¹: $t_R$=1.08 min, [M+1]⁺=595.06.

Example 49

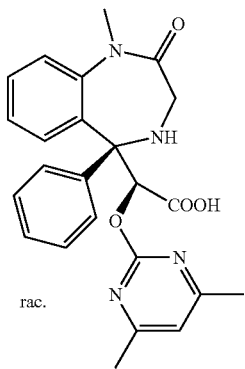

(±)-(S*)-(4,6-dimethyl-pyrimidin-2-yloxy)-((5S*)-1-methyl-2-oxo-5-phenyl-2,3,4,5-tetrahydro-1H-benzo[e][1,4]diazepin-5-yl)-acetic acid is prepared in analogy to Example 39. LC-MS¹: $t_R$=0.82 min, [M+1]⁺=433.05.

Example 50

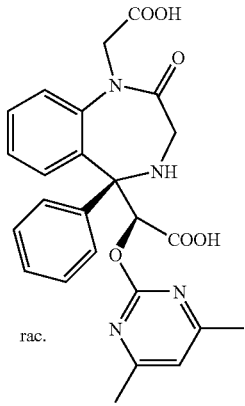

a) To a suspension of NaH (60% in mineral oil) (230 mg, 5.75 mmol) in dry DMF (15 ml) 5-phenyl-1,3-dihydro-benzo[e][1,4]diazepin-2-one (1.0 g, 4.23 mmol, Example 38) is added in two portions. The mixture is diluted with dry DMF (40 ml) and ethyl bromoacetate (932 mg, 6.09 mmol) is added. The mixture becomes clear again upon stirring at room temperature for 1 h and is diluted with EA. The organic phase is washed with water, the aqueous phase is extracted with EA. The combined organic phase is washed three more times with water, dried over MgSO₄ and evaporated. The resulting oil is treated several times with hexane which is decanted. The remaining orange oil is dried under vacuum to give (2-oxo-5-phenyl-2,3-dihydro-benzo[e][1,4]diazepin-1-yl)-acetic acid ethyl ester (1.2 g) as a yellow foam/gum. LC-MS²: $t_R$=4.09 min [M+1]⁺=323.20.

b) To a solution of (2-oxo-5-phenyl-2,3-dihydro-benzo[e][1,4]diazepin-1-yl)-acetic acid ethyl ester (1.2 g, 3.72 mmol) in dry DCM (20 ml) is added benzyloxy-acetic acid (928 mg, 5.58 mmol, Example 18) followed by triethylamine (2.59 ml, 18.6 mmol). The solution is cooled with an ice-bath and bis(2-oxo-3-oxazolidinyl)phosphinic chloride (1.90 g, 7.46 mmol) is added in two portions. The mixture is stirred at 0° C. and is allowed to slowly come to rt. Stirring is continued for 16 h before the mixture is diluted with DCM and washed with sat. aq. NaHCO₃. The aqueous phase is extracted twice with DCM. The combined organic phase is dried over MgSO₄ and evaporated. The crude product is purified by column chromatography (silica gel, heptane:EA 1:1) to give (±)-((1S*, 9bS*)-1-benzyloxy-2,4-dioxo-9b-phenyl-1,3,4,9b-tetrahydro-2H-2a,5'-diaza-benzo[a]cyclobuta[c]cyclo-hepten-5-yl)-acetic acid ethyl ester (1.56 g) as an almost colourless foam. LC-MS²: $t_R$=5.04 min, [M+1]⁺=471.29.

c) To a suspension of 10% Pd on charcoal (250 mg) in ethanol (5 ml) a solution of (±)-((1S*, 9bS*)-1-benzyloxy-2,4-dioxo-9b-phenyl-1,3,4,9b-tetrahydro-2H-2a,5'-diaza-benzo[a]cyclobuta[c]cyclo-hepten-5-yl)-acetic acid ethyl ester (1.55 g, 3.29 mmol) in ethanol (15 ml) and THF (5 ml) is added and the resulting reaction mixture is stirred at rt for 1 h under 2 atm of H₂. Then acetic acid (0.5 ml, 8.74 mmol) is added and stirring is continued at 40° C. for 16 h under 7 atm of H₂. Further 10% Pd on charcoal (200 mg), suspended in ethanol (3 ml), is added and stirring is continued for another 5 h at 40° C. under 7 atm of H₂. The catalyst is filtered off through celite and the colourless filtrate is evaporated to give (±)-((1S*, 9bS*)-1-hydroxy-2,4-dioxo-9b-phenyl-1,3,4,9b-tetrahydro-2H-2a,5-diaza-benzo[a]cyclobuta[c]cyclohepten-5-yl)-acetic acid ethyl ester (1.25 g) as a colourless foam. LC-MS²: $t_R$=3.86 min, [M+1]⁺=381.29, [M-1]⁻=379.09.

d) To a suspension of NaH (60% in mineral oil) (60 mg, 1.5 mmol) in dry THF (6 ml) and dry DMF (2 ml) (±)-((1S*, 9bS*)-hydroxy-2,4-dioxo-9b-phenyl-1,3,4,9b-tetrahydro-2H-2a,5-diaza-benzo[a]cyclobuta[c]cyclo-hepten-5-yl)-acetic acid ethyl ester (400 mg, 1.05 mmol) is added. The mixture is stirred at rt for 10 min before 2-methanesulfonyl-4,6-dimethyl-pyrimidine (Example 7b) (255 mg, 1.37 mmol) is added. Stirring is continued for 6 h. Further NaH (30 mg, 750 μmol) and 2-methanesulfonyl-4,6-dimethyl-pyrimidine (100 mg, 537 μmol) is added. After 2 h at rt the reaction mixture is diluted with EA, washed with sat. aq. NaHCO₃, followed twice by water. The organic phase is evaporated and dried before it is dissolved again in dry THF (6 ml) and dry DMF (2 ml). NaH (50 mg, 1.25 mmol) followed by 2-methanesulfonyl-4,6-dimethyl-pyrimidine (180 mg, 967 μmol) is added and the resulting mixture is stirred at rt for 45 min The reaction mixture is extracted again as described above. The organic phase is evaporated. The resulting oil is purified by column chromatography (silica gel, heptane:EA 1:1) to give (±)-[(1S*, 9bS*)-1-(4,6-dimethyl-pyrimidin-2-yloxy)-2,4-dioxo-9b-phenyl-1,3,4,9b-tetrahydro-2H-2a,5-diaza-benzo[a]cyclo-buta[c]cyclohepten-5-yl]-acetic acid ethyl ester (483 mg) as a colourless foam. LC-MS²: $t_R$=4.74 min, [M+1]⁺=487.14, [M-1]⁻=484.90.

e) A solution of (±)-(1S*, 9bS*)-1-(4,6-dimethyl-pyrimidin-2-yloxy)-2,4-dioxo-9b-phenyl-1,3,4,9b-tetrahydro-2H-2a,5-diaza-benzo[a]cyclo-buta[c]cyclohepten-5-yl]-acetic acid ethyl ester (250 mg, 514 μmol) in THF (8 ml), methanol (6 ml) and 2 N aq. lithium hydroxide (4 ml) is stirred at 65° C. for 2 h. The organic solvents are evaporated and the remaining solution is acidified by adding of 10% aq. acetic acid (8 ml), diluted with water (10 ml) and washed three times with DCM. The aqueous phase is partially evaporated and the crude product is purified by preparative HPLC to give (±)-(S*)-((5S*)-1-Carboxymethyl-2-oxo-5-phenyl-2,3,4,5-tetrahydro-1H-benzo[e][1,4]diazepin-5-yl)-(4,6-dimethyl-pyrimidin-2-yloxy)-acetoc acid (58 mg) as a white lyophilisate. LC-MS$^2$: $t_R$=3.40 min, [M+1]$^+$=477.39, [M−1]$^-$=475.08.

Example 51

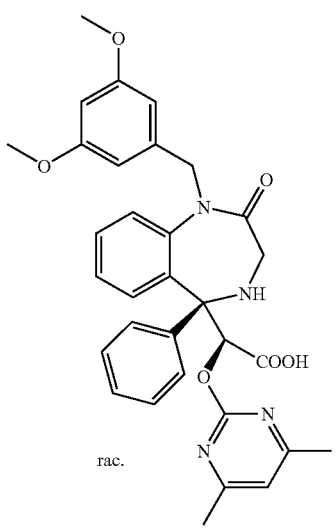

(±)-(S*)-[(5S*)-1-(3,5-Dimethoxy-benzyl)-2-oxo-5-phenyl-2,3,4,5-tetra-hydro-1H-benzo[e][1,4]diazepin-5-yl]-(4,6-dimethyl-pyrimidin-2-yloxy)-acetic acid is prepared in analogy to Example 40. LC-MS$^1$: $t_R$=0.88 min, [M+1]$^+$=569.22.

Example 52

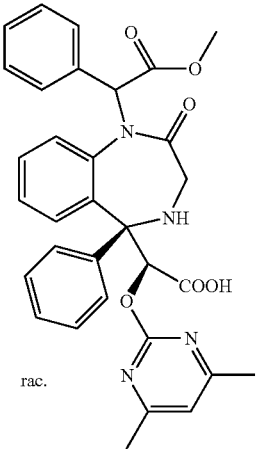

(±)-(S*)-(4,6-Dimethyl-pyrimidin-2-yloxy)-[(5S*)-1-((R/S)-methoxycarbonyl-phenyl-methyl)-2-oxo-5-phenyl-2,3,4,5-tetrahydro-1H-benzo[e][1,4]diazepin-5-yl]-acetic acid is prepared in analogy to Example 41. LC-MS$^1$: $t_R$=0.88 min, [M+1]$^+$=567.19.

Example 53

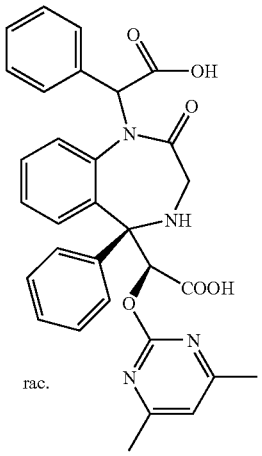

(±)-(S*)-[(5S*)-1-((R/S)-Carboxy-phenyl-methyl)-2-oxo-5-phenyl-2,3,4,5-tetrahydro-1H-benzo[e][1,4]diazepin-5-yl]-(4,6-dimethyl-pyrimidin-2-yloxy)-acetic acid is prepared in analogy to Example 42. LC-MS$^1$: $t_R$=0.79 min, [M+1]$^+$=553.17.

Example 54

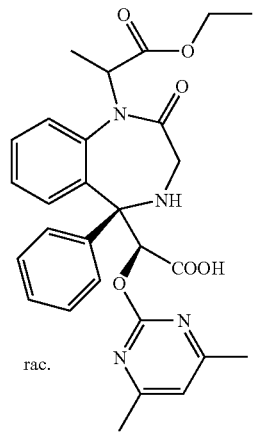

(±)-(2R/S)-2-{(5S*)-5-[(S*)-Carboxy-(4,6-dimethyl-pyrimidin-2-yloxy)-methyl]-2-oxo-5-phenyl-2,3,4,5-tetrahydro-benzo[e][1,4]diazepin-1-yl}-propionic acid ethyl ester is prepared in analogy to Example 43. LC-MS$^1$: $t_R$=0.84 min, [M+1]$^+$=519.28.

Example 55

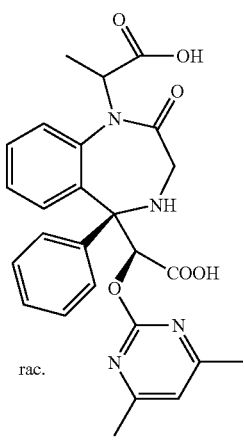

(±)-(R/S)-2-{(5S*)-5-[(S*)-Carboxy-(4,6-dimethyl-pyrimidin-2-yloxy)-methyl]-2-oxo-5-phenyl-2,3,4,5-tetrahydro-benzo[e][1,4]diazepin-1-yl}-propionic acid is prepared in analogy to Example 43. LC-MS$^1$: t$_R$=0.73 min, [M+1]$^+$=491.24.

Example 56

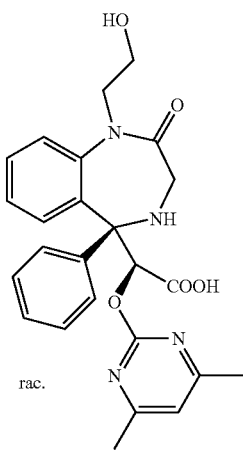

(±)-(S*)-(4,6-Dimethyl-pyrimidin-2-yloxy)-[(5S*)-1-(2-hydroxy-ethyl)-2-oxo-5-phenyl-2,3,4,5-tetrahydro-1H-benzo[e][1,4]diazepin-5-yl]-acetic acid is prepared in analogy to Example 44. LC-MS$^1$: t$_R$=0.77 min, [M+1]$^+$=462.16.

Example 57

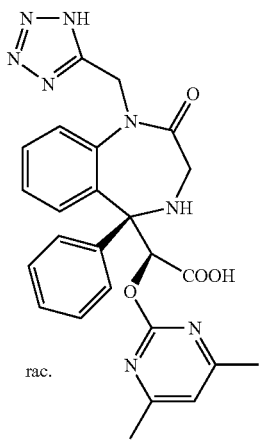

a) (±)-[(1S*, 9bS*)-1-(4,6-Dimethyl-pyrimidin-2-yloxy)-2,4-dioxo-9b-phenyl-1,3,4,9b-tetrahydro-2H-2a,5-diaza-benzo[a]cyclobuta[c]cyclo-hepten-5-yl]-acetonitrile is prepared in analogy to Example 40 starting from 5-phenyl-1,3-dihydro-benzo[e][1,4]diazepin-2-one (Example 27) and chloroacetonitrile. LC-MS$^1$: t$_R$=0.96 min, [M+1]$^+$=440.14.

b) A mixture of (±)-[(1S*, 9bS*)-1-(4,6-dimethyl-pyrimidin-2-yloxy)-2,4-dioxo-9b-phenyl-1,3,4,9b-tetrahydro-2H-2a,5-diaza-benzo[a]cyclo-buta[c]cyclo-hepten-5-yl]-acetonitrile (150 mg, 0.34 mmol), NaN$_3$ (23 mg, 0.36 mmol) and NH$_4$Cl (20 mg, 0.38 mmol) in DMF (4 ml) is stirred at 60° C. for 1 h. Additional NaN$_3$ (23 mg) and NH$_4$Cl (20 mg) is added and stirring is conitued for 17 h. Once more, NaN$_3$ (23 mg) and NH$_4$Cl (20 mg) is added and the mixture is stirred at 60° C. for additional 8 h before it is diluted with 1 N aq. HCl and extracted three times with EA. The organic phase is dried over MgSO$_4$ and evaprorated to give (±)-(1S*, 9bS*)-1-(4,6-dimethyl-pyrimidin-2-yloxy)-9b-phenyl-5-(1H-tetrazol-5-ylmethyl)-5,9b-dihydro-1H-2a,5-diaza-benzo[a]cyclobuta[c]cycloheptene-2,4-dione (160 mg) as a white solid. LC-MS$^1$: t$_R$=0.88 min, [M+1]$^+$=483.17.

c) (±)-(1S*, 9bS*)-1-(4,6-dimethyl-pyrimidin-2-yloxy)-9b-phenyl-5-(1H-tetrazol-5-ylmethyl)-5,9b-dihydro-1H-2a,5-diaza-benzo[a]cyclobuta[c]cycloheptene-2,4-dione (160 mg) is treated with LiOH.H$_2$O (2 ml of a 2 N aq. solution) as described in Example 27 to give (±)-(S*)-(4,6-dimethyl-pyrimidin-2-yloxy)-[(5S*)-2-oxo-5-phenyl-1-(1H-tetrazol-5-ylmethyl)-2,3,4,5-tetrahydro-1H-benzo[e][1,4]diazepin-5-yl]-acetic acid (96 mg) as a white powder. LC-MS$^1$: t$_R$=0.79 min, [M+1]$^+$=501.19.

Example 58

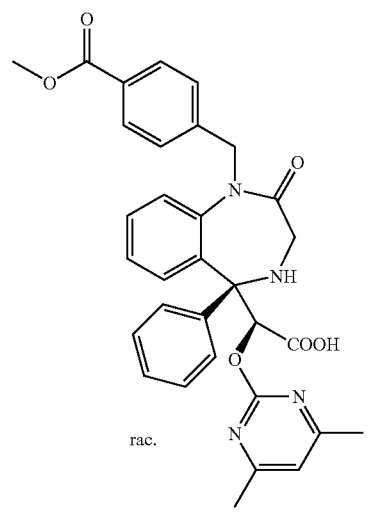

(±)-4-{(5S*)-5-[(S*)-Carboxy-(4,6-dimethyl-pyrimidin-2-yloxy)-methyl]-2-oxo-5-phenyl-2,3,4,5-tetrahydro-benzo[e][1,4]diazepin-1-ylmethyl}-benzoic acid methyl ester is prepared in analogy to Example 45. LC-MS$^1$: t$_R$=0.87 min, [M+1]$^+$=567.20.

Example 59

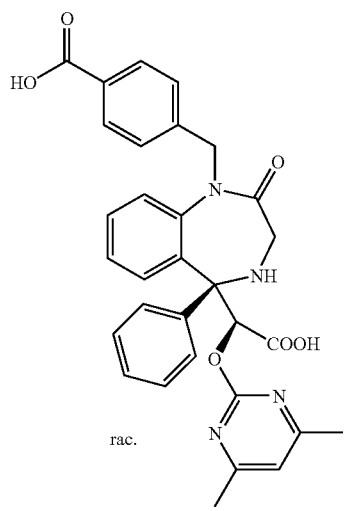

rac.

(±)-4-{(5S*)-5-[(S*)-Carboxy-(4,6-dimethyl-pyrimidin-2-yloxy)-methyl]-2-oxo-5-phenyl-2,3,4,5-tetrahydro-benzo[e][1,4]diazepin-1-ylmethyl}-benzoic acid is prepared in analogy to Example 46. LC-MS[1]: $t_R$=0.77 min, [M+1]$^+$=553.18.

Example 60

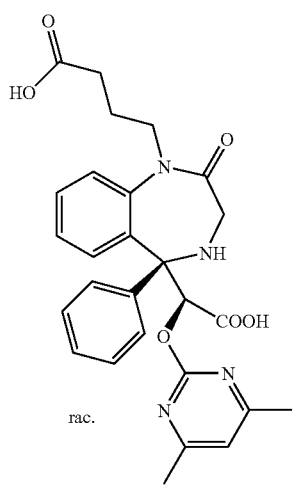

rac.

(±)-4-{(5S*)-5-[(S*)-Carboxy-(4,6-dimethyl-pyrimidin-2-yloxy)-methyl]-2-oxo-5-phenyl-2,3,4,5-tetrahydro-benzo[e][1,4]diazepin-1-yl}-butyric acid is prepared in analogy to Example 47. LC-MS[1]: $t_R$=0.70 min, [M+1]$^+$=505.17.

Example 61

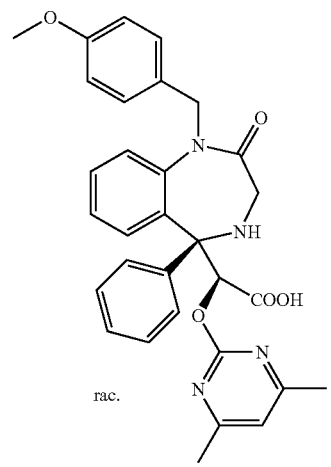

rac.

(±)-(1S*, 9bS*)-1-(4,6-dimethylpyrimidin-2-yloxy)-9b-phenyl-3,4,5,9b-tetrahydro-1H-2a,5-diaza-benzo[a]cyclobuta[c]cyclohepten-2-one (200 mg, 0.38 mmol, prepared in analogy to Example 48) is treated with LiOH.H$_2$O (1.5 ml of a 2 N aq. solution) as described in Example 25 to furnish (±)-(S*)-(4,6-dimethyl-pyrimidin-2-yloxy)-[(5S*)-1-(4-methoxy-benzyl)-2-oxo-5-phenyl-2,3,4,5-tetrahydro-1H-benzo[e][1,4]diazepin-5-yl]-acetic acid (223 mg) as a white solid. LC-MS[2]: $t_R$=4.32 min, [M+1]$^+$=539.47, [M−1]$^-$=536.85.

Examples 62 to 116

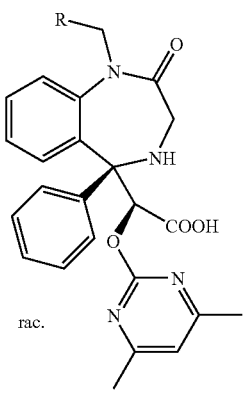

rac.

Examples 62 to 116 are prepared starting from (±)-(1S*, 9bS*)-1-(4,6-dimethylpyrimidin-2-yloxy)-9b-phenyl-3,4,5,9b-tetrahydro-1H-2a,5-diaza-benzo[a]cyclobuta[c]cyclohepten-2-one and the appropriate alkylating agent in analogy to the procedures given in Exampe 48.

| Example | R | $t_R$ (LC-MS¹) [min] | [M + 1]⁺ |
|---|---|---|---|
| 62 | 4-(CF₃)-C₆H₄-CH₂CH₂- | 0.85 | 577.07 |
| 63 | cyclopropyl-CH₂CH₂- | 0.81 | 473.13 |
| 64 | 3-Cl-C₆H₄-CH₂CH₂- | 0.92 | 543.08 |
| 65 | 3,5-(CF₃)₂-C₆H₃-CH₂CH₂- | 1.13 | 645.05 |
| 66 | morpholino-CH₂CH₂CH₂- | 0.63 | 532.12 |
| 67 | 4-phenyl-C₆H₄-CH₂CH₂- | 1.01 | 585.12 |
| 68 | 1-methyl-3-indolyl-CH₂CH₂CH₂- | 0.92 | 576.13 |
| 69 | (CH₃)₂N-CH₂CH₂CH₂- | 0.63 | 490.13 |
| 70 | 4-tBu-C₆H₄-CH₂CH₂- | 0.93 | 565.16 |
| 71 | 2-Cl-C₆H₄-CH₂CH₂- | 0.87 | 542.98 |
| 72 | 4-Cl-C₆H₄-CH₂CH₂- | 0.82 | 543.05 |
| 73 | 3-(CF₃)-C₆H₄-CH₂CH₂- | 0.84 | 577.06 |
| 74 | 2-(OCF₃)-C₆H₄-CH₂CH₂- | 0.85 | 593.09 |
| 75 | 3-(OCF₃)-C₆H₄-CH₂CH₂- | 0.86 | 593.07 |
| 76 | 2-(CF₃)-C₆H₄-CH₂CH₂- | 0.84 | 577.04 |
| 77 | 2-F-C₆H₄-CH₂CH₂- | 0.77 | 527.10 |
| 78 | C₆H₅-CH₂CH₂CH₂- | 0.78 | 523.11 |
| 79 | 2-benzothiazolyl-CH₂CH₂- | 0.78 | 566.03 |
| 80 | 5-methyl-3-isoxazolyl-CH₂CH₂- | 0.67 | 514.07 |
| 81 | 8-quinolinyl-CH₂CH₂- | 0.62 | 560.09 |
| 82 | n-hexyl | 0.84 | 503.10 |
| 83 | 4-(OCF₃)-C₆H₄-CH₂CH₂- | 0.87 | 593.08 |
| 84 | PhSO₂-CH₂-C₆H₄-CH₂CH₂- | 0.75 | 663.08 |
| 85 | 1H-3-indolyl-CH₂CH₂CH₂- | 0.74 | 562.12 |

-continued

| Example | R | $t_R$ (LC-MS[1]) [min] | $[M+1]^+$ |
|---|---|---|---|
| 86 | 4-Br-C6H4-CH2CH2- | 0.84 | 586.98 |
| 87 | Ph-O-CH2CH2CH2- | 0.80 | 553.11 |
| 88 | 4-F-C6H4-CH2CH2- | 0.77 | 527.08 |
| 89 | 2,6-diF-C6H3-CH2CH2- | 0.76 | 545.04 |
| 90 | Ph-CH2CH2CH2- | 0.81 | 537.11 |
| 91 | 3-F-C6H4-CH2CH2- | 0.77 | 527.08 |
| 92 | 3-Br-C6H4-CH2CH2- | 0.83 | 587.00 |
| 93 | CH3-O-CH2CH2-O-CH2CH2CH2- | 0.62 | 521.08 |
| 94 | 2-CH3-C6H4-CH2CH2- | 0.79 | 523.08 |
| 95 | 4-CH3-C6H4-CH2CH2- | 0.81 | 523.09 |
| 96 | 3-CH3-C6H4-CH2CH2- | 0.81 | 523.06 |
| 97 | Cyclohexyl-CH2CH2CH2- | 0.89 | 529.12 |
| 98 | Cyclohexyl-CH2CH2- | 0.84 | 515.08 |
| 99 | 2,4-diF-C6H3-CH2CH2- | 0.80 | 545.03 |
| 100 | 2,3-diF-C6H3-CH2CH2- | 0.80 | 545.04 |
| 101 | 3,5-diCH3-C6H3-CH2CH2- | 0.85 | 537.16 |
| 102 | 3,4-diF-C6H3-CH2CH2- | 0.80 | 545.09 |
| 103 | 3,5-diF-C6H3-CH2CH2- | 0.80 | 545.06 |
| 104 | 2,5-diF-C6H3-CH2CH2- | 0.78 | 544.99 |
| 105 | pentaF-C6-CH2CH2- | 0.82 | 598.99 |
| 106 | 2,3,4-triF-C6H2-CH2CH2- | 0.77 | 563.03 |
| 107 | 2,3,5-triF-C6H2-CH2CH2- | 0.78 | 563.06 |

-continued

| Example | R | $t_R$ (LC-MS[1]) [min] | [M + 1]+ |
|---|---|---|---|
| 108 | (phenethyl) | 0.76 | 509.04 |
| 109 | (2-fluoro-3-methyl-benzyl, ethyl) | 1.04 | 541.07 |
| 110 | (H2N-C(O)-CH2CH2-) | 0.59 | 476.07 |
| 111 | (2,4,6-trimethyl-3-ethyl-phenyl) | 1.15 | 551.12 |
| 112 | (2,3,4-trifluoro-phenethyl) | 1.05 | 563.07 |
| 113 | (4-propyl-phenethyl) | 1.23 | 565.15 |
| 114 | (4-bromo-2-fluoro-phenethyl) | 1.11 | 604.99 |
| 115 | (2,6-dichloro-phenethyl) | 1.06 | 577.03 |
| 116 | (2,4-dichloro-phenethyl) | 1.16 | 577.03 |

Example 117

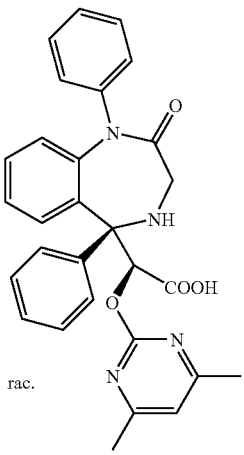

rac.

a) 2-Phenylamino-benzophenone acid is prepared from 2-amino benzophenone according to a procedure described in the literature (J. C. Antilla, S. L. Buchwald, *Org. Lett.* 2 (2001), 2077–2079). $^1$H-NMR(300 MHz, CDCl$_3$): 6.69 (dt, J$_t$=7.0, J$_d$=1.2, 1H), 7.10 (t, J=7.6, 1H), 7.2–7.4 (m, 5H), 7.4–7.6 (m, 5H), 7.69 (d, J=7.0, 2H). LC-MS[2]: $t_R$=6.13 min, [M+1]+=274.

b) To a cooled (0° C.) solution of 2-phenylamino-benzophenone (2.73 g, 10 mmol) in DCM (24 ml), are added water (5 ml) followed by bromoacetyl bromide (2.0 ml, 23 mmol). Stirring is continued at rt for 15 hrs. The layers are partitioned and the organic phase washed with brine, dried over MgSO$_4$ and the solvent removed in vacuo to yield N-(2-benzoyl-phenyl)-2-bromo-N-phenyl-acetamide (3.84 g), which is not further purified. LC-MS[2]: $t_R$=5.27 min, [M+1]+=394.

c) N-(2-Benzoyl-phenyl)-2-bromo-N-phenyl-acetamide (0.27 g, 0.68 mmol) is dissolved in ammonia saturated methanol (7N) and heated to 45° C. for 15 h. The solvent is removed in vacuo, the crude product dissolved in DCM, washed with water, brine, dried over MgSO$_4$ and the solvent removed in vacuo. The crude product is purified over column chromatography on silica (10% EtOAc in Heptane) to afford 1,5-diphenyl-1,3-dihydro-benzo[b]azepin-2-one (0.1 g). $^1$H-NMR(300 MHz, CDCl$_3$): 4.01 (d, J=9.9, 1H), 4.94 (d, J=9.9, 1H), 6.96 (d, J=8.8, 1H), 7.2–7.5 (m, 11H), 7.7 (m, 2H). LC-MS[2]: $t_R$=4.57 min, [M+1]+=313.

d) Triethylamine (0.225 ml, 1.60 mmol) is added dropwise to a cooled (0° C.) solution of 1,5-diphenyl-1,3-dihydro-benzo[b]azepin-2-one (0.1 g, 0.320 mmol) and benzyloxy acetyl chloride (0.066 ml, 0.416 mmol) in DCM (3 ml). The ice bath is allowed to warm to rt over 15 h. The reaction mixture is diluted with EA, extracted with sat. aq. NaHCO$_3$, the aq. phase is extracted with EA (2×). The combined organic phases are washed with brine, dried over MgSO$_4$ and the solvent removed in vacuo to give (±)-(1S*, 9bS*)-1-benzyloxy-5,9b-diphenyl-5,9b-dihydro-1H-2a,5-diaza-benzo[a]cyclobuta[c]cycloheptene-2,4-dione (0.13 g) as a light yellow foam. $^1$H-NMR(300 MHz, CDCl$_3$): 4.03 (d, J=12.8, 1H), 4.12 (s, 1H), 4.50 (d, J=11.1, 1H), 4.58–4.66 (m, 2H), 5.4 (s, 1H), 6.85 (m, 1H), 6.88 (dd, J=1.6, 7.3, 1H), 7.0–7.2 (m, 5H), 7.2–7.5 (m, 8H). LC-MS[2]: $t_R$=5.3 min, [M+1]+=461.

e) To Pd/C (0.03 g, 10%) are added (±)-(1S*, 9bS*)-1-benzyloxy-5,9b-diphenyl-5,9b-dihydro-1H-2a,5-diaza-benzo[a]cyclobuta[c]cycloheptene-2,4-dione (0.13 g, 0.283 mmol), THF (0.8 ml), ethanol (2 ml) and acetic acid (0.03 ml). The reaction mixture is stirred at 50° C. under 7 atm $H_2$ for 20 h. The Pd-catalyst is filtered and the solvent removed in vacuo to afford (±)-(1S*, 9bS*)-1-hydroxy-5,9b-diphenyl-5,9b-dihydro-1H-2a,5-diaza-benzo[a]cyclobuta[c]cycloheptene-2,4-dione (0.07 g) as a white powder, which is used without further purification. LC-MS$^2$: $t_R$=4.04 min, [M+1]$^+$=371.

f) $K_2CO_3$ (4.89 g, 35.4 mmol) is added to a solution of (±)-(1S*, 9bS*)-1-hydroxy-5,9b-diphenyl-5,9b-dihydro-1H-2a,5-diazabenzo[a]cyclobuta[c]cycloheptene-2,4-dione (0.07 g, 0.189 mmol) and 2-methanesulfonyl-4,6-dimethy-pyrimidine (0.042 g, 0.226 mmol, Example 19) in DMF (2 ml). The resulting suspension is heated to 50° C. over 48 h, diluted with DCM, washed with water (2×), brine (2×), dried over $MgSO_4$ and the solvent removed in vacuo. The crude product is suspended in EA to yield (±)-(1S*, 9bS*)-1-(4,6-dimethyl-pyrimidin-2-yloxy)-5,9b-diphenyl-5,9b-dihydro-1H-2a,5-diaza-benzo[a]cyclobuta[c]cycloheptene-2,4-dione (0.05 g) as a white powder. LC-MS$^2$: $t_R$=4.90 min, [M+1]$^+$=477.

g) LiOH.$H_2O$ (0.067 ml of a 2N aq. solution) is added to a solution of (±)-(1S*, 9bS*)-1-(4,6-dimethyl-pyrimidin-2-yloxy)-5,9b-diphenyl-5,9b-dihydro-1H-2a,5-diazabenzo[a]cyclobuta[c]cycloheptene-2,4-dione (0.05 g, 0.105 mmol) in THF (0.55 ml) and methanol (0.2 ml). The mixture is stirred at rt for 15 h, the pH is adjusted to pH=5 with 1 N HCl and the solvents removed in vacuo. The crude product is purified by prep. tlc on silica (5% MeOH in $CH_2Cl_2$) to afford (±)-(S*)-(4,6-dimethyl-pyrimidin-2-yloxy)-[(5S*)-2-oxo-1,5-diphenyl-2,3,4,5-tetrahydro-1H-benzo[e][1,4]diazepin-5-yl]-acetic acid (0.024 g) as a pale yellow powder. $^1$H-NMR(300 MHz, CDCl$_3$): 2.23 (s, 6H), 3.4–3.8 (m, 2H), 6.4–6.6 (m, 3H), 6.89 (s, 1H), 7.0–75 (m, 12H). LC-MS$^2$: $t_R$=4.97 min, [M+1]$^+$=495.

Example 118

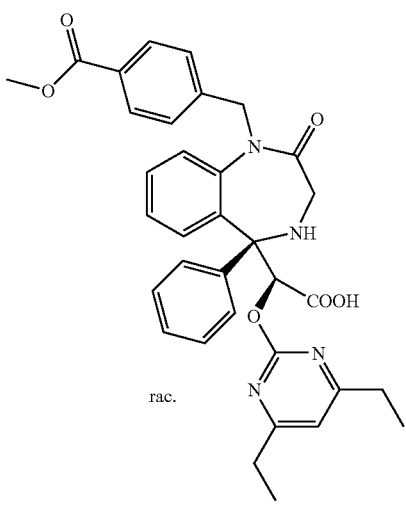

(±)-4-{(5S*)-5-[(S*)-Carboxy-(4,6-diethyl-pyrimidin-2-yloxy)-methyl]-2-oxo-5-phenyl-2,3,4,5-tetrahydro-benzo[e][1,4]diazepin-1-ylmethyl}-benzoic acid methyl ester is prepared in analogy to Examples 29 and 45. LC-MS$^1$: $t_R$=0.96 min, [M+1]$^+$=595.25.

Example 119

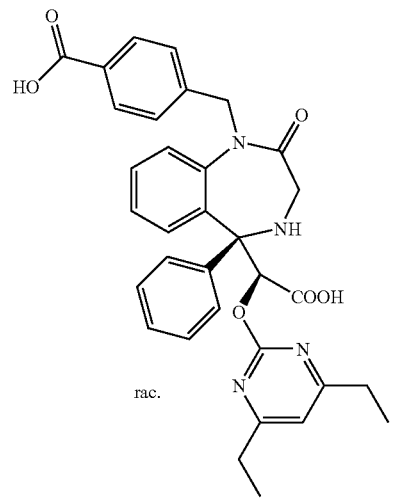

(±)-4-{(5S*)-5-[(S*)-Carboxy-(4,6-diethyl-pyrimidin-2-yloxy)-methyl]-2-oxo-5-phenyl-2,3,4,5-tetrahydro-benzo[e][1,4]diazepin-1-ylmethyl}-benzoic acid is prepared in analogy to Examples 29 and 46. LC-MS$^1$: $t_R$=0.84 min, [M+1]$^+$= 581.22.

Example 120

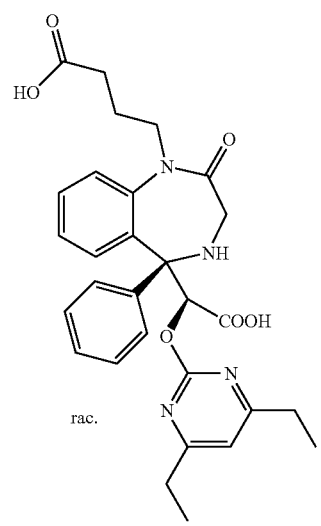

(±)-4-{(5S*)-5-[(S*)-Carboxy-(4,6-diethyl-pyrimidin-2-yloxy)-methyl]-2-oxo-5-phenyl-2,3,4,5-tetrahydro-benzo[e][1,4]diazepin-1-yl}-butyric acid is prepared in analogy to Examples 29 and 47. LC-MS$^1$: $t_R$=0.76 min, [M+1]$^+$= 533.21.

Example 121

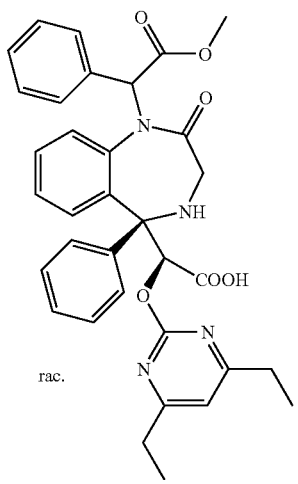

rac.

(±)-(S*)-(4,6-Diethyl-pyrimidin-2-yloxy)-[(5S*)-1-((R/S)-methoxycarbonyl-phenyl-methyl)-2-oxo-5-phenyl-2,3,4,5-tetrahydro-1H-benzo[e][1,4]diazepin-5-yl]-acetic acid is prepared as a racemic mixture of diastereoisomers in analogy to Examples 29 and 41. LC-MS[1]: $t_R$=0.96 min, [M+1]$^+$= 595.26.

Example 122

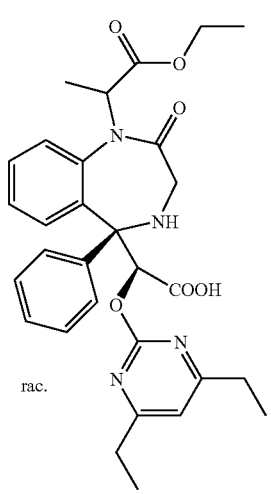

rac.

(±)-(2R/S)-2-{(5S*)-5-[(S*)-Carboxy-(4,6-diethyl-pyrimidin-2-yloxy)-methyl]-2-oxo-5-phenyl-2,3,4,5-tetrahydro-benzo[e][1,4]diazepin-1-yl}-propionic acid ethyl ester is prepared as a racemic mixture of diastereoisomers in analogy to Examples 29 and 43. LC-MS[1]: $t_R$=0.92 min, [M+1]$^+$= 547.19.

Example 123

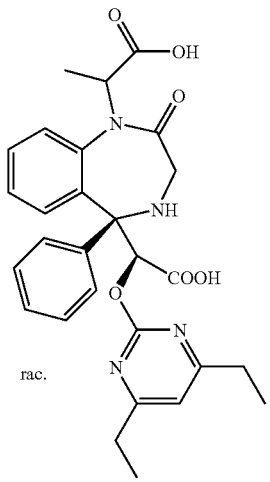

rac.

(±)-(2R/S)-2-{(5S*)-5-[(S*)-Carboxy-(4,6-diethyl-pyrimidin-2-yloxy)-methyl]-2-oxo-5-phenyl-2,3,4,5-tetrahydro-benzo[e][1,4]diazepin-1-yl}-propionic acid is prepared as a racemic mixture of diastereoisomers in analogy to Examples 29 and 43. LC-MS[1]: $t_R$=0.79 min, [M+1]$^+$=519.15.

Example 124

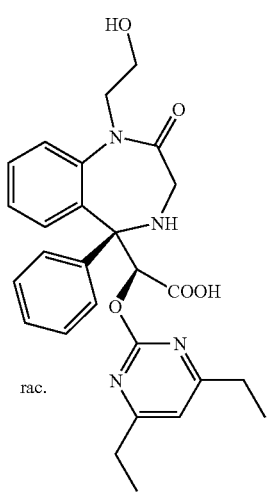

rac.

(±)-(S*)-(4,6-Diethyl-pyrimidin-2-yloxy)-[(5S*)-1-(2-hydroxy-ethyl)-2-oxo-5-phenyl-2,3,4,5-tetrahydro-1H-benzo[e][1,4]diazepin-5-yl]-acetic acid is prepared in analogy to Examples 29 and 44. LC-MS[1]: $t_R$=0.74 min, [M+1]$^+$= 491.16.

Example 125

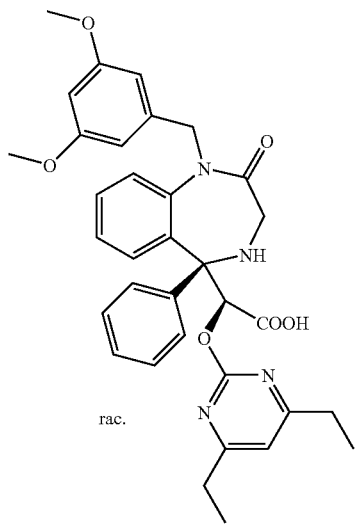

(±)-(S*)-(4,6-Diethyl-pyrimidin-2-yloxy)-[(5S*)-1-(3,5-dimethoxy-benzyl)-2-oxo-5-phenyl-2,3,4,5-tetrahydro-1H-benzo[e][1,4]diazepin-5-yl]-acetic acid is prepared in analogy to Examples 29 and 40. LC-MS$^1$: $t_R$=1.02 min, [M+1]$^+$= 597.27.

Example 126

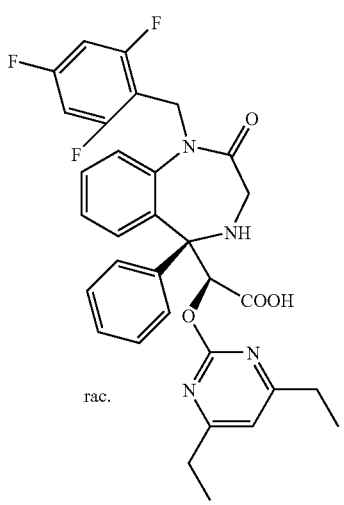

(±)-(S*)-(4,6-Diethyl-pyrimidin-2-yloxy)-[(5S*)-2-oxo-5-phenyl-1-(2,4,6-trifluoro-benzyl)-2,3,4,5-tetrahydro-1H-benzo[e][1,4]diazepin-5-yl]-acetic acid is prepared in analogy to Examples 29 and 48. LC-MS$^2$: $t_R$=5.02 min, [M+1]$^+$= 591.39, [M-1]$^-$=589.29.

Example 127

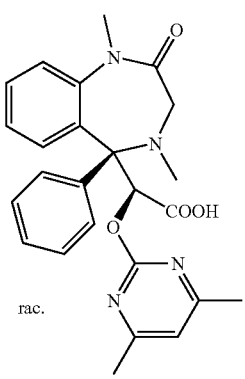

Pd/C (100 mg, 10% Pd) is added to a solution of (±)-(S*)-(4,6-dimethyl-pyrimidin-2-yloxy)-((5S*)-1-methyl-2-oxo-5-phenyl-2,3,4,5-tetrahydro-1H-benzo[e][1,4]diazepin-5-yl)-acetic acid (100 mg, 0.231 mmol, Example 49) in water (8 ml), methanol (8 ml) and aq. formaldehyde solution (0.2 ml, 36%). The mixture is stirred at rt under 3 atm H$_2$ for 18 h before the catalyst is filtered off. The organic solvent of the filtrate is evaporated and the remaining aq. phase is extracted three times with DCM. The organic phase is evaporated and the product is purified by chromatography on prep. tlc-plattes with DCM:methanol 9:1 to give (±)-(S*)-((5S*)-1,4-dimethyl-2-oxo-5-phenyl-2,3,4,5-tetrahydro-1H-benzo[e][1,4]diazepin-5-yl)-(4,6-dimethyl-pyrimidin-2-yloxy)-acetic acid (57 mg) as a white powder. LC-MS$^2$: $t_R$=3.40 min, [M+1]$^+$=447.10, [M-1]$^-$=445.14.

Example 128

(±)-(S*)-(4,6-Dimethyl-pyrimidin-2-yloxy)-[(5S*)-1-(4-methoxy-benzyl)-4-methyl-2-oxo-5-phenyl-2,3,4,5-tetrahydro-1H-benzo[e][1,4]diazepin-5-yl]-acetic acid is prepared starting from (±)-(S*)-(4,6-dimethyl-pyrimidin-2-yloxy)-[(5S*)-1-(4-methoxy-benzyl)-2-oxo-5-phenyl-2,3,4,5-tetrahydro-1H-benzo[e][1,4]diazepin-5-yl]-acetic acid (Example 61) in analogy to Example 127. LC-MS$^1$: $t_R$=0.95 min, [M+1]$^+$=553.16.

Example 129

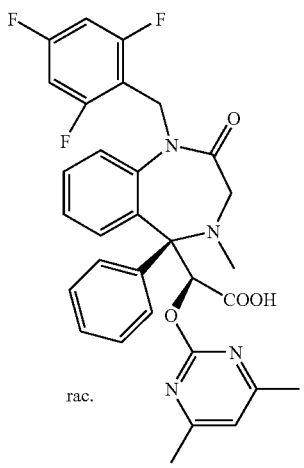

(±)-(S*)-(4,6-Dimethyl-pyrimidin-2-yloxy)-[(5S*)-4-methyl-2-oxo-5-phenyl-1-(2,4,6-trifluoro-benzyl)-2,3,4,5-tetrahydro-1H-benzo[e][1,4]diazepin-5-yl]-acetic acid is prepared starting from (±)-(S*)-(4,6-dimethyl-pyrimidin-2-yloxy)-[(5S*)-2-oxo-5-phenyl-1-(2,4,6-trifluoro-benzyl)-2,3,4,5-tetrahydro-1H-benzo[e][1,4]diazepin-5-yl]-acetic acid (Example 107) in analogy to Example 127. LC-MS[1]: $t_R$=1.06 min, [M+1]$^+$=577.00.

Example 130

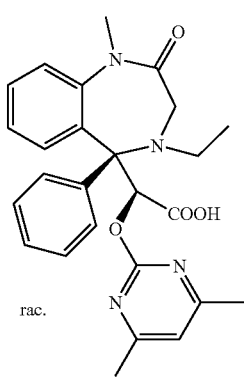

(±)-(S*)-((5S*)-4-ethyl-1-methyl-2-oxo-5-phenyl-2,3,4,5-tetrahydro-1H-benzo[e][1,4]diazepin-5-yl)-(4,6-dimethyl-pyrimidin-2-yloxy)-acetic acid is prepared starting from (±)-(S*)-((5S*)-1-methyl-2-oxo-5-phenyl-2,3,4,5-tetrahydro-1H-benzo[e][1,4]diazepin-5-yl)-(4,6-dimethyl-pyrimidin-2-yloxy)-acetic acid (Example 49) and acetaldehyde in analogy to Example 127. LC-MS[1]: $t_R$=0.75 min, [M+1]$^+$=461.16.

Example 131

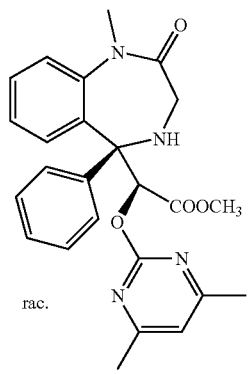

Sodium methylate (10.14 g, 186 mmol) is added at 0° C. to a solution of (±)-(1S*, 9bS*)-1-(4,6-dimethyl-pyrimidin-2-yloxy)-5-methyl-9b-phenyl-5,9b-dihydro-1H-2a,5-diazabenzo[a]cyclobuta[c]cycloheptene-2,4-dione (5.0 g, 12 mmol, Example 49) in methanol (250 ml). The solution is stirred at rt for 3 h, poured into a solution of citric acid (12.6 g, mono hydrate) in water (600 ml) and extracted three times with EA. The organic phase is washed with brine, dried over MgSO$_4$ and evaporated to give (±)-(S*)-(4,6-dimethyl-pyrimidin-2-yloxy)-((5S*)-1-methyl-2-oxo-5-phenyl-2,3,4,5-tetrahydro-1H-benzo[e][1,4]diazepin-5-yl)-acetic acid methyl ester (5.04 g) as a white foam. LC-MS[1]: $t_R$=0.94 min, [M+1]$^+$=447.07.

Example 132

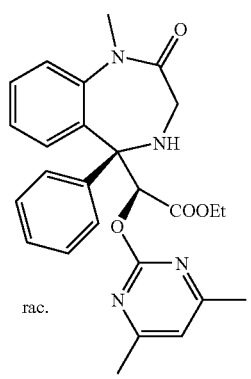

(±)-(S*)-(4,6-dimethyl-pyrimidin-2-yloxy)-((5S*)-1-methyl-2-oxo-5-phenyl-2,3,4,5-tetrahydro-1H-benzo[e][1,4]diazepin-5-yl)-acetic acid ethyl ester is prepared in analogy to Example 131. LC-MS[1]: $t_R$=0.89 min, [M+1]$^+$=461.13.

Example 133

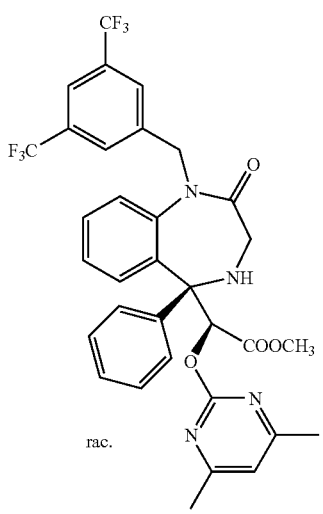

rac.

(±)-(S*)-[(5S*)-1-(3,5-bis-trifluoromethyl-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid methyl ester is prepared starting from (±)-(1S*,9bS*)-5-(3,5-bis-trifluoromethyl-benzyl)-1-(4,6-dimethyl-pyrimidin-2-yloxy)-9b-phenyl-5,9b-dihydro-1H-2a,5-diaza-benzo[a]cyclobuta[c]cycloheptene-2,4-dione (Example 65) in analogy to Example 131. LC-MS¹: $t_R$=1.24 min, [M+1]⁺=659.02.

Example 134

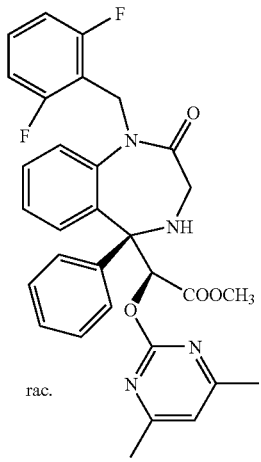

rac.

(±)-(S*)-[(5S*)-1-(2,6-Difluoro-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid methyl ester is prepared starting from (±)-(1S*,9bS*)-5-(2,6-difluoro-benzyl)-1-(4,6-dimethyl-pyrimidin-2-yloxy)-9b-phenyl-5,9b-dihydro-1H-2a,5-diaza-benzo[a]cyclobuta[c]cycloheptene-2,4-dione (Example 89) in analogy to Example 131. LC-MS¹: $t_R$=1.13 min, [M+1]⁺=559.06.

Example 135

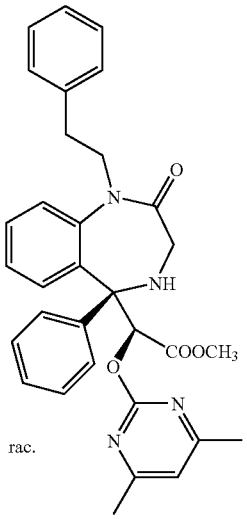

rac.

(±)-(S*)-(4,6-Dimethyl-pyrimidin-2-yloxy)-((5S*)-2-oxo-1-phenethyl-5-phenyl-2,3,4,5-tetrahydro-1H-benzo[e][1,4]diazepin-5-yl)-acetic acid methyl ester is prepared starting from (±)-(1S*,9bS*)-1-(4,6-dimethyl-pyrimidin-2-yloxy)-5-phenethyl-9b-phenyl-5,9b-dihydro-1H-2a,5-diaza-benzo[a]cyclobuta[c]cycloheptene-2,4-dione (Example 78) in analogy to Example 131. LC-MS¹: $t_R$=1.14 min, [M+1]⁺=537.07.

Example 136

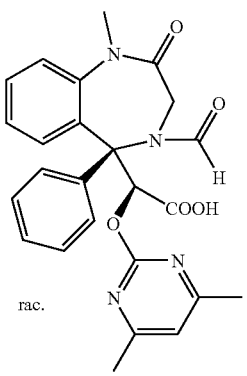

rac.

a) (±)-(S*)-(4,6-dimethyl-pyrimidin-2-yloxy)-((5S*)-1-methyl-2-oxo-5-phenyl-2,3,4,5-tetrahydro-1H-benzo[e][1,4]diazepin-5-yl)-acetic acid methyl ester (447 mg, 1 mmol, Example 131) is added to a mixture of acetic anhydride (1.9 ml) and formic acid (0.76 ml) at 5° C. The mixture is stirred at rt for 1 h before it is poured into cold sat. aq. NaHCO₃. The aq. phase is extracted three times with EA. The organic phase is washed with brine, dried over MgSO₄ and evaporated. The crude product is purified by chromatography on prep. tlc plates with DCM:methanol 9:1 to furnish (±)-(S*)-(4,6-dimethyl-pyrimidin-2-yloxy)-((5S*)-4-formyl-1-methyl-2-oxo-5-phenyl-2,3,4,5-tetrahydro-1H-benzo[e][1,4]diazepin-5-yl)-acetic acid methyl ester (210 mg) as a colourless foam. LC-MS¹: $t_R$=0.97 min, [M+1]⁺=475.06.

b) A solution of (±)-(S*)-(4,6-dimethyl-pyrimidin-2-yloxy)-((5S*)-4-formyl-1-methyl-2-oxo-5-phenyl-2,3,4,5-tetrahydro-1H-benzo[e][1,4]diazepin-5-yl)-acetic acid methyl ester (200 mg, 0.42 mmol) in THF (6 ml), methanol (3 ml), and 2 N aq. LiOH (1 ml) is stirred at rt for 1 h. The solution is poured into 10% aq. citric acid, extracted three times with EA. The organic phase is washed with brine, dried over MgSO$_4$, evaporated and dried under HV to yield (±)-(S*)-(4,6-dimethyl-pyrimidin-2-yloxy)-((5S*)-4-formyl-1-methyl-2-oxo-5-phenyl-2,3,4,5-tetrahydro-1H-benzo[e][1,4]diazepin-5-yl)-acetic acid (220 mg) as a colourless foam. LC-MS[1]: $t_R$=0.89 min, [M+1]$^+$=461.04.

Example 137

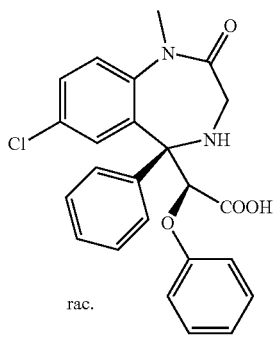

a) (±)-(1S*,9bS*)-8-Chloro-5-methyl-1-phenoxy-9b-phenyl-5,9b-dihydro-1H-2a,5-diaza-benzo[a]cyclobuta[c]cycloheptene-2,4-dione is prepared from 7-chloro-1-methyl-5-phenyl-1,3-dihydro-benzo[e][1,4]diazepin-2-one (Example 39) and phenoxy-acetic acid in analogy to Example 18. LC-MS[2]: $t_R$=5.05 min, [M+1]$^+$=419.16, [M−1]$^−$=417.08.

b) (±)-(S*)-((5S*)-7-Chloro-1-methyl-2-oxo-5-phenyl-2,3,4,5-tetrahydro-1H-benzo[e][1,4]diazepin-5-yl)-phenoxy-acetic acid is prepared from (±)-(1S*,9bS*)-8-chloro-5-methyl-1-phenoxy-9b-phenyl-5,9b-dihydro-1H-2a,5-diaza-benzo[a]cyclobuta[c]cycloheptene-2,4-dione in analogy to Example 38. LC-MS[2]: $t_R$=4.41 min, [M+1]$^+$=437.21, [M−1]$^−$=435.19.

Example 138

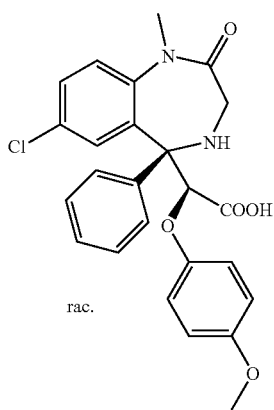

a) (4-Methoxy-phenoxy)-acetic acid ethyl ester is prepared from 4-methoxy-phenol and bromo-acetic acid ethyl ester in analogy to Example 1. LC-MS[2]: $t_R$=4.18 min, [M+1]$^+$=211.06.

b) (4-Methoxy-phenoxy)-acetic acid is obtained from (4methoxy-phenoxy)-acetic acid ethyl ester in analogy to Example 1. LC-MS[2]: $t_R$=3.09 min, [M−1]$^−$=181.04.

c) (±)-(1S*,9bS*)-8-Chloro-1-(4-methoxy-phenoxy)-5-methyl-9b-phenyl-5,9b-dihydro-1H-2a,5-diaza-benzo[a]cyclobuta[c]cycloheptene-2,4-dione is prepared from 7-chloro-1-methyl-5-phenyl-1,3-dihydro-benzo[e][1,4]diazepin-2-one (Example 39) and (4-methoxy-phenoxy)-acetic acid according to Example 18. LC-MS[1]: $t_R$=1.01 min, [M+1]$^+$=449.08.

d) (±)-(S*)-((5S*)-7-Chloro-1-methyl-2-oxo-5-phenyl-2,3,4,5-tetra-hydro-1H-benzo[e][1,4]diazepin-5-yl)-(4-methoxy-phenoxy)-acetic acid is prepared from (±)-(1S*,9bS*)-8-chloro-1-(4-methoxy-phenoxy)-5-methyl-9b-phenyl-5,9b-dihydro-1H-2a,5-diaza-benzo[a]cyclobuta[c]cyclo-heptene-2,4-dione in analogy to Example 18. LC-MS[1]: $t_R$=0.89 min, [M+1]$^+$=467.09.

Example 139

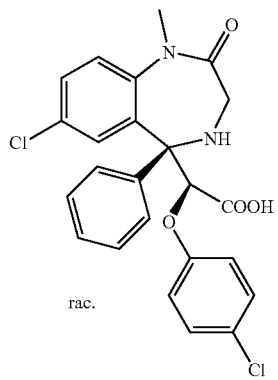

a) (4-Chloro-phenoxy)-acetic acid ethyl ester is prepared from 4-chloro-phenol and bromo-acetic acid ethyl ester in analogy to Example 1.

b) (4-Chloro-phenoxy)-acetic acid is obtained from (4-chloro-phenoxy)-acetic acid ethyl ester according to Example 1.

c) (±)-(1S*,9bS*)-8-Chloro-1-(4-chloro-phenoxy)-5-methyl-9b-phenyl-5,9b-dihydro-1H-2a,5-diaza-benzo[a]cyclobuta[c]cycloheptene-2,4-dione is prepared from 7-chloro-1-methyl-5-phenyl-1,3-dihydro-benzo[e][1,4]diazepin-2-one (Example 39) and (4-chloro-phenoxy)-acetic acid according to Example 18. LC-MS[1]: $t_R$=1.19 min, [M+1]$^+$=453.01.

d) (±)-(S*)-((5S*)-7-Chloro-1-methyl-2-oxo-5-phenyl-2,3,4,5-tetra-hydro-1H-benzo[e][1,4]diazepin-5-yl)-(4-chloro-phenoxy)-acetic acid is prepared from (±)-(1S*,9bS*)-8-chloro-1-(4-chloro-phenoxy)-5-methyl-9b-phenyl-5,9b-dihydro-1H-2a,5-diaza-benzo[a]cyclobuta[c]cycloheptene-2,4-dione in analogy to Example 18. LC-MS[1]: $t_R$=1.07 min, [M+1]$^+$=471.00.

Example 140

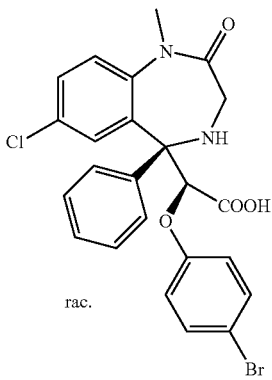

a) (4-Bromo-phenoxy)-acetic acid ethyl ester is prepared from 4-bromo-phenol and bromo-acetic acid ethyl ester in analogy to Example 1.
b) (4-Bromo-phenoxy)-acetic acid is obtained from (4-bromo-phenoxy)-acetic acid ethyl ester according to Example 1 b). LC-MS$^2$: $t_R$=3.78 min, [M−1]$^−$=228.91.
c) (±)-(1S*,9bS*)-1-(4-Bromo-phenoxy)-8-chloro-5-methyl-9b-phenyl-5,9b-dihydro-1H-2a,5-diaza-benzo[a]cyclobuta[c]cycloheptene-2,4-dione is prepared from 7-chloro-1-methyl-5-phenyl-1,3-dihydro-benzo[e][1,4]diazepin-2-one (Example 39) and (4-bromo-phenoxy)-acetic acid according to Example 18. LC-MS$^1$: $t_R$=1.10 min, [M+1]$^+$=498.93.
d) (±)-(S*)-(4-Bromo-phenoxy)-((5S*)-7-chloro-1-methyl-2-oxo-5-phenyl-2,3,4,5-tetrahydro-1H-benzo[e][1,4]diazepin-5-yl)-acetic acid is prepared from (±)-(1S*,9bS*)-1-(4-bromo-phenoxy)-8-chloro-5-methyl-9b-phenyl-5,9b-dihydro-1H-2a,5-diaza-benzo[a]cyclobuta[c]cycloheptene-2,4-dione in analogy to Example 18. LC-MS$^1$: $t_R$=0.97 min, [M+1]$^+$=516.89.

Example 141

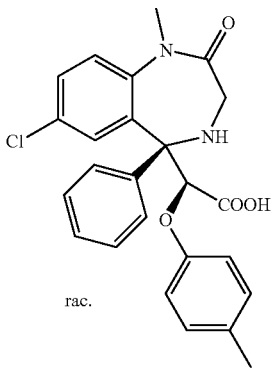

a) p-Tolyloxy-acetic acid ethyl ester is prepared from 4-methyl-phenol and bromo-acetic acid ethyl ester in analogy to Example 1.
b) p-Tolyloxy-acetic acid is obtained from p-tolyloxy-acetic acid ethyl ester according to Example 1.
c) (±)-(1S*,9bS*)-8-Chloro-5-methyl-9b-phenyl-1-p-tolyloxy-5,9b-dihydro-1H-2a,5-diaza-benzo[a]cyclobuta[c]cycloheptene-2,4-dione is prepared from 7-chloro-1-methyl-5-phenyl-1,3-dihydro-benzo[e][1,4]diazepin-2-one (Example 39) and p-tolyloxy-acetic acid according to Example 18. LC-MS$^2$: $t_R$=5.25 min, [M+1]$^+$=433.04.
d) (±)-(S*)-((5S*)-7-Chloro-1-methyl-2-oxo-5-phenyl-2,3,4,5-tetra-hydro-1H-benzo[e][1,4]diazepin-5-yl)-p-tolyloxy-acetic acid is prepared from (±)-(1S*,9bS*)-8-chloro-5-methyl-9b-phenyl-1-p-tolyloxy-5,9b-dihydro-1H-2a,5-diaza-benzo[a]cyclobuta[c]cycloheptene-2,4-dione in analogy to Example 18. LC-MS$^1$: $t_R$=0.94 min, [M+1]$^+$=451.04.

Example 142

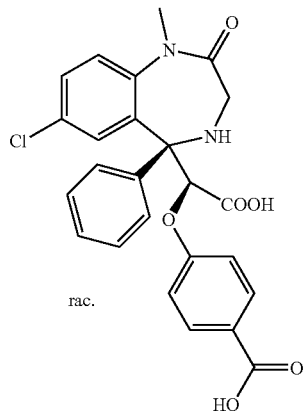

a) 4-tert-Butoxycarbonylmethoxy-benzoic acid methyl ester is prepared from 4-hydroxy-benzoic acid methyl ester and bromo-acetic acid tert-butyl ester in analogy to Example 1.
b) To a solution of 4-tert-butoxycarbonylmethoxy-benzoic acid methyl ester (5 g, 18.8 mmol) in dry DCM (40 ml) is added trifluoro-acetic acid (40 ml) at 0° C. The solution is stirred for 5 h at rt and evaporated in vacuo to give 4-carboxymethoxy-benzoic acid methyl ester 4 g as a white solid. LC-MS$^2$: $t_R$=3.24 min, [M+1]$^+$=211.04, [M−1]$^−$=208.96.
c) (±)-4-((1S*,9bS*)-8-Chloro-5-methyl-2,4-dioxo-9b-phenyl-1,2,3,4,5,9b-hexahydro-2a,5-diaza-benzo[a]cyclobuta[c]cyclohepten-1-yloxy)-benzoic acid methyl ester is prepared from 7-chloro-1-methyl-5-phenyl-1,3-dihydro-benzo[e][1,4]diazepin-2-one (Example 39) and 4-carboxymethoxy-benzoic acid methyl ester according to Example 18. LC-MS$^1$: $t_R$=1.11 min, [M+1]$^+$=477.07.
d) (±)-4-[(S*)-Carboxy-((5S*)-7-chloro-1-methyl-2-oxo-5-phenyl-2,3,4,5-tetrahydro-1H-benzo[e][1,4]diazepin-5-yl)-methoxy]-benzoic acid is prepared from (±)-(1S*,9bS*)-4-(8-chloro-5-methyl-2,4-dioxo-9b-phenyl-1,2,3,4,5,9b-hexahydro-2a,5-diaza-benzo[a]cyclobuta[c]cyclohepten-1-yloxy)-benzoic acid methyl ester in analogy to Example 18. LC-MS$^1$: $t_R$=0.88 min, [M+1]$^+$=481.04.

Example 143

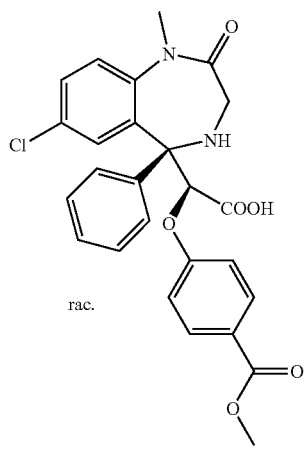

(±)-4-[(S*)-Carboxy-((5S*)-7-chloro-1-methyl-2-oxo-5-phenyl-2,3,4,5-tetrahydro-1H-benzo[e][1,4]diazepin-5-yl)-methoxy]-benzoic acid methyl ester is isolated as a second product in Example 142. LC-MS$^1$: $t_R$=0.99 min, [M+1]$^+$= 495.04.

Example 144

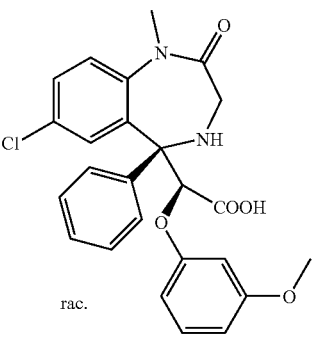

a) (3-Methoxy-phenoxy)-acetic acid ethyl ester is prepared from 3-methoxy-phenol and bromo-acetic acid ethyl ester in analogy to Example 1.
b) (3-Methoxy-phenoxy)-acetic acid is obtained from (3-methoxy-phenoxy)-acetic acid ethyl ester according to Example 1.
c) (±)-(1S*,9bS*)-8-Chloro-1-(3-methoxy-phenoxy)-5-methyl-9b-phenyl-5,9b-dihydro-1H-2a,5-diaza-benzo[a]cyclobuta[c]cycloheptene-2,4-dione is prepared from 7-chloro-1-methyl-5-phenyl-1,3-dihydro-benzo[e][1,4]diazepin-2-one (Example 39) and (3-methoxy-phenoxy)-acetic acid according to Example 18. LC-MS$^1$: $t_R$=1.12 min, [M+1]$^+$=449.03.
d) (±)-(S*)-((5S*)-7-Chloro-1-methyl-2-oxo-5-phenyl-2,3,4,5-tetrahydro-1H-benzo[e][1,4]diazepin-5-yl)-(3-methoxy-phenoxy)-acetic acid is prepared from (±)-(1S*,9bS*)-8-chloro-1-(3-methoxy-phenoxy)-5-methyl-9b-phenyl-5,9b-dihydro-1H-2a,5-diaza-benzo[a]cyclobuta[c]cyclo-heptene-2,4-dione in analogy to Example 18. LC-MS$^1$: $t_R$=0.77 min, [M+1]$^+$=467.05.

Example 145

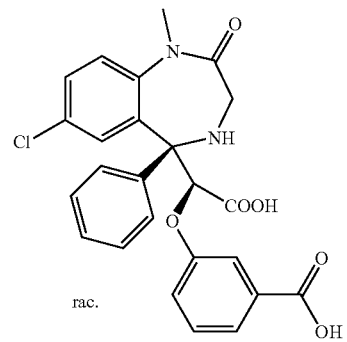

a) 3-Carboxymethoxy-benzoic acid methyl ester is prepared from 3-tert-butoxycarbonylmethoxy-benzoic acid methyl ester as described in Example 1. LC-MS$^2$: $t_R$=3.29 min, [M−1]$^-$=208.97.
b) (±)-3-[(S*)-Carboxy-((5S*)-7-chloro-1-methyl-2-oxo-5-phenyl-2,3,4,5-tetrahydro-1H-benzo[e][1,4]diazepin-5-yl)-methoxy]-benzoic acid is prepared in analogy to Example 142. LC-MS$^1$: $t_R$=0.89 min, [M+1]$^+$=481.04.

Example 146

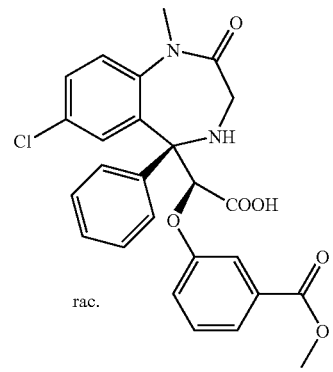

(±)-3-[(S*)-Carboxy-((5S*)-7-chloro-1-methyl-2-oxo-5-phenyl-2,3,4,5-tetrahydro-1H-benzo[e][1,4]diazepin-5-yl)-methoxy]-benzoic acid methyl ester is prepared in analogy to Example 143. LC-MS$^1$: $t_R$=1.00 min, [M+1]$^+$=495.04.

Example 147

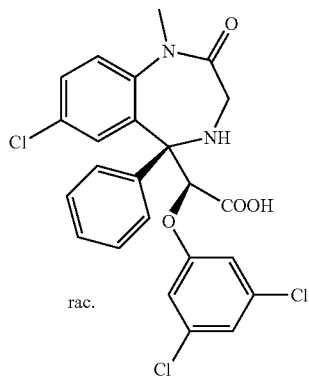

a) (3,5-Dichloro-phenoxy)-acetic acid is obtained from (3,5-dichloro-phenoxy)-acetic acid ethyl ester according to Example 1.
b) (±)-(1S*,9bS*)-8-Chloro-1-(3,5-dichloro-phenoxy)-5-methyl-9b-phenyl-5,9b-dihydro-1H-2a,5-diaza-benzo[a]cyclobuta[c]cycloheptene-2,4-dione is prepared from 7-chloro-1-methyl-5-phenyl-1,3-dihydro-benzo[e][1,4]diazepin-2-one (Example 39) and (3,5-dichloro-phenoxy)-acetic acid according to Example 18. LC-MS[1]: $t_R$=1.28 min, [M+1]$^+$=527.86; $^1$H-NMR (300 MHz, CDCl$_3$): 2.53 (s, 3H), 3.81 (d, J=13.5, 1H), 4.44 (d, J=13.5, 1H), 5.67 (s, 1H), 6.79 (d, J=1.9, 2H), 7.00 (t, J=1.9, 1H), 7.19 (d, J=8.7, 1H), 7.33 (br, 5H), 7.50 (dd, J=2.4, 8.4, 1H), 7.57 (d, J=2.3, 1H).
c) Lithium hydroxyde monohydrate (31 mg, 742 µmol), dissolved in water (500 µl), is added to a solution of (±)-(1S*,9bS*)-8-chloro-1-(3,5-dichloro-phenoxy)-5-methyl-9b-phenyl-5,9b-dihydro-1H-2a,5-diaza-benzo[a]cyclo-buta[c]cycloheptene-2,4-dione (300 mg, 618 µmol) in THF (2 ml) and methanol (500 µl). The solution is stirred for 1 h at rt, then diluted with water and the organic solvents are evaporated in vacuo. The solution is acidified to pH 6 and the mixture lyophilized. The residue is purified by prep. HPLC to give (±)-(S*)-((5S*)-7-chloro-1-methyl-2-oxo-5-phenyl-2,3,4,5-tetrahydro-1H-benzo[e][1,4]diazepin-5-yl)-(3,5-dichloro-phenoxy)-acetic acid (78 mg) as a white powder. LC-MS[1]: $t_R$=1.13 min, [M+1]$^+$=506.92.

Example 148

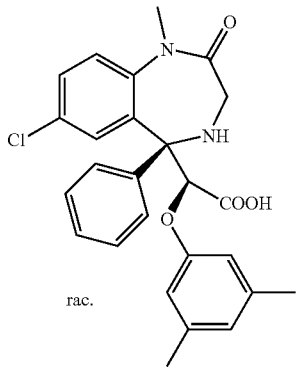

a) (3,5-Dimethyl-phenoxy)-acetic acid is obtained from (3,5-dimethyl-phenoxy)-acetic acid ethyl ester in analogy to Example 1.
b) (±)-(S*)-((5S*)-7-Chloro-1-methyl-2-oxo-5-phenyl-2,3,4,5-tetrahydro-1H-benzo[e][1,4]diazepin-5-yl)-(3,5-dimethyl-phenoxy)-acetic acid is prepared in analogy to Example 18. LC-MS[1]: $t_R$=0.98 min, [M+1]$^+$=465.07.

Example 149

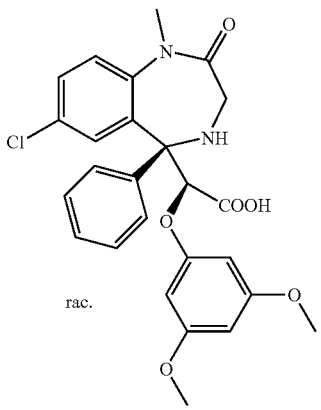

a) (±)-(1S*,9bS*)-8-Chloro-1-(3,5-dimethoxy-phenoxy)-5-methyl-9b-phenyl-5,9b-dihydro-1H-2a,5-diaza-benzo[a]cyclobuta[c]cycloheptene-2,4-dione is prepared from 7-chloro-1-methyl-5-phenyl-1,3-dihydro-benzo[e][1,4]diazepin-2-one (Example 39) and from (3,5-dimethoxyphenoxy)-acetic acid (Example 1) according to Example 18. LC-MS[2]: $t_R$=5.04 min, [M+1]$^+$=479.29, [M−1]$^-$=477.42.
b) A solution of (±)-(1S*,9bS*)-8-chloro-1-(3,5-dimethoxy-phenoxy)-5-methyl-9b-phenyl-5,9b-dihydro-1H-2a,5-diaza-benzo[a]cyclobuta[c]cyclo-heptene-2,4-dione (670 mg, 1.39 mmol) in dioxane (8 ml) and 6 M aq. HCl (6 ml) is heated for 2.5 h at 80° C. After cooling to rt the pH of the solution is adjusted to 7 and the solvents are evaporated. The residue is purified by MPLC to give (±)-(S*)-((5S*)-7-chloro-1-methyl-2-oxo-5-phenyl-2,3,4,5-tetrahydro-1H-benzo[e][1,4]diazepin-5-yl)-(3,5-dimethoxy-phenoxy)-acetic acid (42 mg, 85 µmol) as a white solid. LC-MS[2]: $t_R$=4.51 min, [M+1]$^+$=497.21, [M−1]$^-$=495.19.

Example 150

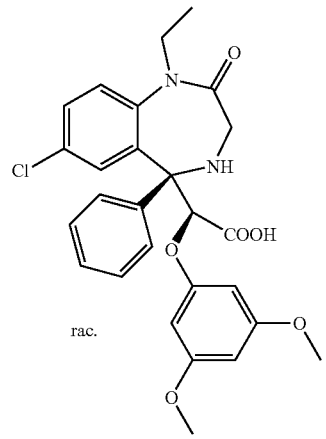

a) 7-Chloro-1-ethyl-5-phenyl-1,3-dihydro-benzo[e][1,4]diazepin-2-one is prepared from 7-chloro-5-phenyl-1,3-dihydro-benzo[e][1,4]diazepin-2-one (Example 39) and iodo-ethane according to Example 39. LC-MS[1]: $t_R$=0.88 min, [M+1]$^+$=299.09.
b) (±)-(1S*,9bS*)-8-Chloro-1-(3,5-dimethoxy-phenoxy)-5-ethyl-9b-phenyl-5,9b-dihydro-1H-2a,5-diaza-benzo[a]cyclobuta[c]cycloheptene-2,4-dione is prepared from 7-chloro-1-ethyl-5-phenyl-1,3-dihydro-benzo[e][1,4]diazepin-2-one and (3,5-dimethoxy-phenoxy)-acetic acid (Example 1) in analogy to Example 18. LC-MS[1]: $t_R$=1.18 min, [M+1]$^+$=493.07.
c) (±)-(S*)-((5S*)-7-Chloro-1-ethyl-2-oxo-5-phenyl-2,3,4,5-tetrahydro-1H-benzo[e][1,4]diazepin-5-yl)-(3,5-dimethoxy-phenoxy)-acetic acid is prepared from (±)-(1S*,9bS*)-8-chloro-1-(3,5-dimethoxy-phenoxy)-5-ethyl-9b-phenyl-5,9b-dihydro-1H-2a,5-diaza-benzo[a]cyclobuta[c]cycloheptene-2,4-dione in analogy to Example 18. LC-MS[1]: $t_R$=1.05 min, [M+1]$^+$=511.06.

Example 151

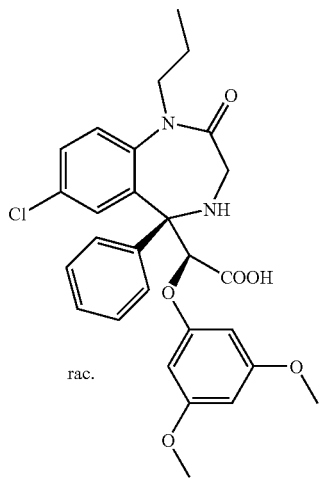

rac.

a) 7-Chloro-5-phenyl-1-propyl-1,3-dihydro-benzo[e][1,4]diazepin-2-one is prepared from 7-chloro-5-phenyl-1,3-dihydro-benzo[e][1,4]diazepin-2-one (Example 39) and 1-bromo-propane according to Example 39. LC-MS$^1$: $t_R$=0.92 min, [M+1]$^+$=313.03.

b) (±)-(1S*,9bS*)-8-Chloro-1-(3,5-dimethoxy-phenoxy)-9b-phenyl-5-propyl-5,9b-dihydro-1H-2a,5-diaza-benzo[a]cyclobuta[c]cycloheptene-2,4-dione is prepared from 7-chloro-5-phenyl-1-propyl-1,3-dihydro-benzo[e][1,4]diazepin-2-one and (3,5-dimethoxy-phenoxy)-acetic acid (Example 1) according to Example 18. LC-MS$^1$: $t_R$=1.22 min, [M+1]$^+$=507.09.

c) (±)-(S*)-((5S*)-7-Chloro-2-oxo-5-phenyl-1-propyl-2,3,4,5-tetrahydro-1H-benzo[e][1,4]diazepin-5-yl)-(3,5-dimethoxy-phenoxy)-acetic acid is prepared from (±)-(1S*,9bS*)-8-chloro-1-(3,5-dimethoxy-phenoxy)-9b-phenyl-5-propyl-5,9b-dihydro-1H-2a,5-diaza-benzo[a]cyclo-buta[c]cycloheptene-2,4-dione in analogy to Example 18. LC-MS$^1$: $t_R$=1.10 min, [M+1]$^+$=525.07.

Example 152

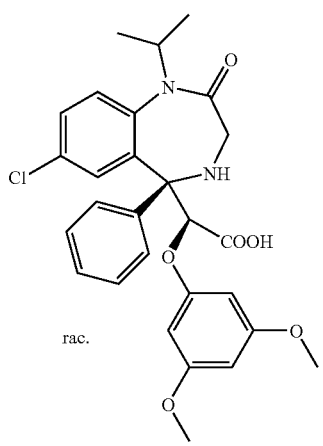

rac.

a) 7-Chloro-1-isopropyl-5-phenyl-1,3-dihydro-benzo[e][1,4]diazepin-2-one is prepared from 7-chloro-5-phenyl-1,3-dihydro-benzo[e][1,4]diazepin-2-one (Example 39) and 2-iodo-propane according to Example 39. LC-MS$^1$: $t_R$=0.91 min, [M+1]$^+$=313.01.

b) (±)-(S*)-((5S*)-7-Chloro-1-isopropyl-2-oxo-5-phenyl-2,3,4,5-tetrahydro-1H-benzo[e][1,4]diazepin-5-yl)-(3,5-dimethoxy-phenoxy)-acetic acid is prepared in analogy to Example 18. LC-MS$^1$: $t_R$=1.09 min, [M+1]$^+$=525.06.

Example 153

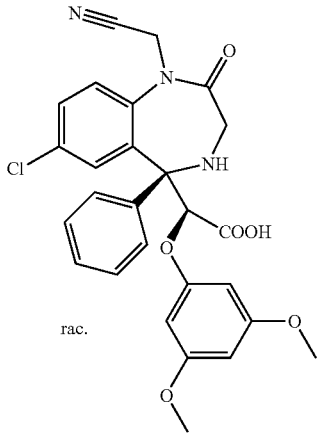

rac.

a) (7-Chloro-2-oxo-5-phenyl-2,3-dihydro-benzo[e][1,4]diazepin-1-yl)-acetonitrile is prepared from 7-chloro-5-phenyl-1,3-dihydro-benzo[e][1,4]diazepin-2-one (Example 39) and chloro-acetonitrile in analogy to Example 39. LC-MS$^1$: $t_R$=0.90 min, [M+1]$^+$=309.97.

b) (±)-(1S*,9bS*)-[8-Chloro-1-(3,5-dimethoxy-phenoxy)-2,4-dioxo-9b-phenyl-1,3,4,9b-tetrahydro-2H-2a,5-diaza-benzo[a]cyclobuta[c]cyclo-hepten-5-yl]-acetonitrile is prepared from (7-chloro-2-oxo-5-phenyl-2,3-dihydro-benzo[e][1,4]diazepin-1-yl)-acetonitrile and (3,5-dimethoxy-phenoxy)-acetic acid (Example 1) in analogy to Example 18. LC-MS$^1$: $t_R$=0.99 min, [M+1]$^+$=504.03.

c) (±)-(S*)-((5S*)-7-Chloro-1-cyanomethyl-2-oxo-5-phenyl-2,3,4,5-tetrahydro-1H-benzo[e][1,4]diazepin-5-yl)-(3,5-dimethoxy-phenoxy)-acetic acid is prepared from (±)-(1S*,9bS*)-[8-chloro-1-(3,5-dimethoxy-phenoxy)-2,4-dioxo-9b-phenyl-1,3,4,9b-tetrahydro-2H-2a,5-diaza-benzo[a]cyclo-buta[c]cyclohepten-5-yl]-acetonitrile in analogy to Example 18. LC-MS$^1$: $t_R$=1.08 min, [M+1]$^+$=522.02.

Example 154

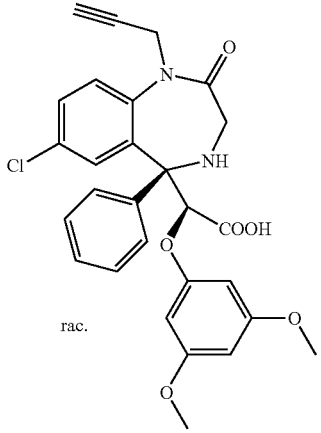

rac.

a) 7-Chloro-5-phenyl-1-prop-2-ynyl-1,3-dihydro-benzo[e][1,4]diazepin-2-one is prepared from 7-chloro-5-phenyl-1,3-dihydro-benzo[e][1,4]diazepin-2-one (Example 39) and 3-bromo-propyne according to Example 39. LC-MS$^1$: $t_R$=0.91 min, [M+1]$^+$=308.98.

b) (±)-(1S*,9bS*)-8-Chloro-1-(3,5-dimethoxy-phenoxy)-9b-phenyl-5-prop-2-ynyl-5,9b-dihydro-1H-2a,5-diaza-benzo[a]cyclobuta[c]cycloheptene-2,4-dione is prepared from 7-chloro-5-phenyl-1-prop-2-ynyl-1,3-dihydro-benzo[e][1,4]diazepin-2-one and (3,5-dimethoxy-phenoxy)-acetic acid (Example 1) according to Example 18. LC-MS[1]: $t_R$=1.16 min, [M+1]$^+$=503.05.

c) (±)-(S*)-((5S*)-7-Chloro-2-oxo-5-phenyl-1-prop-2-ynyl-2,3,4,5-tetrahydro-1H-benzo[e][1,4]diazepin-5-yl)-(3,5-dimethoxy-phenoxy)-acetic acid is prepared from (±)-(1S*,9bS*)-8-chloro-1-(3,5-dimethoxy-phenoxy)-9b-phenyl-5-prop-2-ynyl-5,9b-dihydro-1H-2a,5-diaza-benzo[a]cyclo-buta[c]cycloheptene-2,4-dione in analogy to Example 18. LC-MS[1]: $t_R$=1.07 min, [M+1]$^+$=521.03.

Example 155

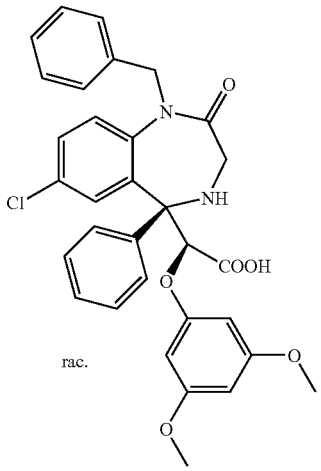

rac.

a) 1-Benzyl-7-chloro-5-phenyl-1,3-dihydro-benzo[e][1,4]diazepin-2-one is prepared from 7-chloro-5-phenyl-1,3-dihydro-benzo[e][1,4]diazepin-2-one (Example 39) and bromomethyl-benzene according to Example 39. LC-MS[1]: $t_R$=0.98 min, [M+1]$^+$=361.03.

b) (±)-(1S*,9bS*)-5-Benzyl-8-chloro-1-(3,5-dimethoxy-phenoxy)-9b-phenyl-5,9b-dihydro-1H-2a,5-diaza-benzo[a]cyclobuta[c]cycloheptene-2,4-dione is prepared from 1-benzyl-7-chloro-5-phenyl-1,3-dihydro-benzo[e][1,4]diazepin-2-one and (3,5-dimethoxy-phenoxy)-acetic acid (Example 1) according to Example 18. LC-MS[1]: $t_R$=1.26 min, [M+1]$^+$=555.09.

c) (±)-(S*)-((5S*)-1-Benzyl-7-chloro-2-oxo-5-phenyl-2,3,4,5-tetrahydro-1H-benzo[e][1,4]diazepin-5-yl)-(3,5-dimethoxy-phenoxy)-acetic acid is prepared from (±)-(1S*,9bS*)-5-benzyl-8-chloro-1-(3,5-dimethoxy-phenoxy)-9b-phenyl-5,9b-dihydro-1H-2a,5-diaza-benzo[a]cyclo-buta[c]cycloheptene-2,4-dione in analogy to Example 18. LC-MS[1]: $t_R$=1.17 min, [M+1]$^+$=573.08.

Example 156

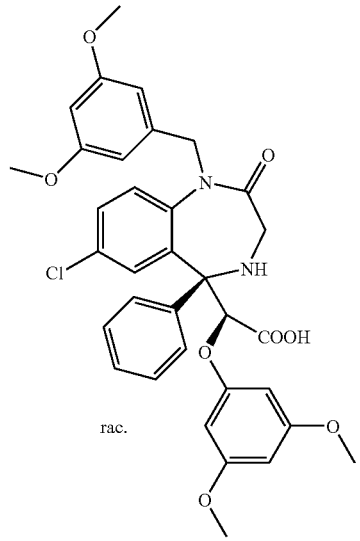

rac.

a) 7-Chloro-1-(3,5-dimethoxy-benzyl)-5-phenyl-1,3-dihydro-benzo[e][1,4]diazepin-2-one is prepared from 7-chloro-5-phenyl-1,3-dihydro-benzo[e][1,4]diazepin-2-one (Example 39) and 1-bromomethyl-3,5-dimethoxy-benzene according to Example 39. LC-MS[1]: $t_R$=1.12 min, [M+1]$^+$=421.03.

b) (±)-(1S*,9bS*)-8-Chloro-5-(3,5-dimethoxy-benzyl)-1-(3,5-dimethoxy-phenoxy)-9b-phenyl-5,9b-dihydro-1H-2a,5-diaza-benzo[a]cyclo-buta[c]cycloheptene-2,4-dione is prepared from 7-chloro-1-(3,5-dimethoxy-benzyl)-5-phenyl-1,3-dihydro-benzo[e][1,4]diazepin-2-one and (3,5-dimethoxy-phenoxy)-acetic acid (Example 1) according to Example 18. LC-MS[1]: $t_R$=1.24 min, [M+1]$^+$=615.05.

c) (±)-(S*)-[(5S*)-7-Chloro-1-(3,5-dimethoxy-benzyl)-2-oxo-5-phenyl-2,3,4,5-tetrahydro-1H-benzo[e][1,4]diazepin-5-yl]-(3,5-dimethoxy-phenoxy)-acetic acid is prepared from (±)-(1S*,9bS*)-8-chloro-5-(3,5-dimethoxy-benzyl)-1-(3,5-dimethoxy-phenoxy)-9b-phenyl-5,9b-dihydro-1H-2a,5-diaza-benzo[a]cyclobuta[c]cycloheptene-2,4-dione in analogy to Example 18. LC-MS[1]: $t_R$=1.16 min, [M+1]$^+$=633.07.

Example 157

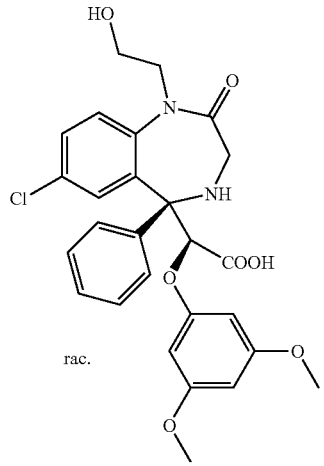

rac.

a) Acetic acid 2-(7-chloro-2-oxo-5-phenyl-2,3-dihydro-benzo[e][1,4]diazepin-1-yl)-ethyl ester is prepared from 7-chloro-5-phenyl-1,3-dihydro-benzo[e][1,4]diazepin-2-one (Example 39) and acetic acid 2-bromo-ethyl ester according to Example 39. LC-MS$^1$: $t_R$=0.98 min, [M+1]$^+$= 356.99; $^1$H-NMR (300 MHz, CDCl$_3$): 1.70 (s, 3H), 3.79 (d, J=10.7, 1H), 3.80–3.88 (m, 1H), 4.08–4.23 (m, 2H), 4.55–4.64 (m, 1H), 4.82 (d, J=10.7; 1H), 5.30 (s 1H), 7.30 (d, J=2.6, 1H), 7.37–7.61 (m, 7H).

b) (±)-Acetic acid 2-[(1S*,9bS*)-8-chloro-1-(3,5-dimethoxy-phenoxy)-2,4-dioxo-9b-phenyl-1,3,4,9b-tetrahydro-2H-2a,5-diaza-benzo[a]cyclo-buta[c]cyclohepten-5-yl]-ethyl ester is prepared from acetic acid 2-(7-chloro-2-oxo-5-phenyl-2,3-dihydrobenzo[e][1,4]diazepin-1-yl)-ethyl ester and (3,5-dimethoxy-phenoxy)-acetic acid (Example 1) according to Example 18. LC-MS$^1$: $t_R$=1.13 min, [M+1]$^+$=550.97.

c) (±)-(S*)-[(5S*)-7-Chloro-1-(2-hydroxy-ethyl)-2-oxo-5-phenyl-2,3,4,5-tetrahydro-1H-benzo[e][1,4]diazepin-5-yl]-(3,5-dimethoxy-phenoxy)-acetic acid is prepared from (±)-acetic acid 2-[(1S*,9bS*)-8-chloro-1-(3,5-dimethoxy-phenoxy)-2,4-dioxo-9b-phenyl-1,3,4,9b-tetrahydro-2H-2a,5-diaza-benzo[a]cyclo-buta[c]cyclohepten-5-yl]-ethyl ester in analogy to Example 18. LC-MS$^1$: $t_R$=0.93 min, [M+1]$^+$=527.03.

Example 158

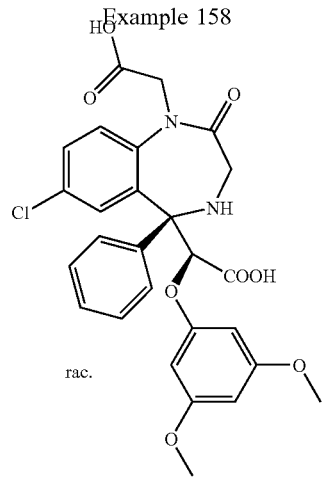

rac.

a) (7-Chloro-2-oxo-5-phenyl-2,3-dihydro-benzo[e][1,4]diazepin-1-yl)-acetic acid ethyl ester is prepared from 7-chloro-5-phenyl-1,3-dihydro-benzo[e][1,4]diazepin-2-one (Example 39) and bromo-acetic acid ethyl ester according to Example 39. LC-MS$^1$: $t_R$=1.04 min, [M+1]$^+$= 357.01.

b) (±)-[(1S*,9bS*)-8-Chloro-1-(3,5-dimethoxy-phenoxy)-2,4-dioxo-9b-phenyl-1,3,4,9b-tetrahydro-2H-2a,5-diaza-benzo[a]cyclobuta[c]cyclo-hepten-5-yl]-acetic acid ethyl ester is prepared from (7-chloro-2-oxo-5-phenyl-2,3-dihydro-benzo[e][1,4]diazepin-1-yl)-acetic acid ethyl ester and (3,5-dimethoxy-phenoxy)-acetic acid (Example 1) according to Example 18. LC-MS$^1$: $t_R$=1.18 min, [M+1]$^+$= 551.02.

c) (±)-(S*)-((5S*)-1-Carboxymethyl-7-chloro-2-oxo-5-phenyl-2,3,4,5-tetrahydro-1H-benzo[e][1,4]diazepin-5-yl)-(3,5-dimethoxy-phenoxy)-acetic acid is prepared from (±)-[(1S*,9bS*)-8-Chloro-1-(3,5-dimethoxy-phenoxy)-2,4-dioxo-9b-phenyl-1,3,4,9b-tetrahydro-2H-2a,5-diaza-benzo[a]cyclobuta[c]cyclo-hepten-5-yl]-acetic acid ethyl ester in analogy to Example 18. LC-MS$^1$: $t_R$=0.94 min, [M+1]$^+$=540.99.

Example 159

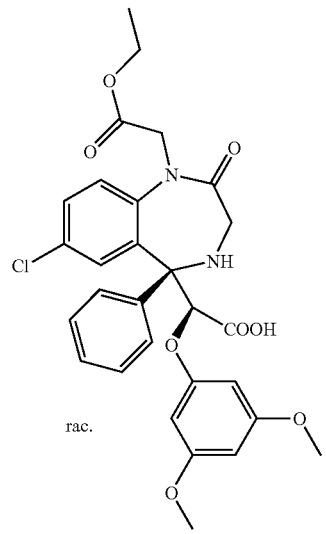

rac.

(±)-(S*)-((5S*)-7-Chloro-1-ethoxycarbonylmethyl-2-oxo-5-phenyl-2,3,4,5-tetrahydro-1H-benzo[e][1,4]diazepin-5-yl)-(3,5-dimethoxy-phenoxy)-acetic acid is isolated as a second product in Example 158. LC-MS$^1$: $t_R$=1.08 min, [M+1]$^+$=569.03.

Example 160

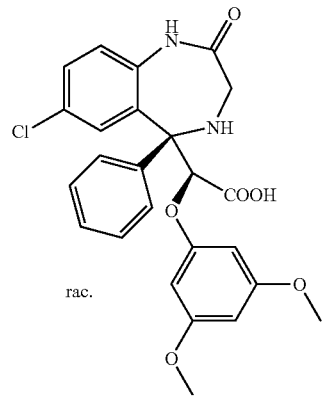

rac.

a) Acetic acid 7-chloro-2-oxo-5-phenyl-2,3-dihydro-benzo[e][1,4]diazepin-1-ylmethyl ester is prepared starting from 7-chloro-5-phenyl-1,3-dihydro-benzo[e][1,4]diazepin-2-one (Example 39) and bromomethyl acetate in analogy to Example 39. LC-MS$^1$: $t_R$=1.04 min, [M+1]$^+$= 343.00.

b) (±)-Acetic acid (1S*,9bS*)-8-chloro-1-(3,5-dimethoxy-phenoxy)-2,4-dioxo-9b-phenyl-1,3,4,9b-tetrahydro-2H-2a,5-diaza-benzo[a]cyclo-buta[c]cyclohepten-5-ylmethyl ester is prepared from acetic acid 7-chloro-2-oxo-5-phenyl-2,3-dihydro-benzo[e][1,4]diazepin-1-ylmethyl ester and (3,5-dimethoxy-phenoxy)-acetic acid (Example 1) in analogy to Example 18. LC-MS$^1$: $t_R$=1.13 min, [M+1]$^+$= 537.01.

c) Treating (±)-acetic acid (1S*,9bS*)-8-chloro-1-(3,5-dimethoxy-phenoxy)-2,4-dioxo-9b-phenyl-1,3,4,9b-tetrahydro-2H-2a,5-diaza-benzo[a]cyclo-buta[c]cyclohepten-5-ylmethyl ester with LiOH.H₂O as described in Example 18 yields (±)-(S)-((5S*)-7-chloro-2-oxo-5-phenyl-2,3,4,5-tetrahydro-1H-benzo[e][1,4]diazepin-5-yl)-(3,5-dimethoxy-phenoxy)-acetic acid. LC-MS¹: $t_R$=0.81 min, [M+1]⁺=482.97.

Example 161

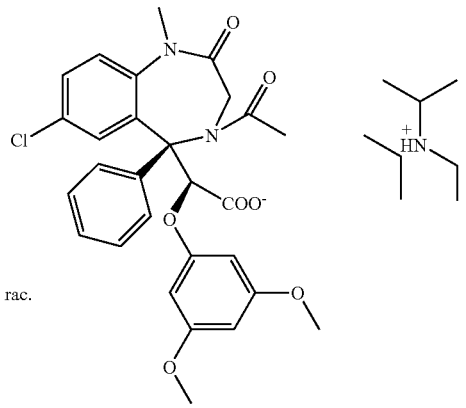

A solution of (±)-(S*)-((5S*)-7-chloro-1-methyl-2-oxo-5-phenyl-2,3,4,5-tetrahydro-1H-benzo[e][1,4]diazepin-5-yl)-(3,5-dimethoxy-phenoxy)-acetic acid (32 mg, 64 µmol) (Example 149), N-ethyldiisopropylamine (55 µl, 320 µmol) and chlorotrimethylsilane (9 µl, 77 µmol) in dry THF (4 ml) is stirred for 1.5 h at 55° C. Acetyl chloride (7 µl, 96 µmol) is added at rt and the mixture is stirred at rt for 2 h. The solution is poured into 0.01 M aq. HCl and extracted twice with DCM. The organic phase is dried over Na₂SO₄ and evaporated. The crude product is purified by MPLC to give ethyl-diisopropyl-ammonium (±)-(1S*)-((5S*)-4-acetyl-7-chloro-1-methyl-2-oxo-5-phenyl-2,3,4,5-tetrahydro-1H-benzo[e][1,4]diazepin-5-yl)-(3,5-dimethoxy-phenoxy)-acetate (14 mg) as a light beige solid. LC-MS²: $t_R$=4.43 min, [M+1]⁺=539.10, [M−1]⁻=537.18.

Example 162

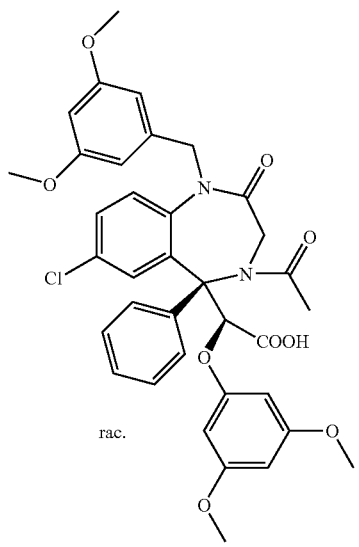

(±)-(S*)-[(5S*)-4-Acetyl-7-chloro-1-(3,5-dimethoxy-benzyl)-2-oxo-5-phenyl-2,3,4,5-tetrahydro-1H-benzo[e][1, 4]diazepin-5-yl]-(3,5-dimethoxy-phenoxy)-acetic acid is prepared from (±)-(S*)-[(5S*)-7-chloro-1-(3,5-dimethoxy-benzyl)-2-oxo-5-phenyl-2,3,4,5-tetrahydro-1H-benzo[e][1,4]diazepin-5-yl]-(3,5-dimethoxy-phenoxy)-acetic acid (Example 156) in analogy to Example 16. LC-MS¹: $t_R$=0.89 min, [M+1]⁺=675.04.

Example 163

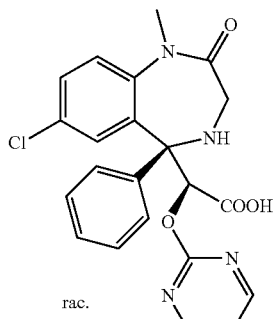

a) (±)-(1S*,9bS*)-1-benzyloxy-8-chloro-5-methyl-9b-phenyl-5,9b-dihydro-1H-2a,5-diaza-benzo[a]cyclo-buta[c]cycloheptene-2,4-dione (Example 39) is subjected to hydrogenolysis as described in Example 18 under 6 atm of H₂ at rt for 75 min. This gives a 4:1 mixture of (±)-(1S*,9bS*)-8-chloro-1-hydroxy-5-methyl-9b-phenyl-5,9b-dihydro-1H-2a,5-diaza-benzo[a]cyclo-buta[c]cyclo-heptene-2,4-dione and (±)-(1S*,9bS*)-1-hydroxy-5-methyl-9b-phenyl-5,9b-dihydro-1H-2a,5-diaza-benzo[a]cyclo-buta[c]cyclo-heptene-2,4-dione which is not separated. LC-MS²: $t_R$=0.88 min, [M+1]⁺=342.91; LC-MS² (dechlorinated product): $t_R$=0.81 min, [M+1]⁺=309.00.

b) A mixture of (±)-(1S*,9bS*)-8-chloro-1-hydroxy-5-methyl-9b-phenyl-5,9b-dihydro-1H-2a,5-diaza-benzo[a]cyclo-buta[c]cycloheptene-2,4-dione (150 mg, 0.44 mmol, containing 20% of (±)-(1S*,9bS*)-1-hydroxy-5-methyl-9b-phenyl-5,9b-dihydro-1H-2a,5-diaza-benzo[a]cyclobuta[c]cyclo-heptene-2,4-dione), NaH (23 mg, 55% in mineral oil, 0.57 mmol) and 2-chloropyrimidine (65 mg, 0.57 mmol) in THF (5 ml) is strirred at rt for 1 h, then at 55° C. for 3.5 h, before it is diluted with water and sat. aq. NaHCO₃, and extracted with EA. The organic phase is washed with brine, dried over MgSO₄ and evaporated. The crude product is purified by column chromatography on silica gel eluting with heptane:EA 2:1 to furnish (±)-(1S*,9bS*)-8-chloro-5-methyl-9b-phenyl-1-(pyrimidin-2-yloxy)-5,9b-dihydro-1H-2a,5-diaza-benzo[a]cyclobuta[c]cycloheptene-2,4-dione (85 mg) as a white solid. LC-MS²: $t_R$=0.98 min, [M+1]⁺=420.98.

c) Treating (±)-(1S*,9bS*)-8-chloro-5-methyl-9b-phenyl-1-(pyrimidin-2-yloxy)-5,9b-dihydro-1H-2a,5-diaza-benzo[a]cyclobuta[c]cycloheptene-2,4-dione with LiOH.H₂O in analogy to Example 18 furnishes (±)-(S*)-((5S*)-7-chloro-1-methyl-2-oxo-5-phenyl-2,3,4,5-tetrahydro-1H-benzo[e][1,4]di-azepin-5-yl)-(pyrimidin-2-yloxy)-acetic acid. LC-MS²: $t_R$=0.66 min, [M+1]⁺=438.99.

Example 164

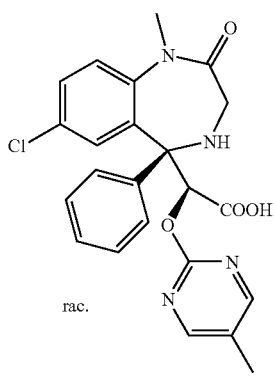

rac.

a) (±)-(1S*,9bS*)-8-Chloro-5-methyl-1-(5-methyl-pyrimidin-2-yloxy)-9b-phenyl-5,9b-dihydro-1H-2a,5-diaza-benzo[a]cyclobuta[c]cycloheptene-2,4-dione is prepared in analogy to Example 163, starting from (±)-(1S*,9bS*)-8-chloro-1-hydroxy-5-methyl-9b-phenyl-5,9b-dihydro-1H-2a,5-diaza-benzo[a]cyclobuta[c]cycloheptene-2,4-dione (Example 163) and 2-chloro-5-methyl-pyrimidine (prepared according to procedures described by T. Ueda, J. J. Fox, J. Med. Chem., 6, (1963), 697–701 and D. J. Brown, T. Nagamatsu, Aust. J. Chem., 30, (1977), 2515–2525). LC-MS¹: $t_R$=1.03 min, [M+1]⁺=435.01.

b) To a solution of (±)-(1S*,9bS*)-8-chloro-5-methyl-1-(5-methyl-pyrimidin-2-yloxy)-9b-phenyl-5,9b-dihydro-1H-2a,5-diaza-benzo[a]cyclobuta[c]cycloheptene-2,4-dione (40 mg, 92 µmol) in THF (2 ml) and methanol (500 µl) is added lithium hydroxyde monohydrate (4.6 mg, 110 µmol), dissolved in water (1 ml). The solution is stirred for 24 h at rt. Lithium hydroxyde monohydrate (4 mg, 95 µmol), dissolved in water (500 µl), is added and the solution is stirred for 6 h at rt. The solution is diluted with water and the organic solvents are evaporated in vacuo. The solution is acidified to pH 6 and the mixture is lyophilized. The residue is purified by prep. HPLC to give (±)-(S*)-((5S*)-7-chloro-1-methyl-2-oxo-5-phenyl-2,3,4,5-tetrahydro-1H-benzo[e][1,4]diazepin-5-yl)-(5-methyl-pyrimidin-2-yloxy)-acetic acid (13 mg) as a white powder. LC-MS¹: $t_R$=0.89 min, [M+1]⁺=452.98.

Example 165

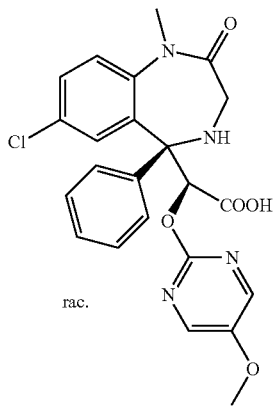

rac.

a) (±)-(1S*,9bS*)-8-Chloro-1-(5-methoxy-pyrimidin-2-yloxy)-5-methyl-9b-phenyl-5,9b-dihydro-1H-2a,5-diaza-benzo[a]cyclobuta[c]cycloheptene-2,4-dione is prepared in analogy to Example 163, starting from 8-chloro-1-hydroxy-5-methyl-9b-phenyl-5,9b-dihydro-1H-2a,5-diaza-benzo[a]cyclobuta[c]cyclo-heptene-2,4-dione (Example 163) and 2-methanesulfonyl-5-methoxy-pyrimidine (prepared according to procedures described by H. C. Koppel, R. H. Springer, R. K. Robins, C. C. Cheng, J. Org. Chem., 27, (1962), 3614–3617 and E. Merifield, E. J. Thomas, J. Chem. Soc., Perkin Trans I, (1999), 3269–3283). LC-MS¹: $t_R$=1.01 min, [M+1]⁺=450.98.

b) (±)-(S*)-((5S*)-7-chloro-1-methyl-2-oxo-5-phenyl-2,3,4,5-tetrahydro-1H-benzo[e][1,4]diazepin-5-yl)-(5-methoxy-pyrimidin-2-yloxy)-acetic acid (44 mg) is obtained by treating (±)-(1S*,9bS*)-8-chloro-1-(5-methoxy-pyrimidin-2-yloxy)-5-methyl-9b-phenyl-5,9b-dihydro-1H-2a,5-diaza-benzo[a]cyclobuta[c]cycloheptene-2,4-dione (110 mg, 244 µmol) with LiOH.H₂O as described in Example 164. LC-MS¹: $t_R$=0.89 min, [M+1]⁺=468.97.

Example 166

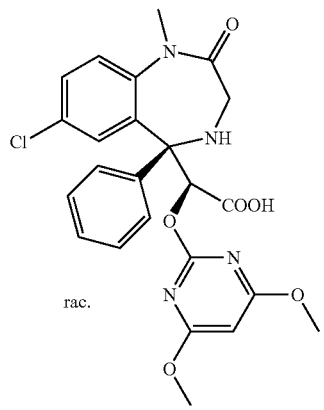

rac.

(±)-(1S*)-((5S*)-7-Chloro-1-methyl-2-oxo-5-phenyl-2,3,4,5-tetrahydro-1H-benzo[e][1,4]diazepin-5-yl)-(4,6-dimethoxy-pyrimidin-2-yloxy)-acetic acid is prepared in analogy to Example 163 starting from (±)-(1S*,9bS*)-8-chloro-1-hydroxy-5-methyl-9b-phenyl-5,9b-dihydro-1H-2a,5-diaza-benzo[a]cyclobuta[c]cycloheptene-2,4-dione (Example 163) and 2-methanesulfonyl-4,6-dimethoxy-pyrimidine (Example 8). LC-MS¹: $t_R$=0.96 min, [M+1]⁺=498.99.

Example 167

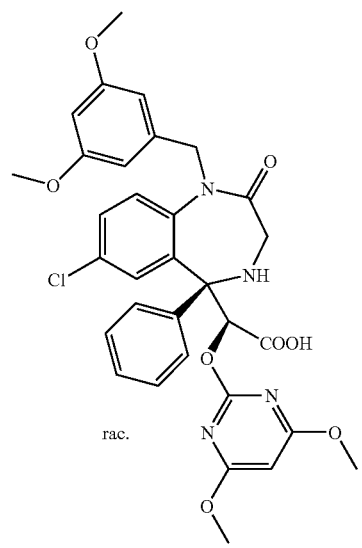

rac.

a) (±)-(1S*,9bS*)-1-Benzyloxy-8-chloro-5-(3,5-dimethoxy-benzyl)-9b-phenyl-5,9b-dihydro-1H-2a,5-diaza-benzo[a]cyclobuta[c]cycloheptene-2,4-dione is obtained from 7-chloro-1-(3,5-dimethoxy-benzyl)-5-phenyl-1,3-dihydro-benzo[e][1,4]diazepin-2-one (Example 156) and benzyloxy-acetic acid (Example 18) according to Example 18. LC-MS$^1$: $t_R$=1.25 min, [M+1]$^+$=569.02.

b) A suspension of (±)-(1S*,9bS*)-1-benzyloxy-8-chloro-5-(3,5-dimethoxy-benzyl)-9b-phenyl-5,9b-dihydro-1H-2a,5-diaza-benzo[a]cyclobuta[c]cyclo-heptene-2,4-dione (540 mg, 949 µmol), 10% Pd on charcoal (100 mg) and acetic acid (217 µl, 3.79 mmol) in THF (10 ml) and ethanol (10 ml) is stirred for 40 min at rt under 6 atm of hydrogen. 10% Pd on charcoal (100 mg) is added and the suspension is stirred for 2 h at rt under 6 atm of hydrogen. Acetic acid (435 µl, 7.61 mmol) is added and the suspension is stirred for 2.5 h at rt under 6 atm of hydrogen. 10% Pd on charcoal (100 mg) is added and the suspension is stirred for 18 h at rt under 6 atm of hydrogen. 10% Pd on charcoal (100 mg) is added and the suspension is stirred for 6 h at rt under 7.5 atm of hydrogen. The suspension is filtered through celite and the filtrate is evaporated in vacuo. The crude product is purified by column chromatography (silicagel, heptane/EA 2:1 to 1:2) to give (±)-(1S*,9bS*)-8-chloro-5-(3,5-dimethoxy-benzyl)-1-hydroxy-9b-phenyl-5,9b-dihydro-1H-2a,5-diaza-benzo[a]cyclobuta[c]cycloheptene-2,4-dione (248 mg) as a white solid. LC-MS$^1$: $t_R$=1.03 min, [M+1]$^+$=479.02.

c) (±)-(1S*,9bS*)-8-Chloro-5-(3,5-dimethoxy-benzyl)-1-(4,6-dimethoxy-pyrimidin-2-yloxy)-9b-phenyl-5,9b-dihydro-1H-2a,5-diaza-benzo[a]cyclobuta[c]cycloheptene-2,4-dione is synthesized from (±)-(1S*,9bS*)-8-chloro-5-(3,5-dimethoxy-benzyl)-1-hydroxy-9b-phenyl-5,9b-dihydro-1H-2a,5-diaza-benzo[a]cyclobuta[c]cycloheptene-2,4-dione and 2-methanesulfonyl-4,6-dimethoxy-pyrimidine (Example 8) in analogy to Example 18. LC-MS$^1$: $t_R$=1.24 min, [M+1]$^+$=617.01.

d) (±)-(1S*)-[(5S*)-7-Chloro-1-(3,5-dimethoxy-benzyl)-2-oxo-5-phenyl-2,3,4,5-tetrahydro-1H-benzo[e][1,4]diazepin-5-yl]-(4,6-dimethoxy-pyrimidin-2-yloxy)-acetic acid is prepared from (±)-(1S*,9bS*)-8-chloro-5-(3,5-dimethoxy-benzyl)-1-(4,6-dimethoxy-pyrimidin-2-yloxy)-9b-phenyl-5,9b-dihydro-1H-2a,5-diaza-benzo[a]cyclobuta[c]cyclo-heptene-2,4-dione in analogy to Example 147. LC-MS$^1$: $t_R$=1.07 min, [M+1]$^+$=635.05.

Example 168

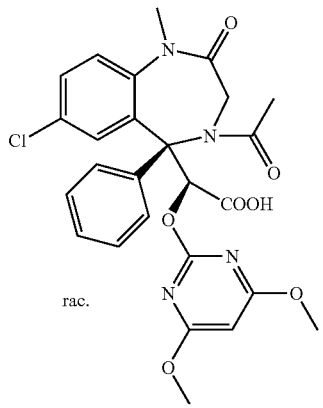

(±)-(1S*)-((5S*)-4-Acetyl-7-chloro-1-methyl-2-oxo-5-phenyl-2,3,4,5-tetrahydro-1H-benzo[e][1,4]diazepin-5-yl]-(4,6-dimethoxy-pyrimidin-2-yloxy)-acetic acid is prepared in analogy to Example 16, starting from of (±)-(1S*)-((5S*)-7-chloro-1-methyl-2-oxo-5-phenyl-2,3,4,5-tetrahydro-1H-benzo[e][1,4]diazepin-5-yl)-(4,6-dimethoxy-pyrimidin-2-yloxy)-acetic acid (Example 166). LC-MS$^1$: $t_R$=0.73 min, [M+1]$^+$=541.03.

Example 169

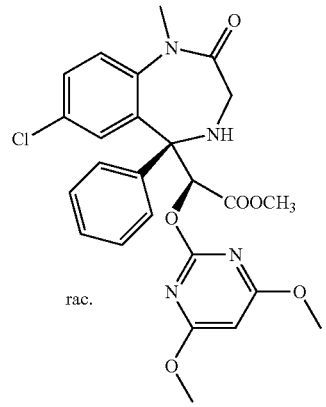

(±)-(S*)-(5S*)-7-Chloro-1-methyl-2-oxo-5-phenyl-2,3,4,5-tetrahydro-1H-benzo[e][1,4]diazepin-5-yl)-(4,6-dimethoxy-pyrimidin-2-yloxy)-acetic acid methyl ester is prepared in analogy to Example 131. LC-MS$^1$: $t_R$=0.94 min, [M+1]$^+$=513.01.

Example 170

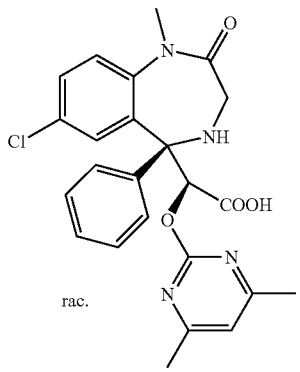

(±)-(1S*)-((5S*)-7-Chloro-1-methyl-2-oxo-5-phenyl-2,3,4,5-tetra-hydro-1H-benzo[e][1,4]diazepin-5-yl)-(4,6-dimethyl-pyrimidin-2-yloxy)-acetic acid is prepared in analogy to Example 163, starting from (±)-(1S*,9bS*)-8-chloro-1-hydroxy-5-methyl-9b-phenyl-5,9b-dihydro-1H-2a,5-diaza-benzo[a]cyclo-buta[c]cyclo-heptene-2,4-dione (Example 163) and 2-methanesulfonyl-4,6-dimethyl-pyrimidine (Example 19). LC-MS$^1$: $t_R$=0.67 min, [M+1]$^+$=467.01.

Example 171

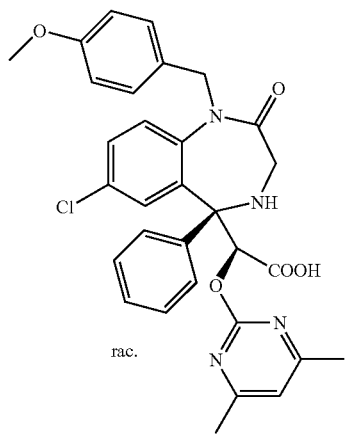

rac.

a) (±)-(1S*,9bS*)-1-Benzyloxy-8-chloro-5-(4-methoxy-benzyl)-9b-phenyl-5,9b-dihydro-1H-2a,5-diaza-benzo[a]cyclobuta[c]cycloheptene-2,4-dione is prepared starting from 7-chloro-1-(4-methoxy-benzyl)-5-phenyl-1,3-dihydro-benzo[e][1,4]diazepin-2-one (prepared in analogy to Example 39) and benzyloxyacetyl chloride in analogy to Example 27. LC-MS[1]: $t_R$=1.26 min, [M+1]$^+$=539.03.

b) A suspension of Pd/C (400 mg, 10% Pd) in THF (5 ml) is added to a solution of (±)-(1S*,9bS*)-1-benzyloxy-8-chloro-5-(4-methoxy-benzyl)-9b-phenyl-5,9b-dihydro-1H-2a,5-diaza-benzo[a]cyclo-buta[c]cycloheptene-2,4-dione (5.0 g, 9.28 mmol) in THF (25 ml), ethanol (25 ml) and 1,2-dichlorobenzene (30 ml). The mixture is stirred at rt under 1 atm H$_2$ for 165 min before the catalyst is filtered off. The filtrate is partially evaporated and the product precipitates from the remaining 1,2-dichlorobenzene. The product is collected, washed with diethyl ether and dried to give (±)-(1S*,9bS*)-8-chloro-1-hydroxy-5-(4-methoxy-benzyl)-9b-phenyl-5,9b-dihydro-1H-2a,5-diaza-benzo[a]cyclobuta[c]cycloheptene-2,4-dione (4.03 g) as a white powder. No dechlorination is observed. LC-MS[1]: $t_R$=1.03 min, [M+1]$^+$=448.99.

c) (±)-(1S*,9bS*)-8-chloro-1-hydroxy-5-(4-methoxy-benzyl)-9b-phenyl-5,9b-dihydro-1H-2a,5-diaza-benzo[a]cyclobuta[c]cycloheptene-2,4-dione is reacted with 2-methanesulfonyl-4,6-dimethyl-pyrimidine (Example 19) as described in Example 25 to give (±)-(1S*,9bS*)-8-chloro-1-(4,6-dimethyl-pyrimidin-2-yloxy)-5-(4-methoxy-benzyl)-9b-phenyl-5,9b-dihydro-1H-2a,5-diaza-benzo[a]cyclobuta[c]cycloheptene-2,4-dione. LC-MS[1]: $t_R$=1.20 min, [M+1]$^+$=555.04.

d) (±)-(1S*,9bS*)-8-chloro-1-(4,6-dimethyl-pyrimidin-2-yloxy)-5-(4-methoxy-benzyl)-9b-phenyl-5,9b-dihydro-1H-2a,5-diaza-benzo[a]cyclo-buta[c]cycloheptene-2,4-dione is treated with LiOH.H$_2$O as described in Example 25 to furnish (±)-(S*)-[(5S*)-7-chloro-1-(4-methoxy-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid. LC-MS[1]: $t_R$=1.09 min, [M+1]$^+$=573.07.

Example 172

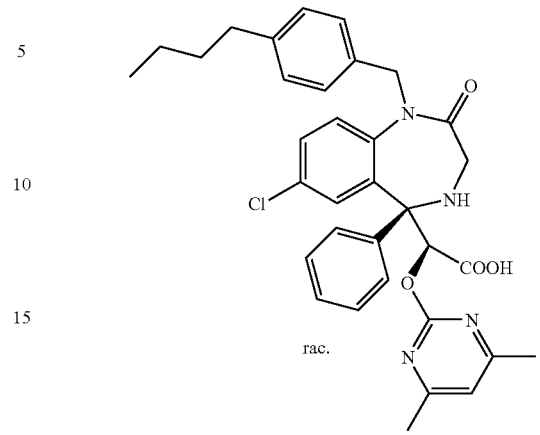

rac.

a) (±)-(1S*,9bS*)-8-chloro-1-(4,6-dimethyl-pyrimidin-2-yloxy)-5-(4-methoxy-benzyl)-9b-phenyl-5,9b-dihydro-1H-2a,5-diaza-benzo[a]cyclo-buta[c]cycloheptene-2,4-dione (Example 171) is treated with ammonium cerium (IV)nitrate as described in Example 48 to furnish (±)-(1S*,9bS*)-8-chloro-1-(4,6-dimethyl-pyrimidin-2-yloxy)-9b-phenyl-5,9b-dihydro-1H-2a,5-diaza-benzo[a]cyclobuta[c]cycloheptene-2,4-dione. LC-MS[1]: $t_R$=0.99 min, [M+1]$^+$=435.03.

b) In analogy to Example 48, (±)-(S*)-[(5S*)-1-(4-butyl-benzyl)-7-chloro-2-oxo-5-phenyl-2,3,4,5-tetrahydro-1H-benzo[e][1,4]diazepin-5-yl]-(4,6-dimethyl-pyrimidin-2-yloxy)-acetic acid is obtained starting from (±)-(1S*,9bS*)-8-chloro-1-(4,6-dimethyl-pyrimidin-2-yloxy)-9b-phenyl-5,9b-dihydro-1H-2a,5-diaza-benzo[a]cyclobuta[c]cycloheptene-2,4-dione and 4-butylbenzyl bromide (prepared from 4-butylbenzylalcohol). LC-MS[1]: $t_R$=1.32 min, [M+1]$^+$=599.14.

Example 173 to 178

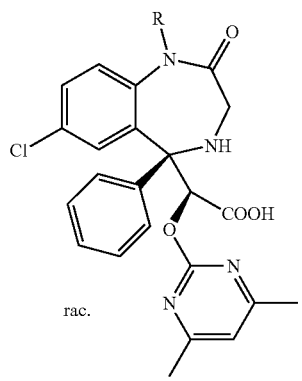

rac.

In analogy to Example 172 the following compounds are prepared:

| Example | R | $t_R$ (LC-MS[1]) [min] | [M + 1]+ |
|---|---|---|---|
| 173 | (2,4,6-trifluorobenzyl) | 1.12 | 597.05 |
| 174 | (2,3,4-trifluorobenzyl) | 1.14 | 597.06 |
| 175 | (2,6-dichlorobenzyl) | 1.15 | 611.01 |
| 176 | (2,3,6-trifluorobenzyl) | 1.10 | 597.05 |
| 177 | (3,4,5-trifluorobenzyl) | 1.14 | 597.03 |
| 178 | (2,4,5-trifluorobenzyl) | 1.13 | 597.02 |

Example 179

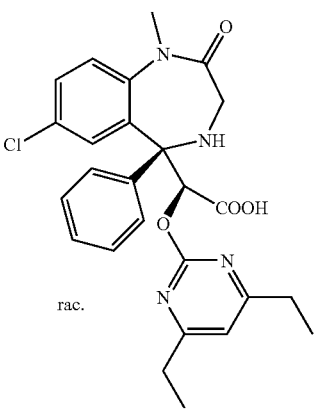

(±)-(S*)-((5S*)-7-Chloro-1-methyl-2-oxo-5-phenyl-2,3,4,5-tetrahydro-1H-benzo[e][1,4]diazepin-5-yl)-(4,6-di-ethyl-pyrimidin-2-yloxy)-acetic acid is prepared in analogy to Examples 29 and 163. LC-MS[1]: $t_R$=1.01 min, [M+1]+= 495.06.

Example 180

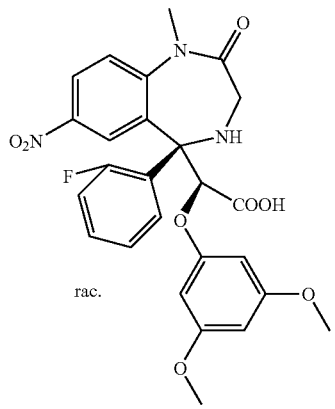

(±)-(S*)-(3,5-Dimethoxy-phenoxy)-[(5S*)-5-(2-fluoro-phenyl)-1-methyl-7-nitro-2-oxo-2,3,4,5-tetrahydro-1H-benzo[e][1,4]diazepin-5-yl]-acetic acid is prepared starting from flunitrazepam (5-(2-fluoro-phenyl)-1-methyl-7-nitro-1,3-dihydro-benzo[e][1,4]diazepin-2-one) and (3,5-dimethoxy-phenoxy)-acetic acid (Example 1) in analogy to Example 18. LC-MS[1]: $t_R$=0.82 min, [M+1]+=526.02.

Example 181

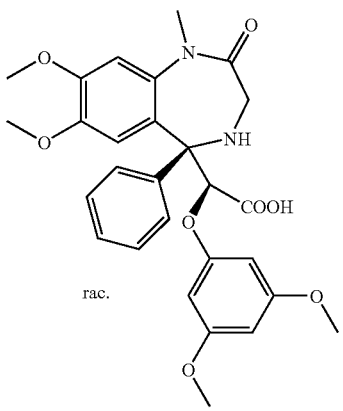

a) A solution of 2-amino-4,5-dimethoxybenzonitrile (8.0 g, 45 mmol) in THF (50 ml) is added dropwise at 5° C. to a solution of phenyl magnesiumbromide (45 ml 3 M in diethyl ether, 135 mmol) in THF (100 ml). The resulting orange brown solution is stirred at rt for 1 h, at 55° C. for 2.5 h before the reaction is quenched at 0° C. with 2 N aq. HCl. The mixture is stirred at acidic pH, then neutralized with aq. NaOH. The organic phase is separated, the aq. phase is extracted three times with EA. The combined organic phase is washed with brine, dried over MgSO4 and evaporated to give 2-(imino-phenyl-methyl)-4,5-dimethoxy-phenylamine (12.0 g) as a brown oil. LC-MS[1]: $t_R$=1.10 min, [M+1]+=257.10.

b) (In analogy to a procedure described by L. Berger, L. H. Sternbach, in U.S. Pat. No. 3,268,586) A solution of 2-(imino-phenyl-methyl)-4,5-dimethoxy-phenylamine (2.0 g, 7.77 mol) and glycine ethyl ester hydrochloride (1.74 g, 12.4 mmol) in pyridine (50 ml) is stirred at reflux for 8 h before it is evaporated. Remaining pyridine is coevaporated with toluene. The product is crystallised from methanol at 0° C. The material is collected and dried to give 7,8-dimethoxy-5-phenyl-1,3-dihydro-benzo[e][1,4]diazepin-2-one (1.35 g) as a beige powder. LC-MS[1]: $t_R$=0.71 min, [M+1]$^+$=297.04.

c) 7,8-Dimethoxy-5-phenyl-1,3-dihydro-benzo[e][1,4]diazepin-2-one is methylated as described in Example 39 to give 7,8-dimethoxy-1-methyl-5-phenyl-1,3-dihydro-benzo[e][1,4]diazepin-2-one as a yellow foam. $^1$H-NMR (300 MHz, CDCl$_3$): 3.39 (s, 3H), 3.74 (s, 3H), 3.79 (d, J=10.5, 1H), 3.97 (s, 3H), 4.79 (d, J=10.5, 1H), 6.69 (s, 1H), 6.77 (s, 1H), 7.36–7.46 (m, 3H), 7.62–7.68 (m, 2H). LC-MS[1]: $t_R$=0.73 min, [M+1]$^+$=311.04.

d) (±)-(S*)-((5S*)-7,8-Dimethoxy-1-methyl-2-oxo-5-phenyl-2,3,4,5-tetrahydro-1H-benzo[e][1,4]diazepin-5-yl)-(3,5-dimethoxy-phenoxy)-acetic acid is obtained in analogy to Example 18. LC-MS[1]: $t_R$=0.77 min, [M+1]$^+$=523.10.

Example 182

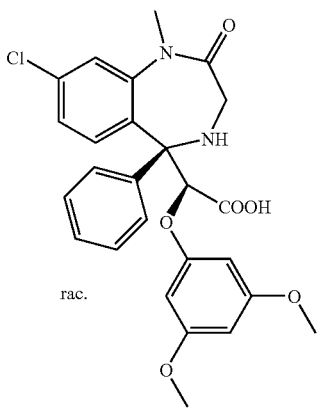

(±)-(S*)-((5S*)-8-Chloro-1-methyl-2-oxo-5-phenyl-2,3,4,5-tetrahydro-1H-benzo[e][1,4]diazepin-5-yl)-(3,5-dimethoxy-phenoxy)-acetic acid is prepared in analogy to Example 181. LC-MS[1]: $t_R$=0.91 min, [M+1]$^+$=497.02.

Example 183

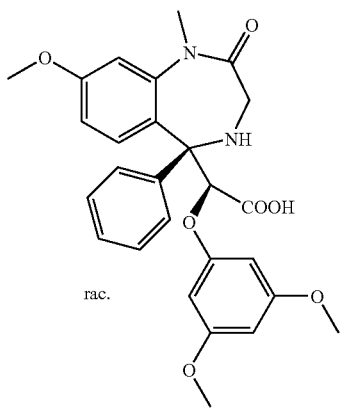

a) 4-Methoxy-2-nitro-benzonitrile is obtained from 4-methoxy-2-nitro-phenylamine according to procedures described by J. Qiu, S. H. Stevenson, M. J. O'Beirne, R. B. Silverman, *J. Med. Chem.*, 42, (1999), 329–332.

b) A suspension of 4-methoxy-2-nitro-benzonitrile (7.24 g, 40.6 mmol) and 10% Pd on charcoal (724 mg) in dry ethanol (100 ml) is stirred for 2 h under an atmosphere of hydrogen gas (balloon). The mixture is filtered through celite and the filtrate evaporated. The crude product is purified by column chromatography (silica gel, heptane/EA 3:1) to give 2-amino-4-methoxy-benzonitrile (1.8 g) as a green powder. LC-MS[2]: $t_R$=3.43 min, [M+1]$^+$=149.02.

c) A 3 M solution of phenyl magnesium bromide in diethylether (18.9 ml, 56.7 mmol) is diluted with dry THF (30 ml) and cooled to 0° C. 2-Amino-4-methoxy-benzonitrile (2.8 g, 18.9 mmol), dissolved in dry THF (20 ml), is added. The suspension is stirred for 30 min at 0° C., then for 2 h at rt and for 18 h at 40° C. The mixture is acidified with 2 M aq. HCl, then basified with 2 M aq NaOH. The aqueous phase is extracted three times with diethylether. The organic phase is washed with sat. aq. NaCl, dried over MgSO$_4$ and evaporated to give (2-amino-4-methoxy-phenyl)-phenyl-methanone (3.2 g) as an orange-brown oil. LC-MS[1]: $t_R$=0.73 min, [M+1]$^+$=227.12.

d) 8-methoxy-5-phenyl-1,3-dihydro-benzo[e][1,4]diazepin-2-one is obtained from (2-amino-4-methoxy-phenyl)-phenyl-methanone and glycine methyl ester hydrochloride in analogy to procedures described by H. Umemiya, H. Fukasawa, M. Ebisawa, L. Eyrolles, E. Kawachi, G. Eisenmann, H. Gronemeyer, Y. Hashimoto, K. Shudo, H. Kagechika, *J. Med. Chem.*, 40, (1997), 4222–4234. LC-MS[1]: $t_R$=0.73 min, [M+1]$^+$=267.00.

e) To a solution of 8-methoxy-5-phenyl-1,3-dihydro-benzo[e][1,4]diazepin-2-one (1 g, 3.76 mmol) in dry DMF (25 ml) is slowly added NaH (60% in mineral oil) (180 mg, 4.50 mmol) at 0° C. The suspension is stirred at 0° C. and allowed to slowly warm to rt. Stirring is continued for 16 h. The mixture is again cooled to 0° C. and iodomethane (258 µl, 4.13 mmol), dissolved in dry DMF (5 ml), is added. The suspension is stirred for 30 min at rt. Iodomethane (65 µl, 1.04 mmol), dissolved in dry DMF (2 ml), is added and the mixture stirred for 30 min at rt. The solution is poured into water. The aqueous phase is extracted three times with EA. The organic phase is dried over MgSO$_4$ and evaporated to give 8-methoxy-1-methyl-5-phenyl-1,3-dihydro-benzo[e][1,4]diazepin-2-one (1 g) as a yellow thick oil. LC-MS[1]: $t_R$=0.75 min, [M+1]$^+$=281.07.

f) (±)-(1S*,9bS*)-1-(3,5-dimethoxy-phenoxy)-7-methoxy-5-methyl-9b-phenyl-5,9b-dihydro-1H-2a,5-diaza-benzo[a]cyclobuta[c]cycloheptene-2,4-dione is prepared from 8-methoxy-1-methyl-5-phenyl-1,3-dihydro-benzo[e][1,4]diazepin-2-one and (3,5-dimethoxy-phenoxy)-acetic acid (Example 1b)) as described in Example 18. LC-MS[1]: $t_R$=1.07 min, [M+1]$^+$=475.06.

g) (±)-(S*)-(3,5-Dimethoxy-phenoxy)-((5S*)-8-methoxy-1-methyl-2-oxo-5-phenyl-2,3,4,5-tetrahydro-1H-benzo[e][1,4]diazepin-5-yl)-acetic acid is prepared from (±)-(1S*,9bS*)-1-(3,5-dimethoxy-phenoxy)-7-methoxy-5-methyl-9b-phenyl-5,9b-dihydro-1H-2a,5-diaza-benzo[a]cyclobuta[c]cycloheptene-2,4-dione in analogy to Example 18. LC-MS[1]: $t_R$=0.94 min, [M+1]$^+$=493.09.

Example 184

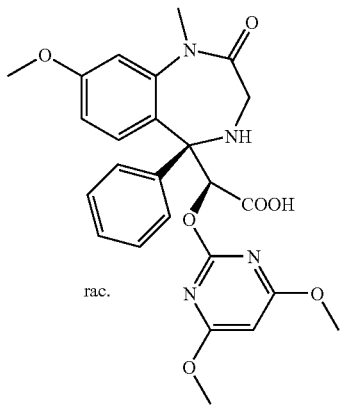
rac.

a) (±)-(1S*,9bS*)-1-Benzyloxy-7-methoxy-5-methyl-9b-phenyl-5,9b-dihydro-1H-2a,5-diaza-benzo[a]cyclobuta[c]cycloheptene-2,4-dione is obtained from 8-methoxy-1-methyl-5-phenyl-1,3-dihydro-benzo[e][1,4]diazepin-2-one (Example 183) and benzyloxyacetic acid (Example 18) in analogy to Example 18. LC-MS[1]: $t_R$=1.09 min, [M+1]$^+$=429.09.

b) A suspension of (±)-(1S*,9bS*)-1-benzyloxy-7-methoxy-5-methyl-9b-phenyl-5,9b-dihydro-1H-2a,5-diaza-benzo[a]cyclobuta[c]cycloheptene-2,4-dione (638 mg, 1.49 mmol), 10% Pd on charcoal (100 mg) and acetic acid (340 µl, 5.95 mmol) in THF (10 ml) and ethanol (6 ml) is stirred for 30 min at rt under 6 atm of hydrogen. 10% Pd on charcoal (100 mg) is added and the mixture is stirred for 16 h at rt under 6 atm of hydrogen. The suspension is filtered through celite and the filtrate evaporated to give (±)-(1S*,9bS*)-1-hydroxy-7-methoxy-5-methyl-9b-phenyl-5,9b-dihydro-1H-2a,5-diaza-benzo[a]cyclobuta[c]cycloheptene-2,4-dione (557 mg) as a light grey oil. LC-MS[1]: $t_R$=0.83 min, [M+1]$^+$=338.99.

c) (±)-(1S*,9bS*)-1-(4,6-Dimethoxy-pyrimidin-2-yloxy)-7-methoxy-5-methyl-9b-phenyl-5,9b-dihydro-1H-2a,5-diaza-benzo[a]cyclo-buta[c]cycloheptene-2,4-dione is obtained from (±)-(1S*,9bS*)-1-hydroxy-7-methoxy-5-methyl-9b-phenyl-5,9b-dihydro-1H-2a,5-diaza-benzo[a]cyclobuta[c]cycloheptene-2,4-dione and 2-methanesulfonyl-4,6-dimethoxy-pyrimidine (Example 8) in analogy to Example 18. LC-MS[1]: $t_R$=1.06 min, [M+1]$^+$=477.05.

d) (±)-(S*)-(4,6-Dimethoxy-pyrimidin-2-yloxy)-((5S*)-8-methoxy-1-methyl-2-oxo-5-phenyl-2,3,4,5-tetrahydro-1H-benzo[e][1,4]diazepin-5-yl)-acetic acid is prepared from (±)-(1S*,9bS*)-1-(4,6-dimethoxy-pyrimidin-2-yloxy)-7-methoxy-5-methyl-9b-phenyl-5,9b-dihydro-1H-2a,5-diaza-benzo[a]cyclobuta[c]cycloheptene-2,4-dione in analogy to Example 18.
LC-MS[1]: $t_R$=0.88 min, [M+1]$^+$=494.99.

Example 185

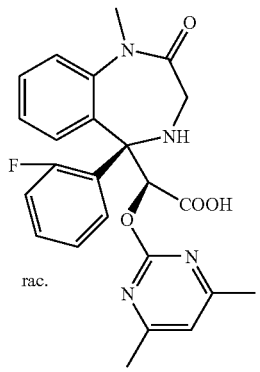
rac.

a) 7-Chloro-5-(2-fluoro-phenyl)-1-methyl-1,3-dihydro-benzo[e][1,4]diazepin-2-one is prepared in analogy to Example 39. LC-MS[2]: $t_R$=4.29 min, [M+1]$^+$=303.11.

b) (±)-(1S*,9bS*)-1-Benzyloxy-8-chloro-9b-(2-fluoro-phenyl)-5-methyl-5,9b-dihydro-1H-2a,5-diaza-benzo[a]cyclobuta[c]cycloheptene-2,4-dione is prepared in analogy to Example 25. LC-MS[2]: $t_R$=4.97 min, [M+1]$^+$=451.24.

c) Hydrogenolysis of (±)-(1S*,9bS*)-1-Benzyloxy-8-chloro-9b-(2-fluoro-phenyl)-5-methyl-5,9b-dihydro-1H-2a,5-diaza-benzo[a]cyclobuta[c]cyclo-heptene-2,4-dione as described in Example 25 gives (±)-(1S*,9bS*)-9b-(2-fluoro-phenyl)-1-hydroxy-5-methyl-5,9b-dihydro-1H-2a,5-diaza-benzo[a]cyclobuta[c]cycloheptene-2,4-dione. LC-MS[2]: $t_R$=3.33 min, [M+1]$^+$=327.17.

d) The introduction of the 4,6-dimethylpyrimidine and the β-lactam cleavage are carried out as described in Example 25 to give (±)-(S*)-(4,6-dimethyl-pyrimidin-2-yloxy)-[(5S*)-5-(2-fluoro-phenyl)-1-methyl-2-oxo-2,3,4,5-tetrahydro-1H-benzo[e][1,4]diazepin-5-yl]-acetic acid. LC-MS[2]: $t_R$=3.56 min, [M+1]$^+$=451.20, [M−1]$^−$=449.21.

Example 186

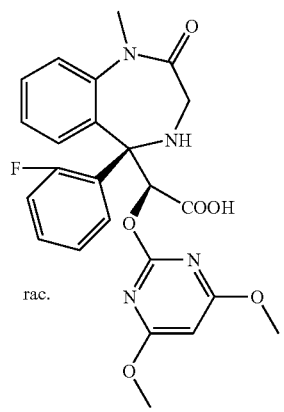
rac.

(±)-(S*)-(4,6-Dimethoxy-pyrimidin-2-yloxy)-[(5S*)-5-(2-fluoro-phenyl)-1-methyl-2-oxo-2,3,4,5-tetrahydro-1H-benzo[e][1,4]diazepin-5-yl]-acetic acid is prepared in analogy to the procedures given in Example 185. LC-MS[2]: $t_R$=3.80 min, [M+1]$^+$=483.24, [M−1]$^−$=481.20.

Example 187

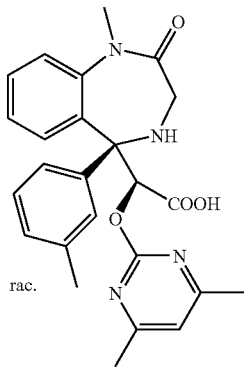

(±)-(S*)-(4,6-Dimethyl-pyrimidin-2-yloxy)-[(5S*)-1-methyl-2-oxo-5-m-tolyl-2,3,4,5-tetrahydro-1H-benzo[e][1,4]diazepin-5-yl]-acetic acid is obtained as a light yellow powder starting from (±)-(1S*,9bS*)-1-(4,6-dimethyl-pyrimidin-2-yloxy)-5-(4-methoxy-benzyl)-9b-m-tolyl-5,9b-dihydro-1H-2a,5-diaza-benzo[a]cyclobuta[c]cycloheptene-2,4-dione (Example 188), following the procedures described in Example 191. $^1$H-NMR (300 MHz, CDCl$_3$): 2.07 (s, 3H), 2.14 (s, 6H), 2.25 (s, 3H), 3.49 (s, 2H), 6.36 (s, 1H), 6.46 (s, 1H), 6.6–6.9 (m, 4H), 7.06 (dd, J=1.2, 7.6, 1H), 7.33 (t, J=7.02, 1H), 7.4 (td, J$_d$=1.2, J$_t$=7.6, 1H), 7.8 (m, 1H). LC-MS$^1$: t$_R$=0.84 min, [M+1]$^+$=447.

Example 188

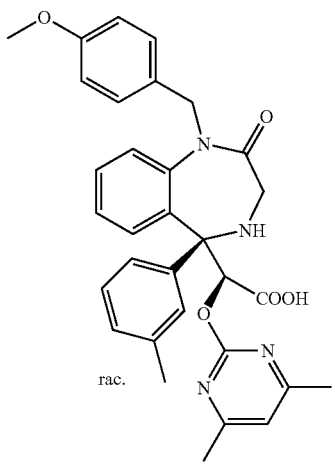

a) Toluene-3-magnesium bromide is prepared under Grignard conditions from magnesium turnings (2.67 g, 0.110 mol) and 3-bromo toluene (10 ml, 82.4 mmol) in anhydrous diethyl ether (45 ml). After refluxing the reaction mixture for 1 h, it is cooled to rt. A solution of 2-aminobenzo nitrile (3.24 g, 27.5 mmol) in diethylether (25 ml) is added dropwise. Upon completion of the addition, the Grignard solution is heated to reflux for 1 h, then cooled to rt. To the reaction mixture is added ice and the Grignard complex is decomposed with HCl conc. (25 ml), the solution is stirred at RT over 30 min, cooled to RT and rendered alkaline with 10% NaOH. The layers are separated, the aq. phase is extracted with diethylether (2×), the combined organic phases are washed with brine, dried over MgSO$_4$ and the solvent removed in vacuo to yield 2-(imino-m-tolyl-methyl)-phenylamine (5 g), which is not further purified. LC-MS$^1$: t$_R$=0.67 min, [M+1]$^+$=211.

b) 2-(imino-m-tolyl-methyl)-phenylamine (4.28 g, 20.3 mmol) and glycine ethylester hydrochloride (4.52 g, 32.4 mmol) are dissolved in abs. pyridine (70 ml) and heated to reflux over 15 h. Upon completion of the reaction, the solvent is removed in vacuo with toluene. The crude residue is purified by column chromatography on silica (0%–50% EA in DCM) to give 5-m-tolyl-1,3-dihydro-benzo[e][1,4]diazepin-2-one (1.0 g) as an orange foam. $^1$H-NMR (300 MHz, CDCl$_3$): 2.36 (s, 3H), 4.32 (s, 2H), 7.11–7.18 (m, 3H), 7.25 (d, J=1.3, 3H), 7.35 (dd, J=1.4, 7, 1H), 7.41 (s, 1H), 7.5 (m, 1H), 9.20 (s, 1H). LC-MS$^1$: t$_R$=0.68 min, [M+1]$^+$=251.

The the [2+2]-cycloaddition, the hydrogenation, the introduction of the 4,6-dimethyl pyrimidine moiety and the β-lactam cleavage are carried out as described in the procedures given in Example 192 to give (±)-(S*)-(4,6-dimethyl-pyrimidin-2-yloxy)-[(5S*)-1-(4-methoxy benzyl)-2-oxo-5-m-tolyl-2,3,4,5-tetrahydro-1H-benzo[e][1,4]diazepin-5-yl]-acetic acid. $^1$H-NMR 300 MHz, CDCl$_3$): 2.13 (s, 3H), 2.23 (s, 6H), 2.80 (d, J=14.6, 1H), 3.58 (m, 2H), 3.75 (s, 3H), 4.14 (d, J=14.6, 1H), 6.45 (s, 2H), 6.77 (d, J=8.8, 4H), 6.92 (d, J=7.6, 2H), 7.02 (d, J=8.8, 2H), 7.23–7.35 (m, 2H), 7.78 (m, 1H). LC-MS$^1$: t$_R$=1.01 min, [M+1]$^+$=553.

Example 189

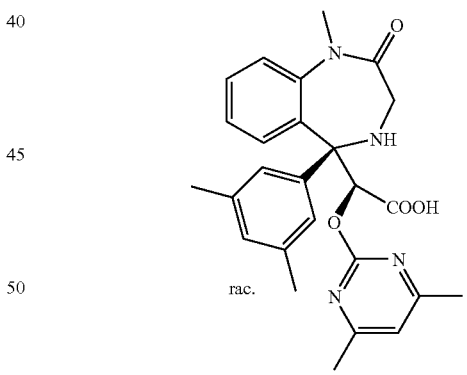

(±)-(S*)-[(5S*)-5-(3,5-Dimethyl-phenyl)-1-methyl-2-oxo-2,3,4,5-tetrahydro-1H-benzo[e][1,4]diazepin-5-yl]-(4,6-dimethyl-pyrimidin-2-yloxy)-acetic acid is obtained as a light yellow powder starting from (±)-(1S*,9bS*)-9b-(3,5-dimethyl-phenyl)-1-(4,6-dimethyl-pyrimidin-2-yloxy)-5-(4-methoxy-benzyl)-5,9b-dihydro-1H-2a,5-diaza-benzo[a]cyclobuta[c]cycloheptene-2,4-dione (Example 190), following the procedures described in Example 191. $^1$H-NMR (300 MHz, CDCl$_3$): 2.09 (s, 6H), 2.22 (s, 6H), 2.35 (s, 3H), 3.57 (s, 2H), 6.44 (s, 1H), 6.50 (s, 1H), 6.57 (s, 1H), 7.14 (dd, J=1.7, 7.9, 1H), 7.21 (m, 1H), 7.36–7.53 (m, 3H), 7.83 (m, 1H). LC-MS$^1$: t$_R$=0.87 min, [M+1]$^+$=461.

Example 190

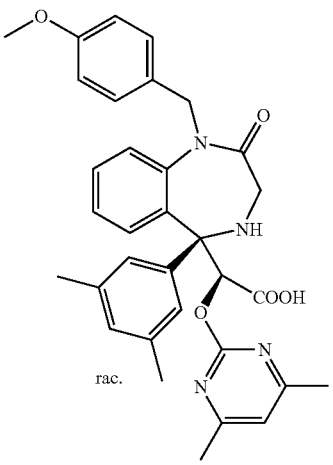

(±)-(S*)-[(5S*)-5-(3,5-Dimethyl-phenyl)-1-(4-methoxy-benzyl)-2-oxo-2,3,4,5-tetrahydro-1H-benzo[e][1,4]diazepin-5-yl]-(4,6-dimethyl-pyrimidin-2-yloxy)-acetic acid is prepared as described in Example 192. $^1$H-NMR (300 MHz, CDCl$_3$): 2.12 (s, 6H), 2.23 (s, 6H), 2.77 (d, J=15.2, 1H), 3.64 (s, 2H), 3.77 (s, 3H), 4.24 (d, J=15.2, 1H), 6.44 (s, 1H), 6.53 (s, 1H), 6.60 (s, 1H), 6.78 (d, J=8.2, 2H), 6.95 (dd, J=1.2, 7.6, 1H), 7.02 (d, J=8.2, 2H), 7.32 (t, J=7.6, 1H) 7.40 (t, J=7.6, 1H), 7.83 (d, J=7.6, 1H). LC-MS$^1$: t$_R$=1.04 min, [M+1]$^+$=567.

Example 191

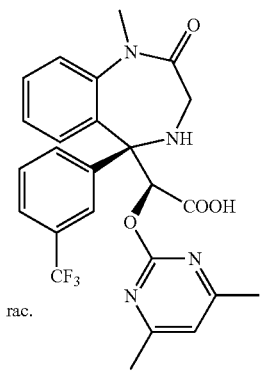

(±)-(1S*,9bS*)-1-(4,6-Dimethyl-pyrimidin-2-yloxy)-5-(4-methoxy-benzyl)-9b-(3-trifluoromethylphenyl)-5,9b-dihydro-1H-2a,5-diazabenzo[a]cyclobuta[c]cycloheptene-2,4-dione is prepared as described in Example 192.

a) An aqueous solution of cerium ammonium nitrate (10.48 g, 19.1 mmol in 33 ml H$_2$O) is added dropwise to a cooled (0° C.) solution of (±)-(1S*,9bS*)-1-(4,6-dimethyl-pyrimidin-2-yloxy)-5-(4-methoxy-benzyl)-9b-(3-trifluoromethylphenyl)-5,9b-dihydro-1H-2a,5-diaza-benzo[a]cyclobuta[c]cycloheptene-2,4-dione (3.75 g, 6.4 mmol) in acetonitrile (87 ml). The reaction mixture is stirred at 0° C. for 1 h, followed by 4 h at rt, diluted with DCM and the layers are separated. The aq. phase is extracted with DCM (2×), the combined organic phases are washed with brine, dried over MgSO$_4$ and the solvent removed in vacuo. The crude product is precipitated from diethylether to yield (±)-(1S*,9bS*)-1-(4,6-dimethyl-pyrimidin-2-yloxy)-9b-(3-trifluoromethyl-phenyl)-5,9b-dihydro-1H-2a,5-diaza-benzo[a]cyclobuta[c]cycloheptene-2,4-dione (2.33 g) as a white powder. LC-MS$^1$: t$_R$=0.99 min, [M+1]$^+$=469.

b) Methyliodide (0.692 ml, 7.5 mmol) is added to a suspension of (±)-(1S*,9bS*)-1-(4,6-dimethyl-pyrimidin-2-yloxy)-9b-(3-trifluoromethyl-phenyl)-5,9b-dihydro-1H-2a,5-diaza-benzo[a]cyclobuta[c]cycloheptene-2,4-dione (2.33 g, 5 mmol) and potassium carbonate (2.07 g, 15 mmol) in DMF (50 ml). The reaction is heated to 60° C. for 15 h, then partitioned between water and DCM. The layers are separated, the aq. layer is extracted with DCM (2×), the combined organic extracts are washed with brine, dried over MgSO$_4$ and the solvent removed in vacuo to give (±)-(1S*,9bS*)-1-(4,6-dimethyl-pyrimidin-2-yloxy)-5-methyl-9b-(3-trifluoromethyl-phenyl)-5,9b-dihydro-1H-2a,5-diaza-benzo[a]cyclobuta[c]cycloheptene-2,4-dione (1.7 g), which is not further purified. LC-MS$^1$: t$_R$=1.05 min, [M+1]$^+$=483.

c) An aqueous solution of LiOH.H$_2$O (0.177 g, 4.2 mmol in 2 ml water) is added to a solution of (±)-(1S*,9bS*)-1-(4,6-dimethyl-pyrimidin-2-yloxy)-5-methyl-9b-(3-trifluoromethyl-phenyl-5,9b-dihydro-1H-2a,5-diaza-benzo[a]cyclobuta[c]cycloheptene-2,4-dione (1.7 g, 3.5 mmol) in THF (8 ml) and methanol (3 ml). Stirring is continued for 1 h, the pH adjusted to 5 with 1 N HCl and the reaction mixture is diluted with DCM. The layers are separated, the organic phase is washed with brine, dried over MgSO$_4$ and the solvent removed in vacuo. The crude product is purified by HPLC on Rp-C$_{18}$ silica gel to afford (±)-(S*)-(4,6-dimethyl-pyrimidin-2-yloxy)-[(5S*)-1-methyl-2-oxo-5-(3-trifluoromethyl-phenyl)-2,3,4,5-tetrahydro-1H-benzo[e][1,4]diazepin-5-yl]-acetic acid (0.02 g) as a white powder. $^1$H-NMR (300 MHz, CDCl$_3$): 2.21 (s, 6H), 2.33 (s, 3H), 3.63 (d, J=14.7, 1H), 3.56 (d, J=13.5, 1H), 6.46 (s, 1H), 6.53 (s, 1H), 7.16–7.57 (m, 7H), 7.83 (m, 1H). LC-MS$^1$: t$_R$=0.93 min, [M+1]$^+$=501.

Example 192

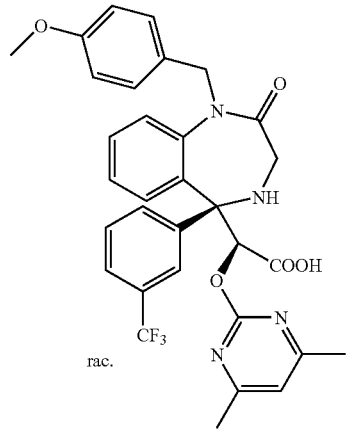

a) 3-(Trifluoromethyl)benzyl-1-magnesium bromide is prepared under Grignard conditions from magnesium turnings (4.22 g, 0.173 mol) and 1-bromo-3-(trifluoromethyl)benzene (17.5 ml, 127 mmol) in anhydrous diethyl ether (65 ml). After refluxing the reaction mixture for 4 h, it is cooled to rt. A solution of 2-aminobenzo nitrile (5 g, 42.3 mmol) in diethylether (35 ml) is added dropwise. Upon completion of the addition, the Grignard solution is heated to reflux over 4 h, then cooled to rt. The Grignard complex is decomposed with 2M HCl mixed with ice, the solution is refluxed over 2 h, cooled to RT and rendered alkaline with 10% NaOH. The layers are separated, the aq. phase is extracted with diethylether, the combined organic phases are washed with brine, dried over MgSO$_4$ and the solvent removed in vacuo to yield 2-amino-3'-(trifluoromethyl)benzophenone (11.72 g) as a light yellow powder, which is not further purified. LC-MS$^1$: $t_R$=1.14 min, [M+1]$^+$=266.

b) 2-Amino-3'-(trifluoromethyl) benzophenone (11.72 g, 44.2 mmol) is dissolved in abs. pyridine (250 ml), glycine ethylester hydrochloride (9.9 g, 70.7 mmol) is added and the reaction mixture heated to reflux over 72 h. Upon completion of the reaction, the solvent is removed in vacuo with toluene. The reaction mixture is partitioned between water and EA, the layers are separated, the aq. phase is extracted once again with EA and the combined organic phases are washed with brine, dried over MgSO$_4$ and the solvent removed in vacuo. The residue is purified over silica (0% –70% EA in heptane) to yield 5-(3-trifluoromethylphenyl)-1,3-dihydro-benzo[e][1,4]diazepin-2-one (4.96 g) as an orange powder. LC-MS$^1$: $t_R$=0.92 min, [M+1]$^+$=305.

c) 4-Methoxy benzyl chloride (2.32 ml, 17.1 mmol) is added to a suspension of 5-phenyl-1,3-dihydro-benzo[e][1,4]diazepin-2-one (4.96 g, 16.3 mmol) and potassium carbonate (6.76 g, 48.9 mmol) in DMF (100 ml). The suspension is stirred at rt over 15 h, diluted with EA and extracted with water. The aq. phase is extracted with EA (2×), the combined organic layers are washed with brine, dried over MgSO$_4$ and the solvent removed in vacuo. The crude residue is precipitated from diethylether to afford 1-(4-methoxy-benzyl)-5-(3-trifluoromethylphenyl)-1,3-dihydro-benzo[e][1,4]diazepin-2-one (6.35 g) as a white crystalline powder. $^1$H-NMR (300 MHz, CDCl$_3$): 3.68 (s, 3H), 3.87 (d, J=10.5, 1H), 4.65 (d, J=14.6, 1H), 4.89 (d, J=14.6, 1H), 5.63 (d, J=14.6, 1H), 6.62 (d, J=8.8, 2H), 6.93 (d, J=8.8, 2H), 7.11 (m, 2H), 7.42–7.56 (m, 4H), 7.63–7.7 (m, 2H). LC-MS$^1$: $t_R$=1.14 min, [M+1]$^+$=425.

d) 1-(4-Methoxy-benzyl)-5-(3-trifluoromethylphenyl)-1,3-dihydro-benzo[e][1,4]diazepin-2-one (6.33 g, 14.9 mmol) is dissolved in DCM (65 ml), cooled to 0° C., benzyloxy acetylchloride (3 ml, 19.4 mmol) is added, followed by triethylamine (6.2 ml, 44.7 mmol). The ice bath is let expire over 15 h. The reaction mixture is partitioned between sat. aq. NaHCO$_3$ and EA, the layers are separated. The aq. phase is extracted with EA (2×), the combined organic phases are washed with brine, dried over MgSO$_4$ and the solvent removed in vacuo. The crude product is suspended in diethylether to give (±)-(1S*, 9bS*)-1-benzyloxy-5-(4-methoxy-benzyl)-9b-(3-trifluoromethyl-phenyl)-5,9b-dihydro-1H-2a,5-diazabenzo[a]cyclobuta[c]cycloheptene-2,4-dione (6.73 g) as a white powder. $^1$H-NMR (300 MHz, CDCl$_3$): 3.33 (d, J=15.2, 1H), 3.76 (s, 3H), 3.83 (d, J=13.5, 1H), 4.51–4.55 (m, 4H), 5.26 (s, 1H), 6.71 (d, J=8.8, 2H), 6.92 (d, J=8.8, 2H), 6.99–7.06 (m, 3H), 7.23–7.36 (m, 6H), 7.5–7.6 (m, 2H). LC-MS$^1$: $t_R$=1.22 min, [M+1]$^+$=573.

e) To Pd/C (1.5 g, 10%) are added (±)-(1S*,9bS*)-1-benzyloxy-5-(4-methoxy-benzyl)-9b-(3-trifluoromethyl-phenyl)-5,9b-dihydro-1H-2a,5-diaza-benzo[a]cyclobuta[c]cycloheptene-2,4-dione (6.73 g, 11.8 mmol), THF (70 ml), ethanol (20 ml) and acetic acid (1.5 ml). The reaction mixture is stirred at 50° C. under 7 atm H$_2$ for 14 h. The Pd-catalyst is filtered and the solvent removed in vacuo to afford (±)-(1S*,9bS*)-1-hydroxy-5-(4-methoxy-benzyl)-9b-(3-trifluoromethyl-phenyl)-5,9b-dihydro-1H-2a,5-diazabenzo[a]cyclobuta[c]cycloheptene-2,4-dione (5.67 g) as a white crystalline foam, which is used without further purification. LC-MS$^1$: $t_R$=1.03 min, [M+1]$^+$=483.

f) Potassium carbonate (4.89 g, 35.4 mmol) is added to a solution of (±)-(1S*,9bS*)-1-hydroxy-5-(4-methoxy-benzyl)-9b-(3-trifluoromethyl-phenyl)-5,9b-dihydro-1H-2a, 5diazabenzo[a]cyclobuta[c]cycloheptene-2,4-dione (5.67 g, 11.8 mmol) and 2-methanesulfonyl-4,6-dimethyl-pyrimidine (2.63 g, 14.1 mmol, Example 19) in DMF (60 ml). The resulting suspension is heated to 50° C. over 48 h, diluted with DCM, washed with water (2×), brine (2×), dried over MgSO$_4$ and the solvent removed in vacuo. The crude product is suspended in diethylether to yield (±)-(1S*,9bS*)-1-(4,6-dimethyl-pyrimidin-2-yloxy)-5-(4-methoxy-benzyl)-9b-(3-trifluoromethylphenyl)-5,9b-dihydro-1H-2a,5-diazabenzo[a]cyclobuta[c]cycloheptene-2,4-dione (4.06 g) as a white powder. LC-MS$^1$: $t_R$=1.17 min, [M+1]$^+$=589.

g) An aqueous solution of LiOH.H$_2$O (0.026 g, 0.61 mmol in 1 ml water) is added to a solution of (±)-(1S*,9bS*)-1-(4,6-dimethyl-pyrimidin-2-yloxy)-5-(4-methoxy-benzyl)-9b-(3-trifluoromethyl-phenyl)-5,9b-dihydro-1H-2a, 5-diaza-benzo[a]cyclobuta[c]cycloheptene-2,4-dione (0.3 g, 0.51 mmol) in THF (3 ml) and methanol (1 ml). The mixture is stirred at rt for 2 h, the pH is adjusted to pH=5 with 1 N HCl and the solvents removed in vacuo. The crude product is purified by prep. tlc on silica (MeOH: CH$_2$Cl$_2$=2:8) to afford (±)-(S*)-(4,6-dimethyl-pyrimidin-2-yloxy)-[(5S*)-1-(4-methoxy-benzyl)-2-oxo-5-(3-trifluoromethyl-phenyl)-2,3,4,5-tetrahydro-1H-benzo[e][1, 4]diazepin-5-yl]-acetic acid (0.1 g) as a white powder. $^1$H-NMR (300 MHz, CDCl$_3$): 2.25 (s, 6H), 2.78 (d, J=15.8, 1H), 3.5 (m, 1H), 3.61 (m, 1H), 3.74 (s, 3H), 4.06 (d, J=14.7, 1H), 6.37 (s, 1H), 6.52 (s, 1H), 6.76 (d, J=8.2, 2H), 6.93–7.54 (m, 8H), 7.76 (m, 1H). LC-MS$^1$: $t_R$=1.09 min, [M+1]$^+$=607.

Example 193

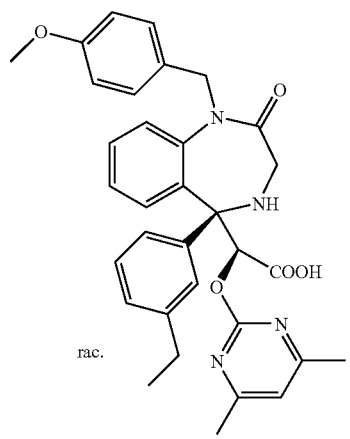

rac.

a) (2-Amino-phenyl)-(3-ethyl-phenyl)-methanone is prepared starting from 2-aminobenzonitrile and 1-bromo-3-ethylbenzene in analogy to Example 192. LC-MS$^2$: $t_R$=5.21 min, [M+1]$^+$=226.08.

b) 5-(3-Ethyl-phenyl)-1-(4-methoxy-benzyl)-1,3-dihydro-benzo[e][1,4]di-azepin-2-one is prepared in analogy to Example 39. LC-MS$^1$: $t_R$=0.99 min, [M+1]$^+$=385.02.

c) (±)-(S*)-(4,6-Dimethyl-pyrimidin-2-yloxy)-[(5S*)-5-(3-ethyl-phenyl)-1-(4-methoxy-benzyl)-2-oxo-2,3,4,5-tetrahydro-1H-benzo[e][1,4]diazepin-5-yl]-acetic acid is prepared in analogy to Example 192. LC-MS[1]: $t_R$=1.06 min, [M+1]$^+$=567.09.

Examples 194 to 200

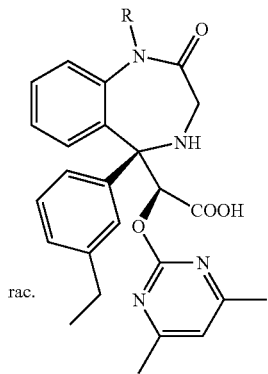

The following examples are prepared starting from (±)-(1S*,9bS*)-1-(4,6-dimethyl-pyrimidin-2-yloxy)-9b-(3-ethyl-phenyl)-5-(4-methoxy-benzyl)-5,9b-dihydro-1H-2a,5-diaza-benzo[a]cyclobuta[c]cycloheptene-2,4-dione (Example 193) in analogy to the procedures given in Example 48:

| Example | R | $t_R$ (LC-MS[1]) [min] | [M + 1]$^+$ |
|---|---|---|---|
| 194 | F,F,ethyl,F-phenyl | 1.08 | 591.08 |
| 195 | trimethyl-phenyl | 1.26 | 579.15 |
| 196 | F,F,F,ethyl-phenyl | 1.13 | 591.11 |
| 197 | F,F,ethyl,F-phenyl | 1.10 | 591.11 |
| 198 | propyl-ethyl-phenyl | 1.30 | 593.19 |
| 199 | F,ethyl,F-phenyl | 1.07 | 573.11 |
| 200 | F,F,ethyl,F-phenyl | 1.12 | 591.10 |

Example 201

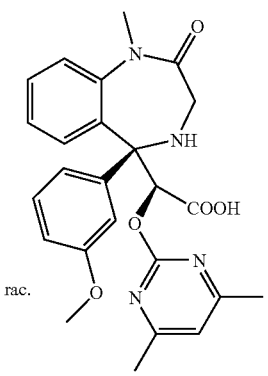

(±)-(S*)-(4,6-Dimethyl-pyrimidin-2-yloxy)-[(5S*)-5-(3-methoxy-phenyl)-1-methyl-2-oxo-2,3,4,5-tetrahydro-1H-benzo[e][1,4]diazepin-5-yl]-acetic acid is prepared in analogy to Example 191. LC-MS[1]: $t_R$=0.83 min, [M+1]$^+$=463.15.

Example 202

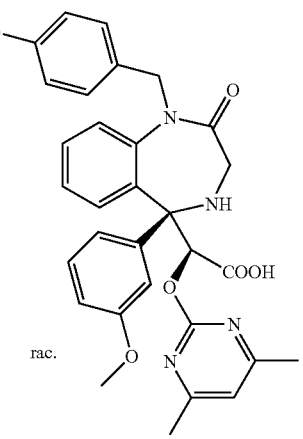

(±)-(S*)-(4,6-Dimethyl-pyrimidin-2-yloxy)-[(5S*)-1-(4-methoxy-benzyl)-5-(3-methoxy-phenyl)-2-oxo-2,3,4,5-tetrahydro-1H-benzo[e][1,4]diazepin-5-yl]-acetic acid is prepared in analogy to Example 192. LC-MS$^1$: $t_R$=0.99 min, [M+1]$^+$=569.08.

Examples 203 to 207

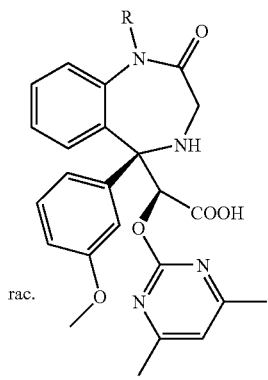

rac.

The following examples are prepared starting from (±)-(1S*,9bS*)-(4,6-dimethyl-pyrimidin-2-yloxy)-9b-(3-methoxy-phenyl)-5-(4-methoxy-benzyl)-5,9b-dihydro-1H-2a,5-diaza-benzo[a]cyclobuta[c]cycloheptene-2,4-dione (Example 202) in analogy to the procedures given in Example 48:

| Example | R | $t_R$ (LC-MS$^1$) [min] | [M + 1]$^+$ |
|---|---|---|---|
| 203 | 2,4,6-trifluoro-3-ethylphenyl | 1.01 | 593.01 |
| 204 | HOOC-CH(CH$_3$)- | 0.79 | 506.99 |
| 205 | 2,3,6-trifluoro-4-ethylphenyl | 1.01 | 593.04 |
| 206 | 2,6-dimethyl-4-ethylphenyl | 1.16 | 581.13 |
| 207 | 2,3-difluoro-6-ethylphenyl | 1.05 | 593.11 |

Example 208

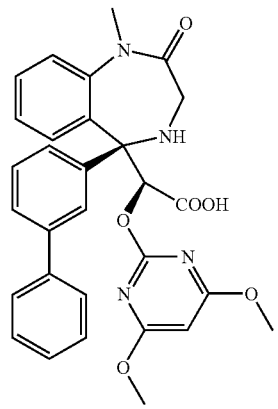

rac.

a) (2-Amino-phenyl)-biphenyl-3-yl-methanone is prepared starting from 2-aminobenzonitrile and 3-bromobiphenyl in analogy to Example 192. LC-MS$^2$: $t_R$=5.32 min, [M+1]$^+$=274.11.

b) 5-Biphenyl-3-yl-1-methyl-1,3-dihydro-benzo[e][1,4]diazepin-2-one is prepared in analogy to Example 39. LC-MS$^2$: $t_R$=4.61 min, [M+1]$^+$=327.27.

c) (±)-(S*)-((5S*)-5-Biphenyl-3-yl-1-methyl-2-oxo-2,3,4,5-tetrahydro-1H-benzo[e][1,4]di-azepin-5-yl)-(4,6-dimethoxy-pyrimidin-2-yloxy)-acetic acid is prepared in analogy to Example 192. LC-MS$^2$: $t_R$=4.39 min, [M+1]$^+$= 541.41, [M−1]$^-$=539.20.

Example 209

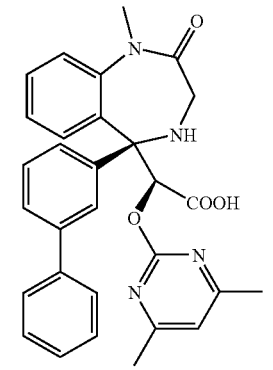

rac.

(±)-(S*)-((5S*)-5-Biphenyl-3-yl-1-methyl-2-oxo-2,3,4,5-tetrahydro-1H-benzo[e][1,4]diazepin-5-yl)-(4,6-dimethyl-pyrimidin-2-yloxy)-acetic acid is prepared in analogy to Example 208. LC-MS$^2$: $t_R$=4.17 min, [M+1]$^+$=509.20, [M−1]$^-$=507.21.

Example 210

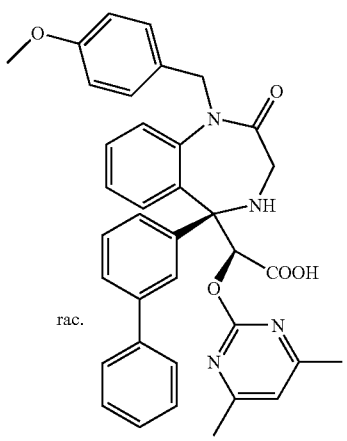

(±)-(S*)-[(5S*)-5-Biphenyl-3-yl-1-(4-methoxy-benzyl)-2-oxo-2,3,4,5-tetrahydro-1H-benzo[e][1,4]diazepin-5-yl]-(4,6-dimethyl-pyrimidin-2-yloxy)-acetic acid is prepared in analogy to Example 193. LC-MS¹: $t_R$=1.13 min, [M+1]⁺= 615.14.

Example 211 to 213

The following examples are prepared starting from (±)-(1S*,9bS*)-9b-biphenyl-3-yl-1-(4,6-dimethyl-pyrimidin-2-yloxy)-5-(4-methoxy-benzyl)-5,9b-dihydro-1H-2a,5-diaza-benzo[a]cyclobuta[c]cycloheptene-2,4-dione (Example 210) in analogy to the procedures given in Example 48:

| Example | R | $t_R$ (LC-MS¹) [min] | [M + 1]⁺ |
|---|---|---|---|
| 211 | F-substituted phenyl | 1.15 | 639.02 |
| 212 | HOOC— | 0.89 | 553.02 |
| 213 | F-substituted phenyl | 1.13 | 639.04 |

Example 214

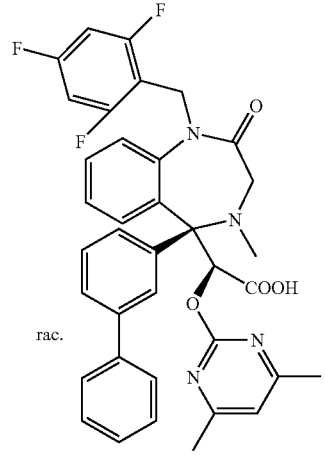

(±)-(S*)-[(5S*)-5-Biphenyl-3-yl-4-methyl-2-oxo-1-(2,4,6-trifluoro-benzyl)-2,3,4,5-tetrahydro-1H-benzo[e][1,4]diazepin-5-yl]-(4,6-dimethyl-pyrimidin-2-yloxy)-acetic acid is prepared starting from (±)-(S*)-[(5S*)-5-biphenyl-3-yl-2-oxo-1-(2,4,6-trifluoro-benzyl)-2,3,4,5-tetrahydro-1H-benzo[e][1,4]di-azepin-5-yl]-(4,6-dimethyl-pyrimidin-2-yloxy)-acetic acid (Example 211) in analogy to Example 127. LC-MS¹: $t_R$=1.17 min, [M+1]⁺=653.08.

Example 215

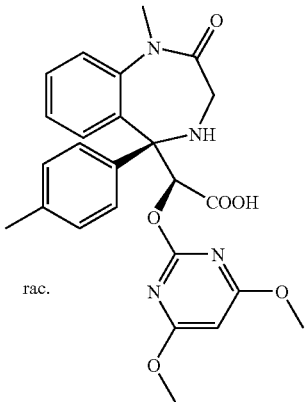

(±)-(S*)-(4,6-Dimethoxy-pyrimidin-2-yloxy)-((5S*)-1-methyl-2-oxo-5-p-tolyl-2,3,4,5-tetrahydro-1H-benzo[e][1,4]diazepin-5-yl)-acetic acid is prepared in analogy to Example 39 and 27 starting from (2-amino-phenyl)-p-tolyl-methanone. LC-MS²: $t_R$=3.84 min, [M+1]⁺=479.40, [M–1]⁻= 477.27.

Example 216

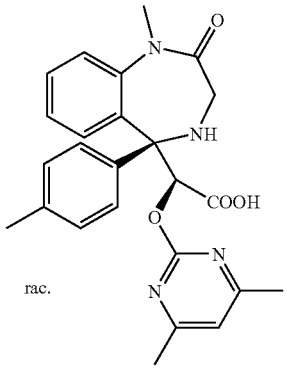

(±)-(S*)-(4,6-Dimethyl-pyrimidin-2-yloxy)-((5S*)-1-methyl-2-oxo-5-p-tolyl-2,3,4,5-tetrahydro-1H-benzo[e][1,4]diazepin-5-yl)-acetic acid is prepared in analogy to Example 39 and 27 starting from (2-amino-phenyl)-p-tolyl-methanone. LC-MS²: $t_R$=3.67 min, [M+1]⁺=447.43, [M−1]⁻= 445.24.

Example 217

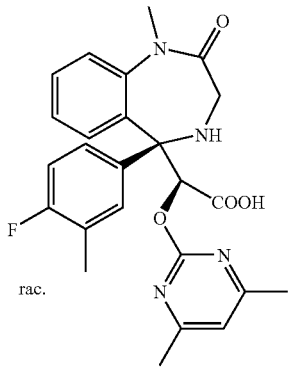

rac.

(±)-(S*)-(4,6-Dimethyl-pyrimidin-2-yloxy)-[(5S*)-5-(4-fluoro-3-methyl-phenyl)-1-methyl-2-oxo-2,3,4,5-tetrahydro-1H-benzo[e][1,4]diazepin-5-yl]-acetic acid is obtained as a light yellow powder starting from (±)-(1S*,9bS*)-1-(4,6-dimethyl-pyrimidin-2-yloxy)-9b-(4-fluoro-3-methyl-phenyl)-5-(4-methoxy-benzyl)-5,9b-dihydro-1H-2a,5-diaza-benzo[a]cyclo-buta[c]cycloheptene-2,4-dione (Example 218) following procedures described in Example 191. ¹H-NMR (300 MHz, CDCl₃): 2.05 (s, 3H), 2.22 (s, 6H), 2.40 (s, 3H), 3.47 (d, J=13.4, 1H), 3.54 (d, J=12.3, 1H), 6.37 (s, 1H), 6.49 (s, 1H), 6.68 (t, J=8.2, 1H), 6.83–6.96 (m, 2H), 7.12 (d, J=7.6, 1H), 7.36 (t, J=7.6, 1H), 7.4 (t, J=7.6, 1H), 7.77 (m, 2H). LC-MS¹: $t_R$=0.86 min, [M+1]⁺=465.

Example 218

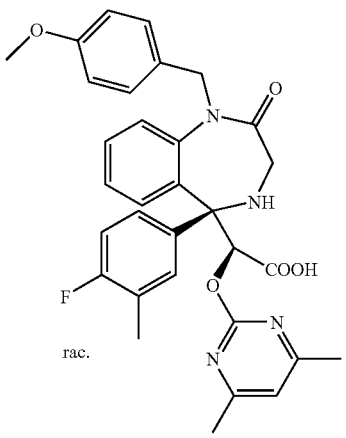

rac.

(±)-(S*)-(4,6-Dimethyl-pyrimidin-2-yloxy)-[(5S*)-5-(4-fluoro-3-methyl-phenyl)-1-(4-methoxy-benzyl)-2-oxo-2,3,4,5-tetrahydro-1H-benzo[e][1,4]diazepin-5-yl]-acetic acid is prepared as described in Example 192, by reacting 5-bromo-2-fluoro-toluene under Grignard conditions with 2-amino benzonitrile and ring cyclization to the corresponding benzodiazepinone intermediate.

a) 5-(4-Fluoro-3-methyl-phenyl)-1,3-dihydro-benzo[e][1,4]diazepin-2-one is obtained as a brown powder. ¹H-NMR (300 MHz, CDCl₃): 2.28 (s, 3H), 4.29 (s, 2H), 6.98 (t, J=8.8, 1H), 7.13–7.2 (m, 1H), 7.24–7.33 (m, 2H), 7.44–7.53 (m, 2H), 9.33 (s, 1H). LC-MS¹: $t_R$=0.70 min, [M+1]⁺=269.

b) The (±)-(S*)-(4,6-dimethyl-pyrimidin-2-yloxy)-[(5S*)-5-(4-fluoro-3-methyl-phenyl)-1-(4-methoxy-benzyl)-2-oxo-2,3,4,5-tetrahydro-1H-benzo[e][1,4]diazepin-5-yl]-acetic acid is obtained from the alkaline hydrolysis of (±)-(1S*,9bS*)-1-(4,6-dimethyl-pyrimidin-2-yloxy)-9b-(4-fluoro-3-methyl-phenyl)-5-(4-methoxy-benzyl)-5,9b-dihydro-1H-2a,5-diaza-benzo[a]cyclobuta[c]cycloheptene-2,4-dione (0.213 g, 0.419 mmol) as a white solid (0.071 g), after purification by prep. tlc on silica (DCM: MeOH=9:1). ¹H-NMR (300 MHz, CDCl₃): 1.98 (s, 3H), 2.16 (s, 6H), 2.84 (d, J=15.8, 1H), 3.51 (m, 2H), 3.69 (s, 3H), 4.17 (d, J=14.6, 1H), 6.32 (s, 1H), 6.42 (s, 1H), 6.61 (m, 1H), 6.70 (d, J=8.8, 2H), 6.98–7.0 (m, 5H), 7.24 (m, 2H), 7.72 (m, 1H). LC-MS¹: $t_R$=1.02 min, [M+1]⁺=571.

Example 219

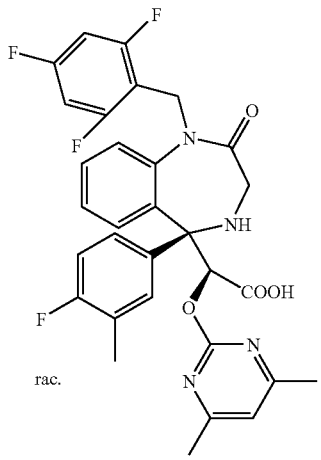

rac.

(±)-(S*)-(4,6-Dimethyl-pyrimidin-2-yloxy)-[(5S*)-5-(4-fluoro-3-methyl-phenyl)-2-oxo-1-(2,4,6-trifluoro-benzyl)-2,3,4,5-tetrahydro-1H-benzo[e][1,4]diazepin-5-yl]-acetic acid is prepared starting from (±)-(1S*,9bS*)-1-(4,6-Dimethyl-pyrimidin-2-yloxy)-9b-(4-fluoro-3-methyl-phenyl)-5-(4-methoxy-benzyl)-5,9b-dihydro-1H-2a,5-diaza-benzo[a]cyclobuta[c]cyclo-heptene-2,4-dione (Example 218) in analogy to Example 48. LC-MS¹: $t_R$=1.04 min, [M+1]⁺= 595.08.

Example 220

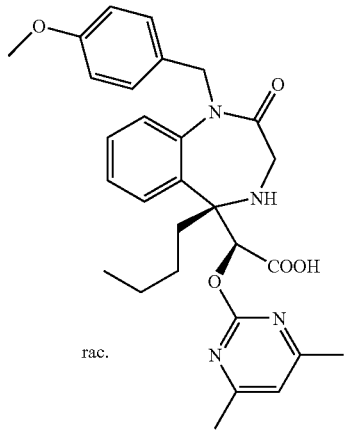

rac.

(±)-(S*)-(4,6-Dimethyl-pyrimidin-2-yloxy)-[(5S*)-1-(4-methoxy-benzyl)-2-oxo-5-pentyl-2,3,4,5-tetrahydro-1H-benzo[e][1,4]diazepin-5-yl]-acetic acid is obtained as described in Example 193, by reacting 1-bromo pentane under Grignard conditions with 2-amino benzonitrile and ring cyclization to the corresponding benzodiazepinone intermediate.

a) 5-Pentyl-1,3-dihydro-benzo[e][1,4]diazepin-2-one is isolated as an orange viscous oil. $^1$H-NMR (300 MHz, CDCl$_3$): 0.82 (t, J=7.0, 3H), 1.24 (m, 4H), 1.56 (m, 2H), 2.76 (t, J=7.6, 2H), 4.10 (s, 2H), 7.42 (dt, J$_d$=1.5, J$_t$=7.0, 1H), 7.53 (d, J=7.6, 1H), 9.61 (s, 1H). LC-MS$^1$: t$_R$=0.74 min, [M+1]$^+$=231.

b) (±)-(S*)-(4,6-Dimethyl-pyrimidin-2-yloxy)-[(5S*)-1-(4-methoxy-benzyl)-2-oxo-5-pentyl-2,3,4,5-tetrahydro-1H-benzo[e][1,4]diazepin-5-yl]-acetic acid is obtained from the alkaline hydrolysis of (±)-(1S*,9bS*)-1-(4,6-dimethyl-pyrimidin-2-yloxy)-5-(4-methoxy-benzyl)-9b-pentyl-5,9b-dihydro-1H-2a,5-diaza-benzo[a]cyclobuta[c]cycloheptene-2,4-dione (0.5 g, 0.97 mmol) as a white powder (0.1 g), after purification by HPLC on Rp-C$_{18}$ silica gel.

$^1$H-NMR (300 MHz, CDCl$_3$): 0.72–1.25 (m, 8H), 1.85 (m, 1H), 2.03 (m, 1H), 2.34 (m, 1H), 2.4 (s, 6H), 3.51–3.77 (m, 3H), 3.8 (s, 3H), 6.36 (s, 1H), 6.7 (s, 1H), 6.86 (d, J=8.8, 2H), 7.23–7.29 (m, 5H), 7.56 (d, J=5.3, 2H). LC-MS$^1$: t$_R$=0.97 min, [M+1]$^+$=533.

Example 221

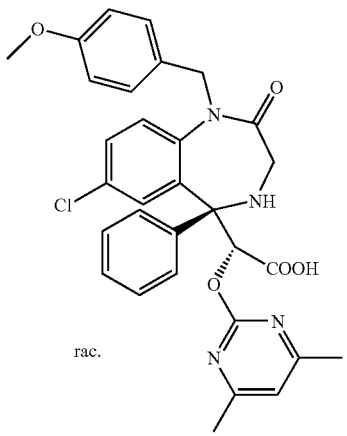

rac.

a) (±)-(1R*,9bS*)-8-chloro-1-(4,6-dimethyl-pyrimidin-2-yloxy)-5-(4-methoxy-benzyl)-9b-phenyl-5,9b-dihydro-1H-2a,5-diaza-benzo[a]cyclo-buta[c]cycloheptene-2,4-dione is isolated as a second product in step c) in Example 171. LC-MS$^1$: t$_R$=1.24 min, [M+1]$^+$=555.06.

b) (±)-(1R*,9bS*)-8-chloro-1-(4,6-dimethyl-pyrimidin-2-yloxy)-5-(4-methoxy-benzyl)-9b-phenyl-5,9b-dihydro-1H-2a,5-diaza-benzo[a]cyclo-buta[c]cycloheptene-2,4-dione is treated with LiOH.H$_2$O as described in Example 25 to furnish (±)-(R*)-[(5S*)-7-chloro-1-(4-methoxy-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid. LC-MS$^1$: t$_R$=1.09 min, [M+1]$^+$=573.09. The material is not identical to the product isolated in Example 171.

Example 222

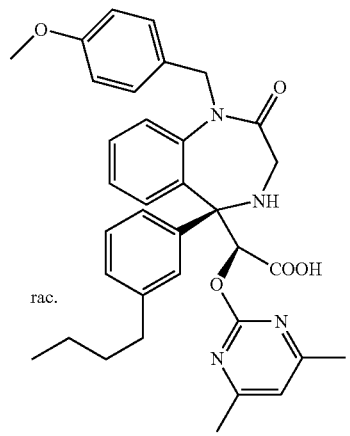

rac.

a) A freshly prepared solution of propyl magnesiumbromide (prepared from magnesium (5.35 g, 0.22 mol) and 1-bromopropane (29.53 g, 0.24 mol)) in THF (200 ml) is slowly added at –70° C. to a solution of 3-bromobenzylbromide (50 g, 0.2 mol) in THF (100 ml). During the addition the temperature is kept below –60° C. To the resulting suspension Li$_2$CuCl$_4$ (10 ml of 0.1 M solution in THF) is added. The reaction mixture is allowed to come slowly to rt, and an exothermic reaction starts. The temperature reaches 40° C. and the mixture is again cooled to 10° C. The dark suspension is stirred for 2 h before it is treated with sat. aq. NH$_4$Cl (100 ml). Stirring is continued for 20 min, the mixture is diluted with diethyl ether and water, the organic phase is separated and washed with brine. The dark blue aq. phase is extracted once more with diethyl ether. The combined organic phase is dried over MgSO$_4$ and evaporated. The crude product was purified by column chromatography on silica gel eluting with hexane to furnish 1-bromo-3-butyl-benzene (16.42 g) as a colourless oil.

$^1$H-NMR (300 MHz, CDCl$_3$): 0.94 (t, J=7.6, 3H), 1.36 (oct, J=7.6, 2H), 1.52–1.65 (m, 2H), 2.59 (t, J=7.6, 2H), 7.07–7.16 (m, 2H), 7.27–7.34 (m, 2H).

b) (±)-(S*)-[(5S*)-5-(3-Butyl-phenyl)-1-(4-methoxy-benzyl)-2-oxo-2,3,4,5-tetrahydro-1H-benzo[e][1,4]diazepin-5-yl]-(4,6-dimethyl-pyrimidin-2-yloxy)-acetic acid is prepared starting from 1-bromo-3-butyl-benzene in analogy to Example 193. LC-MS$^1$: t$_R$=1.17 min, [M+1]$^+$= 595.28.

Example 223 to 229

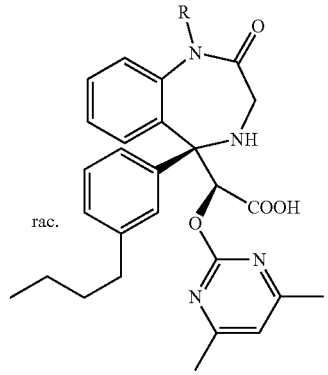

rac.

The following examples are prepared starting from (±)-(1S*,9bS*)-9b-(3-butyl-phenyl)-1-(4,6-dimethyl-pyrimidin-2-yloxy)-5-(4-methoxy-benzyl)-5,9b-dihydro-1H-2a,5-diaza-benzo[a]cyclobuta[c]cycloheptene-2,4-dione (Example 222) in analogy to the procedures given in Example 48:

| Example | R | $t_R$ (LC-MS[1]) [min] | $[M+1]^+$ |
|---|---|---|---|
| 223 | | 1.39 | 621.33 |
| 224 | | 1.20 | 619.24 |
| 225 | | 1.27 | 633.17 |
| 226 | | 1.18 | 619.21 |
| 227 | | 1.23 | 619.21 |
| 228 | | 1.22 | 619.19 |
| 229 | | 1.21 | 619.20 |

Example 230

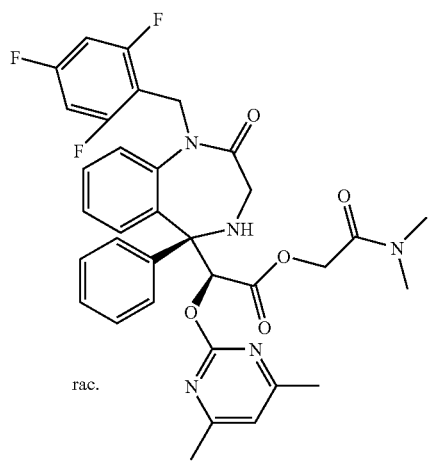

rac.

A solution of (±)-(S*)-(4,6-dimethyl-pyrimidin-2-yloxy)-[(5S*)-2-oxo-5-phenyl-1-(2,4,6-trifluoro-benzyl)-2,3,4,5-tetrahydro-1H-benzo[e][1,4]di-azepin-5-yl]-acetic acid (150 mg, 0.266 mmol, Example 107) in DMF (5 ml) is treated with triethylamine (162 mg, 1.60 mmol) and 2-chloro-dimethylacetamide (162 mg, 1.38 mmol). The mixture is stirred at rt for 18 h before it is diluted with EA, washed twice with water, dried over MgSO$_4$ and evaporated. The crude product is purified by chromatography on prep. tlc plates (DCM with 10% methanol) and crystallisation from diethyl ether/hexane to give (±)-(S*)-(4,6-dimethyl-pyrimidin-2-yloxy)-[(5S*)-2-oxo-5-phenyl-1-(2,4,6-trifluoro-benzyl)-2,3,4,5-tetrahydro-1H-benzo[e][1,4]diazepin-5-yl]-acetic acid dimethylcarbamoylmethyl ester (151 mg) as a white powder. LC-MS[1]: $t_R$=1.10 min, $[M+1]^+$=648.15.

The invention claimed is:

1. A compound of Formula 1,

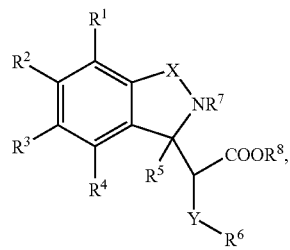

Formula I wherein

X represents —CH$_2$—CH$_2$—CH$_2$—; —NR$^9$—C(=O)—CH$^2$—; —NR$^{10}$—CH$_2$—CH$_2$—; —C(=O)—CH$_2$—CH$_2$—;
—CH$_2$—C(=O)—CH$_2$—; —O—CH$_2$—CH$_2$—; —S—CH$_2$—CH$_2$; —SO$_2$—CH$_2$—CH$_2$—; —NR$^9$—C(=O)—CH$_2$—CH$_2$—;
—NR$^{10}$—CH$_2$—CH$_2$—CH$_2$—; —O—CH$_2$—CH$_2$—CH$_2$—;

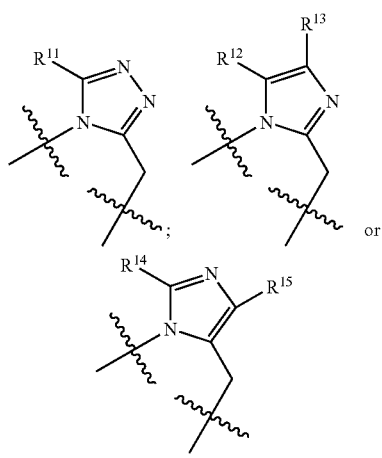

Y represents O; S; NH; N—CH₃ or CH₂;

R¹, R², R³, R⁴ represent hydrogen; or one or two of R¹, R², R³, R⁴ independently represent halogen; hydroxy; lower alkyl; lower alkyloxy; lower alkyloxycarbonyl; hydroxy carbonyl; amino; lower alkylamino; di-(lower alkyl)-amino; lower alkylcarbonylamino; or trifluoromethyl; and the others are hydrogen;

R⁵ represents hydrogen; lower alkyl; phenyl; mono-, di-, or tri-substituted phenyl, substituted with lower alkyl, lower alkyloxy, halogen, amino, lower alkylamino, di-(lower alkyl)-amino, or lower alkylthio; mono- or di-substituted phenyl, substituted with trifluoromethyl; pyridyl; benzyl or mono- or disubstituted benzyl, substituted at the phenyl ring with lower alkyl, lower alkyloxy, halogen, amino, lower alkylamino, di-(lower alkyl)-amino, trifluoromethyl, or lower alkylthio;

R⁶ represents phenyl; mono-, di-, or tri-substituted phenyl, substituted with lower alkyl, lower alkyloxy, halogen, amino, lower alkylamino, di-(lower alkyl)-amino, lower alkylthio, alkylene-dioxy, or ethylenoxy; mono- or di-substituted phenyl, substituted with trifluoromethyl; pyridyl; mono- or di-substituted pyridyl, substituted with lower alkyl, lower alkyloxy, halogen, amino, lower alkylamino, di-(lower alkyl)-amino, trifluoromethyl, or lower alkylthio; pyrimidinyl; mono- or di-substituted pyrimidinyl, substituted with lower alkyl, lower alkyloxy, halogen, amino, lower alkylamino, di-(lower alkyl)-amino, or lower alkylthio; or mono-substituted pyrimidinyl, substituted with trifluoromethyl;

R⁷ represents hydrogen; lower alkyl; cycloalkyl; lower alkylcarbonyl; benzyl; or optionally substituted benzyl, substituted at the phenyl ring with lower alkyl, lower alkyloxy, halogen, amino, lower alkylamino, di-(lower alkyl)-amino, trifluoromethyl, lower alkylthio, alkylene-dioxy, or ethylenoxy;

R⁸ represents hydrogen; lower alkyl; or lower alkylcarbonyloxy-lower alkyl;

R⁹ represents hydrogen; lower alkyl; lower alkenyl; lower alkynyl; hydroxycarbonyl-lower alkyl whereby lower alkyl can be substituted with phenyl; lower alkyloxycarbonyl-lower alkyl whereby lower alkyl can be substituted with phenyl; tetrazol-5-yl-lower alkyl; 2,5-dihydro-5-oxo-4H-1,2,4-oxadiazol-3-yl-lower alkyl; 2,5-dihydro-5-oxo-4H-1,2,4-thiadiazol-3-yl-lower alkyl; 2,5-dihydro-5-thioxo-4H-1,2,4-oxadiazol-3-yl-lower alkyl; 2-oxo-3H-1,2,3,5-oxathiadiazol-4-yl-lower alkyl; amino-lower alkyl; lower alkylamino-lower alkyl; di-(lower alkyl)-amino-lower alkyl; aminocarbonyl-lower alkyl; lower alkylamino carbonyl-lower alkyl; di-(lower alkyl)-aminocarbonyl-lower alkyl; hydroxy-lower alkyl; lower alkyloxy-lower alkyl; benzyl; or mono- or di-substituted benzyl substituted at the phenyl ring with lower alkyl, lower alkyloxy, halogen, amino, lower alkylamino, di-(lower alkyl)-amino, trifluoromethyl, lower alkylthio, alkylene-dioxy, or ethylenoxy;

R¹⁰ represents hydrogen; lower alkyl; lower alkenyl; lower alkynyl; hydroxycarbonyl-lower alkyl whereby lower alkyl can be substituted with phenyl; lower alkyloxycarbonyl-lower alkyl whereby lower alkyl can be substituted with phenyl; tetrazol-5-yl-lower alkyl; 2,5-dihydro-5-oxo-4H-1,2,4-oxadiazol-3-yl-lower alkyl; 2,5-dihydro-5-oxo-4H-1,2,4-thiadiazol-3-yl-lower alkyl; 2,5-dihydro-5-thioxo-4H-1,2,4-oxadiazol-3-yl-lower alkyl; 2-oxo-3H-1,2,3,5-oxathiadiazol-4-yl-lower alkyl; amino-lower alkyl; lower alkylamino-lower alkyl; di-(lower alkyl)-amino-lower alkyl; aminocarbonyl-lower alkyl; hydroxy-lower alkyl; lower alkyloxy-lower alkyl; benzyl; mono- or di-substituted benzyl substituted at the phenyl ring with lower alkyl, lower alkyloxy, halogen, amino, lower alkylamino, di-(lower alkyl)-amino, trifluoromethyl, lower alkylthio, alkylene-dioxy, or ethylenoxy; benzylcarbonyl; mono- or di-substituted benzylcarbonyl substituted at the phenyl ring with lower alkyl, lower alkyloxy, halogen, amino, lower alkylamino, di-(lower alkyl)-amino, trifluoromethyl, lower alkylthio, alkylene-dioxy, or ethylenoxy; lower alkylcarbonyl; phenylcarbonyl; mono- or di-substituted phenylcarbonyl substituted with lower alkyl, lower alkyloxy, halogen, amino, lower alkylamino, di-(lower alkyl)-amino, trifluoromethyl, lower alkylthio, alkylene-dioxy, or ethylenoxy; lower alkylcarbonyl; lower alkyloxy-lower alkylcarbonyl; or hydroxycarbonyl-lower alkylcarbonyl;

R¹¹ represents hydrogen; lower alkyl; cycloalkyl; lower alkyloxy-lower alkyl; lower alkyloxycarbonyl; hydroxycarbonyl; lower alkyloxycarbonyl-lower alkyl; hydroxycarbonyl-lower alkyl; phenyl; mono- or di-substituted phenyl substituted with lower alkyl, lower alkyloxy, halogen, amino, lower alkylamino, di-(lower alkyl)-amino, trifluoromethyl, or lower alkylthio; benzyl; or mono- or di-substituted benzyl substituted at the phenyl ring with lower alkyl, lower alkyloxy, halogen, amino, lower alkylamino, di-(lower alkyl)-amino, or lower alkylthio;

R¹² represents hydrogen; lower alkyl; cycloalkyl; lower alkyloxy-lower alkyl; phenyl; or mono- or di-substituted phenyl substituted with lower alkyl, lower alkyloxy, halogen, amino, lower alkylamino, di-(lower alkyl)-amino, trifluoromethyl, or lower alkylthio;

R¹³ represents hydrogen; lower alkyl; cycloalkyl; or lower alkyloxy-lower alkyl;

R¹⁴ represents hydrogen; lower alkyl; cycloalkyl; lower alkyloxy-lower alkyl; phenyl; mono- or di-substituted phenyl substituted with lower alkyl, lower alkyloxy, halogen, amino, lower alkylamino, di-(lower alkyl)-amino, trifluoromethyl, or lower alkylthio; benzyl; mono- or di-substituted benzyl substituted at the phenyl ring with lower alkyl, lower alkyloxy, halogen, amino, lower alkylamino, di-(lower alkyl)-amino, or lower alkylthio; lower alkyloxycarbonyl; hydroxycarbonyl; lower alkyloxycarbonyl-lower alkyl; hydroxycarbonyl-lower alkyl lower; aminocarbonyl; alkylaminocarbonyl; or di-(lower alkyl)-aminocarbonyl; and $R^{15}$ represents hydrogen; lower alkyl; cycloalkyl; lower alkyloxy-lower alkyl; lower alkyloxycarbonyl; hydroxycarbonyl; lower alkyloxycarbonyl-lower alkyl; hydroxycarbonyl-lower alkyl; aminocarbonyl; lower alkylaminocarbonyl; or di-(lower alkyl)-aminocarbonyl, or an optically pure enantiomer, a mixture of enantiomers, a racemate, a pure diastereomer, a mixture of diastereomers, a diastereomeric racemate, a mixture of diastereomeric racemates, a meso-form, or a pharmaceutically acceptable salt thereof.

2. A compounds of claim 1, wherein $R^6$ represents pyrimidinyl; mono- or di-substituted pyrimidinyl, substituted with lower alkyl, lower alkyloxy, halogen, amino, lower alkylamino, di-(lower alkyl)-amino, or lower alkylthio; or mono-substituted pyrimidinyl, substituted with trifluoromethyl, and Y represents oxygen, or a pharmaceutically acceptable salt thereof.

3. A compounds of claim 1, wherein $R^5$ represents phenyl; mono-, di-, or tri-substituted phenyl, substituted with lower alkyl, lower alkyloxy, halogen, amino, lower alkylamino, di-(lower alkyl)-amino, or lower alkylthio; or mono-, or di-substituted phenyl, substituted with trifluoromethyl, or a pharmaceutically acceptable salt thereof.

4. A compounds of claim 1, wherein
X represents —$NR^9$—C(=O)—$CH_2$—,
or a pharmaceutically acceptable salt thereof.

5. A compounds of claim 1, wherein
$R^2$ represents hydrogen,
or a pharmaceutically acceptable salt thereof.

6. A compounds of claim 1, wherein
$R^1$ represents hydrogen,
$R^2$ represents hydrogen, and
$R^4$ represents hydrogen,
or a pharmaceutically acceptable salt thereof.

7. A compounds of claim 1, wherein
$R^1$ represents hydrogen,
$R^2$ represents hydrogen,
$R^3$ represents hydrogen or halogen, and
$R^4$ represents hydrogen,
or a pharmaceutically acceptable salt thereof.

8. A compounds of claim 1, wherein
$R^1$ represents hydrogen,
$R^2$ represents hydrogen,
$R^3$ represents hydrogen or halogen,
$R^4$ represents hydrogen,
$R^5$ represents phenyl; mono-, di-, or tri-substituted phenyl, substituted with lower alkyl, lower alkyloxy, halogen, amino, lower alkylamino, di-(lower alkyl)-amino, or lower alkylthio; or mono- or di-substituted phenyl, substituted with trifluoromethyl,
$R^6$ represents pyrimidinyl; mono- or di-substituted pyrimidinyl, substituted with lower alkyl, lower alkyloxy, halogen, amino, lower alkylamino, di-(lower alkyl)-amino, or lower alkylthio; or mono-substituted pyrimidinyl, substituted with trifluoromethyl,
$R^7$ represents hydrogen,
$R^8$ represents hydrogen,
$R^9$ represents lower alkyl; lower alkenyl; lower alkynyl; hydroxycarbonyl-lower alkyl whereby lower alkyl can be substituted with phenyl; lower alkyloxycarbonyl-lower alkyl whereby lower alkyl can be substituted with phenyl; hydroxy-lower alkyl; lower alkyloxy-lower alkyl; tetrazol-5-yl-lower alkyl; 2,5-dihydro-5-oxo-4H-1,2,4-oxadiazol-3-yl-lower alkyl; 2,5-dihydro-5-oxo-4H-1,2,4-thiadiazol-3-yl-lower alkyl; 2,5-dihydro-5-thioxo-4H-1,2,4-oxadiazol-3-yl-lower alkyl; 2-oxo-3H-1,2,3,5-oxathiadiazol-4-yl-lower alkyl; benzyl; or mono- or di-substituted benzyl substituted at the phenyl ring with lower alkyl, lower alkyloxy, halogen, amino, lower alkylamino, di-(lower alkyl)-amino, trifluoromethyl, lower alkylthio, alkylene-dioxy, or ethylenoxy, X represents —$NR^9$—C(=O)—$CH_2$—, and Y represents oxygen, or a pharmaceutically acceptable salt thereof.

9. A Compound selected from the group consisting of:

(±)-(S*)-(4,6-dimethyl-pyrimidin-2-yloxy)-((6S*)-1-methyl-6-phenyl-5,6-dihydro-4H-2,3,5,10b-tetraaza-benzo[e]azulen-6-yl)-acetic acid;

(±)-(S*)-(4,6-dimethyl-pyrimidin-2-yloxy)-((6S*)-6-phenyl-5,6-dihydro-4H-2,3,5,10b-tetraaza-benzo[c]azulen-6-yl)-acetic acid;

(±)-(S*)-((5S*)-7-chloro-1-methyl-2-oxo-5-phenyl-2,3,4,5-tetrahydro-1H-benzo[e][1,4]diazepin-5-yl)-(4,6-dimethoxy-pyrimidin-2-yloxy)-acetic acid;

(±)-(S*)-[(5S*)-1-(3,5-dimethoxy-benzyl)-2-oxo-5-phenyl-2,3,4,5-tetrahydro-1H-benzo[e][1,4]diazepin-5-yl]-(4,6-dimethoxy-pyrimidin-2-yloxy)-acetic acid;

(±)-4-{(5S*)-5-[(S*)-Carboxy-(4,6-dimethoxy-pyrimidin-2-yloxy)-methyl]-2-oxo-5-phenyl-2,3,4,5-tetrahydro-benzo[e][1,4]diazepin-1-ylmethyl}-benzoic acid methyl ester;

(±)-(S*)-(4,6-dimethoxy-pyrimidin-2-yloxy)-[(5S*)-5-phenyl-1-(2,4,6-trifluoro-benzyl)-2,3,4,5-tetra-hydro-1H-benzo[e][1,4]diazepin-5-yl]-acetic acid;

(±)-(S*)-(4,6-dimethyl-pyrimidin-2-yloxy)-((5S*)-1-methyl-2-oxo-5-phenyl-2,3,4,5-tetrahydro-1H-benzo[e][1,4]diazepin-5-yl)-acetic acid;

(±)-(S*)-((5S*)-1-Carboxymethyl-2-oxo-5-phenyl-2,3,4,5-tetrahydro-1H-benzo[e][1,4]diazepin-5-yl)-(4,6-dimethyl-pyrimidin-2-yloxy)-acetic acid;

(±)-(S*)-[(5S*)-1-(3,5-Dimethoxy-benzyl)-2-oxo-5-phenyl-2,3,4,5-tetra-hydro-1H-benzo[e][1,4]diazepin-5-yl]-(4,6-dimethyl-pyrimidin-2-yloxy)-acetic acid;

(±)-(S*)-(4,6-Dimethyl-pyrimidin-2-yloxy)-[(5S*)-1-(2-hydroxy-ethyl)-2-oxo-5-phenyl-2,3,4,5-tetrahydro-1H-benzo[e][1,4]diazepin-5-yl]-acetic acid;

(±)-(S*)-(4,6-dimethyl-pyrimidin-2-yloxy)-[(5S*)-2-oxo-5-phenyl-1-(1H-tetrazol-5-ylmethyl)-2,3,4,5-tetrahydro-1H-benzo[e][1,4]diazepin-5-yl]-acetic acid;

(±)-4-{(5S*)-5-[(S*)-Carboxy-(4,6-dimethyl-pyrimidin-2-yloxy)-methyl]-2-oxo-5-phenyl-2,3,4,5-tetrahydro-benzo[e][1,4]diazepin-1-ylmethyl}-benzoic acid methyl ester;

(±)-(S*)-(4,6-dimethyl-pyrimidin-2-yloxy)-[(5S*)-1-(4-methoxy-benzyl)-2-oxo-5-phenyl-2,3,4,5-tetrahydro-1H-benzo[e][1,4]diazepin-5-yl]-acetic acid;

(±)-(S*)-(4,6-dimethyl-pyrimidin-2-yloxy)-[(5S*)-2-oxo-5-phenyl-1-(4-trifluoromethyl-benzyl)-2,3,4,5-tetrahydro-1H-benzo[e][1,4]diazepin-5-yl]-acetic acid;

(±)-(S*)-[(5S*)-1-(3-chloro-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-[(5S*)-1-(3,5-bis-trifluoromethyl-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-(4,6-dimethyl-pyrimidin-2-yloxy)-{(5S*)-1-[2-(1-methyl-1H-indol-3-yl)-ethyl]-2-oxo-5-phenyl-2,3,4,5-tetrahydro-1H-benzo[e][1,4]diazepin-5-yl}-acetic acid;

(±)-(S*)-[(5S*)-1-(2-chloro-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-(4,6-dimethyl-pyrimidin-2-yloxy)-(5S*)-2-oxo-1-phenethyl-5-phenyl-2,3,4,5-tetrahydro-1H-benzo[e][1,4]diazepin-5-yl)-acetic acid;

(±)-(S*)-(4,6-dimethyl-pyrimidin-2-yloxy)-[(5S*)-2-oxo-5-phenyl-1-(4-trifluoromethoxy-benzyl)-2,3,4,5-tetrahydro-1H-benzo[e][1,4]diazepin-5-yl]-acetic acid;

(±)-(S*)-[(5S*)-1-(2,6-difluoro-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-(4,6-dimethyl-pyrimidin-2-yloxy)-{(5S*)-1-[2-(2-methoxy-ethoxy)-ethyl]-2-oxo-5-phenyl-2,3,4,5-tetrahydro-1H-benzo[e][1,4]diazepin-5-yl}-acetic acid;

(±)-(S*)-[(5S *)-1-(2,4-difluoro-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-(4,6-dimethyl-pyrimidin-2-yloxy)-[(5S*)-2-oxo-5-phenyl-1-(2,3,6-trifluoro-benzyl)-2,3,4,5-tetrahydro-1H-benzo[e][1,4]diazepin-5-yl]-acetic acid;

(±)-(S*)-(4,6-dimethyl-pyrimidin-2-yloxy)-[(5S*)-2-oxo-5-phenyl-1-(2,4,6-trifluoro-benzyl)-2,3,4,5-tetrahydro-1H-benzo[e][1,4]diazepin-5-yl]-acetic acid;

(±)-(S*)-(4,6-dimethyl-pyrimidin-2-yloxy)-[(5S*)-2-oxo-5-phenyl-1-(2,4,6-trimethyl-benzyl)-2,3,4,5-tetrahydro-1H-benzo[e][1,4]diazepin-5-yl]-acetic acid;

(±)-(S*)-(4,6-dimethyl-pyrimidin-2-yloxy)-[(5S*)-2-oxo-5-phenyl-1-(2,3,4-trifluoro-benzyl)-2,3,4,5-tetrahydro-1H-benzo[e][1,4]diazepin-5-yl]-acetic acid;

(±)-(S*)-[(5S*)-1-(4-butyl-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-[(5S*)-1-(2,6-dichloro-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-(4,6-dimethyl-pyrimidin-2-yloxy)-((5S*)-2-oxo-1,5-diphenyl-2,3,4,5-tetrahydro-1H-benzo[e][1,4]diazepin-5-yl)-acetic acid;

(±)-4-{(5S*)-5-[(S*)-carboxy-(4,6-diethyl-pyrimidin-2-yloxy)-methyl]-2-oxo-5-phenyl-2,3,4,5-tetrahydro-benzo[e][1,4]diazepin-1-ylmethyl}-benzoic acid methyl ester;

(±)-(S*)-(4,6-diethyl-pyrimidin-2-yloxy)-[(5S*)-1-(2-hydroxy-ethyl)-2-oxo-5-phenyl-2,3,4,5-tetrahydro-1H-benzo[e][1,4]diazepin-5-yl]-acetic acid;

(±)-(S*)-(4,6-diethyl-pyrimidin-2-yloxy)-[(5S*)-1-(3,5-dimethoxy-benzyl)-2-oxo-5-phenyl-2,3,4,5-tetrahydro-1H-benzo[e][1,4]diazepin-5-yl]-acetic acid;

(±)-(S*)-(4,6-diethyl-pyrimidin-2-yloxy)-[(5S*)-2-oxo-5-phenyl-1-(2,4,6-trifluoro-benzyl)-2,3,4,5-tetrahydro-1H-benzo[e][1,4]diazepin-5-yl]-acetic acid;

(±)-(S*)-(4,6-dimethyl-pyrimidin-2-yloxy)-[(5S*)-4-methyl-2-oxo-5-phenyl-1-(2,4,6-trifluoro-benzyl)-2,3,4,5-tetrahydro-1H-benzo[e][1,4]diazepin-5-yl]-acetic acid;

(±)-(S*)-[(5S*)-7-chloro-1-(3,5-dimethoxy-benzyl)-2-oxo-5-phenyl-2,3,4,5-tetrahydro-1H-benzo[e][1,4]diazepin-5-yl]-(3,5-dimethoxy-phenoxy)-acetic acid;

(±)-(1S*)-((5S*)-7-chloro-1-methyl-2-oxo-5-phenyl-2,3,4,5-tetrahydro-1H-benzo[e][1,4]diazepin-5-yl)-(4,6-dimethoxy-pyrimidin-2-yloxy)-acetic acid;

(±)-(1S*)-[(5S*)-7-chloro-1-(3,5-dimethoxy-benzyl)-2-oxo-5-phenyl-2,3,4,5-tetrahydro-1H-benzo[e][1,4]diazepin-5-yl]-(4,6-dimethoxy-pyrimidin-2-yloxy)-acetic acid;

(±)-(1S*)-((5S*)-7-chloro-1-methyl-2-oxo-5-phenyl-2,3,4,5-tetra-hydro-1H-benzo[e][1,4]diazepin-5-yl)-(4,6-dimethyl-pyrimidin-2-yloxy)-acetic acid;

(±)-(S*)-[(5S*)-7-chloro-1-(4-methoxy-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-[(5S*)-1-(4-butylbenzyl)-7chloro-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-[(5S*)-7-chloro-2-oxo-5-phenyl-1-(2,4,6-trifluoro-benzyl)-2,3,4,5-tetrahydro-1H-benzo[e][1,4]diazepin-5-yl]-(4,6-dimethyl-pyrimidin-2-yloxy)-acetic acid;

(±)-(S*)-[(5S*)-7-chloro-1-(2,6-dichloro-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-((5S*)-7-chloro-1-methyl-2-oxo-5-phenyl-2,3,4,5-tetrahydro-1H-benzo[e][1,4]diazepin-5-yl)-(4,6-diethyl-pyrimidin-2-yloxy)-acetic acid;

(±)-(S*)-(4,6-dimethyl-pyrimidin-2-yloxy)-[(5S*)-1-(4-methoxy-benzyl)-2-oxo-5-m-tolyl-2,3,4,5-tetrahydro-1H-benzo[e][1,4]diazepin-5-yl]-acetic acid;

(±)-(S*)-(4,6-dimethyl-pyrimidin-2-yloxy)-[(5S*)-5-(3-ethyl-phenyl)-1-(4-methoxy-benzyl)-2-oxo-2,3,4,5-tetrahydro-1H-benzo[e][1,4]diazepin-5-yl]-acetic acid;

(±)-(S*)-(4,6-dimethyl-pyrimidin-2-yloxy)-[(5S*)-5-(3-ethyl-phenyl)-2-oxo-1-(2,4,6-trimethyl-benzyl)-2,3,4,5-tetrahydro-1H-benzo[e][1,4]diazepin-5-yl]-acetic acid;

(±)-(S*)-(4,6-dimethyl-pyrimidin-2-yloxy)-[(5S*)-5-(3-ethyl-phenyl)-2-oxo-1-(2,3,4-trifluoro-benzyl)-2,3,4,5-tetrahydro-1H-benzo[e][1,4]diazepin-5-yl]-acetic acid;

(±)-(S*)-(4,6-dimethyl-pyrimidin-2-yloxy)-[(5S*)-5-(3-ethyl-phenyl)-2-oxo-1-(2,4,6-trifluoro-benzyl)-2,3,4,5-tetrahydro-1H-benzo[e][1,4]diazepin-5-yl]-acetic acid;

(±)-(S*)-(4,6-dimethyl-pyrimidin-2-yloxy)-[(5S*)-1-(4-methoxy-benzyl)-5-(3-methoxy-phenyl)-2-oxo-2,3,4,5-tetrahydro-1H-benzo[e][1,4]diazepin-5-yl]-acetic acid;

(±)-(S*)-(4,6-dimethyl-pyrimidin-2-yloxy)-[(5S*)-5-(3-methoxy-phenyl)-2-oxo-1-(2,4,6-trifluoro-benzyl)-2,3,4,5-tetrahydro-1H-benzo[e][1,4]diazepin-5-yl]-acetic acid;

(±)-(S*)-[(5S*)-1-carboxymethyl-5-(3-methoxy-phenyl)-2-oxo-2,3,4,5-tetrahydro-1H-benzo[e][1,4]diazepin-5-yl]-(4,6-dimethyl-pyrimidin-2-yloxy)-acetic acid;

(±)-(S*)-(4,6-dimethyl-pyrimidin-2-yloxy)-[(5S*)-5-(3-methoxy-phenyl)-2-oxo-1-(2,3,6-trifluoro-benzyl)-2,3,4,5-tetrahydro-1H-benzo[e][1,4]diazepin-5-yl]-acetic acid;

(±)-(S*)-[(5S*)-5-biphenyl-3-yl-1-(4-methoxy-benzyl)-2-oxo-2,3,4,5-tetrahydro-1H-benzo[e][1,4]diazepin-5-yl]-(4,6-dimethyl-pyrimidin-2-yloxy)-acetic acid;

(±)-(S*)-((5S*)-5-biphenyl-3-yl-2-oxo-1-(2,4,6-trifluoro-benzyl)-2,3,4,5-tetrahydro-1H-benzo[e][1,4]diazepin-5-yl]-(4,6-dimethyl-pyrimidin-2-yloxy)-acetic acid;

(±)-(S*)-((5S*)-5-biphenyl-3-yl-1-carboxymethyl-2-oxo-2,3,4,5-tetrahydro-1H-benzo[e][1,4]diazepin-5-yl)-(4,6-dimethyl-pyrimidin-2-yloxy)-acetic acid;

(±)-(S*)-[(5S*)-5-biphenyl-3-yl-2-oxo-1-(2,3,6-trifluoro-benzyl)-2,3,4,5-tetrahydro-1H-benzo[e][1,4]diazepin-5-yl]-(4,6-dimethyl-pyrimidin-2-yloxy)-acetic acid;

(±)-(S*)-(4,6-dimethyl-pyrimidin-2-yloxy)-[(5S*)-5-(4-fluoro-3-methyl-phenyl)-1-(4-methoxy-benzyl)-2-oxo-2,3,4,5-tetrahydro-1H-benzo[e][1,4]diazepin-5-yl]-acetic acid;

(±)-(S*)-[(5S*)-5-butyl-1-(4-methoxy-benzyl)-2-oxo-2,3,4,5-tetrahydro-1H-benzo[e][1,4]diazepin-5-yl]-(4,6-dimethyl-pyrimidin-2-yloxy)-acetic acid;

(±)-(R*)-[(5S*)-7-chloro-1-(4-methoxy-benzyl)-2-oxo-5-phenyl-2,3,4,5-tetrahydro-1H-benzo[e][1,4]diazepin-5-yl]-(4,6-dimethyl-pyrimidin-2-yloxy)-acetic acid;

(±)-(S*)-[(5S*)-1-(4-butyl-benzyl)-5-(3-butyl-phenyl)-2-oxo-2,3,4,5-tetrahydro-1H-benzo[e][1,4]diazepin-5-yl]-(4,6-dimethyl-pyrimidin-2-yloxy)-acetic acid;

(±)-(S*)-[(5S*)-5-(3-butyl-phenyl)-2-oxo-1-(2,4,6-trifluoro-benzyl)-2,3,4,5-tetrahydro-1H-benzo[e][1,4]diazepin-5-yl]-(4,6-dimethyl-pyrimidin-2-yloxy)-acetic acid;

(±)-(S*)-[(5S*)-5-(3-Butyl-phenyl)-1-(2,6-dichloro-benzyl)-2-oxo-2,3,4,5-tetrahydro-1H-benzo[e][1,4]diazepin-5-yl]-(4,6-dimethyl-pyrimidin-2-yloxy)-acetic acid; and (±)-(S*)-(4,6-dimethyl-pyrimidin-2-yloxy)-[(5S*)-2-oxo-5-phenyl-1-(2,4,6-trifluoro-benzyl)-2,3,4,5-tetrahydro-1H-benzo[e][1,4]diazepin-5-yl]-acetic acid dimethylcarbamoylmethyl ester, or a pharmaceutically acceptable salt thereof.

10. A pharmaceutical composition comprising the compound of any one of claims 1 to 9 and a pharmaceutically acceptable carrier and/or an adjuvant.

11. A process for the manufacture of a compound as claimed in any one of claims 1 to 9, which process comprises:

a) in case Y represents $CH_2$ and $R^6$ represents phenyl, substituted phenyl, pyridinyl, substituted pyridinyl, pyrimidinyl, or substituted pyrimidinyl, in Formula I, reacting a compound of Formula IV with an ester of a compound of Formula V in the presence of a strong base, b) in case Y represents $N—CH_3$ and $R^6$ represents phenyl or substituted phenyl in Formula I, reacting a compound of Formula IV with an ester of a compound of Formula V in the presence of a strong base, c) in case Y represents O or S and $R^6$ represents phenyl or substituted phenyl in Formula I, reacting a compound of Formula IV with a compound of Formula V in the presence of a base and an activating agent, d) in case Y represents NH and $R^6$ represents phenyl or substituted phenyl in Formula I, reacting a compound of Formula IV with a compound of Formula V, wherein NH is previously derivatized with a protective group, in the presence of a base and an activating agent, and subsequently deprotecting the amine,

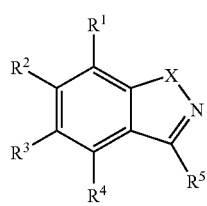

Formula IV

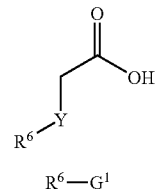

Formula V

-continued

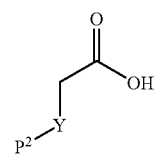

Formula VII e) in case Y represents O, S, NH or $N—CH_3$ and $R^6$ represents a pyridinyl, a substituted pyridinyl, a pyrimidinyl or a substituted pyrimidinyl group, in Formula I, reacting a compound of Formula VIII with a compound of Formula VII, wherein $G^1$ represents a reactive group, in the presence of a base,

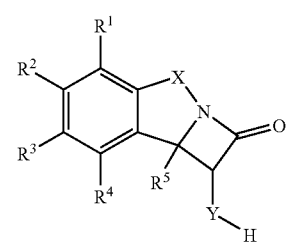

Formula VIII f) cleaving the protecting group $P^2$ in a compound of Formula IX which is prepared by reacting a compound of Formula IV with a compound of Formula X,

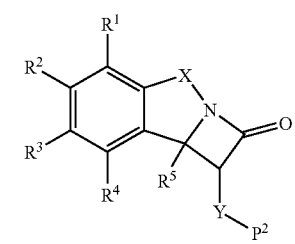

Formula IX

Formula X g) reacting a compound of the Formula III with water or an alcohol $R^8—OH$ in the presence of either a base or an acid in the presence or absence of an additional solvent at a temperature between zero and 100° C.,

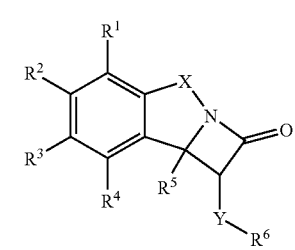

Formula III h) in case $R^7$ in Formula I does not represent a hydrogen atom, reacting a compound of Formula II with an alkylating or acylating agent $R^7$—$G^1$, wherein $G^1$ represents a reactive group, in order to obtain a compound of Formula I, wherein $R^7$ does not represent a hydrogen atom and wherein $R^8$ represents a lower alkyl group, or i) reacting a compound of Formula II

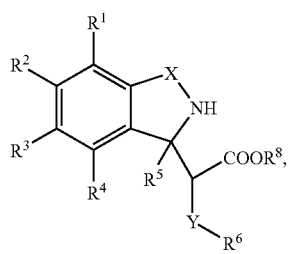

Formula II wherein $R^8$ represents a lower alkyl group, in water in the presence of a base or an acid in the presence or absence of an additional solvent to obtain a compound of Formula I, wherein $R^7$ does not represent a hydrogen atom and wherein $R^8$ represents a hydrogen atom.

12. A process for manufacturing a pharmaceutical composition according to claim 10, comprising mixing one or more of the compounds with a pharmaceutically acceptable excipient.

* * * * *